US009850501B2

(12) United States Patent
Udagawa

(10) Patent No.: US 9,850,501 B2
(45) **Date of Patent: *Dec. 26, 2017**

(54) SIMULTANEOUS SITE-SPECIFIC INTEGRATIONS OF MULTIPLE GENE-COPIES

(71) Applicant: Novozymes A/S, Bagsvaerd (DK)

(72) Inventor: Hiroaki Udagawa, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,757

(22) Filed: Jan. 17, 2017

(65) Prior Publication Data

US 2017/0191081 A1 Jul. 6, 2017

Related U.S. Application Data

(62) Division of application No. 14/118,995, filed as application No. PCT/EP2012/059597 on May 23, 2012, now Pat. No. 9,574,199.

(60) Provisional application No. 61/489,610, filed on May 24, 2011.

(30) Foreign Application Priority Data

May 23, 2011 (EP) .................................... 11167051

(51) Int. Cl.
*C12N 15/80* (2006.01)
*C12N 15/90* (2006.01)

(52) U.S. Cl.
CPC .......... *C12N 15/902* (2013.01); *C12N 15/80* (2013.01)

(58) Field of Classification Search
None
See application file for complete search history.

(56) References Cited

U.S. PATENT DOCUMENTS

2007/0250941 A1 10/2007 Baldwin et al.
2011/0223671 A1 9/2011 Yoder et al.

FOREIGN PATENT DOCUMENTS

WO 0149832 A2 7/2001
WO 2006042548 A1 4/2006

OTHER PUBLICATIONS

Florea et al, 2009, Fungal Gent Biol 46 (10), 721-730.
Forment et al, 2006, Curr Genet 50 (3), 217-224.
Hartman et al, 2010, Appl Environ Microbiol 76 (18), 6613-6617.
Kopke et al, 2010, Appl Environ Microbiol 76 (14), 4664-4674.
Krappman et al, 2005, Eukaryotic Cell 4 (7), 1298-1307.
Sauer et al, 1996, Nucl Acids Res 24 (23), 4608-4613.
Buchholz et al., 1998, Nature Biotech, 16, 657-662.
Ke Wei et al, 1996, J Biol Chem 271 (7), 3812-3816.
Pel et al, 2011, GenBank No. AM26996.

*Primary Examiner* — Jim Ketter
(74) *Attorney, Agent, or Firm* — Robert Starnes

(57) ABSTRACT

The invention relates to a method for the simultaneous integration of two or more copies of a polynucleotide of interest into the chromosome of a fungal host cell comprising at least two pairs of recognition sequences of a site-specific recombinase, each pair flanking a resident negative selection marker; transformation of the cell with a construct carrying a gene of interest also flanked by the recognition sequences to ensure double-crossover events after transient expression of the recombinase, followed by selection for excision of all negative selection markers from the cell.

15 Claims, 21 Drawing Sheets

SIMULTANEOUS SITE-SPECIFIC INTEGRATIONS OF MULTIPLE GENE-COPIES

CROSS-REFERENCE TO RELATED APPLICATIONS

This application is a continuation of U.S. patent application Ser. No. 14/118,995 filed on Nov. 20, 2013, now U.S. Pat. No. 9,574,199, which is a 35 U.S.C. §371 national application of PCT/EP2012/059597 filed on May 23, 2012, which claims priority or the benefit under 35 U.S.C. §119 of U.S. Provisional. Application No. 61/489,610 filed on May 24, 2011, and European Patent Application No. 11167051.9 filed on May 23, 2011, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method for the simultaneous site-specific integrations of multiple copies of a polynucleotide of interest into the genome of a fungal host cell using a transiently expressed recombinase together with suitable resident selection markers.

BACKGROUND OF THE INVENTION

A large number of naturally-occurring organisms have been found to produce useful polypeptide products, e.g., enzymes, the large scale production of which is desirable for research and commercial purposes. Once such a polypeptide product has been identified, efforts are often made to develop manufacturing methods having an improved productivity. One widely used method, which is based on recombinant DNA techniques, is to clone a gene encoding the product and insert the gene into a suitable expression system in order to express the product in a suitable host cell, either integrated in the chromosome or as an extrachromosomal entity, under conditions conducive for the expression of the product.

Irrespective of which production method is used, it is normally desirable to increase the production level of a given polypeptide or protein. Thus, efforts are being made to increase the production, e.g., by inserting the gene encoding the product under the control of a strong expression signal, increasing the stability of the transcribed mRNA or by increasing the number of copies of the gene in the production organism in question. This latter approach may be accomplished by inserting the gene into a multicopy plasmid which generally, however, tends to be unstable in the host cell in question, or by integrating multiple copies of the gene into the chromosome of the production organism, an approach which generally is considered more attractive because the stability of the construct tends to be higher.

Construction of host cells has been described, wherein a highly expressed chromosomal gene is replaced with a recognition sequence of a site-specific recombinase to allow subsequent insertion of a single product-encoding polynucleotide into that site by the use of a recombinase recognizing said sequence (EP 1 405 908 A1; ProBioGen AG).

It has been disclosed to insert DNA at a known location in the genome (O'Gorman et al., 1991 Science, 251:1351-55; Baubonis and Sauer, 1993 Nucl., Acids Res., 21:2025-29; Albert et al., 1995 Plant J., 7:649-59). These methods make use of site-specific recombination systems that are freely reversible. These reversible systems include the following: the Cre-lox system from bacteriophage P1 (Baubonis and Sauer, 1993, supra; Albert et al., 1995 Plant J., 7549-59), the FLP-FRT system of *Saccharomyces cerevisiae* (O'Gorrnan et al., 1991, supra), the R-RS system of *Zygosaccharonzyces rouxii* (Onouchi et al., 1995 Mol. Gen. Genet. 247: 653-660), a modified Gin-gix system from bacteriophage Mu (Maeser and Kahmann, 1991 Mol. Gen. Genet., 230: 170-76), the beta-recombinase-six system from a *Bacillus subtilis* plasmid (Diaz et al., 1999 J. Biol. Chem. 274: 6634-6640), and the delta-gamma-res system from the bacterial transposon Tn1000 (Schwikardi and Dorge, 2000 E B S let. 471: 147-150). Cre, FLP, R, Gin, beta-recombinase and gamma-delta are the recombinases, and lox, FRT, RS, gix, six and res the respective recombination sites (reviewed by Sadowslu, 1993 FASEB J., 7:750-67; Ow and Medberry, 1995 Crit. Rev. Plant Sci. 14: 239-261). Multiplex Cre/lox recombination permits selective site-specific DNA targeting to both a natural and an engineered site in the yeast genome (Sauer, B. Nucleic Acids Research. 1996, Vol. 24(23): 4608-4613). It has been shown that infection of host cells having a natural attachment site, attB as well as an ectopically introduced attB site, with a derivative of the *Streptomyces* phage ΦC31, resulted in the integration of the phage into both attB sites (Smith et al. 2004. Switching the polarity of a bacteriophage integration system. Mol Microbiol 51(6): 1719-1728). Multiple copies of a gene can be introduced into a cell comprising multiple attachment sites recognized by the M×9 integrase using the M×9 phage transformation system, (WO 2004/018635 A2). The temperal Lactococcal bacteriophage TP901-1 integrase and recognition sequences are well-characterized (Breüner et al. (1990) Novel Organization of Genes Involved in Prophage Excision Identified in the Temperate Lactococcal Bacteriophage TP901-1. J Bacteriol 181(23): 7291-7297; Breüner et al. 2001. Resolvase-like recombination performed by the TP901-1 integrase. Microbiology 147: 2051-2063).

The site-specific recombination systems above have in common the property that a single polypeptide recombinase catalyzes the recombination between two sites of identical or nearly identical sequences. Each recombination site consists of a short asymmetric spacer sequence where strand exchange tales place, flanked by an inverted repeat where recombinases bind. The asymmetry of the spacer sequence gives an orientation to the recombination site, and dictates the outcome of a recombination reaction. Recombination between directly or indirectly oriented sites in cis excises or inverts the intervening DNA, respectively. Recombination between sites in trans causes a reciprocal translocation of two linear DNA molecules, or co-integration if at least one of the two molecules is circular. Since the product-sites generated by recombination are themselves substrates for subsequent recombination, the reaction is freely reversible. In practice, however, excision is essentially irreversible because the probability of an intramolecular interaction, where the two recombination-sites are closely linked, is much higher than an intermolecular interaction between unlinked sites. The corollary is that the DNA molecule inserted into a genomic recombination site will readily excise out.

Methods for the replacement, translocation and stacking of DNA in eukaryotic genomes have been disclosed, where multiple genes may be integrated stepwise (WO 02/08409). The simultaneous genomic integration of multiple copies of a promoterless open reading frame or operon by a site-specific and transiently expressed integrase in a microorganism host cell has previously been shown in a *Bacillus* host (WO 2006/042548).

SUMMARY OF THE INVENTION

The present invention is directed to a process for the integration of two or more copies of a polynucleotide of interest into the chromosome of a fungal host cell, by the steps of:

(a) providing a fungal host cell comprising in its chromosome at least two integration sites, each integration site comprising a pair of recognition sequences of a site-specific recombinase, each pair flanking a resident selection marker;

(b) introducing into said cell a nucleic acid construct comprising a pair of recognition sequences of the site-specific recombinase, said pair flanking the polynucleotide of interest;

(c) transiently expressing the site-specific recombinase in the cell, whereby the chromosomal recognition sequence pairs are recombined with the corresponding recognition sequence pair of the nucleic acid construct by the recombinase so that at the least two integration sites, the resident selection marker in the chromosome is excised while a copy of the polynucleotide of interest is integrated in its place to produce a fungal host cell comprising two or more copies of the polynucleotide of interest integrated into the chromosome of the fungal host cell.

As exemplified in the examples section below, the primary aspect of the present invention provides a method for the simultaneous integration of two or more copies of a polynucleotide of interest into the chromosome of a fungal host cell, said method comprising the steps of:

(a) providing a fungal host cell comprising in its chromosome at least two pairs of recognition sequences of a site-specific recombinase, each pair flanking a resident negative selection marker;

(b) introducing into said cell a nucleic acid construct comprising a pair of recognition sequences of the site-specific recombinase, said pair flanking the polynucleotide of interest;

(c) transiently expressing the site-specific recombinase in the cell, whereby the chromosomal recognition sequence pairs are recombined with the corresponding recognition sequence pair of the nucleic acid construct by the recombinase, so that every resident negative selection marker in the chromosome is excised while a copy of the polynucleotide of interest is integrated in its place; and then (d) cultivating the cell in a selective medium and selecting a cell, wherein every negative selection marker has been replaced with two or more copies of the polynucleotide of interest by double homolous recombination.

DEFINITIONS

Figure 1:
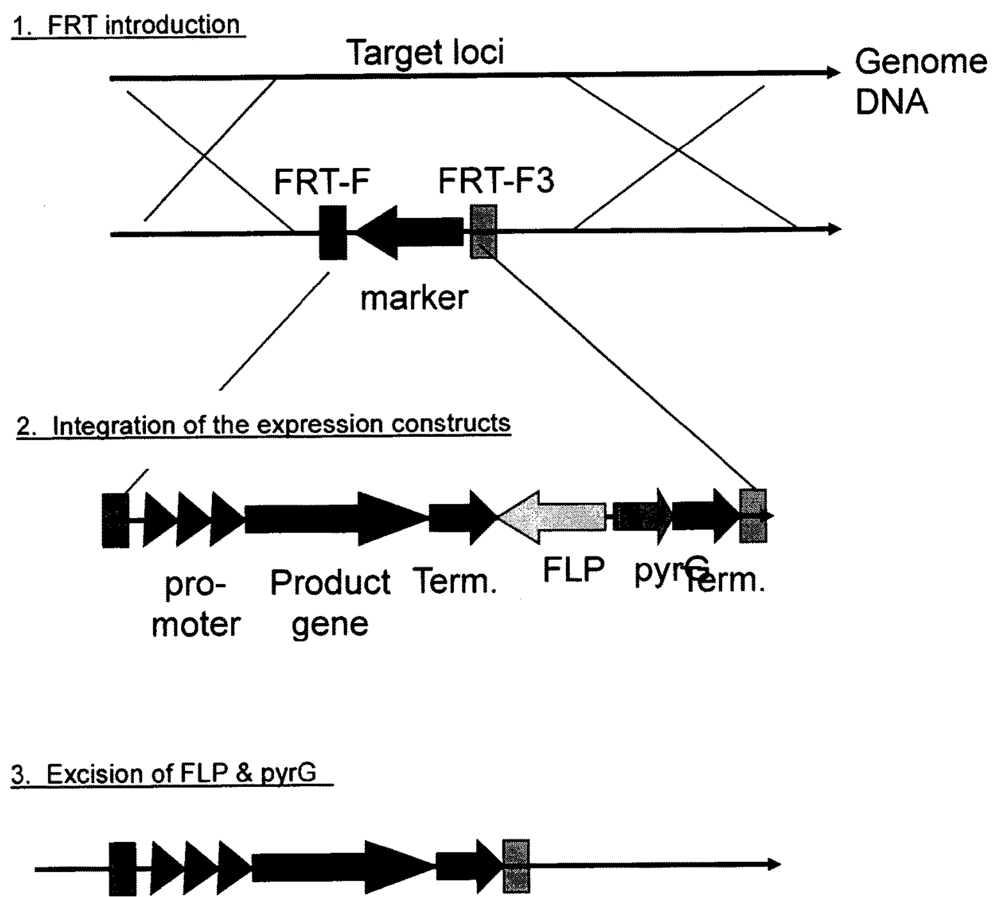
FIG. 1 shows the basic scheme of the method of the invention, herein exemplified using the FRT/FLP recombinase system and pyrG as bi-directional selective marker together with the FLP-encoding gene flanked by two copies of the transcriptional terminator, labelled “Term” that enable the excision of the FLP and pyrG genes by double homologous recombination, which allows transient expression of FLP.

Cytosine deaminase: Cytosine deaminase (EC 3.5.4.1) catalyzes the deamination of cytosine and 5-fluorocytosine (5FC) to form uracil and toxic 5-fluorouracil (5FU), respectively. When genetically modified cells comprising cytosine deaminase are combined with 5FC it is converted to toxic 5FU, so the cytosine deaminase-encoding gene is potentially a potent negative selection marker.

It has also been shown that an inhibitor in the pyrimidine de novo synthesis pathway can be utilized to create a condition in which cells are dependent on the conversion of pyrimidine supplements to uracil by cytosine deaminase. Thus, only cells expressing the cytosine deaminase gene can be rescued in a positive selection medium comprising an inhibitor of the pyrimidine de novo synthesis as well as inosine and cytosine (See FIG. 1 of Wei and Huber, 1996, J Biol Chem 271(7): 3812). The inhibitor is preferably N-(phosphonacetyl)-L-aspartate (PALA), which inhibits aspartate carbamyl transferase.

If necessary, cytosine deaminase activity may be quantitated by a genetic assay (Frederico L. A. et al, 1990, Biochemistry 29: 2532-2537).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids deleted from the amino and/or carboxyl terminus of a mature polypeptide or domain; wherein the fragment has cytosine deaminase activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated or purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Negative selection marker: The term "negative selection marker" means a nucleic acid sequence capable of conferring a selection characteristics so that cells which have the negative selection marker are killed or otherwise identified, e.g., by fluorescence. The negative selection marker is preferably substantially incapable of homologous recombination with the target DNA sequence.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs the expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Simultaneous: The term "simultaneous" as used herein, that is, in reference to the integration of at least two polynucleotides of interest into a host cell, refers to a process by which the integration of at least two copies of the polynucleotide of interest in the the host cell occurs in the same process step that results in the addition of one copy of the polynucleotide of interest, that is, without either the addition of any other materials and/or any additional process steps. Accordingly, the polynucleotide of interest is introduced into the host cell at at least two different integration sites in the same process at the same time or at different times but contemporaneously during the same process.

Subsequence: The term "subsequence" means a polynucleotide having one or more (e.g., several) nucleotides deleted from the 5' and/or 3' end of a mature polypeptide coding sequence; wherein the subsequence encodes a fragment having cytosine deaminase activity.

Variant: The term "variant" means a polypeptide having cytosine deaminase activity comprising an alteration, i.e., a substitution, insertion, and/or deletion of one or more (e.g., several) amino acid residues at one or more positions. A substitution means a replacement of the amino acid occupying a position with a different amino acid; a deletion means removal of the amino acid occupying a position; and an insertion means adding an amino acid adjacent to the amino acid occupying a position.

DETAILED DESCRIPTION OF THE INVENTION

A first aspect of the present invention is directed to a process for the integration of two or more copies of a polynucleotide of interest into the chromosome of a fungal host cell, by the steps of:

(a) providing a fungal host cell comprising in its chromosome at least two integration sites, each integration site comprising a pair of recognition sequences of a site-specific recombinase, each pair flanking a resident selection marker;

(b) introducing into said cell a nucleic acid construct comprising a pair of recognition sequences of the site-specific recombinase, said pair flanking the polynucleotide of interest;

(c) transiently expressing the site-specific recombinase in the cell, whereby the chromosomal recognition sequence pairs are recombined with the corresponding recognition sequence pair of the nucleic acid construct by the recombinase so that at the least two integration sites, the resident selection marker in the chromosome is excised while a copy of the polynucleotide of interest is integrated in its place to produce a fungal host cell comprising two or more copies of the polynucleotide of interest integrated into the chromosome of the fungal host cell.

In a particular embodiment, the first aspect of the invention relates to a method for the simultaneous integration of two or more copies of a polynucleotide of interest into the chromosome of a fungal host cell, said method comprising the steps of:

(a) providing a fungal host cell comprising in its chromosome at least two pairs of recognition sequences of a site-specific recombinase, each pair flanking a resident negative selection marker;

(b) introducing into said cell a nucleic acid construct comprising a pair of recognition sequences of the site-specific recombinase, said pair flanking the polynucleotide of interest;

(c) transiently expressing the site-specific recombinase in the cell, whereby the chromosomal recognition sequence pairs are recombined with the corresponding recognition sequence pair of the nucleic acid construct by the recombinase, so that every resident negative selection marker in the chromosome is excised while a copy of the polynucleotide of interest is integrated in its place; and then (d) cultivating the cell in a selective medium and selecting a cell, wherein every negative selection marker has been replaced with two or more copies of the polynucleotide of interest by double homolous recombination.

In a preferred embodiment, the polynucleotide of interest comprises an operon or an open reading frame encoding at least one polypeptide of interest. The polypeptide of interest may encode any protein of interest, such as, for example, cytokines (in particular interleukins, interferons, colony stimulating factors (CSF) and growth factors), anticoagulants, enzymes, and enzyme inhibitors.

Preferably, the polypeptide of interest comprises an enzyme, preferably a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

Site-specific recombination systems that are freely reversible have been described in detail in literature. These reversible systems include the following: the Cre-lox system from bacteriophage P1 (Baubonis and Sauer, 1993, supra; Albert et al., 1995 Plant J., 7549-59), the FLP-FRT system of *Saccharomyces cerevisiae* (O'Gorrnan et al., 1991, supra), the R-RS system of *Zygosaccharonzyces rouxii* (Onouchi et al., 1995 Mol. Gen. Genet. 247: 653-660), a modified Gin-gix system from bacteriophage Mu (Maeser and Kahmann, 1991 Mol. Gen. Genet., 230: 170-76), the beta-recombinase-six system from a *Bacillus subtilis* plasmid (Diaz et al., 1999 J. Biol. Chem. 274: 6634-6640), and the delta-gamma-res system from the bacterial transposon Tn1000 (Schwikardi and Dorge, 2000 E B S let. 471: 147-150). Cre, FLP, R, Gin, beta-recombinase and gamma-delta are the recombinases, and lox, FRT, RS, gix, six and res the respective recombination sites (reviewed by Sadowslu, 1993 FASEB J., 7:750-67; Ow and Medberry, 1995 Crit. Rev. Plant Sci. 14: 239-261). Multiplex Cre/lox recombination permits selective site-specific DNA targeting to both a natural and an engineered site in the yeast genome (Sauer, B. Nucleic Acids Research. 1996, Vol. 24(23): 4608-4613). It has been shown that infection of host cells having a natural attachment site, attB as well as an ectopically introduced attB site, with a derivative of the *Streptomyces* phage ΦC31, resulted in the integration of the phage into both attB sites (Smith et al. 2004. Switching the polarity of a bacteriophage integration system. Mol Microbiol 51(6):1719-1728). Multiple copies of a gene can be introduced into a cell comprising multiple attachment sites recognized by the M×9 integrase using the M×9 phage transformation system, (WO 2004/018635 A2). The temperal Lactococcal bacteriophage TP901-1 integrase and recognition sequences are well-characterized (Breüner et al. (1990) Novel Organization of Genes Involved in Prophage Excision Identified in the Temperate Lactococcal Bacteriophage TP901-1. J Bacteriol 181(23): 7291-7297; Breüner et al. 2001. Resolvase-like recombination performed by the TP901-1 integrase. Microbiology 147: 2051-2063).

The site-specific recombination systems above have in common the property that a single polypeptide recombinase catalyzes the recombination between two sites of identical or nearly identical sequences. Each recombination site consists of a short asymmetric spacer sequence where strand exchange tales place, flanked by an inverted repeat where recombinases bind. The asymmetry of the spacer sequence gives an orientation to the recombination site, and dictates the outcome of a recombination reaction. Recombination between directly or indirectly oriented sites in cis excises or inverts the intervening DNA, respectively. Recombination between sites in trans causes a reciprocal translocation of two linear DNA molecules, or co-integration if at least one of the two molecules is circular. Since the product-sites generated by recombination are themselves substrates for subsequent recombination, the reaction is freely reversible. In practice, however, excision is essentially irreversible because the probability of an intramolecular interaction, where the two recombination-sites are closely linked, is much higher than an intermolecular interaction between unlinked sites. The corollary is that the DNA molecule inserted into a genomic recombination site will readily excise out, unless the recombinase is transiently expressed, in which case, the inserted DNA will remain once the recombinase is no longer expressed.

Accordingly, it is preferred in the method of the first aspect, that the site-specific recombinase and its pair of recognition sequences are from the the Cre-lox system of bacteriophage P1, the FLP-FRT system of *Saccharomyces cerevisiae*, the R-RS system of *Zygosaccharonzyces rouxii*, a modified Gin-gix system from bacteriophage Mu, the beta-recombinase-six system from a *Bacillus subtilis* plasmid, the delta-gamma-res system from the bacterial transposon Tn1000, the *Streptomyces* phage ΦC31, the M×9 phage transformation system or the Xis-att system of the temperate Lactococcal bacteriophage TP901-1.

In an embodiment, the site-specific recombinase and its pair of recognition sequences are from the FLP-FRT system. In a particular embodiment, the FLP recombinase is an FLP recombinase variant as described in Buchholz, Frank, *Improved properties of FLP recombinase evolved by cycling mutagenesis*, Nature Biotechnology Volume: 16 Issue: 7 (1998 Jul. 1) p. 657-662. In another particular embodiment, the FLP recombinase is a thermostable recombinase variant designated “FLPe” having amino acid alterations P2S, L33S, Y108N, S294P. The nucleic acid sequence and corresponding amino acid sequence for FLPe is shown as SEQ ID NO:106 and SEQ ID NO:107, respectively.

In a preferred embodiment of the first aspect, the negative selection marker encodes a polypeptide confers resistance to an antibiotic to the host cell and the selective medium comprises an inhibitory concentration of the antibiotic.

Alternatively, in another preferred embodiment of the first aspect, the negative selection marker encodes a cytosine deaminase and the selective medium comprises sufficient amounts of 5-fluorocytosin, to be converted to an inhibitory concentration of toxic 5-fluorouracil by said cytosine deaminase.

In an embodiment, the negative selection marker encodes a cytosine deaminase polypeptide having a sequence identity to SEQ ID NO:60 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the polypeptides differ by no more than ten amino acids, e.g., nine amino acids, eight amino acids, seven amino acids, six amino acids, five amino acids, four amino acids, three amino acids, two amino acids, or one amino acid from SEQ ID NO:60.

The encoded cytosine deaminase polypeptide of the present invention preferably comprises or consists of the amino acid sequence of SEQ ID NO:60 or an allelic variant thereof; or is a fragment thereof having cytosine deaminase activity. In another aspect, the polypeptide comprises or consists of the polypeptide of SEQ ID NO:60.

In another embodiment, the negative selection marker encodes a cytosine deaminase polypeptide and hybridizes under very low stringency conditions, low stringency conditions, medium stringency conditions, medium-high stringency conditions, high stringency conditions, or very high stringency conditions with (i) the polypeptide coding sequence of SEQ ID NO:59, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO:59 or a subsequence thereof, as well as the polypeptide of SEQ ID NO:60 or a fragment thereof, may be used to design nucleic acid probes to identify and clone DNA encoding polypeptides having cytosine deaminase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cytosine deaminase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:59 or a subsequence thereof, the carrier material is preferably used in a Southern blot.

For purposes of the present invention, hybridization indicates that the polynucleotide hybridizes to a labeled nucleic acid probe corresponding to (i) SEQ ID NO:59; (ii) the polypeptide coding sequence of SEQ ID NO:59; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film.

For probes of at least 100 nucleotides in length, very low stringency conditions are defined as prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours optimally. The carrier material is finally washed three times each for 15 minutes using 2×SSC, 0.2% SDS at 45° C.

For probes of at least 100 nucleotides in length, low stringency conditions are defined as prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours optimally. The carrier material is finally washed three times each for 15 minutes using 2×SSC, 0.2% SDS at 50° C.

For probes of at least 100 nucleotides in length, medium stringency conditions are defined as prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours optimally. The carrier material is finally washed three times each for 15 minutes using 2×SSC, 0.2% SDS at 55° C.

For probes of at least 100 nucleotides in length, medium-high stringency conditions are defined as prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours optimally. The carrier material is finally washed three times each for 15 minutes using 2×SSC, 0.2% SDS at 60° C.

For probes of at least 100 nucleotides in length, high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours optimally. The carrier material is finally washed three times each for 15 minutes using 2×SSC, 0.2% SDS at 65° C.

For probes of at least 100 nucleotides in length, very high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours optimally. The carrier material is finally washed three times each for 15 minutes using 2×SSC, 0.2% SDS at 70° C.

In another embodiment, the negative selection marker of the first aspect has a sequence identity to the polypeptide coding sequence of SEQ ID NO:59 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the negative selection marker encodes a variant of the cytosine deaminase polypeptide of SEQ ID NO:60 comprising a substitution, deletion, and/or insertion at one or more (e.g., several) positions. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cytosine deaminase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In an embodiment, the number of amino acid substitutions, deletions and/or insertions introduced into the polypeptide of SEQ ID NO:60 is not more than 10, e.g., 1, 2, 3, 4, 5, 6, 7, 8 or 9. The polypeptide may be a hybrid polypeptide in which a region of one polypeptide is fused at the N-terminus or the C-terminus of a region of another polypeptide.

Sources of Polypeptides Having Cytosine Deaminase Activity

A polynucleotide encoding a polypeptide having cytosine deaminase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted.

The cytosine deaminase polypeptide may be a fungal polypeptide. For example, the polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicolalanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide.

It will be understood that for the aforementioned species the invention encompasses both the perfect and imperfect states, and other taxonomic equivalents, e.g., anamorphs, regardless of the species name by which they are known.

Those skilled in the art will readily recognize the identity of appropriate equivalents. Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Nucleic Acid Constructs

The present invention also relates to nucleic acid constructs or expression vectors comprising a selection marker and a polynucleotide of interest operably linked to one or more control sequences that direct their expression in a suitable expression host cell. In a particular embodiment, the present invention also relates to nucleic acid constructs or expression vectors comprising a negative selection marker and a polynucleotide of interest operably linked to one or more control sequences that direct their expression in a suitable expression host cell.

A polynucleotide may be manipulated in a variety of ways to provide for expression of an encoded polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* gene encoding a neutral alpha-amylase in which the untranslated leader has been replaced by an untranslated leader from an *Aspergillus* gene encoding a triose phosphate isomerase; non-limiting examples include modified promoters from an *Aspergillus niger* gene encoding neutral alpha-amylase in which the untranslated leader has been replaced by an untranslated leader from an *Aspergillus nidulans* or *Aspergillus oryzae* gene encoding a triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals, and as described herein, a pair of recognition sequences of the site-specific recombinase flanking the polynucleotide of interest, the promoter, and the transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which, for example, provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The procedures used to ligate the elements described above to construct the recombinant expression vectors of the present invention are well known to one skilled in the art (see, e.g., Sambrook et al., 1989, supra).

Host Cells

The present invention also relates to recombinant host cells transformed by the methods of the present invention. The present invention also relates to recombinant host cells, suitable for transformation with an integrative nucleic acid construct comprising a polynucleotide of interest flanked by regions of homology to either the cytosine deaminase encoding gene, or regions up and downstream of that gene, respectively, in the host cell genome, which direct chromosomal integration by site-specific double homologous recombination, whereby the polynucleotide of interest is integrated into the genome of the host cell while the cytosine deaminase encoding gene is partially or fully excised and thereby inactivated. The successful inactivation of the residing cytosine deaminase encoding gene is selectable in a medium comprising medium comprising 5-fluorocytosin, which is converted to toxic 5-fluorouracil by cytosine deaminase. So, in such a transformation method, the cytosine deaminase encoding gene functions as a negative selection marker, as outlined in the method of the invention.

A host cell with no measurable cytosine deaminase activity is suitable for a transformation method, where the host cell is transformed with a nucleic acid construct comprising at least one expressible cytosine deaminase-encoding polynucleotide, which is then used as a positive selection marker in a growth medium comprising a de novo pyrimidine synthesis inhibitor under conditions conducive for the expression of the cytosine deaminase. Preferably, the de novo pyrimidine synthesis inhibitor is N-(phosphonacetyl)-L-aspartate (PALA), which inhibits aspartate carbamyl transferase.

The term "host cell" encompasses any progeny of a parent cell that is not identical to the parent cell due to mutations that occur during replication. The choice of a host cell will to a large extent depend upon the gene encoding the polypeptide and its source.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subver-*

*mispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Removal or Reduction of Cytosine Deaminase Activity

The present invention also relates to methods of producing a mutant of a parent cell, which comprises inactivating, disrupting or deleting a polynucleotide of the first aspect, or a portion thereof, encoding a cytosine deaminase, which results in the mutant cell producing less or none of the encoded cytosine deaminase compared with the parent cell, when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cytosine deaminase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the polypeptide coding sequence of SEQ ID NO:59 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the cytosine deaminase polypeptide or a control sequence thereof or a silenced gene encoding the polypeptide, which results in the mutant cell producing less of the cytosine deaminase or no cytosine deaminase compared to the parent cell.

The cytosine deaminase-deficient mutant cells are particularly useful as host cells for transformation with genes encoding native and heterologous proteins of interest. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

Transient Expression of Recombinase

There are numerous well-known and simple ways to bring about the transient expression of the site-specific recombinase of step (c) in the first aspect of the invention.

First of all, it could be advantageous to include the polynucleotide encoding the recombinase in the nucleic acid construct introduced into the cell, albeit in such a manner that it could easily be removed from the cell again after its integration, while leaving the remaining integrated polynucleotide of interest in the chromosome. One such method is employed in the examples and also outlined in FIG. 1, where a preferred recognition-site pair is indicated, namely FRT-F and FRT-F3, together with the FLP recombinase-encoding gene and the bi-directional pyrG marker as well as the doubled transcriptional terminators (denoted "Term" in FIG. 1), which serve as homology boxes for later excision of the FLP gene and the pyrG marker by double homologous recombination. Of course, the terms in FIG. 1 are mere examples and are not intended to limit the scope of the invention, the may be substituted for other well-known markers, recognition sequence pairs etc.

In a preferred embodiment of the first aspect, the nucleic acid construct further comprises, also flanked by the pair of recognition sequences: an incoming selection marker and a polynucleotide encoding the site-specific recombinase, in turn flanked by a pair of homology-boxes, which is all integrated with the polynucleotide of interest in step (c). Preferably, the incoming selection marker enables positive selection or negative selection or is bi-directional. It is then envisioned, that the method of the first aspect comprises the positively selecting for the integration in step (c) by double homologous recombination of the polynucleotide of interest along with the incoming selection marker and the polynucleotide encoding the site-specific recombinase, wherein the two latter are flanked by homology boxes. Further, the method comprises a step of negatively selecting for the excision of every integrated copy of the incoming selection marker and the polynucleotide encoding the site-specific recombinase by double homologous recombination between the homology boxes flanking them.

In another preferred embodiment, a second nucleic acid construct is introduced in said cell in step (b), which is either non-replicating or temperature-sensitively replicating, and which comprises a polynucleotide encoding the site-specific recombinase and a selection marker, which enables positive or negative selection or is bi-directional, and which is maintained in said cell transiently by selective pressure or growth at the permissive temperature, respectively, so that the site-specific recombinase can be transiently expressed in step (c).

In a final preferred embodiment, the cell in step (a) comprises in its chromosome at least one copy of a polynucleotide encoding the site-specific recombinase operably linked with a tightly regulated promoter, which can be turned on and off by modifying a growth condition, e.g., by providing a specific carbon source or inducer, so as to enable the transient expression of the site-specific recombinase in step (c).

EXAMPLES

Molecular cloning techniques are described in Sambrook, J., Fritsch, E. F., Maniatis, T. (1989) Molecular cloning: a laboratory manual (2nd edn.) Cold Spring Harbor Laboratory, Cold Spring Harbor, N.Y.

Enzymes

Enzymes for DNA manipulations (e.g., restriction endonucleases, ligases etc.) are obtainable from New England Biolabs, Inc. and were used according to the manufacturer's instructions.

Media and Reagents

The following media and reagents were used unless otherwise specified: Chemicals used for buffers and substrates were commercial products of analytical grade.

Cove: 342.3 g/L Sucrose, 20 ml/L Cove salt solution, 10 mM acetamide, 30 g/L noble agar.

Cove top agar: 342.3 g/L sucrose, 20 ml/L Cove salt solution, 10 mM acetamide, 10 g/L low melt agarose Cove-2: 30 g/L sucrose, 20 ml/L Cove salt solution, 10 mM acetamide, 30 g/L noble agar.

Cove-N (tf) plates are composed of 342.3 g sucrose, 20 ml Cove salt solution, 3 g $NaNO_3$, and 30 g Noble agar and water to 1 liter.

Cove-N plates are composed of 30 g sucrose, 20 ml Cove salt solution, 3 g $NaNO_3$, and 30 g Noble agar and water to 1 liter.

Cove salt solution is composed of 26 g KCl, 26 g $MgSO_4.7H_2O$, 76 g $KH_2PO_4$ and 50 ml Cove trace metals and water to 1 liter.

Trace metal solution for COVE is composed of 0.04 g $NaB_4O_7.10H_2O$, 0.4 g $CuSO_4.5H_2O$, 1.2 g $FeSO_4.7H_2O$, 1.0 g $MnSO_4.H_2O$, 0.8 g Neutral amylase II $MoO_2.2H_2O$, and 10.0 g $ZnSO_4.7H_2O$ and water to 1 liter.

Cove-N top agarose is composed of 342.3 g sucrose, 20 ml COVE salt solution, 3 g $NaNO_3$, and 10 g low melt agarose and water to 1 liter.

amyloglycosidase trace metal solution is composed of 6.8 g $ZnCl_2.7H_2O$, 2.5 g $CuSO_4.5H_2O$, 0.24 g $NiCl_2.6H_2O$, 13.9 g $FeSO_4.7H_2O$, 13.5 g $MnSO_4.H_2O$ and 3 g citric acid, water to 1 liter.

YPG is composed of 4 g yeast extract, 1 g of $KH_2PO_4$, 0.5 g $MgSO_4.7H_2O$ and 15 g glucose (pH 6.0) and water to 1 liter.
STC buffer is composed of 0.8 M sorbitol, 25 mM Tris (pH 8), and 25 mM $CaCl_2$ and water to 1 liter.
STPC buffer is composed of 40% PEG4000 in STC buffer.
MLC is composed of 40 g glucose, 50 g soybean powder, 4 g citric acid (pH 5.0) and water to 1 liter.
MSS is composed of 70 g sucrose, 100 g soybean powder (pH 6.0), and water to 1 liter. MU-1 is composed 260 g maltodextrin, 3 g $MgSO_4.7H_2O$, 5 g $KH_2PO_4$, 6 g $K_2SO_4$, amyloglycosidase trace metal solution 0.5 ml and urea 2 g (pH 4.5) and water to 1 liter.
KCl plates are composed of 0.6 M KCl, 20 ml of Cove salt solution, 3 g of $NaNO_3$, and 30 g of Noble agar and water to 1 liter.
5-fluorocytosine stock solution: 1000 mg 5-fluorocytosine dissolved in 1 ml 0.91 NaCl solution.
Purchased Material (*E. coli*, Plasmid and Kits)

*E. coli* DH5-alpha (Toyobo) is used for plasmid construction and amplification. The commercial plasmids/vectors TOPO cloning kit (Invitrogen) and pBluescript II SK- (Stratagene #212206) are used for cloning of PCR fragments. Amplified plasmids are recovered with Qiagen® Plasmid Kit (Qiagen). Ligation is done with DNA ligation kit (Takara) or T4 DNA ligase (Boehringer Mannheim). Polymerase Chain Reaction (PCR) is carried out with Expand TM PCR system (Boehringer Mannheim). QIAquick™ Gel Extraction Kit (Qiagen) is used for the purification of PCR fragments and extraction of DNA fragment from agarose gel.
Strains

*Aspergillus oryzae* BECh-2 is described in WO 2000/039322. *Aspergillus nidulans* strain NRRL 1092 was used as a donor strain.

The expression host strain *Aspergillus niger* NN059095 was isolated by Novozymes and is a derivative of *Aspergillus niger* NN049184 which was isolated from soil. NN059095 was genetically modified to disrupt expression of amyloglycosidase activities. *Aspergillus oryzae* ToC1512 is described in WO2005/070962, example 11.
Plasmids The expression plasmid pHUda440 and the nucleotide sequences of amyloglucosidase from *Trametes cingulata* are described in patent application WO2006/069289.

Plasmid pJaL574 and the nucleotide sequences of herpes simplex virus (HSV) thymidine kinase gene (TK), *A. nidulans* glyceraldehyde-3-phosphate dehydrogenase promoter (Pgpd) and *A. nidulans* tryptophane synthase terminator (TtrpC) are described in example 9 in WO07045248.
The expression cassette plasmid pJaL790 and the nucleotide sequences of neutral amylase II promoter (Pna2) is described in patent publication WO2005070962.

The JA126 amylase expression vector is described in patent application 10729.000-US.
Plasmid pDV8 is described in patent WO 2001/068864, example 8.
Plasmid pJaL504 is described in example 10.
Plasmid pJaL504-delta-BglII is described in example 10.
Plasmid pJaL554 is described in patent WO2000/050567A1, example 1.
Plasmid pJaL574 is described in example 10.
Plasmid pJaL835 is described in example 10.
Plasmid pJaL955 is described in example 10.
Plasmid pJaL1022 is described in example 10.
Plasmid pJaL1025 is described in example 10.
Plasmid pJaL1027 is described in example 10.
Plasmid pJaL1029 is described in example 10.
Plasmid pJaL1120 is described in example 10.
Plasmid pJaL1123 is described in example 10.
Plasmid pJaL1183 is described in example 10.
Plasmid pJaL1194 is described in example 10.
Plasmid pJaL1202 is described in example 10.
Plasmid pToC65 is described in patent WO 91/17243
Plasmid pUC19: The construction is described in Vieira et al, 1982, Gene 19:259-268.
Plasmid pCR®4Blunt TOPO® from Invitrogen
Transformation of *Aspergillus*

Transformation of *Aspergillus* species can be achieved using the general methods for yeast transformation. The preferred procedure for the invention is described below.

The *Aspergillus niger* host strain was inoculated into 100 ml YPG medium supplemented with 10 mM uridine and incubated for 16 hrs at 32° C. at 80 rpm. Pellets were collected and washed with 0.6 M KCl, and resuspended in 20 ml 0.6 M KCl containing a commercial β-glucanase product (GLUCANEX™, Novozymes A/S, Bagsvrd, Denmark) at a final concentration of 20 mg per ml. The suspension was incubated at 32° C. with shaking (80 rpm) until protoplasts were formed, and then washed twice with STC buffer. The protoplasts were counted with a hematometer and resuspended and adjusted in an 8:2:0.1 solution of STC:STPC:DMSO to a final concentration of 2.5×107 protoplasts/ml. Approximately 4 μg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. Cove or Cove-N top agarose, the reaction was poured onto Cove or Cove-N (tf) agar plates and the plates were incubated at 32° C. for 5 days.

Transformation of other fungal hosts, such as, *Trichoderma* species, can also be achieved using the general methods for fungal transformation.
PCR Amplification

| | |
|---|---|
| 5× PCR buffer (incl. MgCl2) | 20 μl |
| 2.5 mM dNTP mix | 10 μl |
| Forward primer (100□ μM) | 1 μl |
| Reverse primer (100 μM) | 1 μl |
| Expand High Fidelity polymerase (Roche) | 1 μl |
| Template DNA (50-100 ng/μl) | 1 μl |
| Distilled water to | 100 μl |

PCR Conditions

| | | |
|---|---|---|
| 94 C. | 2 min | 1 cycle |
| 92 C. | 1 min | 30 cycles |
| 55 C. | 1 min | |
| 72 C. | 1-2 min | |
| 72 C. | 7 min | 1 cycle |

SF Cultivation for Glucoamylase Production

Spores of the selected transformants were inoculated in 100 ml MLC media and cultivated at 30° C. for 2 days. 10 ml of MLC was inoculated to 100 ml of MU-1 medium and cultivated at 30° C. for 7 days. The supernatant was obtained by centrifugation.
Southern Hybridization Mycelia of the selected transformants were harvested from overnight culture in 100 ml YPG medium, rinsed with distilled water, dried and frozen at −80° C. Ground mycelia were incubated with Proteinase K and RNaseA at 65° C. for 1 hrs. Genome DNA was recovered by phenol/CHCl3 extraction twice followed by EtOH precipitation and resuspended in distilled water.

Non-radioactive probes were synthesized using a PCR DIG probe synthesis kit (Roche Applied Science, Indianapolis Ind.) followed by manufacture's instruction. DIG labeled probes were gel purified using a QIAquick™ Gel Extraction Kit (QIAGEN Inc., Valencia, Calif.) according to the manufacturer's instructions.

Five micrograms of genome DNA was digested with appropriate restriction enzymes completely for 16 hours (40 μl total volumes, 4 U enzyme/μl DNA) and run on a 0.8% agarose gel. The DNA was fragmented in the gel by treating with 0.2 M HCl, denatured (0.5 M NaOH, 1.5 M NaCl) and neutralized (1 M Tris, pH7.5; 1.5 M NaCl) for subsequent transfer in 20×SSC to Hybond N+ membrane (Amersham). The DNA was UV cross-linked to the membrane and prehybridized for 1 hour at 42° C. in 20 ml DIG Easy Hyb (Roche Diagnostics Corporation, Mannheim, Germany). The denatured probe was added directly to the DIG Easy Hyb buffer and an overnight hybridization at 42° C. was done. Following the post hybridization washes (twice in 2×SSC, roome temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker.

Glucoamylase Activity

Glucoamylase activity is measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes. An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Amyloglycosidase Incubation:
Substrate: maltose 23.2 mM
Buffer: acetate 0.1 M
pH: 4.30±0.05
Incubation temperature: 37° C.±1
Reaction time: 5 minutes
Enzyme working range: 0.5-4.0 AGU/mL Color Reaction:
GlucDH: 430 U/L
Mutarotase: 9 U/L
NAD: 0.21 mM
Buffer: phosphate 0.12 M; 0.15 M NaCl
pH: 7.60±0.05
Incubation temperature: 37° C.±1
Reaction time: 5 minutes
Wavelength: 340 nm Determination of Acid Alpha-Amylase Activity When used according to the present invention the activity of any acid alpha-amylase may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions. Acid alpha-amylase, i.e., acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

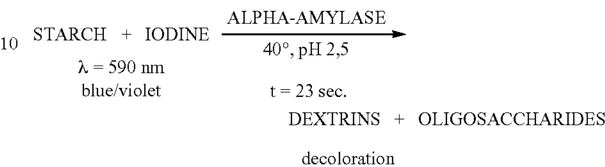

Standard Conditions/Reaction Conditions:
Substrate: Soluble starch, approx. 0.17 g/L
Buffer: Citrate, approx. 0.03 M
Iodine (12): 0.03 g/L
CaCl2: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL

Example 1. Introduction of FRT Sites at the Neutral Amylase I (NAI) Locus in *Aspergillus niger* NN059095

Construction of Hygromycin B Resistance Gene Expression Plasmid pHUda966

The following primers Tef-F and Tef-R which introduce EcoRI/SpeI and a BamHI site, respectively, were designed to isolate a promoter region of *A. oryzae* tef1 (translation elongation factor 1/Ptef1) based on the nucleotide sequences information in GENBANK (ID#AB007770):

```
Tef-F (SEQ ID NO: 1):
gaattcactagtggggttcaaatgcaaacaa

Tef-R (SEQ ID NO: 2):
ggatcctggtgcgaactttgtagtt
```

A PCR reaction with the genome DNA of the *Aspergillus oryzae* strain BECh2 as template was performed using a primer pair of Tef-F and Tef-R. The reaction products were isolated on a 1.0% agarose gel and 0.7 kb product band was excised from the gel. The 0.7 kb amplified DNA fragment was digested with BamHI and EcoRI, and ligated into the *Aspergillus* expression cassette pHUda440 digested with BamHI and EcoRI to create pHUda440-Ptef.

The following primers nia-F and nia-R which introduce an XhoI and an XbaI site, respectively, were designed to isolate a terminator region of *A. oryzae* nitrate reductase (niaD) (Tniad) based on the nucleotide sequences information in EMBL:D49701:

```
nia-F (SEQ ID NO: 3):
ctcgagattatccaagggaatgac

nia-R (SEQ ID NO: 4):
tctagaaagtattttcggtacgatt
```

A PCR reaction with the genome DNA of the *Aspergillus oryzae* strain BECh2 as template was performed using a primer pair of nia-F and nia-R. The reaction products were isolated on a 1.0% agarose gel and 0.5 kb product band was excised from the gel. The 0.5 kb amplified DNA fragment was digested with XhoI and XbaI, and ligated into the *Aspergillus* expression cassette pHUda440-Ptef digested with XhoI and XbaI to create pHUda440-Ptef-Tnia.

The following primers hph-F and hph-R which introduce a BamH and an XhoI site, respectively, were designed to isolate a coding region of hygromycin B resistance gene based on the nucleotide sequences information in EMBL: AR109978:

hph-F (SEQ ID NO: 5): ggatcctacacctcagcaatgtcgcctgaa hph-R (SEQ ID NO:6): ctcgagctattcctttgccctcggacgagtgct A PCR reaction with pJaL154 harboring the hygromycin B resistance gene (hph) as template was performed using a primer pair of hph-F and hph-R. The reaction products were isolated on a 1.0% agarose gel and 1.0 kb product band was excised from the gel. The 1.0 kb amplified DNA fragment was digested with BamHI and XhoI, and ligated into the *Aspergillus* expression cassette pHUda440-Ptef-Tnia digested with BamHI and XhoI to create pHUda966. The nucleotide sequences of hygromycin B resistance gene (hph) expression parts in pHUda966 are shown in SEQ ID NO:7, with indications of the features positions of the primers used for the construction, the encoded hygromycin B resistance factor is shown in SEQ ID NO:8.

Construction of pHUda981 for Introduction of FRT Sites at the NA1 Loci

The 2.5 kb DNA fragment containing herpes simplex virus (HSV) thymidine kinase gene (TK) was recovered from pJaL574 by XhoI and EcoRI digestion. The recovered 2.5 kb fragment was ligated to XhoI and EcoRI digested pBluescript II SK-. The ligation mixture was transformed into *E. coli* DH5α to create the expression plasmid pTK.

The nucleotide sequences of the FRT-F and FRT-F3 sites are:

```
FRT-F (SEQ ID NO: 9):
ttgaagttcctattccgagttcctattctctagaaagtataggaacttc

FRT-F3 (SEQ ID NO: 10):
ttgaagttcctattccgagttcctattcttcaaatagtataggaacttca
```

The following primers 3NA1-F and 3NA1-R which introduce an EcoRI and a SpeI site, respectively, were designed to isolate 3' flanking region of *Aspergillus niger* neutral amylase I (NAI) fused with FRT-F3 recognition site based on the nucleotide sequences information in EMBL: AM270106 and EMBL: DJ052242, respectively:

```
3NA1-F (SEQ ID NO: 11):
actagtttgaagttcctattccgagttcctattcttcaaatagtatagg
aacttcaactagagtatatgatggtact

3NA1-R (SEQ ID NO: 12):
gaattcgcattctcctagttactgatgacttt
```

A PCR reaction with the genome DNA of *Aspergillus niger* NN059095 as template was performed using a primer pair of 3NA1-F and 3NA1-R. The reaction products were isolated on a 1.0% agarose gel and 1.0 kb product band was excised from the gel. The 1.5 kb amplified DNA fragment was digested with SpeI and EcoRI, and ligated into the *Aspergillus* expression cassette pTK digested with EcoRI and SpeI to create pHUdaTK-3NA1.

The following primers 5NA1-F and 5NA1-R which introduce a NotI and a SpeI site, respectively, were designed to isolate 5' flanking region of *Aspergillus niger* neutral amylase I (NAI) fused with FRT-F recognition site based on the nucleotide sequences information in EMBL:AM270106 and EMBL: DJ052242, respectively:

```
5NA1-F (SEQ ID NO: 13):
gcggccgcgtttaaacctatctgttccc

5NA1-R (SEQ ID NO: 14):
actagtgctagcgaagttcctatactttctagagaataggaactcggaat
aggaacttcaagatgaattcgcggcctacatg
```

A PCR reaction with the genome DNA of *Aspergillus niger* NN059095 as template was performed using a primer pair of 5NA1-F and 5NA1-R. The reaction products were isolated on a 1.0% agarose gel and 1.8 kb product band was excised from the gel. The 1.8 kb amplified DNA fragment was digested with NotI and SpeI, and ligated into the *Aspergillus* expression cassette pTK-3NA1 digested with NotI and SpeI to create pHUdaTK-3NA1-5NA1.

The 2.2 kb DNA fragment containing hybromycin B resistance gene driven by *Aspergillus oryzae* tef1 promoter (Ptef) and niaD terminator (Tniad) was recovered from pHUda966 by XbaI and NheI digestion. The recovered 2.2 kb fragment was ligated to SpeI digested pHUdaTK-3NA1-5NA1. The ligation mixture was transformed into *E. coli* DH5α to create the expression plasmid pHUda981.

Figure 2:
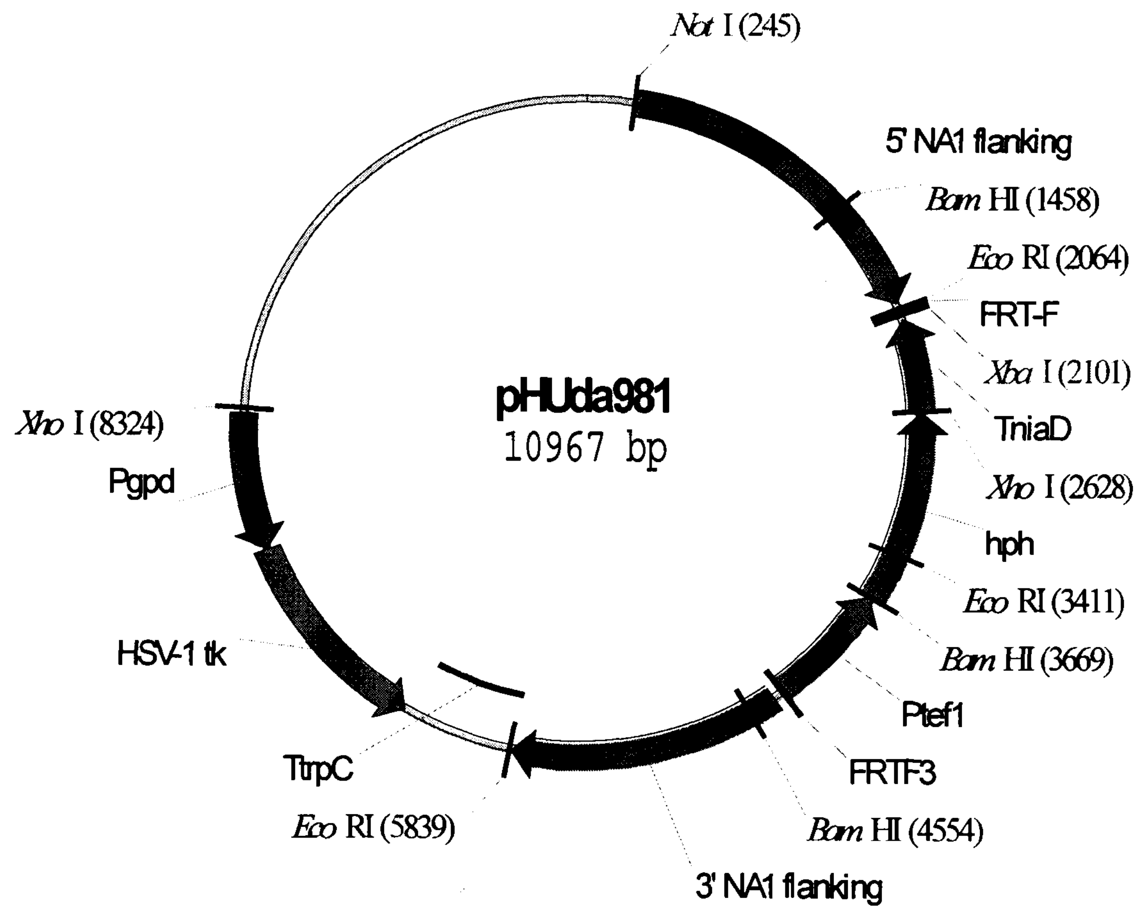
FIG. 2 shows a plasmid map of pHUda981 (Pgpd, HSV1 tk, TtrpC are described in WO07045248).

The nucleotide sequence of the NA1-encoding part and flanking regions of pHUda981 is shown in SEQ ID NO:15, the NA1 is shown in SEQ ID NO: 16 and a plasmid map is shown in FIG. 2.

Introduction of FRT Sites at the NA1 Locus in *A. Niger* NN059095

The pHUda981 was introduced into *Aspergillus niger* strain NN059095. Transformants were selected from the Cove-N (tf) supplemented with 10 mM uridine and 1 mM hygromycin B. Randomly selected transformants were inoculated onto Cove-N plates with 10 mM uridine, 1 mM hygromycin B and 2.5 μM 5-Flouro-2-deoxyuridine (FdU), an agent which kills cells expressing the herpes simplex virus (HSV) thymidine kinase gene (TK) harbouring in pHUda981. Strains which grew well on Cove-N plates supplemented with 2.5 μM FdU were purified and subjected to Southern blotting analysis to confirm whether the FRT sites in pHUda981 was introduced correctly or not.

The following set of primers to make a non-radioactive probe was used to analyze the selected transformants. For the 5' NA1 flanking region:

```
Forward primer (SEQ ID NO: 17):
aatccggatcctttcctata

Reverse primer (SEQ ID NO: 18):
gatggagcgcgcctagaagc
```

Genomic DNA extracted from the selected transformants was digested by NcoI and Southern blotting analysis was preformed using the above probe. Strains of interest were identified by the disappearance of a 2.8 kb NcoI band and the appearance of a 3.1 kb NcoI band. Among the strains given the right integration events, a strain denoted NN059180 was selected.

Example 2. Introduction of FRT Sites at the Acid Stable Amylase Locus in *A. niger* NN059095

Construction of *A. Nidulans* Acetoamidase Gene (amdS) Expression Plasmid pHUda976.

The following primers amdS-F and amdS-R which introduce a BamHI and an XhoI site, respectively, were designed to isolate a coding region of amdS gene based on the nucleotide sequences information in EMBL:AF348620:

```
amdS-F (SEQ ID NO: 19):
ggatccaccatgcctcaatcctgg

amdS-R (SEQ ID NO: 20):
ctcgagctatggagtcaccacatttcccag
```

A PCR reaction with genome DNA of *Aspergillus nidulans* strain NRRL 1092 as template was performed using a primer pair of amdS-F and amdS-R. The reaction products were isolated on a 1.0% agarose gel and 1.0 kb product band was excised from the gel. The 1.9 kb amplified DNA fragment was digested with BamHI and XhoI, and ligated into the *Aspergillus* expression cassette pHUda440-Ptef-Tnia digested with BamHI and XhoI to create pHUda976.

The nucleotide sequence of the *Aspergillus nidulans* acetoamidase gene (amdS) expression parts in pHUda976 is shown in SEQ ID NO:21 with gene features positions of the primers used, the encoded acetoamidase amino acid sequence is shown in SEQ ID NO:22.

Construction of pHUda1019 for Introduction of FRT Sites at the Acid Stable Amylase Locus The following primers 3SP-F and 3SP-R which introduce an EcoRI and a SpeI site, respectively, were designed to isolate 3' flanking region of *Aspergillus niger* acid stable amylase fused with FRT-F3 recognition site based on the nucleotide sequences information in EMBL:AM270232 and EMBL: DJ052242, respectively:

```
3SP-F (SEQ ID NO: 23):
actagtttgaagttcctattccgagttcctattcttcaaatagtatagga
acttcaactagagaatgcaatcataacagaaagta

3SP-R (SEQ ID NO: 24):
gaattcttaattaaatcacggcaagggtttac
```

A PCR reaction with the genome DNA of *Aspergillus niger* NN059095 as template was performed using a primer pair of 3SP-F and 3SP-R. The reaction products were isolated on a 1.0% agarose gel and 1.8 kb product band was excised from the gel. The 1.8 kb amplified DNA fragment was digested with SpeI and EcoRI, and ligated into the *Aspergillus* expression cassette pTK digested with EcoRI and SpeI to create pHUdaTK-3SP.

The following primers 5SP-F and 5SP-R which introduce a SacII and a SpeI site, respectively, were designed to isolate 5' flanking region of *Aspergillus niger* acid stable amylase fused with FRT-F recognition site based on the nucleotide sequences information in EMBL:AM270232 and EMBL: DJ052242, respectively:

```
5SP-F (SEQ ID NO: 25):
ccgcggcaacaggcagaatatcttcc

5SP-R (SEQ ID NO: 26):
actagtgaagttcctatactttctagagaataggaactcggaataggaac
ttcaaacgggatcttggacgcattcca
```

A PCR reaction with the genome DNA of *Aspergillus niger* NN059095 as template was performed using a primer pair of 5SP-F and 5SP-R. The reaction products were isolated on a 1.0% agarose gel and 2.0 kb product band was excised from the gel. The 2.0 kb amplified DNA fragment was digested with SacII and SpeI, and ligated into the *Aspergillus* expression cassette pTK-3SP digested with SacII and SpeI to create pHUdaTK-3SP-5SP.

The 3.1 kb DNA fragment containing the amdS gene driven by *Aspergillus oryzae* tef1 promoter and niaD terminator was recovered from pHUda976 by XbaI and NheI digestion. The recovered 3.1 kb fragment was ligated to SpeI digested pHUdaTK-3SP-5SP. The ligation mixture was transformed into *E. coli* DH5α to create the expression plasmid pHUda1019.

Figure 3:
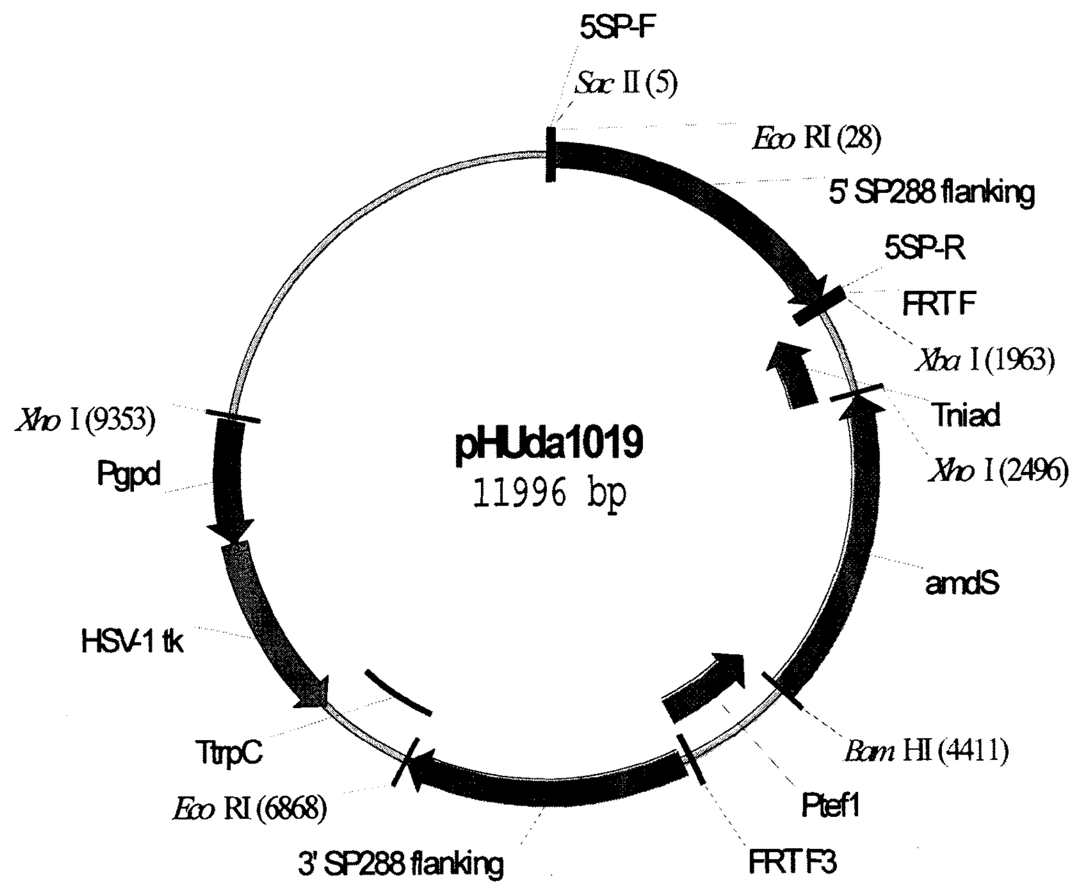
FIG. 3 shows a plasmid map of pHUda1019.

The nucleotide sequence of the *A. niger* acid stable amylase gene with the flanking sequences of pHUda1019 are shown in SEQ ID NO:27 and the encoded amylase amino acid sequence is shown in SEQ ID NO:28; a plasmid map is shown in FIG. 3.

Introduction of FRT Sites at the Locus in *A. niger* NN059180

The pHUda1019 was introduced into *Aspergillus niger* strain NN059180. Transformants were selected from the Cove (tf) supplemented with 10 mM uridine. Randomly selected transformants were inoculated onto Cove-2 plates with 10 mM uridine and 2.5 μM 5-Flouro-2-deoxyuridine (FdU), an agent which kills cells expressing the herpes simplex virus (HSV) thymidine kinase gene (TK) harbouring in pHUda1019. Strains which grew well on Cove-2 plates with 2.5 μM FdU were purified and subjected to Southern blotting analysis to confirm whether the FRT sites in pHUda1019 was introduced correctly or not.

The following set of primers to make non-radioactive probe was used to analyze the selected transformants. For 5' acid stable amylase flanking region:

```
Forward primer (SEQ ID NO: 29):
cgtacaccttgggattatgcgctg

Reverse primer (SEQ ID NO: 30):
cacaaaggcgcaaagcataccatc
```

Genomic DNA extracted from the selected transformants was digested by XhoI. The right integration event were identified by the disappearance of a 6.2 kb XhoI band and the appearance of a 4.1 XhoI band. Among the strains given the right integration events, a strain denoted NN059183 was selected.

Example 3. Simultaneous Site Specific-Integration by FLP in the Two Loci

Construction of *A. nidulans* pyrG Gene Expression Plasmid pHUda794

The following primers pyr-F introducing a PacI site and pyr-R were designed to isolate a promoter and coding region of *A. nidulans* pyrG gene based on the nucleotide sequences information in EMBL:m19132:

```
pyr-F (SEQ ID NO: 31):
ttaattaaactaaatgacgtttgtgaaca

pyr-R (SEQ ID NO: 32):
ctaccgccaggtgtcagtcaccctcaaagtccaactcttttc
```

The following primers Tamg-F and Tamg-R introducing a SphI site were designed to isolate a terminator region of *A. niger* amyloglucosidase (Tamg) gene fused with FRT-F3 recognition site based on the nucleotide sequences information in EMBL:am270061 and DJ052242:

```
Tamg-F (SEQ ID NO: 33):
agagttggactttgagggtgactgacacctggcggtag

Tamg-R (SEQ ID NO: 34):
gcatgcactagctagttgaagttcctatactatttgaagaataggaactc
ggaataggaacttcaacctagaggagagagttg
```

A PCR reaction with genome DNA of *Aspergillus nidulans* strain NRRL 1092 as template was performed using a primer pair of pyr-F and pyr-R. The reaction products were isolated on a 1.0% agarose gel and 1.4 kb product band was excised from the gel.

A PCR reaction with the genome DNA of *Aspergillus niger* NN059095 as template was performed using a primer pair of Tamg-F and Tamg-R. The reaction products were isolated on a 1.0% agarose gel and 0.8 kb product band was excised from the gel.

A PCR reaction with the 1.4 kb and 0.8 kb amplified DNA fragment was performed using a primer pair of pyr-F and Tamg-R. The reaction products were isolated on a 1.0% agarose gel and 2.2 kb product band was excised from the gel.

The 2.2 kb amplified DNA fragment was packed into the TOPO cloning vector (pCR2.1 TOPO) provided by Invitrogen followed by the protocol with the kit to create pHUda794.

The nucleotide sequence of the *A. nidulans* pyrG gene with flanking sequences in pHUda794 is shown in SEQ ID NO:35 along with features and positions of primers used; the amino acid seqeunce of the encoded PyrG is shown in SEQ ID NO:36.

Construction of Synthetic Version of FLP Gene Expression Plasmid pHUda996

The following primers xln-F and xln-R introducing a SphI site and a BamHI, respectively, were designed to isolate a promoter region of *A. nidulans* xlnA gene (PxlnA) based on the nucleotide sequences information in EMBL:z49892:

```
xln-F (SEQ ID NO: 37):
gcatgcttaattaatggaagtgcgttgatcatt

xln-R (SEQ ID NO: 38):
ggatcccctgtcagttggg
```

A PCR reaction with genome DNA of *Aspergillus nidulans* strain NRRL 1092 as template was performed using a primer pair of xln-F and xln-R. The reaction products were isolated on a 1.0% agarose gel and 0.7 kb product band was excised from the gel. The 0.7 kb amplified DNA fragment was digested with BamHI and SphI, and ligated into the *Aspergillus* expression cassette pHUda966 digested with BamHI and SphI to create pHUda966-PxlnA.

The 1.3 kb DNA fragment containing synthetic version of FLP gene (sFLP) was recovered from pJaL1008 by BamHI and XhoI digestion. The recovered 1.3 kb fragment was ligated to BamHI and XhoI digested pHUda966-PxlnA. The ligation mixture was transformed into *E. coli* DH5α to create the expression plasmid pHUda996.

The nucleotide sequences of the synthetic version of FLP expression parts in pHUda996 is shown in SEQ ID NO:39 together with features and positions of the primers used; the amino acid sequence of the encoded sFLP is shown in SEQ ID NO:40.

Construction of pHUda1000 for Simultaneous Site Specific-Integration at the Neutral Amylase 1 (NA1) and the Acid Stable Amylase Loci in NN059183

The following primers Pna-F and Pna-R introducing an EcoRI site and a BamHI site, respectively, were designed to isolate a promoter region of *A. niger* neutral amylase II (NA2) gene (Pna2) put triple in tandem fused with FRT-F recognition site based on the nucleotide sequences information in pJaL790 and EMBL:DJ052242:

```
Pna-F (SEQ ID NO: 41):
gaattcatcttgaagttcctattccgagttcctattctctagaaagtat
aggaacttcgctagccgagagcagcttgaaga

Pna-R (SEQ ID NO: 42):
ggatcccccagttgtgtatatagaggatt
```

A PCR reaction with pJaL790 as template was performed using a primer pair of Pna-F and Pna-R. The reaction products were isolated on a 1.0% agarose gel and 1.7 kb product band was excised from the gel. The 1.7 kb amplified DNA fragment was digested with EcoRI and BamHI, and ligated into the *Aspergillus* expression cassette pHUda440 harboring amyloglucosidase gene from *Trametes cingulata* (T.c. GA) digested with EcoRI and BamHI to create pHUda440-FRT.

The 2.2 kb DNA fragment containing *A. nidulans* pyrG gene was recovered from pHUda794 by PacI and SphI digestion. The recovered 2.2 kb fragment was ligated to PacI and SphI digested pHUda440-FRT. The ligation mixture was transformed into *E. coli* DH5α to create the expression plasmid pHUda440-FRT-pyrG.

Figure 4:
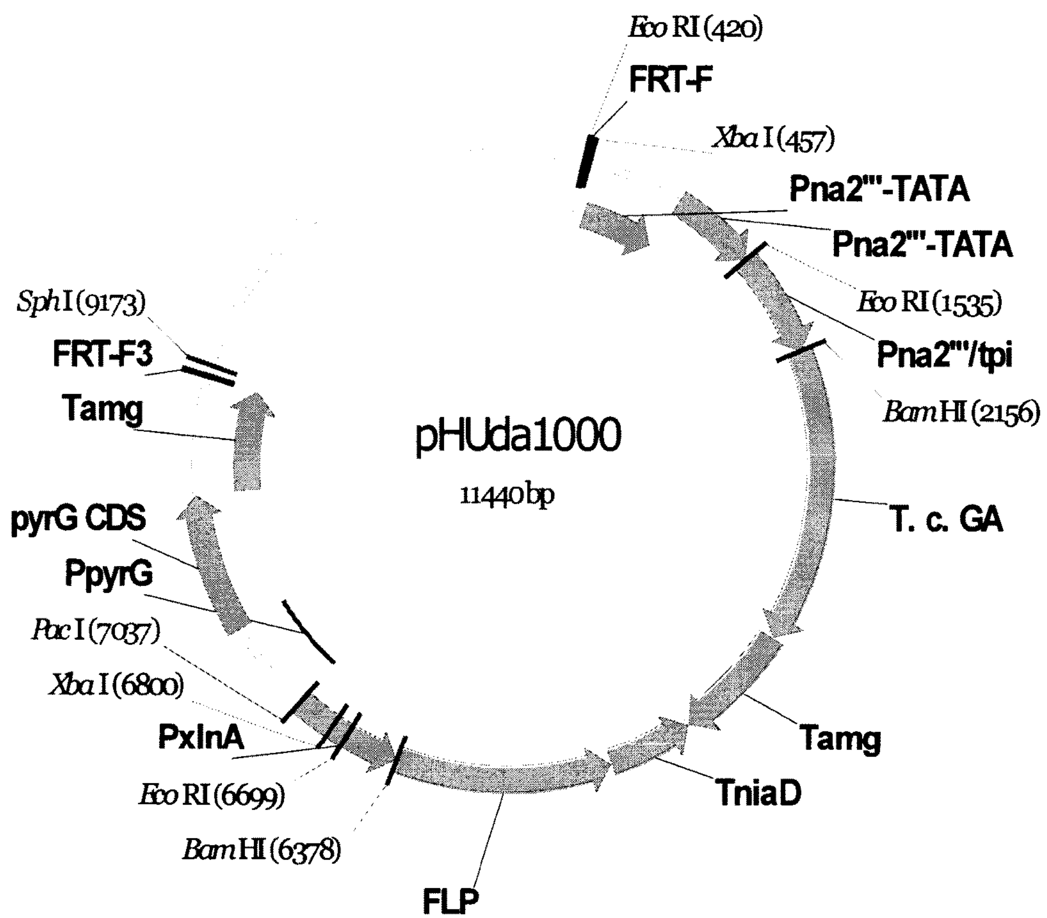
FIG. 4 shows a plasmid map of pHUda1000.

The 2.4 kb DNA fragment containing FLP gene driven by xlnA promoter and niaD terminator was recovered from pHUda996 by PacI and XbaI digestion. The recovered 2.4 kb fragment was ligated to PacI and XbaI digested pHUda440-FRT-pyrG. The ligation mixture was transformed into *E. coli* DH5α to create the expression plasmid pHUda1000. A plasmid map is shown in FIG. 4.

Simultaneous Site Specific-Integration by FLP

The pHUda1000 was introduced into *Aspergillus niger* strain NN059183. Transformants were selected from the Cove-N (tf) supplemented with 1% D-xylose. Randomly selected transformants were inoculated onto Cove-N plates. Strains which grew well on Cove-N plates were purified and subjected to Southern blotting analysis to confirm whether the expression part in pHUda1000 was introduced correctly or not.

The following set of primers to make a non-radioactive probe was used to analyze the selected transformants. For T.c.GA coding region:

```
Forward primer (SEQ ID NO: 43):
tcgagtgcggccgacgcgtacgtc

Reverse primer (SEQ ID NO: 44):
cagagagtgttggtcacgta
```

Genomic DNA extracted from the selected transformants was digested by HindIII and Southern blotting analysis was preformed using the above probe. Strains of interest were identified by the disappearance of a 2.8 kb NcoI band and the appearance of a 3.1 kb NcoI band. By the right integration event, two hybridized signals of the size 7.2 kb and 5.7 kb introduced at NA1 and acid stable amylase loci, respectively, were seen.

Figure 5A:
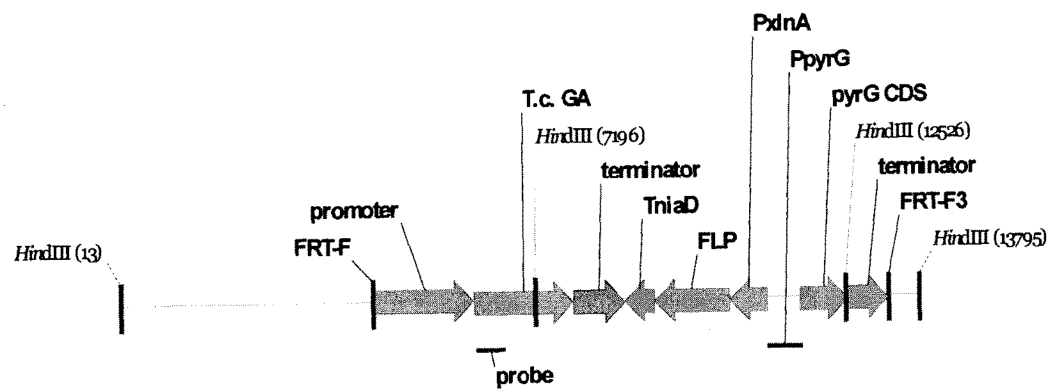
FIG. 5A shows the schematic NA1 locus after the pHUda1000 was introduced correctly in NN059183.
Figure 5B:
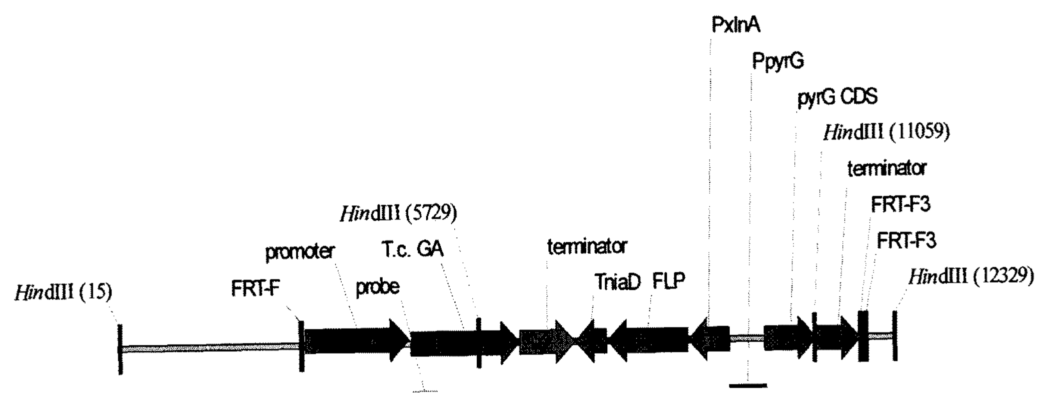
FIG. 5B shows the schematic acid stable amylase locus after the pHUda1000 was introduced correctly in NN059183.

FIG. 5A shows the schematic NA1 locus and FIG. 5B shows the schematic acid stable amylase locus when the pHUda1000 was introduced correctly in NN059183.

Example 4. *A. niger* Ku70 Gene Disruption in NN059183

Construction of the *A. niger* Ku70 Gene Disruption Vector pHUda801

The following primers 3ku-F and 3ku-R introducing an EcoRI site and a SpeI site, respectively, were designed to isolate a 3' flanking region of *A. niger* ku70 gene based on the nucleotide sequences information in EMBL:am270339:

```
3ku-F (SEQ ID NO: 45):
actagttctagaagccgtgggtatttttatgaa

3ku-R (SEQ ID NO: 46):
gaattcgtttaaacttggcggctgccaagcttcc
```

A PCR reaction with genome DNA of *Aspergillus niger* strain NN059183 as template was performed using a primer pair of 3ku-F and 3ku-R. The reaction products were isolated on a 1.0% agarose gel and 2.0 kb product band was excised from the gel. The 2.0 kb amplified DNA fragment was digested with EcoRI and SpeI, and ligated into the pTK digested with EcoRI and SpeI to create pTK-3ku.

The following primers 5ku-F and 5ku-R introducing a NotI site and a SpeI site, respectively, were designed to isolate a 5' flanking region of *A. niger* ku70 gene based on the nucleotide sequences information in EMBL:am270339:

```
5ku-F (SEQ ID NO: 47):
gcggccgctcattcagagagctacccgt

5ku-R (SEQ ID NO: 48):
actagttaattaagaggaccgcatctttga
```

A PCR reaction with genome DNA of *Aspergillus niger* strain NN059183 as template was performed using a primer pair of 5ku-F and 5ku-R. The reaction products were isolated on a 1.0% agarose gel and 1.3 kb product band was excised from the gel. The 1.3 kb amplified DNA fragment was digested with NotI and SpeI, and ligated into the pTK-3ku digested with NotI and SpeI to create pTK-3ku-5ku.

The 2.2 kb DNA fragment containing *A. nidulans* pyrG gene was recovered from pHUda794 by SpeI and XbaI digestion. The recovered 2.2 kb fragment was ligated to SpeI and XbaI digested pTK-3ku-5ku. The ligation mixture was transformed into *E. coli* DH5α to create the expression plasmid pHUda801.

Figure 6:
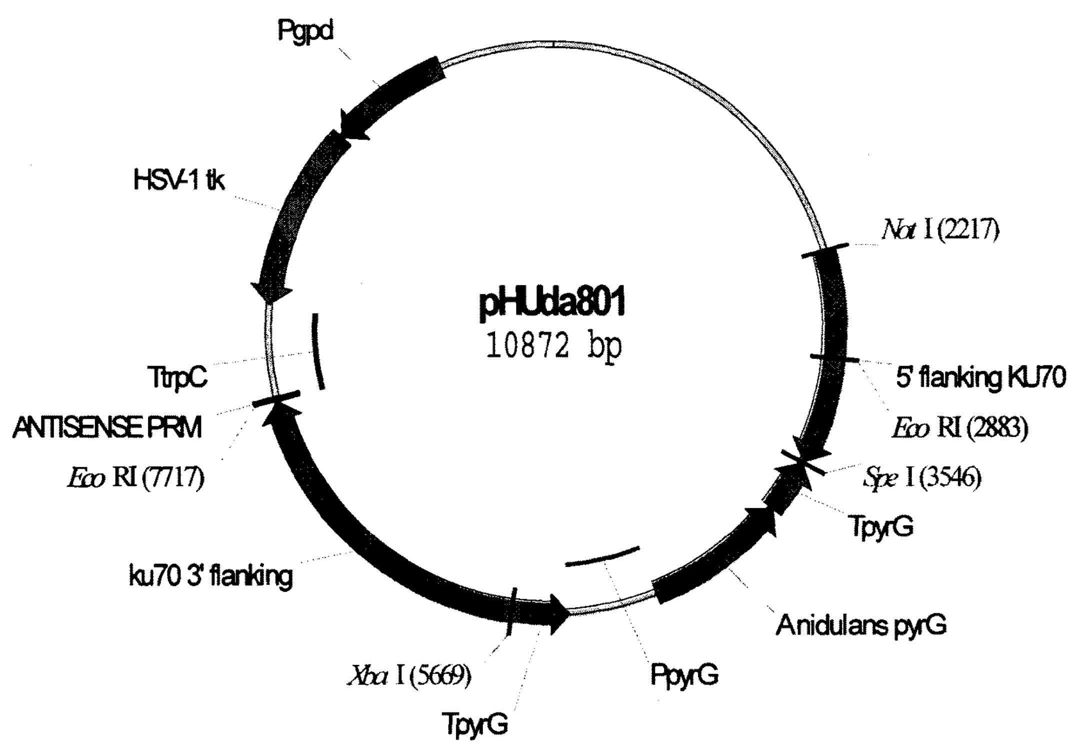
FIG. 6 shows a plasmid map of pHUda801.

The nucleotide sequence of the *A. niger* ku70 gene and flanking sequences of pHUda801 are shown in SEQ ID NO:49; the amino acid sequence of the ku70-encoded polypeptide is shown in SEQ ID NO:50. A plasmid map is shown in FIG. 6.

The Ku70 Gene Disruption in NN059183

The pHUda801 was introduced into *Aspergillus niger* strain NN059183. Transformants were selected from the Cove-N (tf). Randomly selected transformants were inoculated onto Cove-N plates with 2.5 μM 5-Flouro-2-deoxyuridine (FdU), an agent which kills cells expressing the herpes simplex virus (HSV) thymidine kinase gene (TK) harboured in pHUda801. Strains which grew well on Cove-N plates with 2.5 μM FdU were purified and subjected to Southern blotting analysis to confirm whether the ku70 gene was disrupted correctly or not.

The following set of primers to make a non-radioactive probe was used to analyze the selected transformants. For the 3' ku70 flanking region:

```
Forward primer (SEQ ID NO: 51):
acggtatgcgtacaatgatca

Reverse primer (SEQ ID NO: 52):
atttgagggcaccagcacccc
```

Genomic DNA extracted from the selected transformants was digested by SpeI. By the right gene disruption event, a hybridized signal of the size of 8.3 kb by SpeI digestion was shifted to 5.1 kb probed described above. Among the strains given the right integration events, a strain denoted C1997 was selected.

Example 5. Simultaneous Site Specific-Integration by FLP in the Two Loci in C1997

PyrG Gene Rescue in C1997

At first, the introduced pyrG gene at the ku70 loci in C1997 was rescued as follows. The strain C1997 was inoculated once on Cove-N media containing 10 mM uridine and 1 g/L 5-fluoro-orotic acid (5-FOA). Strains in which the pyrG gene has been deleted will grow in the presence of 5-FOA; those that retain the gene will convert 5-FOA to 5-fluoro-UMP, a toxic intermediate. The colonies that grew more quickly were isolated. The isolated strain was named M1117.

Simultaneous Site Specific-Integration by FLP in M1117

The pHUda1000 was introduced into *Aspergillus niger* strain M1117. Transformants were selected from the Cove-N (tf) supplemented with 1 g/L D-xylose. Randomly selected transformants were inoculated onto Cove-N plates. Strains which grew well on Cove-N plates were purified and subjected to Southern blotting analysis to confirm whether the expression part in pHUda1000 was introduced correctly or not.

The following set of primers to make a non-radioactive probe was used to analyze the selected transformants. For the T.c.GA coding region:

```
Forward primer (SEQ ID NO: 53):
tcgagtgcggccgacgcgtacgtc

Reverse primer (SEQ ID NO: 54):
cagagagtgttggtcacgta
```

Genomic DNA extracted from the selected transformants was digested by HindIII. By the right integration event, two hybridized signals at the size of 7.2 kb and 5.7 kb introduced at NA1 and acid stable amylase loci, respectively, were seen.

The frequency of the simultaneous integration with the ku70 gene disruption (M1117) was approx. 20% whereas that without ku70 gene disruption (NN059183) was around 4-5%. It suggested that the ku70 gene disruption played a great role in improving the locus specific integration frequency by FLP.

Example 6. *A. niger* Fcy1 Gene Disruption in NN059183

Construction of the *A. niger* (Cytosine Deaminase) Fcy1 Gene Disruption Vector pHUda1043

The following primers 3fcy-F and 3fcy-R introducing a XbaI site and a PmeI site, respectively, were designed to isolate a 3' flanking region of *A. niger* fcy1 gene based on the nucleotide sequences information in EMBL:am269962:

```
3fcy-F (SEQ ID NO: 55):
tctagaattgaaagctagttctggtcgcat

3fcy-R (SEQ ID NO: 56):
gtttaaactccttgcttcgcatacatgcccac
```

A PCR reaction with genome DNA of *Aspergillus niger* strain NN059183 as template was performed using a primer pair of 3fcy-F and 3fcy-R. The reaction products were isolated on a 1.0% agarose gel and 2.0 kb product band was excised from the gel. The 2.0 kb amplified DNA fragment was digested with XbaI and PmeI, and ligated into the pHUda801 digested with XbaI and PmeI to create pHUda801-3fcy.

The following primers 5fcy-F and 5fcy-R introducing a NotI site and a SpeI site, respectively, were designed to isolate a 5' flanking region of *A. niger* fcy1 gene based on the nucleotide sequences information in EMBL:am269962:

```
5fcy-F (SEQ ID NO: 57):
gcggccgccgccgccgaagaactgagcaaa

5fcy-R (SEQ ID NO: 58):
actagtatatcttcttatcgcagagattg
```

A PCR reaction with genome DNA of *Aspergillus niger* strain NN059183 as template was performed using a primer pair of 5fcy-F and 5fcy-R. The reaction products were isolated on a 1.0% agarose gel and 2.1 kb product band was excised from the gel. The 2.1 kb amplified DNA fragment was digested with NotI and SpeI, and ligated into the pHUda801-3fcy digested with NotI and SpeI to create pHUda1043.

Figure 7:
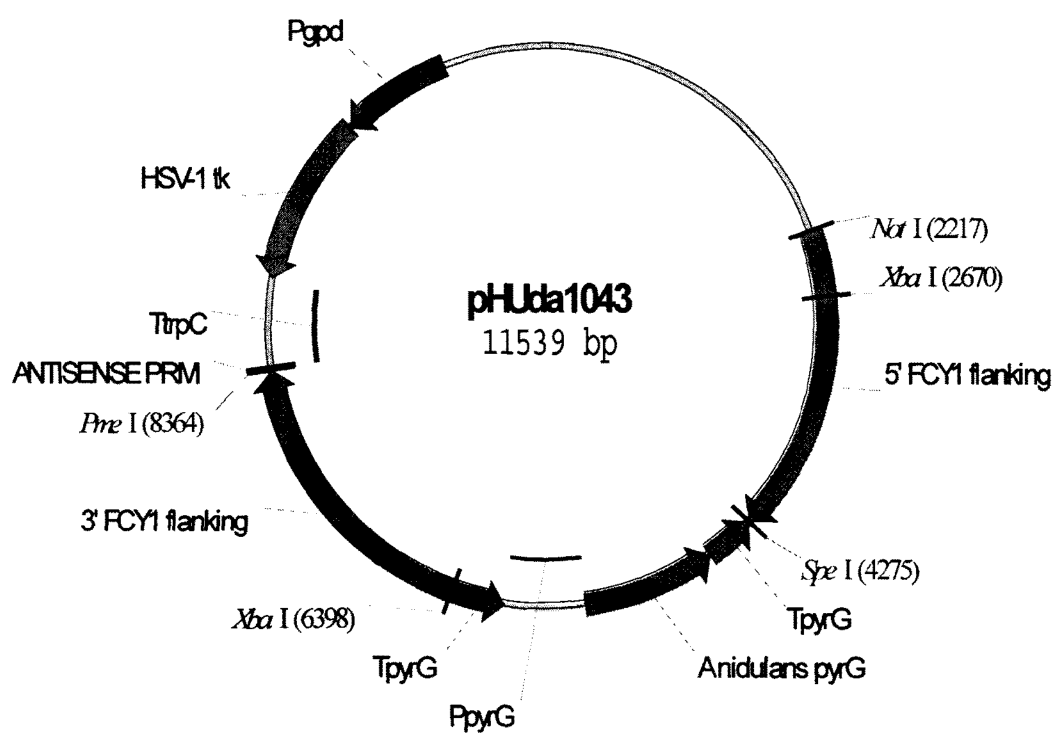
FIG. 7 shows a plasmid map of pHUda1043.

The nucleotide sequence of the *A. niger* fcy1 gene and flanking sequences in pHUda1043 is shown in SEQ ID NO:59; the amino acid sequence of the fcy1-encoded polypeptide is shown in SEQ ID NO:60. A plasmid map is shown in FIG. 7.

The Fcy1 Gene Disruption in NN059183

The pHUda1043 was introduced into *Aspergillus niger* strain NN059183. Transformants were selected from the Cove-N (tf). Randomly selected transformants were inoculated onto Cove-N plates with 2.5 μM FdU, an agent which kills cells expressing the herpes simplex virus (HSV) thymidine kinase gene (TK) harbouring in pHUda1043. Strains which grew well on Cove-N plates with 2.5 μM FdU and Cove-N plates with 10 μg/ml 5-fluorocytosine (5FC) were purified and subjected to Southern blotting analysis to confirm whether the fcy1 gene was disrupted correctly or not.

The following set of primers to make a non-radioactive probe was used to analyze the selected transformants. For the 3' fcy1 flanking region:

```
Forward primer (SEQ ID NO: 61):
gaaagctagttctggtcgcattgagc

Reverse primer (SEQ ID NO: 62):
gaagttgaaggagatgggtctgga
```

Genomic DNA extracted from the selected transformants was digested by NheI and XhoI and Southern blotting analysis was preformed using the above probe. Strains of interest were identified by the disappearance of a 3.1 kb NheI-XhoI band and the appearance of a 2.0 kb NheI-XhoI band. Among the strains given the right integration events, a strain NN059186 was selected.

Example 7. Introduction of FRT Sites and *A. niger* Fcy1 Gene at the Neutral Amylase II (NA2) Locus in *A. niger* NN059186

The pyrG Gene Rescue in NN059186

At first, the introduced pyrG gene at the fcy1 loci in NN059186 was rescued as follows. The strain NN059186 was inoculated once on Cove-N media containing 10 mM uridine and 1 g/L 5-fluoro-orotic acid (5-FOA). Strains in which the pyrG gene has been deleted will grow in the presence of 5-FOA; those that retain the gene will convert 5-FOA to 5-fluoro-UMP, a toxic intermediate. The colonies that grew more quickly were isolated. The isolated strain was named NN059200.

Construction of pHUda1078 for Introduction of FRT Sites and *A. niger* Fcy1 at the NA2 Loci The following primers 3na2-F and 3na2-R introducing a XbaI site and a PmeI site, respectively, were designed to isolate a 3' flanking region of *A. niger* NA2 gene fused with FRT-F3 site based on the nucleotide sequences information in EMBL:am270278 and DJ052242:

```
3na2-F (SEQ ID NO: 63):
tctagattgaagttcctattccgagttcctattcttcaaatagtatagga
acttcatgtctccatgtttcttgagcggaagtact

3na2-R (SEQ ID NO: 64):
gtttaaacgaagactgatattatggcggaa
```

A PCR reaction with genome DNA of *Aspergillus niger* strain NN059183 as template was performed using a primer pair of 3na2-F and 3na2-R. The reaction products were isolated on a 1.0% agarose gel and 2.1 kb product band was excised from the gel. The 2.1 kb amplified DNA fragment was digested with XbaI and PmeI, and ligated into the pHUda801 digested with XbaI and PmeI to create pHUda801-3na2.

The following primers 5na2-F and 5na2-R introducing a NotI site and a SpeI site, respectively, were designed to isolate a 5' flanking region of *A. niger* NA2 gene fused with FRT-F site based on the nucleotide sequences information in EMBL:am270278 and DJ052242:

```
5na2-F (SEQ ID NO: 65):
gcggccgcaagagtcaaaagatagcagagc

5na2-R (SEQ ID NO: 66):
actagtgctagcgaagttcctatacttgaataggaactcggaataggaac
ttcaagatgaattcgcggccggccgcatg
```

A PCR reaction with genome DNA of *Aspergillus niger* strain NN059183 as template was performed using a primer pair of 5na2-F and 5na2-R. The reaction products were isolated on a 1.0% agarose gel and 2.0 kb product band was excised from the gel. The 2.0 kb amplified DNA fragment was digested with NotI and SpeI, and ligated into the pHUda801-3na2 digested with NotI and SpeI to create pHUda801-3na2-5na2.

The 4.3 kb DNA fragment containing T.c.GA gene driven by triple tandem NA2 promoter (Pna2) and AMG terminator (Tamg) was recovered from pHUda440-FRT by NheI and XbaI digestion. The recovered 4.3 kb fragment was ligated to NheI and XbaI digested pHUda801-3na2-5na2. The ligation mixture was transformed into *E. coli* DH5α to create the expression plasmid pHUda801-3na2-5na2-TC.

The 2.1 kb DNA fragment containing *A. nidulans* pyrG gene was recovered from pHUda794 by SpeII and XbaI digestion. The recovered 2.1 kb fragment was ligated to XbaI partially digested pHUda801-3na2-5na2-TC. The ligation mixture was transformed into *E. coli DH5α* to create the expression plasmid pHUda801-3na2-5na2-TC-pyrG.

The following primers fcy-F and fcy-R introducing a NheI site at both sites were designed to isolate an entire region of *A. niger* fcy1 gene based on the nucleotide sequences information in EMBL:am269962:

```
fcy-F (SEQ ID NO: 67):
gctagcgcgaggctatcacggaggctgtgg

fcy-R (SEQ ID NO: 68):
gctagcttctgtggttcttgccatgatcgt
```

A PCR reaction with genome DNA of *Aspergillus niger* strain NN059183 as template was performed using a primer pair of fcy-F and fcy-R. The reaction products were isolated on a 1.0% agarose gel and 1.5 kb product band was excised from the gel. The 1.5 kb amplified DNA fragment was digested with NheI, and ligated into the pHUda801-3na2-5na2-TC-pyrG digested with NheI to create pHUda1078.

Figure 8:
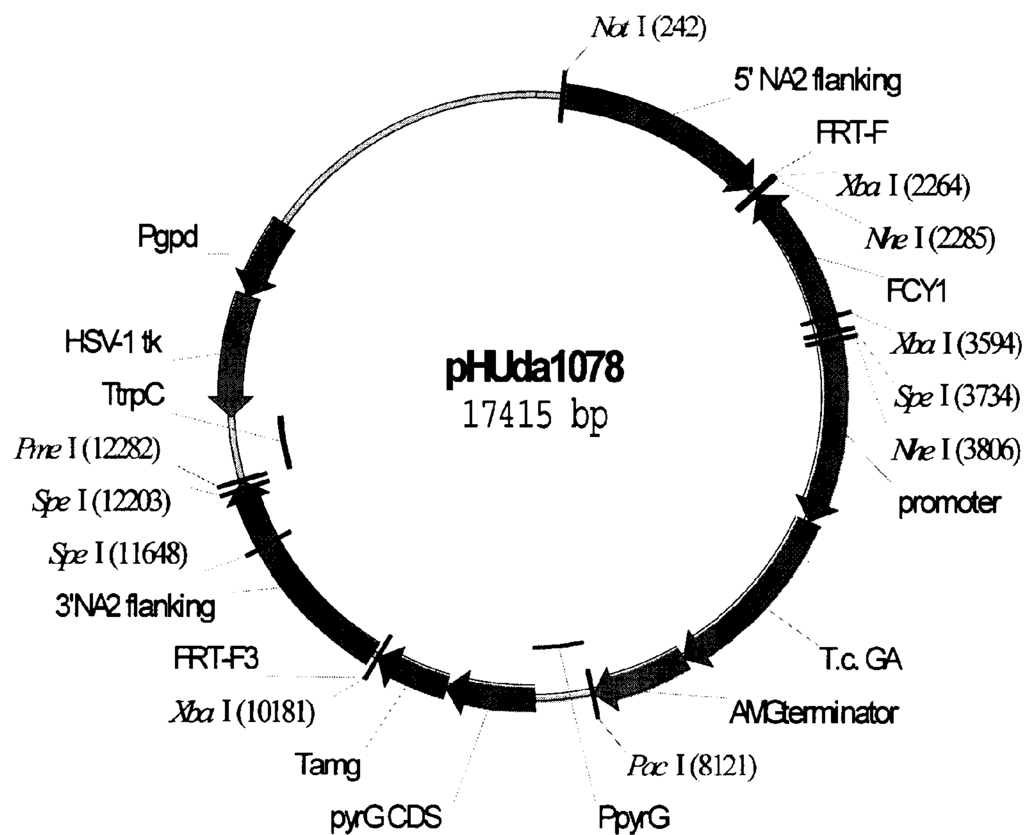
FIG. 8 shows a plasmid map of pHUda1078.

The nucleotide sequence of the *A. niger* NA2 gene with flanking sequences in pHUda1078 is shown in SEQ ID NO:69; the amino acid sequence of the NA2-encoded polypeptide is shown in SEQ ID NO:70. The nucleotide sequence of *A. niger* fcy1 in pHUda1078 & 1067 (see below) is shown in SEQ ID NO:71 and the fcy1-encoded amino acid sequence in SEQ ID NO:72. A plasmid map of pHUda1078 is shown in FIG. 8.

Introduction of FRT Sites and *A. niger* Fcy1 Gene Plus T.c. GA at the NA2 Locus in *A. niger* NN059200

The pHUda1078 was introduced into *Aspergillus niger* strain NN059200. Transformants were selected from the Cove-N (tf). Randomly selected transformants were inoculated onto Cove-N plates with 2.5 μM 5-Flouro-2-deoxyuridine (FdU). Strains which grew well on Cove-N plates with 2.5 μM FdU and hardly grew on Cove-N plates with 10 μg/ml 5-fluorocytosine (5FC) were purified and subjected to Southern blotting analysis to confirm whether the FRT sites and fcy1/T.c.GA genes were introduced correctly at the NA2 locus or not.

The following set of primers to make a non-radioactive probe was used to analyze the selected transformants. For the T.c.GA coding region:

```
Forward primer (SEQ ID NO: 73):
tcgagtgcggccgacgcgtacgtc

Reverse primer (SEQ ID NO: 74):
cagagagtgttggtcacgta
```

Genomic DNA extracted from the selected transformants was digested by SpeI. By the right gene introduction event, a hybridized signal of the size of 4.4 kb by SpeI digestion was observed probed described above. Among the strains given the right integration events, a strain NN059203 was selected.

Example 8. Introduction of FRT Sites and the *A. niger* Fcy1 Gene as Well as the T.c.GA Gene at the Neutral Amylase I (NA1) and Acid Stable Amylase Locus in *A. niger* NN059203

The pyrG Gene Rescue in NN059203

The introduced pyrG gene at the NA2 loci in NN059203 was rescued as follows. The strain NN059203 was inoculated once on Cove-N media containing 10 mM uridine and 1 g/L 5-fluoro-orotic acid (5-FOA). Strains in which the pyrG gene has been deleted will grow in the presence of 5-FOA; those that retain the gene will convert 5-FOA to 5-fluoro-UMP, a toxic intermediate. The colonies that grew more quickly were isolated. The isolates strain was named NN059207.

Construction of pHUda1067 for Introduction of FRT Sites and *A. niger* Fcy1 at the NA1 and Acid Stable Amylase Loci The following primers bac-F and bac-R introducing a XbaI site at both sites were designed to isolate a vector sequence of pBluescript II SK-fused with FRT-F and FRT-F3 sites:

```
bac-F (SEQ ID NO: 75):
tctagagaataggaactcggaataggaacttcaagatgaattcgcggccg
cg

bac-R (SEQ ID NO: 76):
tctagattgaagttcctattccgagttcctattcttcaaatagtatagga
acttcagcatgcaagcttggcctccgc
```

A PCR reaction with pBluescript II SK- as template was performed using a primer pair of bac-F and bac-R. The reaction products were isolated on a 1.0% agarose gel and 2.7 kb product band was excised from the gel. The 2.7 kb amplified DNA fragment was digested with XbaI, and ligated into the pHUda1078 digested with XbaI to create pHUda1078-NA2.

The following primers FLP-F and FLP-R introducing a PacI site at both sites were designed to isolate a FLP expression cassette driven by *A. nidulans* xylanase promoter (PxlnA) and *A. oryzae* niaD terminator (TniaD):

```
FLP-F (SEQ ID NO: 77):
ttaattaatggaagtgcgttgatcattatt

FLP-R (SEQ ID NO: 78):
ttaattaaactagtggagcgaaccaagtga
```

Figure 9:
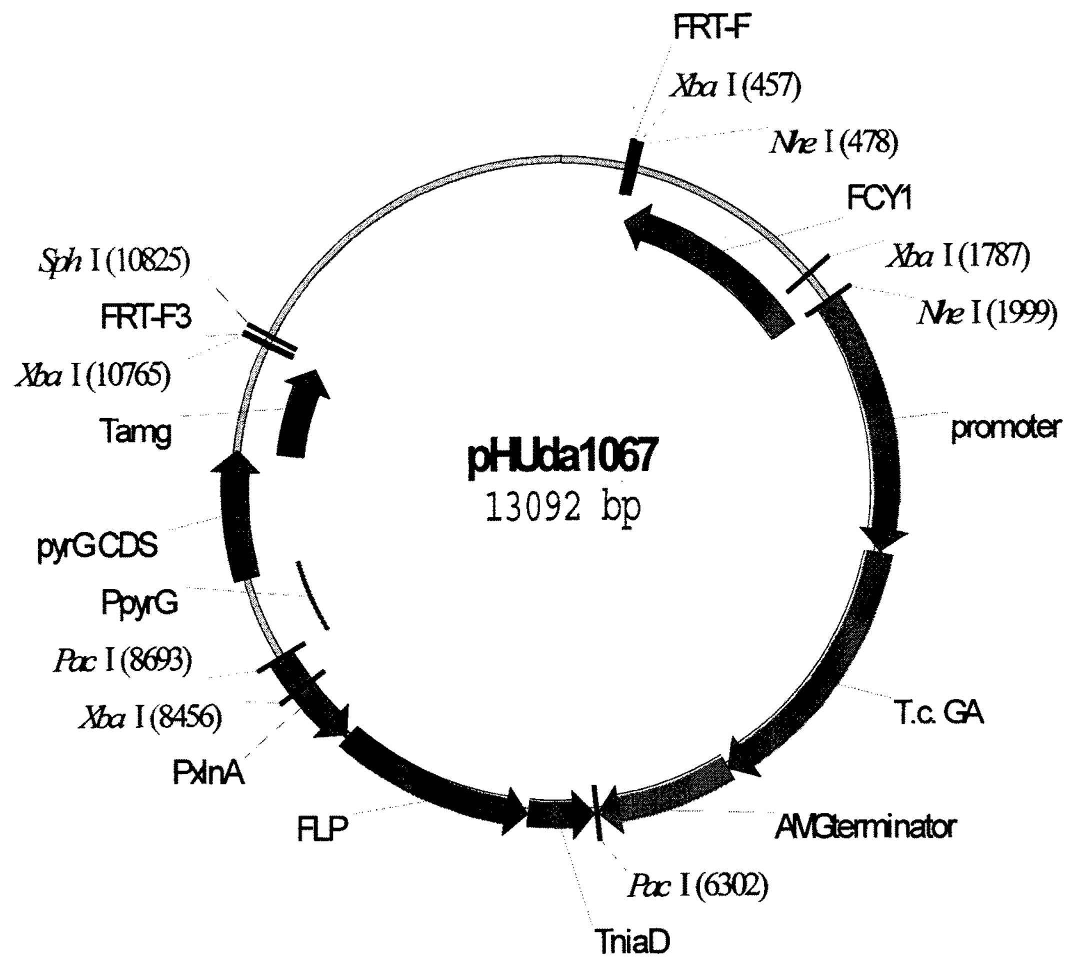
FIG. 9 shows a plasmid map of pHUda1067.

A PCR reaction with pHUda996 as template was performed using a primer pair of FLP-F and FLP-R. The reaction products were isolated on a 1.0% agarose gel and 2.4 kb product band was excised from the gel. The 2.4 kb amplified DNA fragment was digested with PacI, and ligated into the pHUda1078-NA2 digested with PacI to create pHUda1067. A plasmid map is shown in FIG. 9.

Introduction of FRT Sites and *A. niger* Fcy1 Gene and T.c.GA Gene at the NA1 and Acid Stable Amylase Loci in *A. niger* NN059207

The pHUda1067 was introduced into *Aspergillus niger* strain NN059207. Transformants were selected from the Cove-N (tf) supplemented with 1% D-xylose. Randomly selected transformants were inoculated onto Cove-N plates. Strains which grew well on Cove-N plates were purified and subjected to Southern blotting analysis to confirm whether the FRT sites and fcy1 gene in pHUda1067 was introduced at NA1 and acid stable amylase loci correctly or not.

The following set of primers to make a non-radioactive probe was used to analyze the selected transformants. For the T.c.GA coding region:

```
Forward primer (SEQ ID NO: 79):
tcgagtgcggccgacgcgtacgtc

Reverse primer (SEQ ID NO: 80):
cagagagtgttggtcacgta
```

Genomic DNA extracted from the selected transformants was digested by HindIII. By the right gene introduction event, hybridized signals of the size of 8.7 kb (NA1), 7.2 kb (acid stable amylase) and 5.6 kb (NA2) by HindIII digestion was observed when probed as described above. Among the strains with the right 3-copy integration events, a strain denoted NN059208 was selected.

Figure 10A:
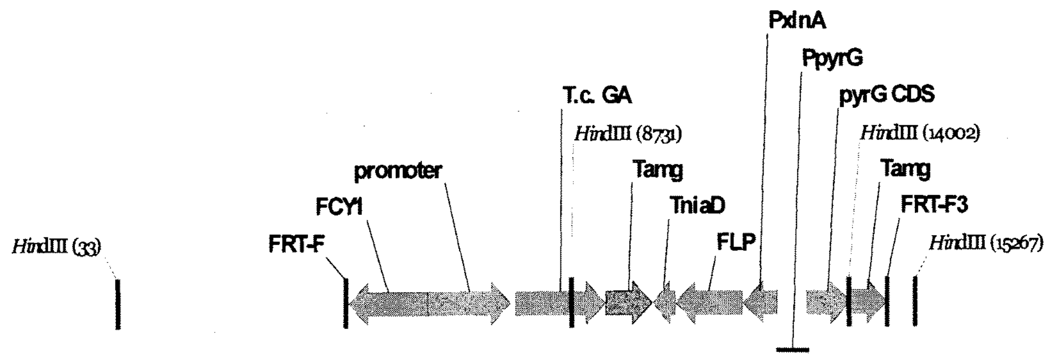
FIG. 10A shows the schematic NA1 locus in NN059208.
Figure 10B:
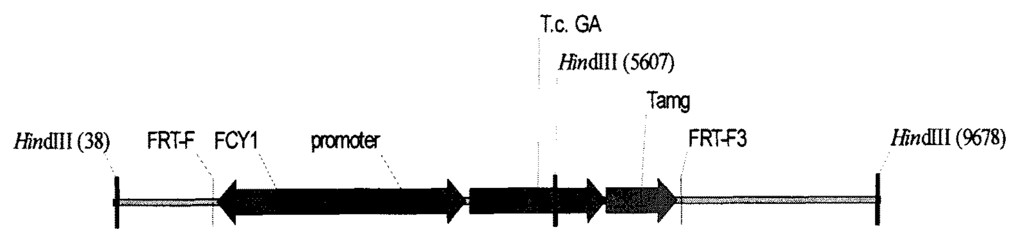
FIG. 10B shows the schematic NA2 locus in NN059208.
Figure 10C:
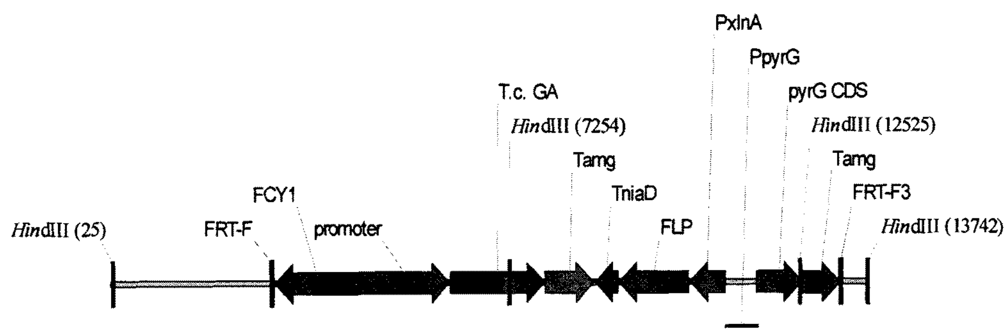
FIG. 10C shows the schematic acid stable amylase locus in NN059208.

FIG. 10A shows the schematic NA1 locus, FIG. 10B shows the schematic NA2 locus and FIG. 10C shows the schematic acid stable amylase locus in NN059208.

NN059203 and NN059208 having 1-copy and 3-copy-T.c.GA genes, respectively, were fermented in shake flasks and their enzyme activities (AGU activities) were measured followed by the materials and methods described above; results are shown in table 1 below. Two-copy T.c. GA strains (1000-7, 18) generated by transformation of either NN059183 or C1997 with pHUda1000 were also fermented.

TABLE 1

The AGU activity of 1-, 2- and 3-copy strains, wherein NN059203 is normalized to 1.00.

| Strain | Host | plasmid | T.c. GA copies | AGU relative activity |
|---|---|---|---|---|
| NN059203 | NN059183 | pHUda1078 | 1 | 1.00 |
| 1000-7 | NN059183 | pHUda1000 | 2 | 1.98-2.08 |
| 1000-18 | C1997 | pHUda1000 | 2 | 1.96-2.10 |
| NN059208 | NN059203 | pHUda1067 | 3 | 2.87-3.00 |

Example 9. Simultaneous Gene Swapping T.c. GA Gene for JA126 Amylase Gene in the 3 Loci (NA1, NA2 and Acid Stable Amylase) in NN059208 by FLP The pyrG Gene Rescue in NN059208

At first, the introduced pyrG genes at the NA1 and acid stable amylase loci in NN059208 were rescued as follows. The strain NN059208 was inoculated once on Cove-N media containing 10 mM uridine and 1 g/L 5-fluoro-orotic acid (5-FOA). Strains in which the pyrG gene has been deleted will grow in the presence of 5-FOA; those that retain the gene will convert 5-FOA to 5-fluoro-UMP, a toxic intermediate. The colonies that grew more quickly were isolated. The isolated strain was named NN059209.

Construction of pRika147 for Introduction of JA126 Amylase Gene at Three Loci

The 1.5 kb DNA fragment containing *A. niger* fcy1 gene was removed from pHUda1067 by NheI digestion. The recovered 1.5 kb fragment was re-ligated. The ligation mixture was transformed into *E. coli* DH5α to create the expression plasmid pHUda1067-fcy.

The following primers 126-F and 126-R introducing a BamHI site and a PmII site, respectively, were designed to isolate an encoding region of JA126 amylase comprising the secretion signal sequences of *A. niger* acid stable amylase, catalytic domain of amylase from *Rhizomucor pusillus* and linker and starch binding domain from glucoamylase of *Aspergillus niger*:

```
126-F (SEQ ID NO: 81):
ggatccaccatgcggctctccacatcc

126-R (SEQ ID NO: 82):
cacgtgtgattacggacacaatccgttatt
```

The nucleotide sequence of the JA126 amylase gene is shown in SEQ ID NO:83 and the encoded amino acid sequence is shown in SEQ ID NO:84.

Figure 11:
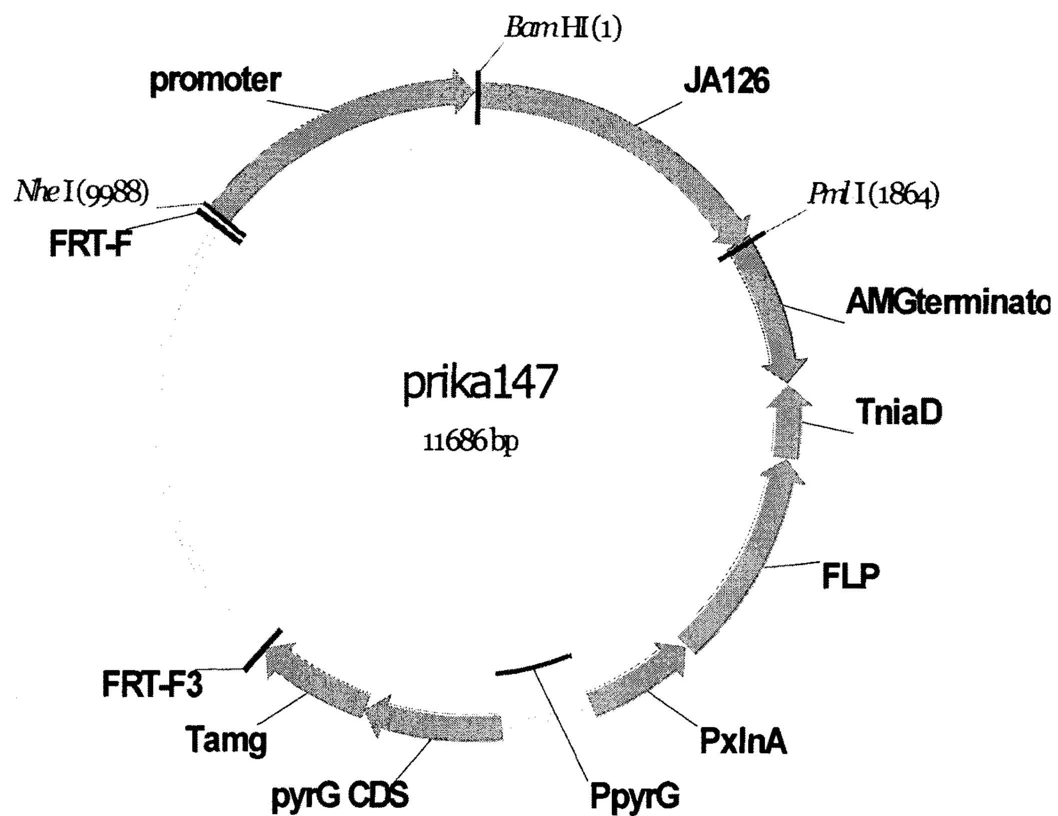
FIG. 11 shows a plasmid map of pRika147.

A PCR reaction with pJA126AN as template was performed using a primer pair of 126-F and 126-R. The reaction products were isolated on a 1.0% agarose gel and 1.9 kb product band was excised from the gel. The 1.9 kb amplified DNA fragment was digested with BamHI and PmII, and ligated into the pHUda1067-fcy digested with BamHI and PmII to create pRika147. A plasmid map is shown in FIG. 11.

Simultaneous Introduction of JA126 Amylase Gene in the 3 Loci (NA1, NA2 and Acid Stable Amylase) in NN059209

The pRika147 was introduced into *Aspergillus niger* strain NN059209. Transformants were selected from the Cove-N (tf) supplemented with 1% D-xylose and 10 μg/ml 5-fluorocytosine (5FC). Randomly selected transformants were inoculated onto Cove-N plates supplemented with 10 μg/ml 5-fluorocytosine (5FC). Strains which grew well on Cove-N plates supplemented with 10 μg/ml 5-fluorocytosine (5FC) were purified and subjected to Southern blotting analysis to confirm whether the JA126 gene in pRika147 was introduced at NA1, NA2 and acid stable amylase loci correctly or not.

The following set of primers to make a non-radioactive probe was used to analyze the selected transformants. For the JA126 coding region:

```
Forward primer (SEQ ID NO: 85):
tcgaacttcggcgacgagtcgcagttgaa

Reverse primer (SEQ ID NO: 86):
cccaacatctcggaaatcctggagaaaccc
```

Genomic DNA extracted from the selected transformants was digested by HindIII and PmII. By the right gene introduction event, hybridized signals of the size of 8.0 kb (NA1), 6.5 kb (acid stable amylase) and 4.8 kb (NA2) by HindIII and PmII digestion was observed when probed as described above.

Figure 12A:
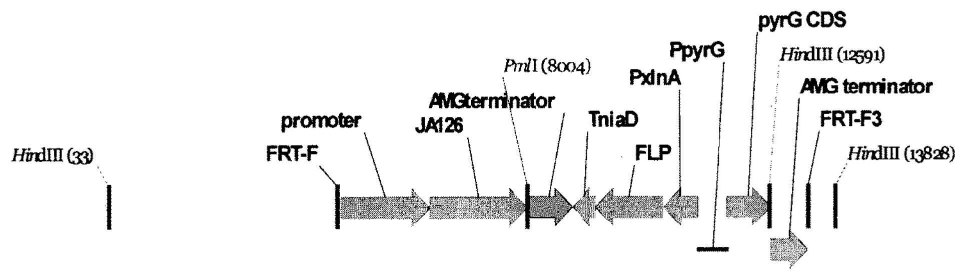
FIG. 12A shows the schematic NA1 locus after the correct integration of pRika147 in NN059208.
Figure 12B:
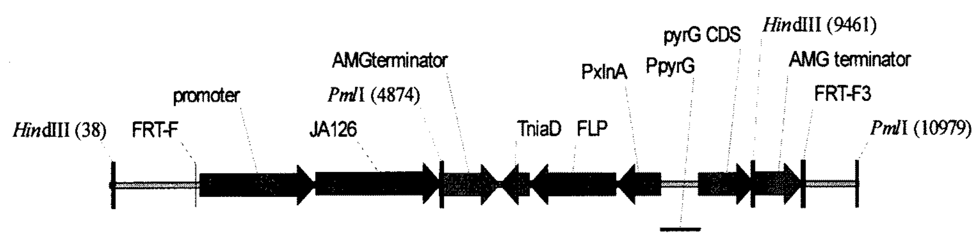
FIG. 12B shows the schematic NA2 locus after the correct integration of pRika147 in NN059208.
Figure 12C:
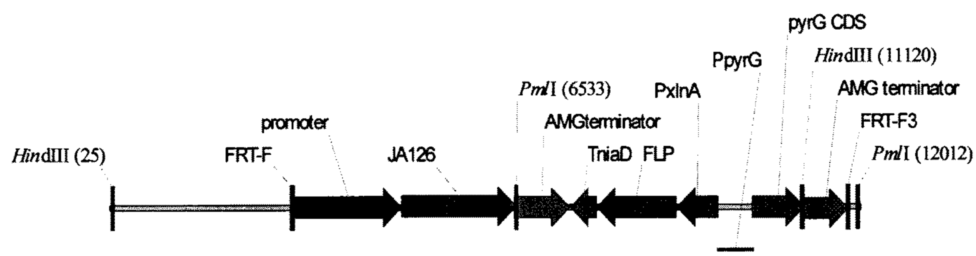
FIG. 12C shows the schematic acid stable amylase locus after the correct integration of pRika147 in NN059208.

FIG. 12A shows the schematic NA1 locus, FIG. 12B shows the schematic NA2 locus and FIG. 12C shows the schematic acid stable amylase locus after the correct integration of pRika147 in NN059208.

The frequencies of generations of transformants by Cove-N plates supplemented with 10 μg/ml 5-fluorocytosine (5FC) was approx. 1/10,000 of those by Cove-N plates without 5FC. However, 50% of the generated strains by Cove-N plates supplemented with 10 μg/ml 5-fluorocytosine (5FC) gave right integration at 3 loci, whereas all strains selected randomly by Cove-N plates without 5FC gave right integration mostly at 1 loci, whereas no strains generated without 5FC showed the right integration events. It indicated that the counter-selection using the fcy1 gene worked very well.

Three strains (R147-17, 26, 34) introducing JA126 amylase gene at 3 loci were fermented in shake flasks and their enzyme activities (AFAU activities) were measured followed by the materials and methods described above; results are shown in table 2 below. As a reference, C2325, a single copy JA126 amylase strain generated by ordinary homologous recombination (not shown) was also fermented.

TABLE 2

The AFAU activity of 1- and 3-copy strains, wherein C2325 is normalized to 1.00.

| Strain | JA126 copies | AFAU relative activity |
|---|---|---|
| C2325 | 1 | 1.00 |
| R147-17 | 3 | 2.75-2.96 |
| R147-26 | 3 | 2.82-3.00 |
| R147-34 | 3 | 3.15-3.18 |

Example 10. Introduction of FRT Sites and TK Gene at the Amylase B (amyB) Locus in *A. oryzae* JaL1338

Construction of a ligD Disruption Plasmid, pJaL1123

Two restriction recognition sites for BamHI and BglII, respectively, were destroyed in pDV8. First pDV8 was digested with BamHI and then the ends were completely filled in by treatment with Klenow enzyme and the four dNTPs. The resulting 6030 bp fragment was re-ligated providing plasmid pJaL504. Secondly pJaL504 was digested with BglII and then the ends were completely filled in by treatment with Klenow enzyme and the 4 dNTPs. The resulting 6034 bp fragment was re-ligated providing plasmid pJaL504-delta-BglII.

By PCR with primers 172450 and 172449 a 2522 bp fragment was amplified containing the HSV-TK gene flank by the *A. nidulans* gpd promoter and TrpC terminator. The PCR fragment was then cloned into the plasmid pCR®4Blunt TOPO® vector resulting in pJaL574.

```
Primer 172449 (SEQ ID NO: 87):
gacgaattccgatgaatgtgtgtcctg

Primer 172450 (SEQ ID NO: 88):
gacgaattctctagaagatctctcgaggagctcaagcttctgtacagtg
accggtgactc
```

The *A. oryzae* pyrG gene from pJaL554 was isolated as 2403 bp StuI-EcoRI fragment, wherein the EcoRI site was completely filled in by treatment with Klenow enzyme and the 4 dNTPs. The fragment was cloned into the unique PmeI site in pJaL574 resulting in plasmid pJaL1022.

Plasmid pJaL1022 was digested with SspB1 and the 8574 bp fragment was isolated and re-ligated, resulting in plasmid pJaL1025. Plasmid pJaL1025 was digested with EcoRI and the 8559 bp fragment was isolated and re-ligated, resulting in plasmid pJaL1027. One of two BamHI sites was destroyed by partial digestion with BamHI following treatment with Klenow enzyme and the four dNTPs, whereby the ends were completely filled in. The 8563 bp fragment was re-ligated resulting in plasmid pJaL1029.

From the publicly available *A. oryzae* RIB40 genome sequence (NITE database (http://www.bio.nite.go.jp/dogan/project/view/AO) primers were designed to PCR amplify the 5' flanking and the 3' flanking sequences of the ligD gene (AO090120000322). The primers for the 5' flanking part, X4407C0 and X4407C07, were tailed with BamHI and EcoRI sites, respectively:

```
Primer X4407C0 (SEQ ID NO: 89):
cagggatccgtctaggctgcaataggc

Primer X4407C07 (SEQ ID NO: 90):
ggagaattcggtcacatc
```

The primers for the 3' flanking part, X7164D09 and X7164D10, were tailed with HindIII and SpeI sites, respectively:

```
Primer X7164D09 (SEQ ID NO: 91):
gacactagtcgtcggcagcaccggtg

Primer X7164D10 (SEQ ID NO: 92):
cagaagcttcagagtgaaatagacgcgg
```

Genomic DNA from ToC1512 was used as template for the PCR reaction. The amplified 5' and 3' fragments on 1114 bp and 914 bp were digested with BamHI-EcoRI and HindIII-SpeI, resulting in an 1102 bp fragment and a 902 bp fragment, respectively. The 3' flanking fragment was cloned into the corresponding sites in pJaL1029 giving pJaL1120. The 5' flanking fragment was then cloned into the corresponding sites in pJaL1120, resulting in pJaL1123.

Construction of a ligD Minus *A. oryzae* Strain, JaL1194.

Plasmid pJaL1123 was linearized with SpeI and used to transform *A. oryzae* ToC1512 and transformants were selected on minimal medium supplemented 0.6 mM 5-fluoro-2'-deoxyuridine (FdU) as described in WO 0168864. A number of transformants were re-isolated twice and genomic DNA was prepared. The chromosomal DNA from each of the transformants was digested with Asp718 and analyzed by Southern blotting, using the 1102 bp 32P-labelled DNA EcoRI-BamHI fragment from pJaL1123 containing the 5' flanks of the *A. oryzae* ligD gene as the probe. Strains of interest were identified by the disappearance of a 3828 bp Asp718 band and the appearance of a 2899 bp Asp718 band. One transformant having the above characteristics was named JaL1194.

Isolation of a pyrG Minus *A. oryzae* Strain, JaL1196

The *A. oryzae* strain JaL1194 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA. One strain, JaL1196, was identifying as being pyrG minus. JaL1196 is uridine dependent, therefore it can be transformed with the wild type pyrG gene and transformants selected by the ability to grow in the absence of uridine.

Construction of a Aflatrem Gene Cluster (Atm) Deletion Plasmid, pJaL1202

*A. oryzae* telomere sequences were introduced around the TK expression cassette by PCR with primers T5483H12 and T5483G10 on pJaL574:

```
Primer T5483H12 (SEQ ID NO: 93):
gcacatatgatttaaatccctaatgttgaccctaatgttgaccctaatgt
tgagcggccgcgtttaaacgaattcgccc

Primer T5483G10 (SEQ ID NO: 94):
cgtaagcttatttaaatccctaatgttgaccctaatgttgaccctaatgt
tgagaccggtgactctttctg
```

The amplified fragment of 2595 bp was digested with NdeI and HindIII and the resulting 2582 bp fragment was cloned into the corresponding sites in pU19 giving pJaL835. Plasmid pJaL835 was digested with HindIII, the ends were filled out by treatment with Klenow enzyme and the four dNTPs and then re-ligated to give pJaL955.

Plasmid pJaL554 was digested with HindIII and Asp718 and the resulting 1994 bp fragment encoding the *A. oryzae* pyrG gene was cloned into the corresponding sites in pToC65 giving pJaL1183. A 1535 bp fragment 5' for the atm was amplified from ToC1512 genomic DNA by primers D5831F08 and D5831F09:

```
Primer D5831F08 (SEQ ID NO: 95):
gacgaattcggcgtgggaaattcctgg

Primer D5831F09 (SEQ ID NO: 96):
ccctacacctggggtacc
```

The amplified fragment was digested with EcoRI and Asp718 and the resulting 1514 bp fragment was cloned into the corresponding sites in pJaL1183 giving pJaL1194. The 3529 bp EcoRI-NotI fragment from pJaL1194 containing the atm 5' flank and the pyrG gene was ligated together with the 3529 bp fragment from pJaL955 containing the TK gene, giving pJaL1202. Plasmid pJaL1202 is a plasmid for deletion of the chromosomal atm gene cluster.

Construction of a Atm Minus *A. oryzae* Strain, JaL1268.

Plasmid pJaL1202 was linearized with SpeI and used to transform *A. oryzae* JaL1196. Transformants were selected on minimal medium supplemented 0.6 mM 5-fluoro-2'-deoxyuridine (FdU) as described in WO 0168864. A number of transformants were re-isolated twice and genomic DNA was prepared. The chromosomal DNA from each of the transformants was digested with SacI and analyzed by Southern blotting, using the 1514 bp 32P-labelled DNA EcoRI-Asp718 fragment from pJaL1194 containing the 5' flanks of the *A. oryzae* atm gene cluster as the probe. Strains of interest were identified by the disappearance of a 3230 bp SacI band and the appearance of a 4436 bp SacI band. One transformant having the above characteristics was named JaL1268.

Isolation of a pyrG Minus *A. oryzae* Strain, JaL1338

The *A. oryzae* strain JaL1268 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA. One strain, JaL1338, was identifying as being pyrG minus. JaL1338 is uridine dependent, therefore it can be transformed with the wild type pyrG gene and transformants selected by the ability to grow in the absence of uridine.

Construction of a Plasmid Containing the TK Gene Flanked by FRT Sites for Integration at the Amylase B Locus, pJaL1258

From the publicly available *A. oryzae* RIB40 genome sequence (NITE database (http://www.bio.nite.go.jp/dogan/project/view/AO) primers were designed to amplify the 5' flanking and the 3' flanks sequences of the amylase B (amyB) gene (AO090023000944). The primers for the 5' flanking part, D5775F04 and D5775D07, were tailed with NotI and HindIII sites, respectively:

```
Primer D5775F04 (SEQ ID NO: 97):
gacgcggccgcgctttgctaaaactttgg

Primer D5775D07 (SEQ ID NO: 98):
gacaagcttatgctcgatggaaacgtgcac
```

The primers for the 3' flanking part, D5775D08 and D5775F05, were tailed with HindIII and NotI sites, respectively:

```
Primer D5775D08 (SEQ ID NO: 99):
gacaagcttacagtagttggactactttac

Primer D5775F05 (SEQ ID NO: 100):
gacgcggccgcgacgagcaactgacggc
```

Genomic DNA from ToC1512 was used as template for the PCR reaction. The amplified 5' and 3' fragments on 1307 bp and 511 bp were digested with NotI and HindIII, resulting in a 1294 bp fragment and a 498 bp fragment, respectively. The 5' and 3' flanking fragments were then cloned into the NotI sites in pToC65, resulting in pJaL1196.

The yeast 2μ plasmid FRT sites F and F3 (Schlake T. and Bode J. Use of mutated FLP recognition target (FRT) sites for the exchange of expression cassettes at defined chromosomal loci. Biochemistry 33: 12746-12751) were cloned into pUC19 by annealing of primers F3-1 and F3-2 to form an adaptor having overhang for cloning into the restriction sites BamHI and PstI of pUC19 giving pJaL952:

```
Primer F3-1 (SEQ ID NO: 101):
gatccttgaagttcctattccgagttcctattcttcaaatagtataggaa
cttcactgca

Primer F3-2 (SEQ ID NO: 102):
tgaagttcctatactatttgaagaataggaactcggaataggaacttcaa
```

The insertion of the FRT F3 site into pUC19 was verified by sequencing. Then the primers F-1 and F-2 were annealed together to form an adaptor having overhang for cloning into the restriction site Asp718 of pJaL952:

```
Primer F-1
                                       (SEQ ID NO: 103)
gtaccttgaagttcctattccgagttcctattctctagaaagtataggaa

cttca

Primer F-2
                                       (SEQ ID NO: 104)
gtactgaagttcctatactttctagagaataggaagtcggaataggaact

tcaa
```

The insertion of the FRT F site in the same orientation as F3 into pJaL952 was verified by sequencing and a correct clone was name pJaL953.

The FRT F-F3 sites were inserted between the amyB flanks by taking a 142 bp Sack HindIII fragment from pJaL963 containing the FRT sites F and F3 and cloning that into pJaL1196 digested with SacI-HindIII, resulting in pJaL1249 which contains the 5' amyB flank followed by the FRT F-F3 sites and the 3' amyB flank.

The pyrG and TK genes were then inserted between the FRT F and FRT F3 sites as follows. A 4838 bp HindIII-SspBI fragment of pJaL1029, where the ends were filled in by treatment with Klenow enzyme and the four dNTP's, was cloned into the SmaI site of pJaL1249, providing a plasmid with the following arrangement of different elements: 5' amyB flank-FRT F-pyrG-TK-FTRT F3-3' amyB flank, which was named pJaL1258.

Construction of a *A. oryzae* Strain Having the FRT, pyrG, and TK Integrated at the amyB Locus, JaL1386.

Plasmid pJaL1258 was linearized with NotI and used to transform *A. oryzae* JaL1338; transformants were selected on minimal medium. A number of transformants were re-isolated twice and genomic DNA was prepared. The chromosomal DNA from each of the transformants was digested with XhoI and analyzed by Southern blotting, using the 1294 bp 32P-labelled DNA NotI-HindIII fragment from pJaL1196 containing the 5' flanks of the *A. oryzae* amyB gene as probe.

Strains of interest were identified by the disappearance of a 4164 bp XhoI band and the appearance of an 8971 bp XhoI band. One transformant having the above characteristics was named JaL1386.

Isolation of a pyrG Minus *A. oryzae* Strain, JaL1394

The *A. oryzae* strain JaL1386 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA. One strain, JaL1394, was identifying as being pyrG minus. JaL1394 is uridine dependent, therefore it can be transformed with the wild type pyrG gene and transformants selected by the ability to grow in the absence of uridine.

Example 11. Site Specific-Integration by FLP into the amyB Locus in JaL1394

Construction of a the Talaromyce *Emersonii* AMG Expression Cassette pRIKA99

A *Talaromyces emersonii* AMG gene containing introns was optimized to provide a synthetic gene (SEQ ID NO:105) for expression in *Aspergillus*. For cloning purposes, BamHI and XhoI restriction sites were added to the 5' end and 3' end, respectively. The synthesized gene was obtained based on the sequence of plasmid pJ241:13509-Huda2. The 2085 bp BamHI-XhoI fragment encoding the *Talaromyce emersonii* AMG gene and the 9510 bp BamHI-XhoI fragment were isolated from plasmid pJ241:13509-Huda2 and pHUda1000, respectively. The two fragments were ligated together to created pRIKA99.

Site Specific-Integration of pRIKA99 in JaL1394 by FLP

The pRIKA99 was introduced into *Aspergillus oryzae* strain JaL1394. Transformants were selected on KCl-plates supplemented with 1% D-xylose and 0.6 mM 5-fluoro-2'-deoxyuridine (FdU). Four transformants were re-isolated twice and genomic DNA was prepared. The chromosomal DNA from each of the four transformants was digested with BglII-DraIII and BglII-KspI and analyzed by Southern blotting, first by using a 2095 bp 32P-labelled DNA BamHI-XhoI fragment from pRIKA99 containing the AMG gene and secondly after stripping of the filter by using a 731 bp 32P-labelled DNA AfeI-PacI fragment from pRIKA99 containing the *A. nidulans* xlnA promoter as the probes.

The right integration event was identified by giving with: 1) the AMG probe: 7145 bp and 3739 bp bands in the BglII-DraIII digestion and a 6845 bp band in the BglII-KspI digestion; 2) the *A. nidulans* xlnA promoter probe a 6845 bp band in the BglII-DraIII digestion and a 4039 bp band in the BglII-KspI digestion.

Example 12. *Aspergillus oryzae* Growth Inhibition by 5-Fluorocytosine (5FC) and Disruption of the Cytosine Aminase To test that *A. oryzae* is growth inhibited by 5-fluorocytosine (5FC), spores of BECh2 were streaked on Cove-N (tf) supplemented with different concentration of 5FC (2.5, 1.5 and 0.625 μg/ml). No growth was detected at the lowest 5FC concentration (0.625 μg/ml) indicating that *A. oryzae* also has a cytosine deaminase. In *A. oryzae* there is only one orthologous gene (AO090003000802 of the public genome sequence) to the *A. niger* fcy1 gene (EMBL:am269962), therefore this has been disrupted to verify that this gene is the cytosine deaminase that causes cell death when growing on 5FC.

The AO090003000802 was disrupted by using the bipartite gene-targeting substrate as described in Nielsen et al (2005) *Efficient PCR-based gene targeting with a recyclable marker for Aspergillus nidulans*, Fungal Gent Biol 43:54-64. Generation of a fragment on 2145 bp containing the 5' flank of the *A. oryzae* AO090003000802 gene and a partial pyrG gene (promoter and ⅔ of the encoding region of the pyrG gene) was amplified by PCR. First, a 1036 bp fragment containing the 5' flank of AO090003000802 was amplified by PCR with primers oJaL132 (CAGATACTGGTTCCTTACGG) (SEQ ID NO:108) and oJaL133 (CGTCCACGCGGGGATTATGCGTAGAATGCAGAGATAGCTG) (SEQ ID NO:109) with BECh2 genomic DNA as template. Then second, a 1129 bp fragment containing the 5' part of the pyrG was amplified by PCR with primers X1111C07 (GCATAATCCCCGCGTGGACG) (SEQ ID NO:110) and oJaL114 (CCAACAGCCGACTCAGGAG) (SEQ ID NO:111) with pJaL554 as template DNA. The amplified products were isolated on a 1.0% agarose gel and mixed together and PCR was done with primers oJaL132 and oJaL114 resulting in an amplification product on 2145 bp, which was purified on a 1.0 agarose gel.

Generation of a fragment on 2436 bp containing the 3' flank of the *A. oryzae* AO090003000802 gene and a partial pyrG gene (⅔ of the encoding region of the pyrG gene and the terminator) was amplified by PCR. First, a 1011 bp fragment containing the 5' flank of AO090003000802 was amplified by PCR with primers oJaL134 (CGATAAGCTCCTTGACGGGGTTGAGCACTGCTTTTGGATC) (SEQ ID NO:112) and oJaL135 (GCTCACCCGGCATAAGTTGC) (SEQ ID NO:113) with BECh2 genomic DNA as template. Then second, a 1445 bp fragment containing the 5' part of the pyrG was amplified by PCR with primers X1111C08 (CCCCGTCAAGGAGCTTATCG) (SEQ ID NO:114) and oJaL113 (GAGCTGCTGGATTTGGCTG) (SEQ ID NO:115)_with pJaL554 as template DNA. The amplified products were isolated on a 1.0% agarose gel and mixed together and PCR was done with primers oJaL1135 and oJaL135 resulting in an amplification product on 2436 bp, which was purified on a 1.0 agarose gel.

For disruption of the AO090003000802 gene the above two amplified fragments on 2145 bp and 2436 bp was mixed, transformed into *A. oryzae* JaL1398 strain and transformants was selected from the COVE-N plates. Southern blot analysis was used for verification of the disruption of the AO090003000802 gene. Genomic DNA extracted from 20 transformants was digested with PvuI-SpeI and Southern blotting analysis was performed using the above amplified PCR 1036 bp fragment was 32P-labeled and used as probe. Strains of interest were identified by the disappearance of a 5.5 kb PvuI-SpeI band and the appearance of a 6.9 kb PvuI-SpeI band. At the same time strains were tested for growth on COVE-N plates containing 0.625 μg/ml 5FC and only strains having the expected band on 6.9 kb show growth, which shows that the AO090003000802 gene is a cytosine deaminase. Among these strains one was selected and named JaL1500.

Example 13. Introduction of FRT Sites and *A. niger* Fcy1 Gene at the PAY (Putative Alkyl Sulfatase) Locus in *A. niger* NN059209

Construction of pHUda1174 (FIG. 13) for Introduction of FRT Sites and *A. niger* Fcy1 at the PAY Locus The following primers 3PAY-F and 3PAY-R introducing a XbaI site and a PmeI site, respectively, were designed to isolate a 3' flanking region of *A. niger* PAY gene based on the nucleotide sequences information in EMBL:am270278.

```
                    (SEQ ID NO: 116)
3PAY-F:   ttgcttctagacttctatttcctaatat

                    (SEQ ID NO: 117)
3PAY-R:   ttgtttaaacttaattaaccgcgccat
```

A PCR reaction with genome DNA of *Aspergillus niger* strain NN059183 as template was performed using a primer pair of 3PAY-F and 3PAY-R. The reaction products were isolated on a 1.0% agarose gel and 2.1 kb product band was excised from the gel. The 2.1 kb amplified DNA fragment was digested with XbaI and PmeI, and ligated into the pHUda801 digested with XbaI and PmeI to create pHUda801-3PAY.

The following primers 5PAY-F and 5PAY-R introducing a NotI site and a SpeI site, respectively, were designed to isolate a 5' flanking region of *A. niger* PAY gene fused with FRT-F site based on the nucleotide sequences information in EMBL:am270278 and DJ052242.

```
5PAY-F:
                    (SEQ ID NO: 118)
ggtggcggccgcgccgacggtgctggagga

5PAY-R:
                    (SEQ ID NO: 119)
tttactagtgaagttcctatactttctagagaataggaactcggaatagg

aacttcaagatgaattcctagtcgg
```

A PCR reaction with genome DNA of *Aspergillus niger* strain NN059183 as template was performed using a primer pair of 5PAY-F and 5PAY-R. The reaction products were isolated on a 1.0% agarose gel and 1.3 kb product band was excised from the gel. The 1.3 kb amplified DNA fragment was digested with NotI and SpeI, and ligated into the pHUda801-3PAY digested with NotI and SpeI to create pHUda801-3PAY-5PAY.

The 4.3 kb DNA fragment containing T.c.GA gene driven by triple tandem NA2 promoter (Pna2) and AMG terminator (Tamg) was recovered from pHUda440-FRT by NheI and XbaI digestion. The recovered 4.3 kb fragment was ligated to NheI and XbaI digested pHUda801-3PAY-5PAY. The ligation mixture was transformed into *E. coli* DH5α to create the expression plasmid pHUda801-3PAY-5PAY-TC.

The following primers pyrG-F and pyrG-R introducing a XbaI site and a SpeI site, respectively, were designed to isolate a *A. nidulans* pyrG gene fused with FRT-F3 site based on the nucleotide sequences information in EMBL: EMBL: M19132 and DJ052242.

```
pyrG-F:
                    (SEQ ID NO: 120)
ttagtactttgaagttcctattccgagttcctattcttcaaatagtatag

gaacttcaactagctagtgcatgcctagtggagcg

pyrG-R:
                    (SEQ ID NO: 121)
aagtctagaagcaagggcgaattccagca
```

A PCR reaction with genome DNA of pHUda794 as template was performed using a primer pair of pyrG-F and pyrG-R. The reaction products were isolated on a 1.0% agarose gel and 2.1 kb product band was excised from the gel. The 2.1 kb amplified DNA fragment was digested with XbaI and SpeI, and ligated into the pHUda801-3PAY-5PAY-TC digested with XbaI to create pHUda801-3PAY-5PAY-TC-pyrG.

The following primers fcy-F and fcy-R introducing a NheI site at both sites were designed to isolate an entire region of *A. niger* fcy1 gene based on the nucleotide sequences information in EMBL:am269962.

```
                    (SEQ ID NO: 122)
fcy-F:   gctagcgcgaggctatcacggaggctgtgg

                    (SEQ ID NO: 123)
fcy-R:   gctagcttctgtggttcttgccatgatcgt
```

Figure 13:
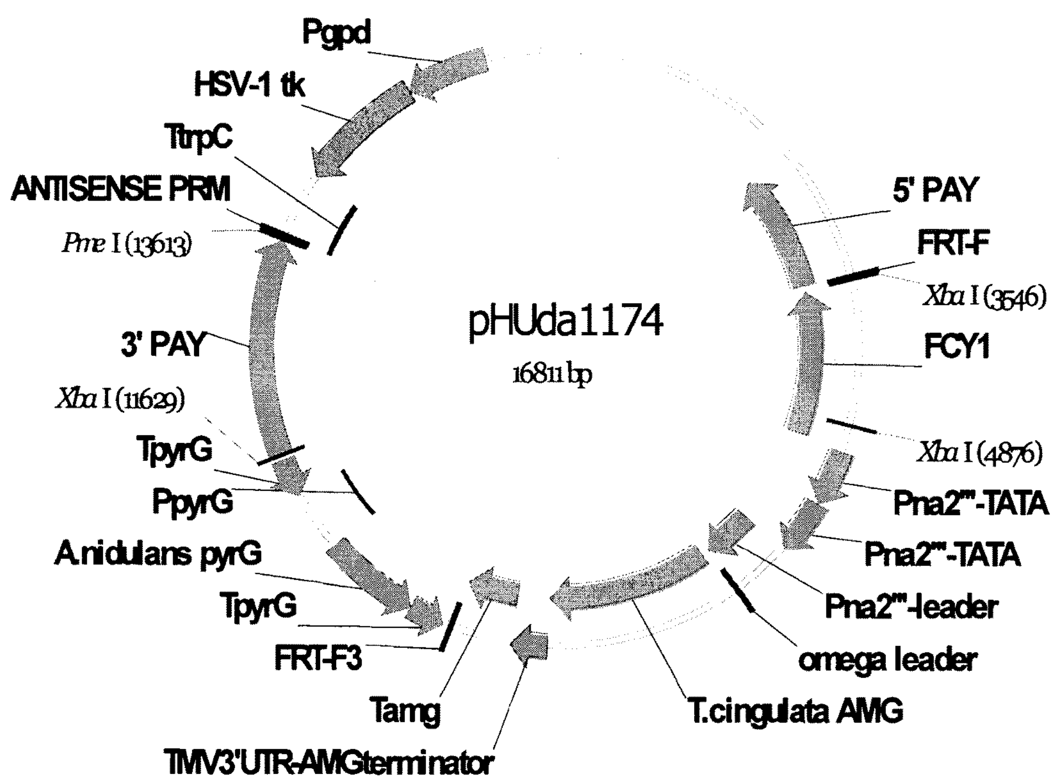
FIG. 13 shows a plasmid map of pHUda1174.
Figure 14:
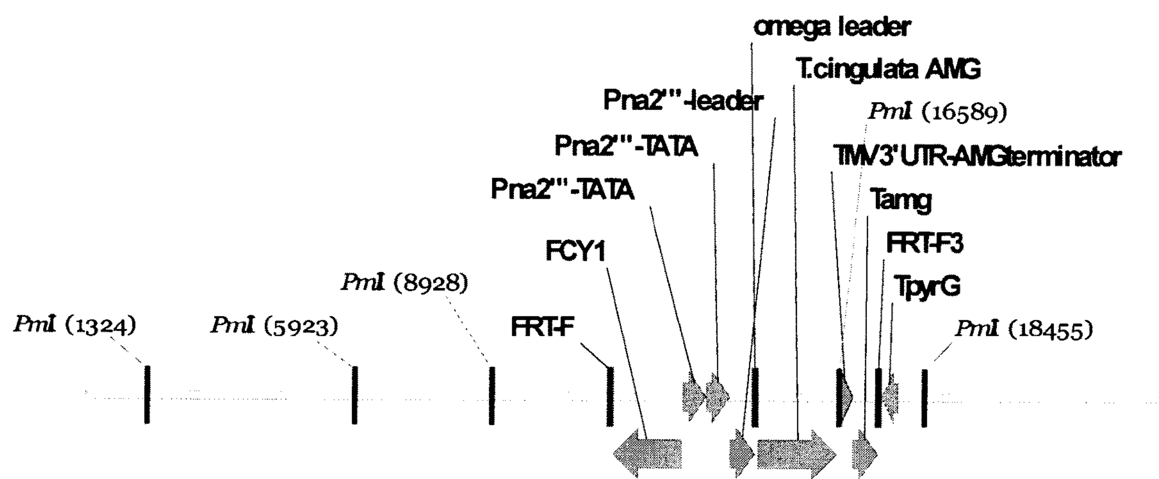
FIG. 14 shows the schematic of the PAY loci (upper) in M1146.

A PCR reaction with genome DNA of *Aspergillus niger* strain NN059183 as template was performed using a primer pair of fcy-F and fcy-R. The reaction products were isolated on a 1.0% agarose gel and 1.5 kb product band was excised from the gel. The 1.5 kb amplified DNA fragment was digested with NheI, and ligated into the pHUda801-3PAY-5PAY-TC-pyrG digested with NheI to create pHUda1174 (FIG. 13).

Introduction of FRT sites and *A. niger* fcy1 gene at the PAY locus in *A. niger* NN059209

The pHUda1174 was introduced into *Aspergillus niger* strain NN059209. Transformants were selected from the Cove-N (tf). Randomly selected transformants were inoculated onto Cove-N plates with 2.5 □M 5-Flouro-2-deoxyuridine (FdU). Strains which grew well on Cove-N plates with 2.5 μM FdU and hardly grew on Cove-N plates with 10 μg/ml 5-fluorocytosine (5FC) were purified and subjected to Southern blotting analysis to confirm whether the FRT sites and fcy1 gene was introduced at PAY loci correctly or not.

The following set of primers to make non-radioactive probe was used to analyze the selected transformants. For T.c.GA coding region, forward primer: tcgagtgcggccgacgcgtacgtc (SEQ ID NO:124), reverse primer: cagagagtgttggtcacgta (SEQ ID NO:125) Genomic DNA extracted from the selected transformants was digested by PmlI.

By the right gene introduction event, a hybridized signal at the size of 7.7 kb by PmlI digestion was observed probed described above. Among the strains given the right integration events, a strain NN059280 was selected.

Example 14. Competitive Gene Swapping for to Create Strains Having Altered Gene Copies of JA126 Amylase The pyrG gene was rescued in NN059280.

The introduced pyrG gene at the PAY loci in NN059280 was rescued as follows. The strain NN059280 was inoculated once on Cove-N media containing 10 mM uridine and 1 g/L 5-fluoro-orotic acid (5-FOA). Strains in which the pyrG gene has been deleted will grow in the presence of 5-FOA; those that retain the gene will convert 5-FOA to 5-fluoro-UMP, a toxic intermediate. The colonies that grew more quickly were isolated. The isolates strain was named M1146.

Figure 15:
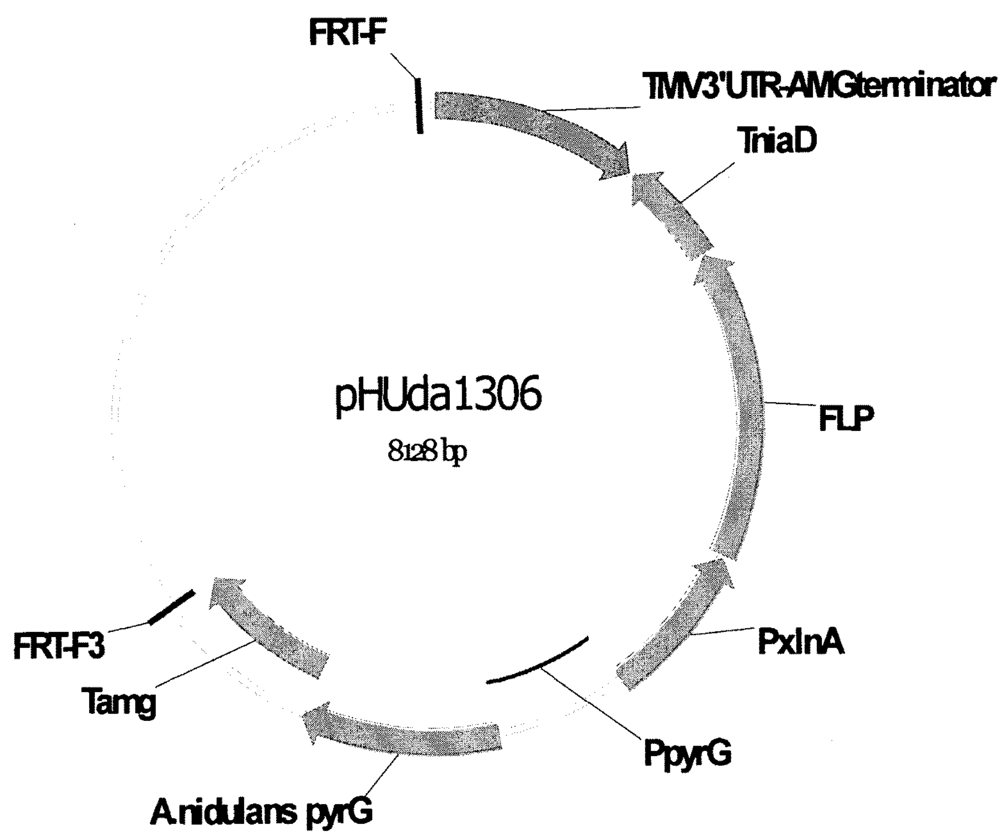
FIG. 15 shows the plasmid map of pHUda1306.
Figure 16A:
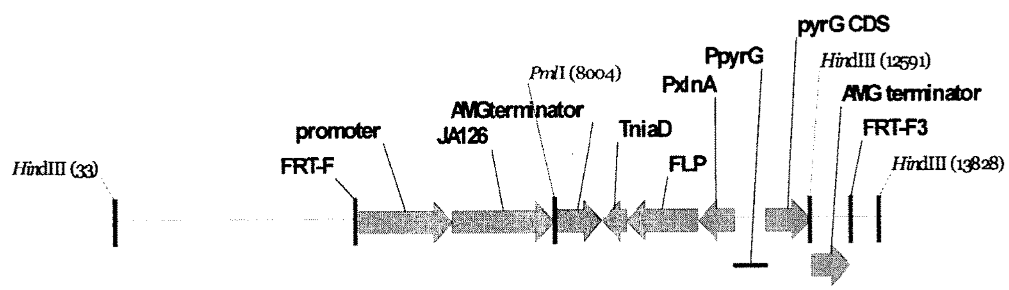
FIG. 16A shows the schematic NA1 locus when pRika147 was introduced in M1146.
Figure 16B:
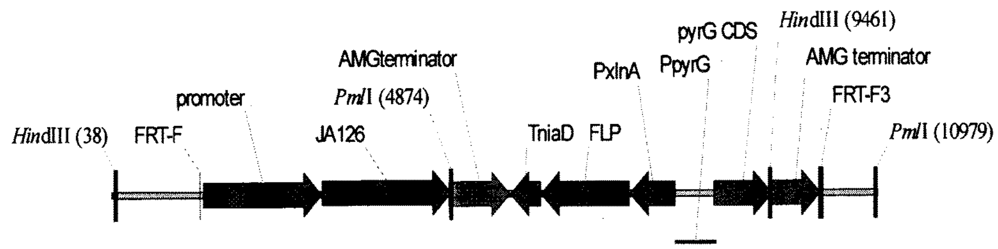
FIG. 16B shows the schematic NA2 locus when pRika147 was introduced in M1146.
Figure 16C:
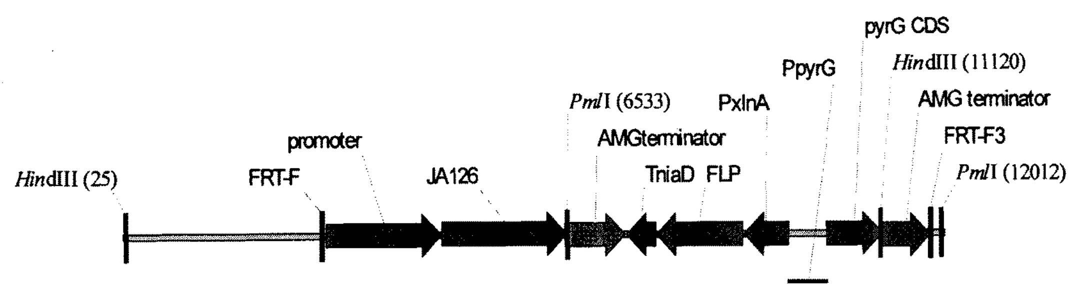
FIG. 16C shows the schematic SP288 locus when pRika147 was introduced in M1146.
Figure 16D:
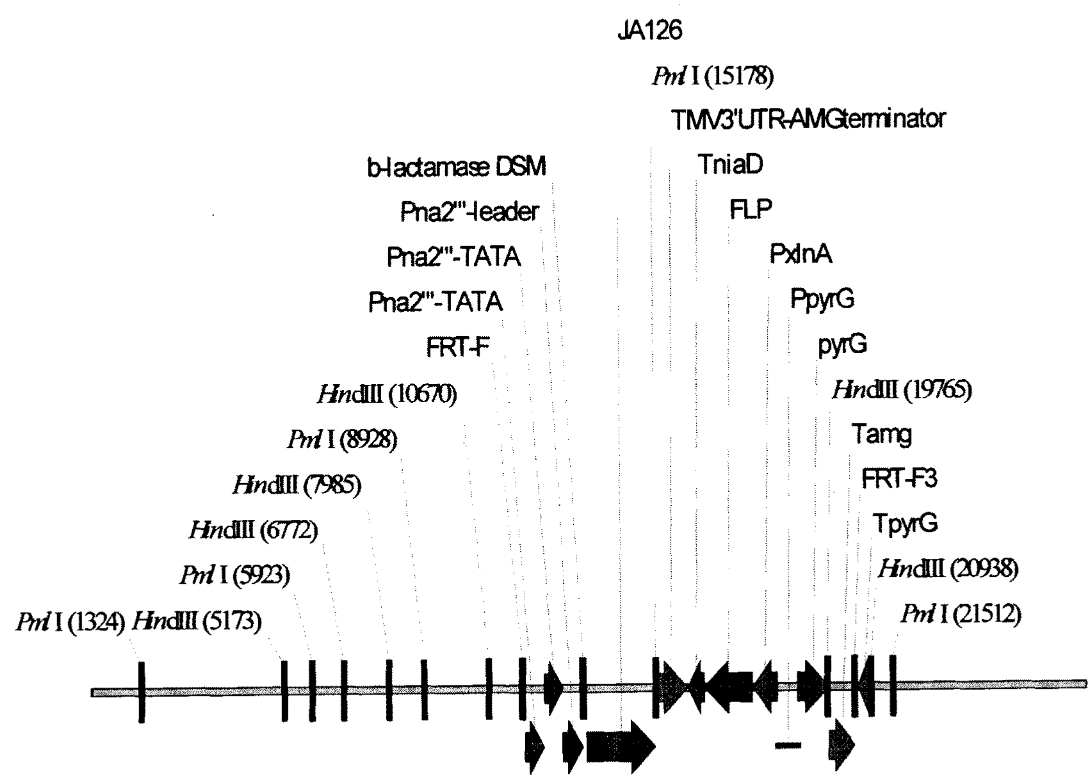
FIG. 16D shows the schematic PAY locus when pRika147 was introduced in M1146.

Construction of an Empty Vector pHUda1306 (FIG. 15)

The pRika147 was digested with NheI and PmII. The 8.1 kb DNA fragment was filled in by T4 DNA polymerase and re-ligated. The resultant plasmid was termed as pHUda1306 (FIG. 15).

Competitive gene swapping using pRika147 and pHUda1306 to create strains having altered gene copies of JA126 amylase; see FIGS. 16A, 16B, 16C, and 16D.

The pRika147 and pHUda1306 were co-introduced into *Aspergillus niger* strain M1146. Transformants were selected from the Cove-N (tf) supplemented with 1% D-xylose and 10 μg/ml 5-fluorocytosine (5FC). Randomly selected transformants were inoculated onto Cove-N plates supplemented with 10 μg/ml 5-fluorocytosine (5FC). Strains which grew well on Cove-N plates supplemented with 10 μg/ml 5-fluorocytosine (5FC) were purified and subjected to Southern blotting analysis to confirm whether the JA126 gene in pRika147 was introduced at NA1, NA2, SP288 or PAY loci correctly or not.

The following set of primers to make non-radioactive probe was used to analyze the selected transformants. For JA126 coding region:

```
forward primer:
tcgaacttcggcgacgagtcgcagttgaa     (SEQ ID NO: 126)

reverse primer:
cccaacatctcggaaatcctggagaaaccc    (SEQ ID NO: 127)
```

Genomic DNA extracted from the selected transformants was digested by HindIII and PmII. By the right gene introduction event, hybridized signals at the size of 8.0 kb (NA1), 6.5 kb (SP288), 4.8 kb (NA2) and 4.5 kb (PAY) by HindIII and PmII digestion was observed probed described above. The frequencies of generations of transformants having 0~4 gene copies of JA126 were mostly identical. Thus, transformants with various copy numbers of the gene in an interest were easily obtained by co-introduction of the expression plasmid and the empty plasmid.

| Copy numbers | Frequencies (%) |
|---|---|
| 0 | 20 |
| 1 | 18 |
| 2 | 16 |
| 3 | 18 |
| 4 | 14 |
| False integrations: | 12 |

Example 15. Simultaneous Gene Swapping T.c. GA Gene for JA126 Amylase Gene in the 4 Loci (NA1, NA2, SP288 and PAY) in NN059280 by FLP and its Thermostable Variant FLPe Construction of a Thermostable FLP Variant (FLPe) Expression Vector pHUda1352

Based on the sequence information on FLPe from literature (Improved properties of FLP recombinase evolved by cycling mutagenesis F. Buchholz, P. O. Angrand, A. F. Stewart. Nat. Biotechnol., 16 (1998), pp. 657-662), the following primers were made.

```
FLPe1:
                                          (SEQ ID NO: 128)
ggatctaccatgtcccagttcgatatcctctgcaagacccccccaaggt

cctcgtccgccagttcgtcgagcgcttcgagcgcccctccggcgagaaga

tcgcctcctgcgccg

FLPe2:
                                          (SEQ ID NO: 129)
atgcttctggccgttgtaggggatgatggt

FLPe3:
                                          (SEQ ID NO: 130)
accatcatcccctacaacggccagaagcat

FLPe4;
                                          (SEQ ID NO: 131)
ttgatggcgaagatggggtagggggcgttc

FLPe5:
                                          (SEQ ID NO: 132)
gaacgcccccctaccccatcttcgccatcaa

FLPe6;
                                          (SEQ ID NO: 133)
ttcggatcagatgcggcggttgatgtagga
```

A PCR reaction with pHUda996 as template was performed using a primer pair of FLPe1 & 2, FLPe 3 &4 and FLPe 5 & 6. The reaction products were isolated on a 1.0% agarose gel and 0.3, 0.6 and 0.5 kb product band was excised from the gel. These three fragments were mixed and used for the 2nd PCR reaction using a primer pair of FLPe 1 & 6. The reaction products were isolated on a 1.0% agarose gel and 1.3 kb product band was excised from the gel. 1.3 kb amplified DNA fragment was digested with BamHI and BstBI, and ligated into the pHUda996 digested with BamHI and BstBI to create pHUda1352.

Figure 17:
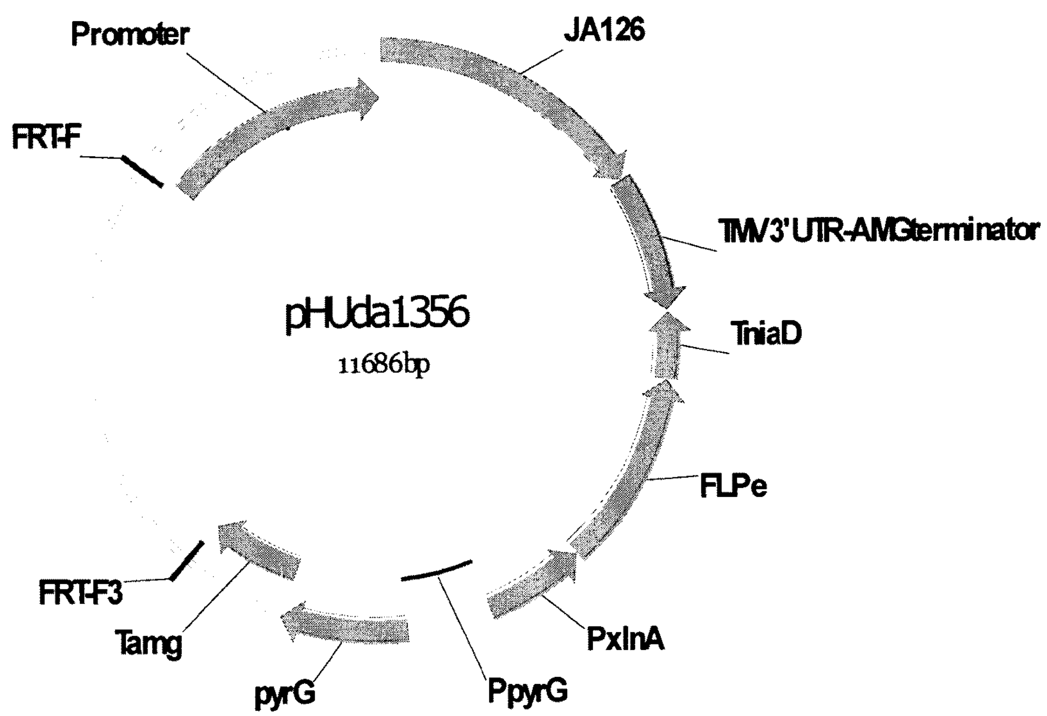
FIG. 17 shows the plasmid map of pHUda1356.

Construction of JA126 Amylase Expression Plasmid Carrying a Thermostable FLP Variant (FLPe) expression vector pHUda1356. The pHUda1352 was digested with BamHI and BstBI. The 1.3 kb DNA fragment was ligated into the pRika147 digested with BamHI and BstBI to create pHUda1356 (FIG. 17).

Comparison of the Simultaneous Gene Swapping Efficiency Between FLP and FLPe

The pRika147 and pHUda1356 were introduced into *Aspergillus niger* strain M1146. Transformants were selected from the Cove-N (tf) supplemented with 1% D-xylose and 10 μg/ml 5-fluorocytosine (5FC). Randomly selected transformants were inoculated onto Cove-N plates supplemented with 10 μg/ml 5-fluorocytosine (5FC). Strains which grew well on Cove-N plates supplemented with 10 μg/ml 5-fluorocytosine (5FC) were purified and subjected to Southern blotting analysis to confirm whether the JA126 gene in pRika147 was introduced at NA1, NA2, SP288 or PAY loci correctly or not.

The following set of primers to make non-radioactive probe was used to analyze the selected transformants. For JA126 coding region:

```
forward primer:
tcgaacttcggcgacgagtcgcagttgaa      (SEQ ID NO: 134)

reverse primer:
cccaacatctcggaaatcctggagaaaccc     (SEQ ID NO: 135)
```

Genomic DNA extracted from the selected transformants was digested by HindIII and PmII. By the right gene introduction event, hybridized signals at the size of 8.0 kb (NA1), 6.5 kb (SP288), 4.8 kb (NA2) and 4.5 kb (PAY) by HindIII and PmII digestion was observed probed described above. The frequency of the simultaneous integration with the FLPe (pHUda1356) was approx. 3 times higher than that with FLP (pRika147), so the thermostable FLP variant FLPe provides an improved locus specific integration frequency.

Example 16. Introduction of FRT Sites and TK Genes at the Loci amyB and #13 in *A. oryzae*

Construction of *A. oryzae* Strain JaL1398

Isolation of a niaD Minus *A. oryzae* Strain, JaL828

First the *A. oryzae* strain 5-58 (WO20099106488) was screened for resistance to chlorate to identify spontaneous niaD mutants on minimal plates (Cove D. J. 1966. Biochem. Biophys. Acta. 113:51-56) supplemented with 1.0 M sucrose as carbon source, 10 mM Na-glutamate as nitrogen source, and 5% Chlorate. One strain, JaL828, was identifying as being niaD minus. Second, the *A. oryzae* strain JaL828 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodium nitrate as nitrogen source, and 0.5 mg/ml FOA. One strain, COIs454, was identifying as being pyrG minus. COIs454 is uridine dependent, therefore it can be transformed with the wild type pyrG gene and transformants selected by the ability to grow in the absence of uridine. Third the *A. oryzae* COIs454 strain was made ligD minus as described in example 10 resulting in *A. oryzae* strain JaL1390. Fourth the *A. oryzae* strain JaL1390 was made pyrG minus as described above resulting in strain JaL1398.

Construction of *A. oryzae* Strain JaL1523 Having the FRT::TK Integrated at the Loci amyB and #13

For integration of the TK flanked by FRT sites plasmid pJaL1258 was linearized with NotI and used to transform *A. oryzae* JaL1398; transformants were selected on minimal medium. A number of transformants were re-isolated twice and genomic DNA was prepared. The chromosomal DNA from each of the transformants was digested with XhoI and analyzed by Southern blotting, using the 1294 bp 32P-labelled DNA NotI-HindIII fragment from pJaL1196 containing the 5' flanks of the *A. oryzae* amyB gene as probe. Strains of interest were identified by the disappearance of a 4164 bp XhoI band and the appearance of an 8971 bp XhoI band. One transformant having the above characteristics was named JaL1450.

Isolation of a pyrG Minus *A. oryzae* Strain, JaL1467

The *A. oryzae* strain JaL1450 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodium nitrate as nitrogen source, and 0.5 mg/ml FOA. One strain, JaL1467, was identifying as being pyrG minus. JaL1467 is uridine dependent, therefore it can be transformed with the wild type pyrG gene and transformants selected by the ability to grow in the absence of uridine.

Construction of a Plasmid Containing the TK Gene Flank by FRT Site for Integration at the #13 Locus, pJaL1313

In plasmid pJaL835 (US2010062491) the single HindIII was destroyed by opening of the plasmid with HindIII and then the ends was fill out by treatment with 4dNTP's and Klenow following re-ligation resulting in plasmid pJaL955.

Out from the *A. oryzae* RIB40 genome sequence (www-.bio.nite.go.jp/dogan/project/view/AO) primers were designed to amplify the 5' flanking and the 3' flanking sequences of the locus #13. The primers for the 5' flanking part, K6763E12: gacgcggccgccgcgtggaggtctaggac (SEQ ID NO:136) and K6763F01: gacaagcttacaaacccgtgacactcc (SEQ ID NO:137) were tailed with NotI and HindIII sites, respectively. The primers for the 3' flanking part K6763F02: gacaagcttacgcatgtatgtatgtgtc (SEQ ID NO:138) and K6763F03: gacgtttaaacggatgggtttgccatac (SEQ ID NO:139) were tailed with HindIII and PmeI sites, respectively. Genomic DNA from ToC1512 was used as template for the PCR reaction. The amplified 5' and 3' fragments on 1065 bp and 1032 bp were digested with NotI-HindIII and HindIII-PmeI, respectively, resulting in a 1052 bp fragment and a 1021 bp fragment, respectively. The 5' and 3' flanking fragments were then clone into the NotI-PmeI sites in pJaL955, resulting in pJaL968. The plasmid pJaL968 was digested with NheI-PmeI and ends were completely filled out by treatment with dNTP's and Klenow. The 4548 bp fragment was purified and self-ligated resulting in plasmid pJaL1285.

The yeast 2μ plasmid FRT sites F and F3 (Schlake T. and Bode J. Use of mutated FLP recognition target (FRT) sites for the exchange of expression cassettes at defined chromosomal loci. Biochemistry 33: 12746-12751) were clone into pUC19 by first annealing of primers F3-1 (SEQ ID NO: 15) and F3-2 (SEQ ID NO: 16) to form an adaptor having overhang for cloning into the restriction sites BamHI and PstI of pUC19 giving pJaL952. The insertion of the FRT F3 site into pUC19 was verified by sequencing. Second the primers F-1 and F-2 was annealed together to form an adaptor having overhang for cloning into the restriction site Asp718 of pJaL952. The insertion of the FRT F site in the right orientation same as F3 into pJaL952 was verified by sequencing and a right clone was name pJaL953. Plasmid pJaL953 was digested with SacI-ScaI and the resulting 1866 bp fragment was ligated to an 920 bp ScaI-SacI fragment from pIC19H, resulting in plasmid pJaL1289.

For insertion of the HSV-TK gene between the FRT sites the 4839 bp HindIII-BsrGI, where the ends are completely fill-out bu treatment with dNTP's and Klenow, where cloned into pJaL1289 digested with SmaI. A plasmid having the different elements in the following way: FRT F_pyrG_HSV-TK_FRT F3 was named pJaL1293.

The 4984 bp HindIII fragment harboring the FRT F_pyrG_HSV-TK_FRT F3 part of pJaL1293 was ligated to the 4548 bp HindIII fragment from pJaL1285. A plasmid having the different elements in the following way: 5' #13 flank_FRT F_pyrG_HSV-TK_FRT F3_3' #13 flank was named pJaL1313.

Construction of an *A. oryzae* Strain Having the FRT, pyrG, and TK Integrated at the #13 Locus, JaL1523.

Plasmid pJaL1313 was linearized with NotI and used to transform *A. oryzae* JaL1467 and transformants were selected on minimal medium. A number of transformants were re-isolated twice and genomic DNA was prepared. The chromosomal DNA from each of the transformants was digested with NheI-NdeI and analyzed by Southern blotting, using the 893 bp 32P-labelled DNA NcoI-HindIII fragment from pJaL1313 containing the 3' flanks of the *A. oryzae* #13 locus as the probe. Strains of interest were identified by the disappearance of a 3896 kb NheI-NdeI band and the appearance of an 5607 kb NheI-NdeI band. One transformant having the above characteristics was named JaL1523.

Isolation of a pyrG Minus *A. oryzae* Strain, JaL1540

The *A. oryzae* strain JaL1523 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodium nitrate as 4nitrogen source, and 0.5 mg/ml FOA. One strain, JaL1540, was identifying as being pyrG minus. JaL1540 is uridine dependent, therefore it can be transformed with the wild type pyrG gene and transformants selected by the ability to grow in the absence of uridine.

Example 17 Utilization of the FRT/FLP Recombination System for Site-Specific Integration in *Trichoderma reesei*

Media and Reagents

The following media and reagents were used:

LB broth+100 μg/ml ampicillin: 10 g tryptone, 5 g yeast extract, 5 g NaCl and 1 ml 100 mg/ml ampicillin, per liter.

2YT amp: 16 g tryptone, 10 g yeast extract, 5 g NaCl, 15 g bacto agar, 1 ml 100 mg/ml ampicillin, per liter.

COVE: 342.3 g sucrose, 20 ml COVE salt solution, 10 ml 1M acetamide, 10 ml 1.5 M CsCl and 25 g Agar Noble, per liter.

COVE2+10 mM Uridine: 30 g sucrose, 20 ml COVE salt solution, 10 mM acetamide, 15 mM CsCl and 25 g Agar Noble, per liter.

CIM: 20 g Arbocel-natural cellulose fibers (J. Rettenmaier USA LP), 10 g corn steep solids (Sigma), 1.45 g (NH4) 2SO4, 2.08 g KH2PO4, 0.28 g CaCl2, 0.42 g MgSO4.7H2O, 0.42 ml *T. reesei* Trace Metals, 2 drops of Pluronic L61 anti-foam. pH 6.0 per liter.

COVE Salt Solution: 26 g KCl, 26 g MgSO4 7H20, 76 g KH2PO4, 50 ml COVE trace elements, per liter.

Cove trace elements: 0.004 g Na2B4O710H2O, 0.4 g CuSO45H2O, 1.2 g FeSO47H2O, 0.7 g MnSO4H2O, 0.8 g Na2MoO22H2O, 10 g ZnSO4.7H2O, per liter.

*T. reesei* Trace Metals: 216 g FeCl3.6H2O, 58 ZnSO4.7H2O, 27 g MnSO4.H2O, 10 g CuSO4.5H2O, 2.4 g H3BO, 336 g citric acid.

PEG: 500 g polyethylene glycol, 10 ml of 1 M Tris pH7.5, 10 ml of 1 M CaCl2, per liter STC: 0.5 L 1 M Sorbitol, 10 ml of 1 M Tris pH7.5, 10 ml of 1 M CaCl2, per liter TrMM: 30 g glucose, 0.6 g CaCl2, 6 g (NH4)2SO4, 20 ml COVE Salt Solution, 25 g Noble Agar, per liter YPG2%: 10 g yeast extract, 20 g peptone, 20 g glucose, per liter.

Plasmid Construction

Figure 18:
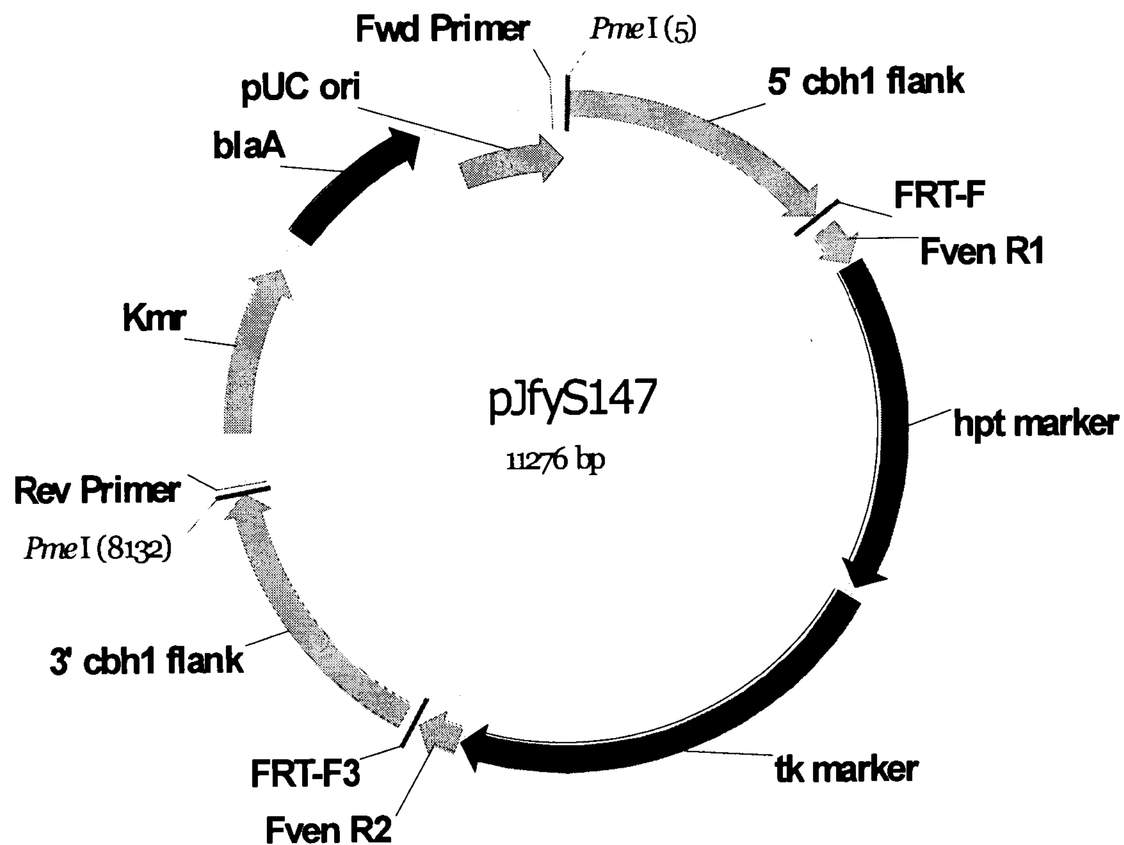
FIG. 18 shows a map of the vector pJfyS147 used to integrate the FRT sites into the *T. reesei* genome at the cbh1 locus.

The FRT site integration vector pJfyS147 was constructed and is shown in FIG. 18.

Figure 19:
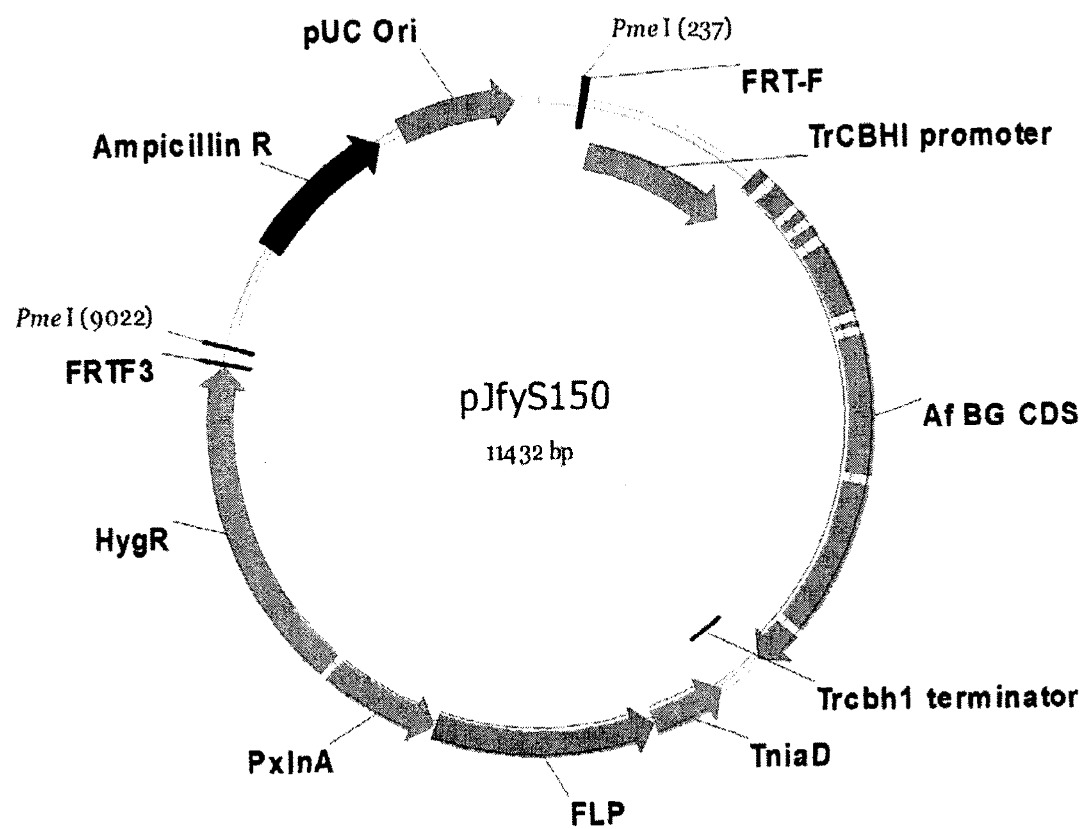
FIG. 19 shows a map of the vector pJfyS150 used to integrate the *A. fumigatus* BG at the cbh1 locus in *T. reesei* strain JfyS147-20B using the FLP/FRT system.

The FRT/FLP expression vector pjfyS150 containing the beta-glucosidase was constructed and is shown in FIG. 19.

*Trichoderma reesei* protoplasting and transformation

Protoplasts of *Trichoderma reesei* strain TV11 were generated as described previously WO 11/075677. Protoplasts were thawed on ice and 5×100 μl protoplast aliquots were transferred to 4×14 ml Falcon 2059 tubes. Pme I-linearized gel purified DNA (~3 μg) was added to each tube to which 250 μl of 60% PEG were added.

The contents of the tubes were gently mixed by inverting gently 5 times and incubating them for 30 minutes at 34° C. To each tube 3 ml STC were added and 1.5 ml were plated to a 150 mm plate containing 50 ml of PDA+1 M Sucrose and spread using a sterile spreader. The plates were incubated at 28° C. for ~18 hrs after which 20 ml of an overlay of PDA+10 mM uridine+35 μg/ml hygromycin B (Invitrogen cat #10687010) were added. Plates were incubated for 6 days at 28° C. until transformants were picked.

Pick Transformants

Transformants were picked with a 10 μl inoculating loop and transferred to a 75 mm diameter plate containing PDA agar and incubated for 5 days at 28° C.

Shake Flask Analysis of Transformants in CIM Media

Spores were collected with a 10 μl inoculation loop and transferred to 125 ml polycarbonate shake flasks, each containing 25 ml CIM media and incubated at 28° C. with shaking for 5 days.

Cure Hpt/Tk Markers

Spores of 7 day old plate were collected in 0.01% Tween-20 and spore concentrations determined with a hemacytometer. Spores were diluted in sterile diH20 and 104, 105 and 106 were plated to 150 mm TrMM+2% glucose plates+1 μM 5-flourodeoxyuridine (FdU). Plates were incubated for 6 days at 28° C. and spore isolates were picked using a 10 μl inoculation loop and transferred to new PDA plates and incubated at 28° C.

Genomic DNA Isolation/Southern Analysis

Spores were collected in 5 ml 0.01% Tween-20 and 2 ml were used to inoculate 50 ml of YPG2% medium in 250 ml baffled shake flasks. The cultures were incubated for 40 hours at 28° C. with shaking at 170 rpm. Agar plugs were removed and the cultures were filtered through MIRACLOTH™. Harvested biomass was frozen with liquid nitrogen and the mycelia were ground using a mortar and pestle.

Genomic DNA was isolated using a DNEASY® Plant Maxi Kit (QIAGEN, Valencia, Calif., USA) according to the manufacturer's instructions except that the lytic incubation period at 65° C. was extended to 1.5 hours from 10 minutes. The concentration of the resulting DNA containing solution was determined using a Nanodrop 1000 spectrophotometer (ThermoFischer Scientific, Waltham, Mass., USA).

Two and a half μg of genomic DNA were digested with 44 units NdeI in a 50 μl reaction volume at 37° C. for 22 hours. The digestion was subjected to 0.9% agarose gel electrophoresis in TAE buffer. The DNA was fragmented in the gel by treating with 0.25 M HCl, denatured with 1.5 M NaCl-0.5 M NaOH, neutralized with 1.5 M NaCl-1 M Tris pH 8, and then transferred in 20×SSC to a NYTRAN® Supercharge nylon membrane using a TURBOBLOTTER™ Kit (both from Whatman, Kent, UK). The DNA was UV crosslinked to the membrane using a UV STRATALINKER™ (Stratagene, La Jolla, Calif., USA) and prehybridized for 1 hour at 42° C. in 20 ml of DIG Easy Hyb (Roche Diagnostics Corporation, Indianapolis, Ind., USA).

A probe hybridizing to the 3' flank of the *T. reesei* cbh2 gene was generated using a PCR Dig Probe Synthesis Kit (Roche Diagnostics Corporation, Indianapolis, Ind., USA) according to the manufacturer's instructions with the forward and reverse primers indicated below. The PCR reaction contained 1× HERCULASE® Reaction Buffer (Stratagene, La Jolla, Calif.), 400 nM each primer, 200 μM DIG-labeled dUTP-containing dNTPs, 125 ng TV10 genomic DNA, and 1.5 units HERCULASE® DNA polymerase. The cycling parameters were as follows: 1 cycle at 95° C. for 2 minute; 25 cycles each at 95° C. for 30 seconds, 55° C. for 30 seconds, and 72° C. for 40 seconds; and 1 cycle at 72° C. for 7 minutes.

```
                                (SEQ ID NO: 140)
Forward (069083):    aaaaaacaaacatcccgttcataac

                                (SEQ ID NO: 141)
Reverse (069084):    aacaaggtttaccggtttcgaaaag
```

The probe reaction was subjected to 1% agarose gel electrophoresis in TAE buffer and the band corresponding to the probe was excised and agarose-extracted using a MINELUTE® Gel Extraction Kit (QIAGEN Inc., Valencia, Calif., USA). The probe was boiled for 5 minutes and added to 10 ml of DIG Easy Hyb to produce the hybridization solution. Hybridization was performed at 42 degree C. for 15-17 hours. The membrane was then washed under high stringency conditions in 2×SSC plus 0.1% SDS for 5 minutes at room temperature followed by two washes in 0.1× SSC plus 0.1% SDS for 15 minutes each at 65° C. The probe-target hybrids were detected by chemiluminescent assay (Roche Diagnostics, Indianapolis, Ind., USA) according to the manufacturer's instructions.

*Trichoderma reesei* Protoplasting and Transformation of the FLP Vector

Protoplasts of *Trichoderma reesei* strain TV11 were generated as described previously (14). Protoplasts were thawed on ice and 5×100 μl protoplasts each were transferred to 4×14 ml Falcon 2059 tubes. Pme I-linearized gel purified DNA (~2 μg) was added to each tube and 250 μl 60% PEG were added. The contents of the tubes were gently mixed by inverting the tubes gently 5 times and incubated for 30 minutes at 34° C. To each tube 3 ml STC were added and 1.5 ml were plated to a 150 mm plate containing 50 ml of PDA+1 M Sucrose and spread using a sterile spreader. The plates were incubated at 28° C. for ~18 hrs after which 20 ml of an overlay of PDA+10 mM uridine+35 μg/ml hygromycin B (Invitrogen cat #10687010) were added. Plates were incubated for 6 days at 28° C. until transformants were picked.

Spore PCR

To screen transformants for the integration of the FLP/FRT vector, transformants were screened by spore PCR. This was accomplished by collecting spores with a sterile 1 μl inoculation loop and transferring them to 25 μl TE buffer in a 0.6 ml Eppendorf tube. Spores were microwaved on high for 1 minute and 1 μl immediately added to an Advantage GC Genomic LA Polymerase PCR mix containing the following components: 1× reaction buffer, 200 μM dNTPs, 400 nM each primer, 1.25 U Polymerase. The PCR products were amplified with the following cycling parameters and the forward and reverse primers indicated below for either the 5' integration or the 3' integration: 95° C.—10 min, 30 cycles of 95° C.—30 seconds, 56° C.—30 seconds, 72° C.—1 minute 40 seconds and a final cycle of 72° C.—7 minutes.

```
5' Recombination Forward (#0611526):
ttcccttcctctagtgttgaat       (SEQ ID NO: 142)

Reverse No integration (#0611527):
tcgtcgaatactaacatcttgc       (SEQ ID NO: 143)

Reverse Integration (#0611528):
cacggacctcgaacctttatat       (SEQ ID NO: 144)

3' Recombination Forward (#999661):
cagcgagagcctgacctattgcatc    (SEQ ID NO: 145)

Reverse No integration (#069084):
aacaaggtttaccggtttcgaaaag    (SEQ ID NO: 146)

Reverse Integration (#0611648):
gtggctgccgaggtgtgtatacca     (SEQ ID NO: 147)
```

The entire PCR reactions were run on a 1% agarose gel in 50 ml TAE buffer containing 500 ng/ml Ethidium Bromide and products visualized with UV light.

Results

The FRT site integration vector, pJfyS147 (FIG. 18) was designed so that the sites would be integrated in the genome at the cbh1 locus. The two FRT sites are slightly different in an attempt to prevent unwanted recombination between them and were named FRT-F and FRT-F3 for the 5' and 3' sites, respectively. The 5' cbh1 flank used to target the vector to the locus was chosen so that the cbh1 coding sequence as well as a 1 kb portion of the promoter would also be deleted as the promoter is also incorporated into the expression vector used later and a successful integration would restore the promoter. Since the vector also deletes the cbh1 gene when correctly integrated at the cbh1 locus this allows for a simple proteomic screen since the SDS-PAGE profile would be substantially altered with the removal of CBH1. When protoplasts of strain TV11 were transformed with pJfyS147, one hundred and thirty-three transformants were obtained. All of these transformants were picked and analyzed in shake flasks under cellulase inducing conditions. Of the 133 transformants analyzed, two showed the proteomic profile consistent with deletion of cbh1.

The two transformants showing the altered proteomic profile were expected to have the FRT integration plasmid at the cbh1 locus. Two strains JfyS147-20 and -73 were plated to *Trichoderma* minimal media containing 5-fluorodeoxyuridine (FdU) in an attempt to facilitate the excision of the hpt/tk cassettes. Seventy-two FdU resistant colonies were obtained on the plates from strain JfyS147-20 and a lawn was obtained from strain JfyS147-73. Eight colonies were picked from JfyS147-20 named JfyS147-20A to -20H and a section of the lawn was picked from JfyS147-73 and the resulting strain was named JfyS147-73A. Four isolates from JfyS147-20 as well as the one isolated region from JfyS147-73, were analyzed by Southern to determine if the FRT cassette had been cleanly integrated and the hpt/tk markers were correctly excised.

Southern analysis showed that one transformant, JfyS47-20, had the deletion cassette at the cbh1 locus as expected and the resulting spore progeny had excised the hpt/tk markers. The other transformant, JfyS147-73, failed to show any hybridization. The region containing the FRTF and FRTF3 sites was PCR amplified from genomic DNA of JfyS147-20B and sequenced to confirm the presence of the two sites. Protoplasts of this stain were generated and transformed with the FLP/FRT integration vector pJfyS150 (FIG. 19).

The expression vector pJfyS150 is a derivative of a *Trichoderma* expression vector containing the cbh1 promoter and terminator with the hygromycin phosphotransferase gene for hygromycin resistance. pJfyS150 differs from its parent in that it also contains the FRT-F and FRTF3 sites that reside in the genome of JfyS147-20B and the codon optimized flippase gene (FLP) cassette derived from pRiKa147 (obtained from HuDa). The reporter used was the *A. fumigatus* BG.

The vector was linearized with Pme I to remove the bacterial propagation part of the plasmid and the resulting gel-purified fragment used to transform JfyS147-20B protoplasts from which twenty transformants were obtained. The 20 transformants obtained here represented an efficiency of 2.5/μg.

The twenty transformants were analyzed by spore PCR to determine if the cassette had been integrated at the desired locus by amplifying the 5' region of the site of insertion. If the integration of the cassette is ectopic a 1 kb fragment results and if the integration happens with the FRT sites the result is a 1.8 kb PCR product. Of the 20 obtained, 18 appeared to have ectopic integrations while two showed a PCR band consistent with integration at the cbh1 locus but the size was smaller than expected. When the PCR fragments were sequenced the results indicated that the recombination had occurred between the FRTF site present at the locus and two different regions in the cbh1 promoter.

1% xylose was added to the protoplast storage solution prior to transformation in an attempt to speed up the required cellular response events. Protoplasts with extra xylose were transformed with the same expression vector as before, pJfyS150, and 19 transformants were obtained. The 19 transformants were analyzed by PCR screen on the 5' end as before as well as by an additional set of primers hybridizing to the 3' region of integration.

The results indicated that that 5 of the 19 transformants had integrated the cassette at the FRTF site in the 5' region. Also 2 transformants gave no band in the PCR screen suggesting that region of the locus had been rearranged during transformation, indicating some sort of inexact locus-specific targeting as seen with the previous set of transformants. The PCR screen of the FRTF3 site region on the 3' end of the transforming integration vector indicated that 5 transformants had undergone the necessary FLP-mediated integration at the 3' end, and that 3 of the 5 had undergone both necessary recombination. When each region was analyzed separately a few of the transformants had undergone the desired recombination at only one of the FRT sites but a nonspecific recombination at the other. 3 transformants had undergone the required recombination at both FRT sites, which was an improvement compared to the process without the addition of xylose into the protoplast storage media.

Accordingly, the FLP/FRT system was successfully utilized in *T. reesei* to introduce an expression plasmid to the cbh1 locus in *T. reesei*. In particular strain JfyS147-20B was generated and contained the FRT sites at the cbh1 locus. A new expression vector was also generated incorporating the cbh1 promoter and terminator, the hpt gene as a selection marker, the *A. fumigatus* BG gene as a reporter, as well as the FRT sites and FLP gene required for the system. This new vector, pJfyS150, was used to insert the *A. fumigatus* BG cassette at the cbh1 locus using the FLP/FRT system with an insertion frequency of 15.7% (or at least 10.5% as one of the strains showed instability of the cassette during propagation in shake flasks).

The invention claimed is:

1. A method for the simultaneous integration of two or more copies of a polynucleotide of interest into the chromosome of a fungal host cell, said method comprising the steps of:

(a) providing a fungal host cell comprising in its chromosome at least two integration sites, each integration site comprising a pair of recognition sequences of a site-specific recombinase, each pair flanking a resident negative selection marker, wherein the site-specific recombinase and its pair of recognition sequences are from the FLP-FRT system of *Saccharomyces cerevisiae* and wherein the negative selection marker encodes a polypeptide having cytosine deaminase activity;

(b) introducing into said cell a nucleic acid construct comprising a pair of recognition sequences of the site-specific recombinase, said pair flanking the polynucleotide of interest;

(c) transiently expressing the site-specific recombinase in the cell, whereby the chromosomal recognition sequence pairs are recombined with the corresponding recognition sequence pair of the nucleic acid construct by the recombinase, so that at the at least two integration sites, the resident negative selection marker in the chromosome is excised while a copy of the polynucleotide of interest is integrated in its place to produce a fungal host cell comprising two or more copies of the polynucleotide of interest integrated into the chromosome of the fungal host cell; and (d) cultivating the fungal host cell of step (c) in a selective medium comprising sufficient amounts of 5-fluorocytosin to be converted to an inhibitory concentration of toxic 5-fluorouracil by said cytosine deaminase, and selecting a cell in which the fungal host cell comprises at least two polynucleotides of interest integrated into the chromosome of the fungal host cell.

2. The method of claim 1, wherein the polynucleotide of interest comprises an operon or an open reading frame encoding at least one polypeptide of interest.

3. The method of claim 1, wherein the polypeptide of interest comprises an enzyme.

4. The method of claim 3, wherein the enzyme is a hydrolase, isomerase, ligase, lyase, oxidoreductase, or transferase.

5. The method of claim 3, wherein the enzyme is an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

6. The method of claim 1, wherein the fungal host cell is a filamentous fungal host cell.

7. The method of claim 6, wherein the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

8. The method of claim 6, wherein the filamentous fungal host cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

9. The method of claim 1, wherein the cytosine deaminase is selected from the group consisting of:

(a) a polypeptide having at least 70% sequence identity to the polypeptide of SEQ ID NO:60; or (b) a polypeptide encoded by a polynucleotide having at least 70% sequence identity to the polypeptide coding sequence of SEQ ID NO:59 or the cDNA sequence thereof.

10. The method of claim 1, wherein the negative selection marker comprises a nucleic acid sequence that has at least 70% sequence identity to the polypeptide coding sequence of SEQ ID NO:59 or the cDNA sequence thereof.

11. The method of claim 1, wherein the negative selection marker encodes a fragment of a polypeptide having the amino acid sequence of SEQ ID NO:60, wherein the fragment has cytosine deaminase activity.

12. The method of claim 1, wherein the negative selection marker encodes a cytosine deaminase polypeptide having the amino acid sequence of SEQ ID NO:60.

13. The method of claim 1, wherein a second nucleic acid construct is introduced in said cell in step (b), which is either non-replicating or temperature-sensitively replicating, and which comprises a polynucleotide encoding the site-specific recombinase and a selection marker, which enables positive or negative selection or is bi-directional, and which is maintained in said cell transiently by selective pressure or growth at the permissive temperature, respectively, so that the site-specific recombinase can be transiently expressed in step (c).

14. The method of claim 1, wherein the site-specific recombinase comprises the amino acid sequence of SEQ ID NO:107.

15. The method of claim 1, wherein the FLP recombinase is a thermostable recombinase variant designated FLPe having amino acid alterations P2S, L33S, Y108N, S294P.

* * * * *

SEQUENCE LISTING

```
<160> NUMBER OF SEQ ID NOS: 147

<210> SEQ ID NO 1
<211> LENGTH: 31
<212> TYPE: DNA
<213> ORGANISM: artificial sequence
<220> FEATURE:
<223> OTHER INFORMATION: Primer Tef-F

<400> SEQUENCE: 1

gaattcacta gtggggttca aatgcaaaca a                                    31


<210> SEQ ID NO 2
<211> LENGTH: 25
<212> TYPE: DNA
<213> ORGANISM: artificial sequence
<220> FEATURE:
<223> OTHER INFORMATION: Primer Tef-R

<400> SEQUENCE: 2

ggatcctggt gcgaactttg tagtt                                           25


<210> SEQ ID NO 3
<211> LENGTH: 24
<212> TYPE: DNA
<213> ORGANISM: artificial sequence
<220> FEATURE:
<223> OTHER INFORMATION: Primer nia-F

<400> SEQUENCE: 3

ctcgagatta tccaagggaa tgac                                            24
```

<210> SEQ ID NO 4
<211> LENGTH: 25
<212> TYPE: DNA
<213> ORGANISM: artificial sequence
<220> FEATURE:
<223> OTHER INFORMATION: Primer nia-R

<400> SEQUENCE: 4
tctagaaagt attttcggta cgatt 25

<210> SEQ ID NO 5
<211> LENGTH: 30
<212> TYPE: DNA
<213> ORGANISM: artificial sequence
<220> FEATURE:
<223> OTHER INFORMATION: Primer hph-F

<400> SEQUENCE: 5
ggatcctaca cctcagcaat gtcgcctgaa 30

<210> SEQ ID NO 6
<211> LENGTH: 33
<212> TYPE: DNA
<213> ORGANISM: artificial sequence
<220> FEATURE:
<223> OTHER INFORMATION: Primer hph-R

<400> SEQUENCE: 6
ctcgagctat tcctttgccc tcggacgagt gct 33

<210> SEQ ID NO 7
<211> LENGTH: 2221
<212> TYPE: DNA
<213> ORGANISM: artificial sequence
<220> FEATURE:
<223> OTHER INFORMATION: Hygromycin B resistance gene (hph) expression parts in plasmid pHUda966.
<220> FEATURE:
<221> NAME/KEY: promoter
<222> LOCATION: (13)..(669)
<223> OTHER INFORMATION: Aspergillus oryzae TEF1 promoter
<220> FEATURE:
<221> NAME/KEY: misc_feature
<222> LOCATION: (651)..(675)
<223> OTHER INFORMATION: Primer tef-R
<220> FEATURE:
<221> NAME/KEY: misc_feature
<222> LOCATION: (670)..(699)
<223> OTHER INFORMATION: Primer hph-F
<220> FEATURE:
<221> NAME/KEY: CDS
<222> LOCATION: (688)..(1710)
<223> OTHER INFORMATION: hph coding sequence
<220> FEATURE:
<221> NAME/KEY: misc_feature
<222> LOCATION: (1711)..(1734)
<223> OTHER INFORMATION: Primer nia-F
<220> FEATURE:
<221> NAME/KEY: terminator
<222> LOCATION: (1717)..(2215)
<223> OTHER INFORMATION: Aspergillus niaD oryzae terminator, TniaD.
<220> FEATURE:
<221> NAME/KEY: misc_feature
<222> LOCATION: (1734)..(1766)
<223> OTHER INFORMATION: Primer hph-R
<220> FEATURE:
<221> NAME/KEY: misc_feature
<222> LOCATION: (2201)..(2221)
<223> OTHER INFORMATION: Primer nia-R

<400> SEQUENCE: 7

```
gaattcacta gtggggttca aatgcaaaca agtacaacac gcagcaaacg aagcagccca     60

ccactgcgtt gatgcccagt ttgactgtcc gaaatccacc ggaaaggtgg aaacatacta    120

tgtaacaatc agagggaaga aaaaattttt atcgacgagg caggatagtg actgatggtg    180

gggtcatggt cgggtctccg agcgaaagag aaccaaggaa acaagatcaa cgaggttggt    240

gtacccaaaa ggccgcagca acaagagtca tcgcccaaaa gtcaacagtc tggaagagac    300

tccgccgtgc agattctgcg tcggtcccgc acatgcgtgg tgggggcatt acccctccat    360

gtccaatgat aagggcggcg gtcgagggct taagcccgcc cactaattcg ccttctcgct    420

tgcccctcca tataaggatt ccccctcctt cccctcccac aactttttc cttctttctc    480

tcttcgtccg catcagtacg tatatctttc ccccatacct cctttcctac tcttcttcca    540

ttcattcaac tcttctcctt actgacatct gttttgctca gtacctctac gcgatcagcc    600

gtagtatctg agcaagcttc tctacagaat ctttctagta tcttacaaag aactacaaag    660

ttcgcaccag gatcctacac ctcagca atg tcg cct gaa ctc acc gcg acg tct    714
                              Met Ser Pro Glu Leu Thr Ala Thr Ser
                              1               5

gtc gag aag ttt ctg atc gaa aag ttc gac agc gtc tcc gac ctg atg      762
Val Glu Lys Phe Leu Ile Glu Lys Phe Asp Ser Val Ser Asp Leu Met
10                  15                  20                  25

cag ctc tcg gag ggc gaa gaa tct cgt gct ttc agc ttc gat gta gga      810
Gln Leu Ser Glu Gly Glu Glu Ser Arg Ala Phe Ser Phe Asp Val Gly
                30                  35                  40

ggg cgt gga tat gtc ctg cgg gta aat agc tgc gcc gat ggt ttc tac      858
Gly Arg Gly Tyr Val Leu Arg Val Asn Ser Cys Ala Asp Gly Phe Tyr
            45                  50                  55

aaa gat cgt tat gtt tat cgg cac ttt gca tcg gcc gcg ctc ccg att      906
Lys Asp Arg Tyr Val Tyr Arg His Phe Ala Ser Ala Ala Leu Pro Ile
        60                  65                  70

ccg gaa gtg ctt gac att ggg gaa ttc agc gag agc ctg acc tat tgc      954
Pro Glu Val Leu Asp Ile Gly Glu Phe Ser Glu Ser Leu Thr Tyr Cys
    75                  80                  85

atc tcc cgc cgt gca cag ggt gtc acg ttg caa gac ctg cct gaa acc     1002
Ile Ser Arg Arg Ala Gln Gly Val Thr Leu Gln Asp Leu Pro Glu Thr
90                  95                  100                 105

gaa ctg ccc gct gtt ctg cag ccg gtc gcg gag gcc atg gat gcg atc     1050
Glu Leu Pro Ala Val Leu Gln Pro Val Ala Glu Ala Met Asp Ala Ile
                110                 115                 120

gct gcg gcc gat ctt agc cag acg agc ggg ttc ggc cca ttc gga ccg     1098
Ala Ala Ala Asp Leu Ser Gln Thr Ser Gly Phe Gly Pro Phe Gly Pro
            125                 130                 135

caa gga atc ggt caa tac act aca tgg cgt gat ttc ata tgc gcg att     1146
Gln Gly Ile Gly Gln Tyr Thr Thr Trp Arg Asp Phe Ile Cys Ala Ile
        140                 145                 150

gct gat ccc cat gtg tat cac tgg caa act gtg atg gac gac acc gtc     1194
Ala Asp Pro His Val Tyr His Trp Gln Thr Val Met Asp Asp Thr Val
    155                 160                 165

agt gcg tcc gtc gcg cag gct ctc gat gag ctg atg ctt tgg gcc gag     1242
Ser Ala Ser Val Ala Gln Ala Leu Asp Glu Leu Met Leu Trp Ala Glu
170                 175                 180                 185

gac tgc ccc gaa gtc cgg cac ctc gtg cac gcg gat ttc ggc tcc aac     1290
Asp Cys Pro Glu Val Arg His Leu Val His Ala Asp Phe Gly Ser Asn
                190                 195                 200

aat gtc ctg acg gac aat ggc cgc ata aca gcg gtc att gac tgg agc     1338
Asn Val Leu Thr Asp Asn Gly Arg Ile Thr Ala Val Ile Asp Trp Ser
            205                 210                 215

gag gcg atg ttc ggg gat tcc caa tac gag gtc gcc aac atc ttc ttc     1386
```

```
Glu Ala Met Phe Gly Asp Ser Gln Tyr Glu Val Ala Asn Ile Phe Phe
        220                 225                 230

tgg agg ccg tgg ttg gct tgt atg gag cag cag acg cgc tac ttc gag     1434
Trp Arg Pro Trp Leu Ala Cys Met Glu Gln Gln Thr Arg Tyr Phe Glu
    235                 240                 245

cgg agg cat ccg gag ctt gca gga tcg ccg cgg ctc cgg gcg tat atg     1482
Arg Arg His Pro Glu Leu Ala Gly Ser Pro Arg Leu Arg Ala Tyr Met
250                 255                 260                 265

ctc cgc att ggt ctt gac caa ctc tat cag agc ttg gtt gac ggc aat     1530
Leu Arg Ile Gly Leu Asp Gln Leu Tyr Gln Ser Leu Val Asp Gly Asn
                270                 275                 280

ttc gat gat gca gct tgg gcg cag ggt cga tgc gac gca atc gtc cga     1578
Phe Asp Asp Ala Ala Trp Ala Gln Gly Arg Cys Asp Ala Ile Val Arg
            285                 290                 295

tcc gga gcc ggg act gtc ggg cgt aca caa atc gcc cgc aga agc gcg     1626
Ser Gly Ala Gly Thr Val Gly Arg Thr Gln Ile Ala Arg Arg Ser Ala
        300                 305                 310

gcc gtc tgg acc gat ggc tgt gta gaa gta ctc gcc gat agt gga aac     1674
Ala Val Trp Thr Asp Gly Cys Val Glu Val Leu Ala Asp Ser Gly Asn
    315                 320                 325

cga cgc ccc agc act cgt ccg agg gca aag gaa tag ctcgagatta          1720
Arg Arg Pro Ser Thr Arg Pro Arg Ala Lys Glu
330                 335                 340

tccaagggaa tgacttaatg agtatgtaag acatgggtca taacggcgtt cgaaacatat   1780

acagggttat gtttgggaat agcacacgaa taataacgtt aataggtacc aaagtccttg   1840

atacattagc acggtagaaa aagaataata caacgagctg ggaatattct ttaatataaa   1900

actccaagaa gagctggtgc ggtggagctt gttttcgact ctcagtaata tttcctcata   1960

tccaagcgcg ctaggaggtg gtcgaataca catgtaggcg cttctctgga tgcaaaagtc   2020

gtgccggacc tgccgaaaga ctttgaagat gcgttcacgc catctaagtt gcgtagataa   2080

ttcacaaaaa gggatgtttg tttccggaat gtagcaaaga gctgatagc aatagcctca    2140

ctttcgtggc gcacgccgct cgttccatcc atcctcgaca atggagcaaa tgtcaaaatc   2200

gtaccgaaaa tactttctag a                                             2221


<210> SEQ ID NO 8
<211> LENGTH: 340
<212> TYPE: PRT
<213> ORGANISM: artificial sequence
<220> FEATURE:
<223> OTHER INFORMATION: Synthetic Construct

<400> SEQUENCE: 8

Met Ser Pro Glu Leu Thr Ala Thr Ser Val Glu Lys Phe Leu Ile Glu
1               5                   10                  15

Lys Phe Asp Ser Val Ser Asp Leu Met Gln Leu Ser Glu Gly Glu Glu
            20                  25                  30

Ser Arg Ala Phe Ser Phe Asp Val Gly Gly Arg Gly Tyr Val Leu Arg
        35                  40                  45

Val Asn Ser Cys Ala Asp Gly Phe Tyr Lys Asp Arg Tyr Val Tyr Arg
   50                  55                  60

His Phe Ala Ser Ala Ala Leu Pro Ile Pro Glu Val Leu Asp Ile Gly
65                  70                  75                  80

Glu Phe Ser Glu Ser Leu Thr Tyr Cys Ile Ser Arg Arg Ala Gln Gly
                85                  90                  95

Val Thr Leu Gln Asp Leu Pro Glu Thr Glu Leu Pro Ala Val Leu Gln
            100                 105                 110
```

```
Pro Val Ala Glu Ala Met Asp Ala Ile Ala Ala Ala Asp Leu Ser Gln
        115                 120                 125

Thr Ser Gly Phe Gly Pro Phe Gly Pro Gln Gly Ile Gly Gln Tyr Thr
    130                 135                 140

Thr Trp Arg Asp Phe Ile Cys Ala Ile Ala Asp Pro His Val Tyr His
145                 150                 155                 160

Trp Gln Thr Val Met Asp Asp Thr Val Ser Ala Ser Val Ala Gln Ala
                165                 170                 175

Leu Asp Glu Leu Met Leu Trp Ala Glu Asp Cys Pro Glu Val Arg His
            180                 185                 190

Leu Val His Ala Asp Phe Gly Ser Asn Asn Val Leu Thr Asp Asn Gly
        195                 200                 205

Arg Ile Thr Ala Val Ile Asp Trp Ser Glu Ala Met Phe Gly Asp Ser
    210                 215                 220

Gln Tyr Glu Val Ala Asn Ile Phe Phe Trp Arg Pro Trp Leu Ala Cys
225                 230                 235                 240

Met Glu Gln Gln Thr Arg Tyr Phe Glu Arg Arg His Pro Glu Leu Ala
                245                 250                 255

Gly Ser Pro Arg Leu Arg Ala Tyr Met Leu Arg Ile Gly Leu Asp Gln
            260                 265                 270

Leu Tyr Gln Ser Leu Val Asp Gly Asn Phe Asp Asp Ala Ala Trp Ala
        275                 280                 285

Gln Gly Arg Cys Asp Ala Ile Val Arg Ser Gly Ala Gly Thr Val Gly
    290                 295                 300

Arg Thr Gln Ile Ala Arg Arg Ser Ala Ala Val Trp Thr Asp Gly Cys
305                 310                 315                 320

Val Glu Val Leu Ala Asp Ser Gly Asn Arg Arg Pro Ser Thr Arg Pro
                325                 330                 335

Arg Ala Lys Glu
            340


<210> SEQ ID NO 9
<211> LENGTH: 49
<212> TYPE: DNA
<213> ORGANISM: artificial sequence
<220> FEATURE:
<223> OTHER INFORMATION: FRT-F site

<400> SEQUENCE: 9

ttgaagttcc tattccgagt tcctattctc tagaaagtat aggaacttc                49


<210> SEQ ID NO 10
<211> LENGTH: 50
<212> TYPE: DNA
<213> ORGANISM: artificial sequence
<220> FEATURE:
<223> OTHER INFORMATION: FRT-F3 site

<400> SEQUENCE: 10

ttgaagttcc tattccgagt tcctattctt caaatagtat aggaacttca               50


<210> SEQ ID NO 11
<211> LENGTH: 77
<212> TYPE: DNA
<213> ORGANISM: artificial sequence
<220> FEATURE:
<223> OTHER INFORMATION: Primer 3NA1-F

<400> SEQUENCE: 11
```

actagtttga agttcctatt ccgagttcct attcttcaaa tagtatagga acttcaacta 60
gagtatatga tggtact 77

<210> SEQ ID NO 12
<211> LENGTH: 32
<212> TYPE: DNA
<213> ORGANISM: artificial sequence
<220> FEATURE:
<223> OTHER INFORMATION: Primer 3NA1-R

<400> SEQUENCE: 12
gaattcgcat tctcctagtt actgatgact tt 32

<210> SEQ ID NO 13
<211> LENGTH: 28
<212> TYPE: DNA
<213> ORGANISM: artificial sequence
<220> FEATURE:
<223> OTHER INFORMATION: Primer 5NA1-F

<400> SEQUENCE: 13
gcggccgcgt ttaaacctat ctgttccc 28

<210> SEQ ID NO 14
<211> LENGTH: 82
<212> TYPE: DNA
<213> ORGANISM: artificial sequence
<220> FEATURE:
<223> OTHER INFORMATION: Primer 5NA1-R

<400> SEQUENCE: 14
actagtgcta gcgaagttcc tatactttct agagaatagg aactcggaat aggaacttca 60
agatgaattc gcggcctaca tg 82

<210> SEQ ID NO 15
<211> LENGTH: 5890
<212> TYPE: DNA
<213> ORGANISM: artificial sequence
<220> FEATURE:
<223> OTHER INFORMATION: NA1-encoding part and flanking regions of pHUda981.
<220> FEATURE:
<221> NAME/KEY: misc_feature
<222> LOCATION: (12)..(1788)
<223> OTHER INFORMATION: 5' flanking pHUda981 region.
<220> FEATURE:
<221> NAME/KEY: CDS
<222> LOCATION: (2406)..(2573)
<220> FEATURE:
<221> NAME/KEY: CDS
<222> LOCATION: (2629)..(2667)
<220> FEATURE:
<221> NAME/KEY: CDS
<222> LOCATION: (2753)..(2868)
<220> FEATURE:
<221> NAME/KEY: CDS
<222> LOCATION: (2938)..(3046)
<220> FEATURE:
<221> NAME/KEY: CDS
<222> LOCATION: (3115)..(3343)
<220> FEATURE:
<221> NAME/KEY: CDS
<222> LOCATION: (3402)..(3564)
<220> FEATURE:
<221> NAME/KEY: CDS
<222> LOCATION: (3630)..(3776)
<220> FEATURE:
<221> NAME/KEY: CDS
<222> LOCATION: (3842)..(4082)

<220> FEATURE:
<221> NAME/KEY: CDS
<222> LOCATION: (4162)..(4446)
<220> FEATURE:
<221> NAME/KEY: misc_feature
<222> LOCATION: (4460)..(5883)
<223> OTHER INFORMATION: 3' flanking pHUda981 region.

<400> SEQUENCE: 15

```
acgaggtcct aaactatctg ttccctcccc cccttttat cttcttgtag tccggccttc     60
tagagaaacc atctgcgctg ttctgctcgc cagggaggta tgaccacgtc agcctaaagc    120
gtccagcgaa taaaatccat ctgttcatcc ttcgattcgt catgctttcc tttagttcgt    180
aagcaaggtt cttgtgatca gtctgtacac gtatgcccgg agatccttcc aaaaggggaa    240
accatttctc tagtgcgtag atcactgcca aaagttctcg ttcggtgacg gtgtagttgc    300
gttcaggtgg ggtcaggcgc cgggaaataa tcgcgcaagt taggccgcct tgcataagtt    360
gggcaccgat tgcaaatgat gacgcgtccg ttctcaaagt gcactttctg gtggggtcga    420
agtaggctgt gtcgagcatc cgttgctcca atcgtttcac attctcaaat gccaagtctt    480
ggcgccaagt ccattttccg tcttgctttg tggcgtcgta aagcggggtc gcgtggtggg    540
ccaacatcgg tatgtaatca cggaaaaagt taaccacgcc caaaaacttc cgaagttctg    600
tcttattcct cggtttcggc cagttgcgta tcgttccatc ggagataacc gggctgcatc    660
tgttgtaact gtatcgatgg ccgcaataaa caacttctcg tacttttcgc tggcatttcc    720
tttctttcaa agccaagccg ttctgcctca ggcgtgtctc aatgccttga caaatcctgt    780
catgttcctg ttcgttgtcg gagaaaacca aaatatcgtc caagtgtatc gtaacattgt    840
taccaagaaa ttcccacagt acattttcga tgtaaatctg ccactctgct ggggccgtgc    900
cgattccgaa tggtaatacc gtgtactggt atgttcccat gtgacatcta aacgtcgtca    960
aaggtctgtc ttctttccgt attgtcatct tgtaatacgc ttcctcaatg tcgtatttcg   1020
aaaagaaacg ggctttcttt atccaatccc tgtggtaaga ttgatcgtca ggagattatc   1080
tgcaggaaac atcatggtgg ggtaaccaag gttgtgtctg tataatatat acatgtaaga   1140
tacatgagct tcggtgatat aatacagaag taccatacag taccgcgtta tgaaaacaca   1200
ttaatccgga tcctttccta taatagacta gcgtgcttgg cattagggtt cgaaaaacaa   1260
tcgaagagta taaggggatg acagcagtaa cgactccaac tgtacgcctc cgggtagtag   1320
accgagcagc cgagccagct cagcgcctaa aacgccttat acaattaagc agttaaagaa   1380
gttagaatct acgcttaaaa agctacttaa aaatcgatct cgcagtcccg attcgcctat   1440
caaaaccagt ttaaatcaac tgattaaagg tgccgaacga gctataaatg atataacaat   1500
attaaagcat taattagagc aatatcaggc cgcgcacgaa aggcaactta aaaagcgaaa   1560
gcgctctact aaacagatta cttttgaaaa aggcacatca gtatttaaag cccgaatcct   1620
tattaagcgc cgaaatcagg cagataaagc catacaggca gatagacctc tacctattaa   1680
atcggcttct aggcgcgctc catctaaatg ttctggctgt ggtgtacagg ggcataaaat   1740
tacgcactac ccgaatcgat agaactactc atttttatat agaagtcaga attcatggtg   1800
ttttgatcat tttaaatttt tatatggcgg gtggtgggca actcgcttgc gcgggcaact   1860
cgcttaccga ttacgttagg gctgatattt acgtaaaaat cgtcaaggga tgcaagacca   1920
aagtagtaaa accccggagt caacagcatc caagcccaag tccttcacgg agaaacccca   1980
gcgtccacat cacgagcgaa ggaccacctc taggcatcgg acgcaccatc caattagaag   2040
cagcaaagcg aaacagccca agaaaaaggt cggcccgtcg gccttttctg caacgctgat   2100
```

```
cacgggcagc gatccaacca acaccctcca gagtgactag ggcggaaat ttaaagggat   2160

taatttccac tcaaccacaa atcacagtcg tccccggtat tgtcctgcag aatgcaattt   2220

aaactcttct gcgaatcgct tggattcccc gcccctggcc gtagagctta aagtatgtcc   2280

cttgtcgatg cgatgtatca caacatataa atactagcaa gggatgccat gcttggagga   2340

tagcaaccga caacatcaca tcaagctctc ccttctctga acaataaacc ccacagaagg   2400

cattt atg atg gtc gcg tgg tgg tct cta ttt ctg tac ggc ctt cag gtc   2450
      Met Met Val Ala Trp Trp Ser Leu Phe Leu Tyr Gly Leu Gln Val
      1               5                   10                  15

gcg gca cct gct ttg gct gca acg cct gcg gac tgg cga tcg caa tcc     2498
Ala Ala Pro Ala Leu Ala Ala Thr Pro Ala Asp Trp Arg Ser Gln Ser
                20                  25                  30

att tat ttc ctt ctc acg gat cga ttt gca agg acg gat ggg tcg acg     2546
Ile Tyr Phe Leu Leu Thr Asp Arg Phe Ala Arg Thr Asp Gly Ser Thr
            35                  40                  45

act gcg act tgt aat act gcg gat cag gtgtgttgtt acctactagc           2593
Thr Ala Thr Cys Asn Thr Ala Asp Gln
        50                  55

tttcagaaag aggaatgtaa actgacttga tatag aaa tac tgt ggt gga aca      2646
                                       Lys Tyr Cys Gly Gly Thr
                                                   60

tgg cag ggc atc atc gac aag gtaaattgcc cctttatcaa aaaaaaagaa        2697
Trp Gln Gly Ile Ile Asp Lys
        65

ggaaaagcag aagaaaaata aaataaaaag aactctagtc ctaaccatca catag ttg    2755
                                                             Leu
                                                             70

gac tat atc cag gga atg ggc ttc aca gcc atc tgg atc acc ccc gtt     2803
Asp Tyr Ile Gln Gly Met Gly Phe Thr Ala Ile Trp Ile Thr Pro Val
                75                  80                  85

aca gcc cag ctg ccc cag acc acc gca tat gga gat gcc tac cat ggc     2851
Thr Ala Gln Leu Pro Gln Thr Thr Ala Tyr Gly Asp Ala Tyr His Gly
            90                  95                  100

tac tgg cag cag gat at  gtaagtcgat ttctttaaat atctacctgt            2898
Tyr Trp Gln Gln Asp Ile
        105

catcttttac atcaatatga actaacttga tggttttag a tac tct ctg aac gaa    2953
                                             Tyr Ser Leu Asn Glu
                                                 110

aac tac ggc act gca gat gac ttg aag gcg ctc tct tcg gcc ctt cat     3001
Asn Tyr Gly Thr Ala Asp Asp Leu Lys Ala Leu Ser Ser Ala Leu His
    115                 120                 125

gag agg ggg atg tat ctt atg gtc gat gtg gtt gct aac cat atg         3046
Glu Arg Gly Met Tyr Leu Met Val Asp Val Val Ala Asn His Met
130                 135                 140

gttcgtggtc ctttgcaact gacttcgcgg atatggttca tttcagtact gacaatgagt   3106

aatatcag ggc tat gat gga gcg ggt agc tca gtc gat tac agt gtg ttt    3156
         Gly Tyr Asp Gly Ala Gly Ser Ser Val Asp Tyr Ser Val Phe
         145                 150                 155

aaa ccg ttc agt tcc caa gac tac ttc cac ccg ttc tgt ttc att caa     3204
Lys Pro Phe Ser Ser Gln Asp Tyr Phe His Pro Phe Cys Phe Ile Gln
    160                 165                 170

aac tat gaa gat cag act cag gtt gag gat tgc tgg cta gga gat aac     3252
Asn Tyr Glu Asp Gln Thr Gln Val Glu Asp Cys Trp Leu Gly Asp Asn
175                 180                 185                 190

act gtc tcc ttg cct gat ctc gat acc acc aag gat gtg gtc aag aat     3300
Thr Val Ser Leu Pro Asp Leu Asp Thr Thr Lys Asp Val Val Lys Asn
```

```
                195                 200                 205

gaa tgg tac gac tgg gtg gga tca ttg gta tcg aac tac tcc a          3343
Glu Trp Tyr Asp Trp Val Gly Ser Leu Val Ser Asn Tyr Ser
            210                 215                 220

gtaagatatt tctccctcat tctacaactt ggctgatcga tgatacttac gaaatcag    3401

tt  gac ggc ctc cgt atc gac aca gta aaa cac gtc cag aag gac ttc    3448
Ile Asp Gly Leu Arg Ile Asp Thr Val Lys His Val Gln Lys Asp Phe
                225                 230                 235

tgg ccc ggg tac aac aaa gcc gca ggc gtg tac tgt atc ggc gag gtg    3496
Trp Pro Gly Tyr Asn Lys Ala Ala Gly Val Tyr Cys Ile Gly Glu Val
            240                 245                 250

ctc gac ggt gat ccg gcc tac act tgt ccc tac cag aac gtc atg gac    3544
Leu Asp Gly Asp Pro Ala Tyr Thr Cys Pro Tyr Gln Asn Val Met Asp
        255                 260                 265

ggc gta ctg aac tat ccc at  gtatggttcc tccaaccatg agccttcttg       3594
Gly Val Leu Asn Tyr Pro Ile
    270                 275

caagtctcat ctcctaacga aacggctaaa accag t tac tat cca ctc ctc aac   3648
                                         Tyr Tyr Pro Leu Leu Asn
                                                         280

gcc ttc aag tca acc tcc ggc agc atg gac gac ctc tac aac atg atc    3696
Ala Phe Lys Ser Thr Ser Gly Ser Met Asp Asp Leu Tyr Asn Met Ile
            285                 290                 295

aac acc gtc aaa tcc gac tgt cca gac tca aca ctc ctg ggc aca ttc    3744
Asn Thr Val Lys Ser Asp Cys Pro Asp Ser Thr Leu Leu Gly Thr Phe
        300                 305                 310

gtc gag aac cac gac aac cca cgg ttc gct tc  gtaagtcttc ccttttattt  3796
Val Glu Asn His Asp Asn Pro Arg Phe Ala Ser
    315                 320

tccgttccca atttccacac agaaccccac ctaacaagag caaag t tac acc aac    3851
                                                    Tyr Thr Asn
                                                    325

gac ata gcc ctc gcc aag aac gtc gca gca ttc atc atc ctc aac gac    3899
Asp Ile Ala Leu Ala Lys Asn Val Ala Ala Phe Ile Ile Leu Asn Asp
        330                 335                 340

gga atc ccc atc atc tac gcc ggc caa gaa cag cac tac gcc ggc gga    3947
Gly Ile Pro Ile Ile Tyr Ala Gly Gln Glu Gln His Tyr Ala Gly Gly
    345                 350                 355

aac gac ccc gcg aac cgc gaa gca acc tgg ctc tcg ggc tac ccg acc    3995
Asn Asp Pro Ala Asn Arg Glu Ala Thr Trp Leu Ser Gly Tyr Pro Thr
360                 365                 370                 375

gac agc gag ctg tac aag tta att gcc tcc gcg aac gca atc cgg aac    4043
Asp Ser Glu Leu Tyr Lys Leu Ile Ala Ser Ala Asn Ala Ile Arg Asn
                380                 385                 390

tat gcc att agc aaa gat aca gga ttc gtg acc tac aag gtaagcacaa     4092
Tyr Ala Ile Ser Lys Asp Thr Gly Phe Val Thr Tyr Lys
            395                 400

cctctaagca taccctaatg gcctatcttc agagtatctg acacaagaga ctaatcactg  4152

gcaatacag aac tgg ccc atc tac aaa gac gac aca acg atc gcc atg cgc  4203
          Asn Trp Pro Ile Tyr Lys Asp Asp Thr Thr Ile Ala Met Arg
          405                 410                 415

aag ggc aca gat ggg tcg cag atc gtg act atc ttg tcc aac aag ggt    4251
Lys Gly Thr Asp Gly Ser Gln Ile Val Thr Ile Leu Ser Asn Lys Gly
    420                 425                 430

gct tcg ggt gat tcg tat acc ctc tcc ttg agt ggt gcg ggt tac aca    4299
Ala Ser Gly Asp Ser Tyr Thr Leu Ser Leu Ser Gly Ala Gly Tyr Thr
435                 440                 445                 450

gcc ggc cag caa ttg acg gag gtc att ggc tgc acg acc gtg acg gtt    4347
```

-continued

```
Ala Gly Gln Gln Leu Thr Glu Val Ile Gly Cys Thr Thr Val Thr Val
                455                 460                 465

ggt tcg gat gga aat gtg cct gtt cct atg gca ggt ggg cta cct agg     4395
Gly Ser Asp Gly Asn Val Pro Val Pro Met Ala Gly Gly Leu Pro Arg
            470                 475                 480

gta ttg tat ccg act gag aag ttg gca ggt agc aag atc tgt agt agc     4443
Val Leu Tyr Pro Thr Glu Lys Leu Ala Gly Ser Lys Ile Cys Ser Ser
        485                 490                 495

tcg tgaagggtgg agagtatatg atggtactgc tattcaatct ggcattggac          4496
Ser

agtgagtttg agtttgatgt acagttggag tcgttactgc tgtcatcccc ttatactctt   4556

cgattgtttt tcgaacccta atgccaagca cgctagtcta ttataggaaa ggatccggat   4616

taatgtgttt tcataacgcg gtactgtatg gtacttctgt attatatcac cgaagctcat   4676

gtatcttaca tgtatatatt atacagacac aaccttggtt acagttggag tcattactgc   4736

tgtcaccccc cccaatactc tttgatcgta tttcgaaccc taatgccaag tgcgctagtc   4796

tacatatgga aggtaaccgt aacattaata ttccggaaat tttgatcgta ctgtattgaa   4856

cagtaaggtt atagaaatag tgtattgagt ttgtatcagt aatctacggt agctggaagc   4916

ttctacactg caaacgcgtc aaacatgaca aagcatgtgc cttgcatctc ccgcaaactg   4976

ttaacattcc ttttgtttgt actgagccac ggttcgatcc tttttgacct taccaggtta   5036

accaagacgg gtagggctac aatactgtac ctgtcttagt tcattgtcca tgaacctgat   5096

cattttactg gttttgttag ctgcacctct tccctcacgg acactcttgc tgggacaccc   5156

atatggtgta ggctaacata tgatgatccc aacactaggc ttctcagtgg catctactgc   5216

cttgagggga tgacgtttag tccttactac gatgacgatg cctctcagct tcagccacct   5276

gatccgtgga tacaaactcc atcgtatgcc cccacccctg gtgacttcgg tagagatcgt   5336

acgccatccg tattttgccc atcacctgaa catgtacttg atgaacctta tactcccttg   5396

catcaatccc agcccaatca tctgggtttc ttccaggagc ccgaagaaag gactacgagg   5456

caacatagag gaaagccttg tattcattat actattgagt ggaaggtaac tctgaacaac   5516

cgaactgtgt caaaggacac tgaacaggac ttggctgtag cacccagttc acactgggcg   5576

aagataacac aggatgctga aaatgttatg cgtcgaaaaa tacgtcacaa ccaacgtgtg   5636

agatcagatg atactacagt cagagtatct gtaaacgaac gtggacaatc tgatctgaac   5696

aaacgttttg acggcactaa tattgattgg aaacctatag agaaacagct cttaatgtgg   5756

ggaaatctgt ttcatattgg caagaagctc aaacttttta tatccataaa ctatatagag   5816

gacagtggcc ctcctctttc acggaataca gataagagag gaaagtcatc agtaactagg   5876

agaatgctta caga                                                     5890
```

```
<210> SEQ ID NO 16
<211> LENGTH: 499
<212> TYPE: PRT
<213> ORGANISM: artificial sequence
<220> FEATURE:
<223> OTHER INFORMATION: Synthetic Construct

<400> SEQUENCE: 16

Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
            20                  25                  30

Tyr Phe Leu Leu Thr Asp Arg Phe Ala Arg Thr Asp Gly Ser Thr Thr
```

```
        35                  40                  45

Ala Thr Cys Asn Thr Ala Asp Gln Lys Tyr Cys Gly Gly Thr Trp Gln
    50                  55                  60

Gly Ile Ile Asp Lys Leu Asp Tyr Ile Gln Gly Met Gly Phe Thr Ala
65                  70                  75                  80

Ile Trp Ile Thr Pro Val Thr Ala Gln Leu Pro Gln Thr Thr Ala Tyr
                85                  90                  95

Gly Asp Ala Tyr His Gly Tyr Trp Gln Gln Asp Ile Tyr Ser Leu Asn
            100                 105                 110

Glu Asn Tyr Gly Thr Ala Asp Asp Leu Lys Ala Leu Ser Ser Ala Leu
        115                 120                 125

His Glu Arg Gly Met Tyr Leu Met Val Asp Val Val Ala Asn His Met
    130                 135                 140

Gly Tyr Asp Gly Ala Gly Ser Ser Val Asp Tyr Ser Val Phe Lys Pro
145                 150                 155                 160

Phe Ser Ser Gln Asp Tyr Phe His Pro Phe Cys Phe Ile Gln Asn Tyr
                165                 170                 175

Glu Asp Gln Thr Gln Val Glu Asp Cys Trp Leu Gly Asp Asn Thr Val
            180                 185                 190

Ser Leu Pro Asp Leu Asp Thr Thr Lys Asp Val Val Lys Asn Glu Trp
        195                 200                 205

Tyr Asp Trp Val Gly Ser Leu Val Ser Asn Tyr Ser Ile Asp Gly Leu
    210                 215                 220

Arg Ile Asp Thr Val Lys His Val Gln Lys Asp Phe Trp Pro Gly Tyr
225                 230                 235                 240

Asn Lys Ala Ala Gly Val Tyr Cys Ile Gly Glu Val Leu Asp Gly Asp
                245                 250                 255

Pro Ala Tyr Thr Cys Pro Tyr Gln Asn Val Met Asp Gly Val Leu Asn
            260                 265                 270

Tyr Pro Ile Tyr Tyr Pro Leu Leu Asn Ala Phe Lys Ser Thr Ser Gly
        275                 280                 285

Ser Met Asp Asp Leu Tyr Asn Met Ile Asn Thr Val Lys Ser Asp Cys
    290                 295                 300

Pro Asp Ser Thr Leu Leu Gly Thr Phe Val Glu Asn His Asp Asn Pro
305                 310                 315                 320

Arg Phe Ala Ser Tyr Thr Asn Asp Ile Ala Leu Ala Lys Asn Val Ala
                325                 330                 335

Ala Phe Ile Ile Leu Asn Asp Gly Ile Pro Ile Ile Tyr Ala Gly Gln
            340                 345                 350

Glu Gln His Tyr Ala Gly Gly Asn Asp Pro Ala Asn Arg Glu Ala Thr
        355                 360                 365

Trp Leu Ser Gly Tyr Pro Thr Asp Ser Glu Leu Tyr Lys Leu Ile Ala
    370                 375                 380

Ser Ala Asn Ala Ile Arg Asn Tyr Ala Ile Ser Lys Asp Thr Gly Phe
385                 390                 395                 400

Val Thr Tyr Lys Asn Trp Pro Ile Tyr Lys Asp Asp Thr Thr Ile Ala
                405                 410                 415

Met Arg Lys Gly Thr Asp Gly Ser Gln Ile Val Thr Ile Leu Ser Asn
            420                 425                 430

Lys Gly Ala Ser Gly Asp Ser Tyr Thr Leu Ser Leu Ser Gly Ala Gly
        435                 440                 445

Tyr Thr Ala Gly Gln Gln Leu Thr Glu Val Ile Gly Cys Thr Thr Val
    450                 455                 460
```

```
Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Ser Ser Ser


<210> SEQ ID NO 17
<211> LENGTH: 20
<212> TYPE: DNA
<213> ORGANISM: artificial sequence
<220> FEATURE:
<223> OTHER INFORMATION: Forward primer

<400> SEQUENCE: 17

aatccggatc ctttcctata                                                20


<210> SEQ ID NO 18
<211> LENGTH: 20
<212> TYPE: DNA
<213> ORGANISM: artificial sequence
<220> FEATURE:
<223> OTHER INFORMATION: Reverse primer

<400> SEQUENCE: 18

gatggagcgc gcctagaagc                                                20


<210> SEQ ID NO 19
<211> LENGTH: 24
<212> TYPE: DNA
<213> ORGANISM: artificial sequence
<220> FEATURE:
<223> OTHER INFORMATION: Primer amdS-F

<400> SEQUENCE: 19

ggatccacca tgcctcaatc ctgg                                           24


<210> SEQ ID NO 20
<211> LENGTH: 30
<212> TYPE: DNA
<213> ORGANISM: artificial sequence
<220> FEATURE:
<223> OTHER INFORMATION: Primer amdS-R

<400> SEQUENCE: 20

ctcgagctat ggagtcacca catttcccag                                     30


<210> SEQ ID NO 21
<211> LENGTH: 3091
<212> TYPE: DNA
<213> ORGANISM: artificial sequence
<220> FEATURE:
<223> OTHER INFORMATION: The Aspergillus nidulans acetoamidase gene
      (amdS) expression parts in pHUda976.
<220> FEATURE:
<221> NAME/KEY: promoter
<222> LOCATION: (13)..(669)
<223> OTHER INFORMATION: A. oryzae TEF1 promoter
<220> FEATURE:
<221> NAME/KEY: misc_feature
<222> LOCATION: (670)..(695)
<223> OTHER INFORMATION: Primer amdS-F
<220> FEATURE:
<221> NAME/KEY: CDS
<222> LOCATION: (681)..(944)
<220> FEATURE:
<221> NAME/KEY: CDS
<222> LOCATION: (1025)..(1165)
```

```
<220> FEATURE:
<221> NAME/KEY: CDS
<222> LOCATION: (1226)..(1646)
<220> FEATURE:
<221> NAME/KEY: CDS
<222> LOCATION: (1760)..(2577)
<220> FEATURE:
<221> NAME/KEY: misc_feature
<222> LOCATION: (2557)..(2580)
<223> OTHER INFORMATION: Primer amdS-R
<220> FEATURE:
<221> NAME/KEY: terminator
<222> LOCATION: (2587)..(3085)
<223> OTHER INFORMATION: The A.oryzae niaD terminator (TniaD).

<400> SEQUENCE: 21

gaattcacta gtggggttca aatgcaaaca agtacaacac gcagcaaacg aagcagccca     60

ccactgcgtt gatgcccagt ttgactgtcc gaaatccacc ggaaaggtgg aaacatacta    120

tgtaacaatc agagggaaga aaaaattttt atcgacgagg caggatagtg actgatggtg    180

gggtcatggt cgggtctccg agcgaaagag aaccaaggaa acaagatcaa cgaggttggt    240

gtacccaaaa ggccgcagca acaagagtca tcgcccaaaa gtcaacagtc tggaagagac    300

tccgccgtgc agattctgcg tcggtcccgc acatgcgtgg tgggggcatt acccctccat    360

gtccaatgat aagggcggcg gtcgagggct taagcccgcc cactaattcg ccttctcgct    420

tgcccctcca tataaggatt cccccctcctt cccctcccac aactttttttc cttctttctc    480

tcttcgtccg catcagtacg tatatctttc cccatacct cctttcctac tcttcttcca    540

ttcattcaac tcttctcctt actgacatct gttttgctca gtacctctac gcgatcagcc    600

gtagtatctg agcaagcttc tctacagaat ctttctagta tcttacaaag aactacaaag    660

ttcgcaccag gatccacaga atg cct caa tcc tgg gaa gaa ctg gcc gct gat    713
                     Met Pro Gln Ser Trp Glu Glu Leu Ala Ala Asp
                     1               5                   10

aag cgc gcc cgc ctc gca aaa acc atc cct gat gaa tgg aaa gtc cag      761
Lys Arg Ala Arg Leu Ala Lys Thr Ile Pro Asp Glu Trp Lys Val Gln
            15                  20                  25

acg ctg cct gcg gaa gac agc gtt att gat ttc cca aag aaa tcg ggt      809
Thr Leu Pro Ala Glu Asp Ser Val Ile Asp Phe Pro Lys Lys Ser Gly
        30                  35                  40

atc ctt tca gag gcc gaa ctg aag atc aca gag gcc tcc gct gca gat      857
Ile Leu Ser Glu Ala Glu Leu Lys Ile Thr Glu Ala Ser Ala Ala Asp
    45                  50                  55

ctt gtg tcc aag ctg gcg gcc gga gag ttg acc tcg gtg gaa gtt acg      905
Leu Val Ser Lys Leu Ala Ala Gly Glu Leu Thr Ser Val Glu Val Thr
60                  65                  70                  75

cta gca ttc tgt aaa cgg gca gca atc gcc cag cag tta gtagggtccc       954
Leu Ala Phe Cys Lys Arg Ala Ala Ile Ala Gln Gln Leu
                80                  85

ctctacctct cagggagatg taacaacgcc accttatggg actatcaagc tgacgctggc   1014

ttctgtgcag aca aac tgc gcc cac gag ttc ttc cct gac gcc gct ctc      1063
           Thr Asn Cys Ala His Glu Phe Phe Pro Asp Ala Ala Leu
               90                  95                  100

gcg cag gca agg gaa ctc gat gaa tac tac gca aag cac aag aga ccc     1111
Ala Gln Ala Arg Glu Leu Asp Glu Tyr Tyr Ala Lys His Lys Arg Pro
            105                 110                 115

gtt ggt cca ctc cat ggc ctc ccc atc tct ctc aaa gac cag ctt cga     1159
Val Gly Pro Leu His Gly Leu Pro Ile Ser Leu Lys Asp Gln Leu Arg
        120                 125                 130

gtc aag gtacaccgtt gcccctaagt cgttagatgt ccctttttgt cagctaacat      1215
Val Lys
```

```
    135

atgccaccag ggc tac gaa aca tca atg ggc tac atc tca tgg cta aac      1264
           Gly Tyr Glu Thr Ser Met Gly Tyr Ile Ser Trp Leu Asn
                           140                 145

aag tac gac gaa ggg gac tcg gtt ctg aca acc atg ctc cgc aaa gcc     1312
Lys Tyr Asp Glu Gly Asp Ser Val Leu Thr Thr Met Leu Arg Lys Ala
    150                 155                 160

ggt gcc gtc ttc tac gtc aag acc tct gtc ccg cag acc ctg atg gtc     1360
Gly Ala Val Phe Tyr Val Lys Thr Ser Val Pro Gln Thr Leu Met Val
165                 170                 175                 180

tgc gag aca gtc aac aac atc atc ggg cgc acc gtc aac cca cgc aac     1408
Cys Glu Thr Val Asn Asn Ile Ile Gly Arg Thr Val Asn Pro Arg Asn
                185                 190                 195

aag aac tgg tcg tgc ggc ggc agt tct ggt ggt gag ggt gcg atc gtt     1456
Lys Asn Trp Ser Cys Gly Gly Ser Ser Gly Gly Glu Gly Ala Ile Val
            200                 205                 210

ggg att cgt ggt ggc gtc atc ggt gta gga acg gat atc ggt ggc tcg     1504
Gly Ile Arg Gly Gly Val Ile Gly Val Gly Thr Asp Ile Gly Gly Ser
        215                 220                 225

att cga gtg ccg gcc gcg ttc aac ttc ctg tac ggt cta agg ccg agt     1552
Ile Arg Val Pro Ala Ala Phe Asn Phe Leu Tyr Gly Leu Arg Pro Ser
    230                 235                 240

cat ggg cgg ctg ccg tat gca aag atg gcg aac agc atg gag ggt cag     1600
His Gly Arg Leu Pro Tyr Ala Lys Met Ala Asn Ser Met Glu Gly Gln
245                 250                 255                 260

gag acg gtg cac agc gtt gtc ggg ccg att acg cac tct gtt gag g       1646
Glu Thr Val His Ser Val Val Gly Pro Ile Thr His Ser Val Glu
                265                 270                 275

gtgagtcctt cgcctcttcc ttcttttcct gctctatacc aggcctccac tgtcctcctt   1706

tcttgctttt tatactatat acgagaccgg cagtcactga tgaagtatgt tag ac       1761
                                                           Asp

ctc cgc ctc ttc acc aaa tcc gtc ctc ggt cag gag cca tgg aaa tac     1809
Leu Arg Leu Phe Thr Lys Ser Val Leu Gly Gln Glu Pro Trp Lys Tyr
            280                 285                 290

gac tcc aag gtc atc ccc atg ccc tgg cgc cag tcc gag tcg gac att     1857
Asp Ser Lys Val Ile Pro Met Pro Trp Arg Gln Ser Glu Ser Asp Ile
        295                 300                 305

att gcc tcc aag atc aag aac ggc ggg ctc aat atc ggc tac tac aac     1905
Ile Ala Ser Lys Ile Lys Asn Gly Gly Leu Asn Ile Gly Tyr Tyr Asn
    310                 315                 320

ttc gac ggc aat gtc ctt cca cac cct cct atc ctg cgc ggc gtg gaa     1953
Phe Asp Gly Asn Val Leu Pro His Pro Pro Ile Leu Arg Gly Val Glu
325                 330                 335                 340

acc acc gtc gcc gca ctc gcc aaa gcc ggt cac acc gtg acc ccg tgg     2001
Thr Thr Val Ala Ala Leu Ala Lys Ala Gly His Thr Val Thr Pro Trp
                345                 350                 355

acg cca tac aag cac gat ttc ggc cac gat ctc atc tcc cat atc tac     2049
Thr Pro Tyr Lys His Asp Phe Gly His Asp Leu Ile Ser His Ile Tyr
            360                 365                 370

gcg gct gac ggc agc gcc gac gta atg cgc gat atc agt gca tcc ggc     2097
Ala Ala Asp Gly Ser Ala Asp Val Met Arg Asp Ile Ser Ala Ser Gly
        375                 380                 385

gag ccg gcg att cca aat atc aaa gac cta ctg aac ccg aac atc aaa     2145
Glu Pro Ala Ile Pro Asn Ile Lys Asp Leu Leu Asn Pro Asn Ile Lys
    390                 395                 400

gct gtt aac atg aac gag ctc tgg gac acg cat ctc cag aag tgg aat     2193
Ala Val Asn Met Asn Glu Leu Trp Asp Thr His Leu Gln Lys Trp Asn
405                 410                 415                 420
```

```
tac cag atg gag tac ctt gag aaa tgg cgg gag gct gaa gaa aag gcc     2241
Tyr Gln Met Glu Tyr Leu Glu Lys Trp Arg Glu Ala Glu Glu Lys Ala
                425                 430                 435

ggg aag gaa ctg gac gcc atc atc gcg ccg att acg cct acc gct gcg     2289
Gly Lys Glu Leu Asp Ala Ile Ile Ala Pro Ile Thr Pro Thr Ala Ala
            440                 445                 450

gta cgg cat gac cag ttc cgg tac tat ggg tat gcc tct gtg atc aac     2337
Val Arg His Asp Gln Phe Arg Tyr Tyr Gly Tyr Ala Ser Val Ile Asn
        455                 460                 465

ctg ctg gat ttc acg agc gtg gtt gtt ccg gtt acc ttt gcg gat aag     2385
Leu Leu Asp Phe Thr Ser Val Val Val Pro Val Thr Phe Ala Asp Lys
    470                 475                 480

aac atc gat aag aag aat gag agt ttc aag gcg gtt agt gag ctt gat     2433
Asn Ile Asp Lys Lys Asn Glu Ser Phe Lys Ala Val Ser Glu Leu Asp
485                 490                 495                 500

gcc ctc gtg cag gaa gag tat gat ccg gag gcg tac cat ggg gca ccg     2481
Ala Leu Val Gln Glu Glu Tyr Asp Pro Glu Ala Tyr His Gly Ala Pro
                505                 510                 515

gtt gca gtg cag gtt atc gga cgg aga ctc agt gaa gag agg acg ttg     2529
Val Ala Val Gln Val Ile Gly Arg Arg Leu Ser Glu Glu Arg Thr Leu
            520                 525                 530

gcg att gca gag gaa gtg ggg aag ttg ctg gga aat gtg gtg act cca     2577
Ala Ile Ala Glu Glu Val Gly Lys Leu Leu Gly Asn Val Val Thr Pro
        535                 540                 545

tagctcgaga ttatccaagg gaatgactta atgagtatgt aagacatggg tcataacggc   2637

gttcgaaaca tatacagggt tatgtttggg aatagcacac gaataataac gttaataggt   2697

accaaagtcc ttgatacatt agcacggtag aaaaagaata atacaacgag ctgggaatat   2757

tctttaatat aaaactccaa gaagagctgg tgcggtggag cttgttttcg actctcagta   2817

atatttcctc atatccaagc gcgctaggag gtggtcgaat acacatgtag gcgcttctct   2877

ggatgcaaaa gtcgtgccgg acctgccgaa agactttgaa gatgcgttca cgccatctaa   2937

gttgcgtaga taattcacaa aaagggatgt ttgtttccgg aatgtagcaa agagctgata   2997

ggcaatagcc tcactttcgt ggcgcacgcc gctcgttcca tccatcctcg acaatggagc   3057

aaatgtcaaa atcgtaccga aaatactttc taga                                3091


<210> SEQ ID NO 22
<211> LENGTH: 548
<212> TYPE: PRT
<213> ORGANISM: artificial sequence
<220> FEATURE:
<223> OTHER INFORMATION: Synthetic Construct

<400> SEQUENCE: 22

Met Pro Gln Ser Trp Glu Glu Leu Ala Ala Asp Lys Arg Ala Arg Leu
1               5                   10                  15

Ala Lys Thr Ile Pro Asp Glu Trp Lys Val Gln Thr Leu Pro Ala Glu
            20                  25                  30

Asp Ser Val Ile Asp Phe Pro Lys Lys Ser Gly Ile Leu Ser Glu Ala
        35                  40                  45

Glu Leu Lys Ile Thr Glu Ala Ser Ala Ala Asp Leu Val Ser Lys Leu
    50                  55                  60

Ala Ala Gly Glu Leu Thr Ser Val Glu Val Thr Leu Ala Phe Cys Lys
65                  70                  75                  80

Arg Ala Ala Ile Ala Gln Gln Leu Thr Asn Cys Ala His Glu Phe Phe
                85                  90                  95

Pro Asp Ala Ala Leu Ala Gln Ala Arg Glu Leu Asp Glu Tyr Tyr Ala
```

```
            100                 105                 110

Lys His Lys Arg Pro Val Gly Pro Leu His Gly Leu Pro Ile Ser Leu
        115                 120                 125

Lys Asp Gln Leu Arg Val Lys Gly Tyr Glu Thr Ser Met Gly Tyr Ile
    130                 135                 140

Ser Trp Leu Asn Lys Tyr Asp Glu Gly Asp Ser Val Leu Thr Thr Met
145                 150                 155                 160

Leu Arg Lys Ala Gly Ala Val Phe Tyr Val Lys Thr Ser Val Pro Gln
                165                 170                 175

Thr Leu Met Val Cys Glu Thr Val Asn Asn Ile Ile Gly Arg Thr Val
            180                 185                 190

Asn Pro Arg Asn Lys Asn Trp Ser Cys Gly Gly Ser Ser Gly Gly Glu
        195                 200                 205

Gly Ala Ile Val Gly Ile Arg Gly Gly Val Ile Gly Val Gly Thr Asp
    210                 215                 220

Ile Gly Gly Ser Ile Arg Val Pro Ala Ala Phe Asn Phe Leu Tyr Gly
225                 230                 235                 240

Leu Arg Pro Ser His Gly Arg Leu Pro Tyr Ala Lys Met Ala Asn Ser
                245                 250                 255

Met Glu Gly Gln Glu Thr Val His Ser Val Val Gly Pro Ile Thr His
            260                 265                 270

Ser Val Glu Asp Leu Arg Leu Phe Thr Lys Ser Val Leu Gly Gln Glu
        275                 280                 285

Pro Trp Lys Tyr Asp Ser Lys Val Ile Pro Met Pro Trp Arg Gln Ser
    290                 295                 300

Glu Ser Asp Ile Ile Ala Ser Lys Ile Lys Asn Gly Gly Leu Asn Ile
305                 310                 315                 320

Gly Tyr Tyr Asn Phe Asp Gly Asn Val Leu Pro His Pro Pro Ile Leu
                325                 330                 335

Arg Gly Val Glu Thr Thr Val Ala Ala Leu Ala Lys Ala Gly His Thr
            340                 345                 350

Val Thr Pro Trp Thr Pro Tyr Lys His Asp Phe Gly His Asp Leu Ile
        355                 360                 365

Ser His Ile Tyr Ala Ala Asp Gly Ser Ala Asp Val Met Arg Asp Ile
    370                 375                 380

Ser Ala Ser Gly Glu Pro Ala Ile Pro Asn Ile Lys Asp Leu Leu Asn
385                 390                 395                 400

Pro Asn Ile Lys Ala Val Asn Met Asn Glu Leu Trp Asp Thr His Leu
                405                 410                 415

Gln Lys Trp Asn Tyr Gln Met Glu Tyr Leu Glu Lys Trp Arg Glu Ala
            420                 425                 430

Glu Glu Lys Ala Gly Lys Glu Leu Asp Ala Ile Ile Ala Pro Ile Thr
        435                 440                 445

Pro Thr Ala Ala Val Arg His Asp Gln Phe Arg Tyr Tyr Gly Tyr Ala
    450                 455                 460

Ser Val Ile Asn Leu Leu Asp Phe Thr Ser Val Val Val Pro Val Thr
465                 470                 475                 480

Phe Ala Asp Lys Asn Ile Asp Lys Lys Asn Glu Ser Phe Lys Ala Val
                485                 490                 495

Ser Glu Leu Asp Ala Leu Val Gln Glu Glu Tyr Asp Pro Glu Ala Tyr
            500                 505                 510

His Gly Ala Pro Val Ala Val Gln Val Ile Gly Arg Arg Leu Ser Glu
        515                 520                 525
```

```
Glu Arg Thr Leu Ala Ile Ala Glu Glu Val Gly Lys Leu Leu Gly Asn
    530                 535                 540

Val Val Thr Pro
545


<210> SEQ ID NO 23
<211> LENGTH: 85
<212> TYPE: DNA
<213> ORGANISM: artificial sequence
<220> FEATURE:
<223> OTHER INFORMATION: Primer 3SP-F

<400> SEQUENCE: 23

actagtttga agttcctatt ccgagttcct attcttcaaa tagtatagga acttcaacta     60

gagaatgcaa tcataacaga aagta                                          85


<210> SEQ ID NO 24
<211> LENGTH: 32
<212> TYPE: DNA
<213> ORGANISM: artificial sequence
<220> FEATURE:
<223> OTHER INFORMATION: Primer 3SP-R

<400> SEQUENCE: 24

gaattcttaa ttaaatcacg gcaagggttt ac                                   32


<210> SEQ ID NO 25
<211> LENGTH: 26
<212> TYPE: DNA
<213> ORGANISM: artificial sequence
<220> FEATURE:
<223> OTHER INFORMATION: Primer 5SP-F

<400> SEQUENCE: 25

ccgcggcaac aggcagaata tcttcc                                          26


<210> SEQ ID NO 26
<211> LENGTH: 77
<212> TYPE: DNA
<213> ORGANISM: artificial sequence
<220> FEATURE:
<223> OTHER INFORMATION: Primer 5SP-R

<400> SEQUENCE: 26

actagtgaag ttcctatact ttctagagaa taggaactcg gaataggaac ttcaaacggg     60

atcttggacg cattcca                                                    77


<210> SEQ ID NO 27
<211> LENGTH: 6950
<212> TYPE: DNA
<213> ORGANISM: Artificial sequence
<220> FEATURE:
<223> OTHER INFORMATION: Acid stable amylase from Aspergillus niger
      with flanking sequence from  plasmid pHUDa1019.
<220> FEATURE:
<221> NAME/KEY: misc_feature
<222> LOCATION: (6)..(1930)
<223> OTHER INFORMATION: 5' flanking region from plasmid pHUDa1019.
<220> FEATURE:
<221> NAME/KEY: CDS
<222> LOCATION: (2735)..(2902)
<220> FEATURE:
<221> NAME/KEY: CDS
<222> LOCATION: (2952)..(2990)
<220> FEATURE:
<221> NAME/KEY: CDS
```

```
<222> LOCATION: (3047)..(3162)
<220> FEATURE:
<221> NAME/KEY: CDS
<222> LOCATION: (3222)..(3330)
<220> FEATURE:
<221> NAME/KEY: CDS
<222> LOCATION: (3391)..(3619)
<220> FEATURE:
<221> NAME/KEY: CDS
<222> LOCATION: (3672)..(3834)
<220> FEATURE:
<221> NAME/KEY: CDS
<222> LOCATION: (3884)..(4030)
<220> FEATURE:
<221> NAME/KEY: CDS
<222> LOCATION: (4085)..(4325)
<220> FEATURE:
<221> NAME/KEY: CDS
<222> LOCATION: (4404)..(4706)
<220> FEATURE:
<221> NAME/KEY: misc_feature
<222> LOCATION: (5229)..(6935)
<223> OTHER INFORMATION: 3' flanking region from plasmid pHUDa1019

<400> SEQUENCE: 27

cggcaacagg cagaatatct tccgaattca atcgactgcg cgatgcaagt tggctagcaa     60

cggcgtacac cttgggatta tgcgctgctc aaccgatggt cagctatcaa acaaaatttg    120

ggaagatcgg gctatactga cggtgacatt atagtacggc aagctgagtg acatctacgg    180

tcgcaagcca ctgcttcttt gggcatatgt tttctttggc gtgggatgca ttatcaggta    240

gatactccct ttttcttata cgctggtttg ctggttcgtg ctgacagctg tttccctagc    300

ggtattggtc gagacatggc gactgtcata ttggggcgtg caatcagcgg aattgggggt    360

gctggaacaa tggcgatggg ctctatcatt atcacaggta ggctagcagc ttatcaggtt    420

gaaagaactg tcactgaaca taggcagata ttgttcctcg tcgagatgtt gcccattggc    480

gggcgtacat caatatcgcg atgactctgg gtcgtagcgc aggaggccca atcggcggat    540

ggctaaccga tacaatcgga tggagatggt atgctttgcg cctttgtgac cgcttctctc    600

actaaattgt ggccaaggtc gtttattatc caaggcccct tagccgctgt ggcagctctg    660

ttggtgatat ggaagctcaa actcgccaat ccagtcactg agaagagcat ccgccgtgtc    720

gactttctcg gaacattcct cctggccgtc ggtattgtta caatcaccgt tatcatggac    780

caagcagggc agtccttcgc atgggcatca ttgtcaacag caatccttgc aactctcagt    840

ctatcagcat tcgtcgcctt cgtccttgtt gaactctacg tagcccctga accgattttc    900

gaacttcgca tgttgcggaa gccgaatgtg acgcccagtt acctgatcgg atcgctgcag    960

atcaccgccc aagttggaat gatgttctcc gtgccgttat attttcaggt gacatcgaaa   1020

gcctctgcca ccgtagctgg agggcatctg gttcctgcag tgatcggaaa cacgcttggc   1080

ggcttaatcg cgggagcctt tatccgtcgc accggccaat tcaaggtcct cttgatcctt   1140

gccggtctcg ttgcgtccgt cgcctatcta ctcctcatcc ttcgctggaa cggtcatact   1200

ggattctggg agtccttgta cattattccc ggtggtatgg gtactggttt ctgctctgca   1260

gctgcttttg tcagtatgac ggcgtttttg atgccgcagg aagtggccat ggcaacagga   1320

ggttacttcc tattattcag cttcgccatg acggccggtg tcactgtcac taacagtctg   1380

ctggggacgg ttttcaagcg ccagatggaa cagcacctga cgggtccagg agccaagaag   1440

gttggtatcc ccgcaccttt tctgcgtcac ttactaacga gtatatgaag atcatcgagc   1500

gcgcgctgtc cgacaccagc tatatcaacg gtttgcaggg tcatgtccgg gatgtagtgg   1560

taaaaggata tgtgactggt ctccgctaca cttactgtaa gtcgtttgaa tcatgcatcc   1620
```

```
accgtccacc ttattaactt ggtgccagta ttttccctca ttctttcgct ccttggatcg   1680

gtcctcgctt ggactgtacg aaaacaccaa ctatgaggaa ccagcacggc agctgatagt   1740

atccgaaagc tgcaaattgc ttcatcgagg ctggcattcg atagaagaaa gaactataga   1800

caactagtct tacaatatga caattctctt tgattaataa atgaaaataa cacttgtgtc   1860

agcctaatag ccgagtggcg ggcatctctg gcggcctccc gagcagcgtg gaatgcgtcc   1920

aagatcccgt ccgcgggtcg tcctccggtc ggaatgatga ctggagcagc agacgatatc   1980

ctgacctgaa tgcatgtgat attcacattc cagggagaat tgtcggctat ttagaaccct   2040

ctcggcttaa aagccctatt agactatggg tgcgctcaag ccactagcca ggaattcccg   2100

ctgaacgctc catcaccttg cagctgaagt gcaacatggg acgggcttta acttttcgta   2160

gatataagtt taatctatcc tctccacacc catagggtcg tatggcgtca accagggcac   2220

tctgcaggat ttcatctcgc ttcgccaagc gaggcgccct aacgggcagc ctgcagctta   2280

ccctgttaac cccggctcac cacccccgca gcaatccgtc gcgtcctcca cgagtcataa   2340

caaggttcgg gcgttgtttc ttacccccac tatcaggcgt attcagttaa cagtcagtag   2400

tcccgtgtcg gagatttgtt gttctgcaac aattaaaggg gaccggggtt aaatcctggc   2460

ccccgaactg atcggagttt cggccaatga gagatgttat atacgcccgt tcctggctga   2520

tggattaatt gccggctcca tttggcatcc atcaagcatc atacgggatt agaagggtag   2580

ttcgtgggtt gatctgccgt gcaaggtgct caaggctctg gagtcatgct gaacgcaaat   2640

atttaagaat cgtcgtcagg gacagcgttc tctggatagt caagctgtgc ttgggacgct   2700

gttctgtcgc tttgtcaaaa cataatttgc agcg atg aga tta tcg act tcg agt   2755
                                      Met Arg Leu Ser Thr Ser Ser
                                      1               5

ctc ttc ctt tcc gtg tct ctg ctg ggg aag ctg gcc ctc ggg ctg tcg     2803
Leu Phe Leu Ser Val Ser Leu Leu Gly Lys Leu Ala Leu Gly Leu Ser
        10                  15                  20

gct gca gaa tgg cgc act cag tcg att tac ttc cta ttg acg gat cgg     2851
Ala Ala Glu Trp Arg Thr Gln Ser Ile Tyr Phe Leu Leu Thr Asp Arg
    25                  30                  35

ttc ggt agg acg gac aat tcg acg aca gct aca tgc gat acg ggt gac     2899
Phe Gly Arg Thr Asp Asn Ser Thr Thr Ala Thr Cys Asp Thr Gly Asp
40                  45                  50                  55

caa gtacgttggt attgcaggac ttccatcatt catctactga cttgaatag atc tat   2957
Gln                                                       Ile Tyr

tgt ggt ggc agt tgg caa gga atc atc aac cat gtttgtgatc acttcatact   3010
Cys Gly Gly Ser Trp Gln Gly Ile Ile Asn His
    60                  65

atccgctgtg cgcgtgtctg actttatttg ctgcag ctg gat tat atc cag ggc     3064
                                        Leu Asp Tyr Ile Gln Gly
                                        70                  75

atg gga ttc acg gcc atc tgg atc tcg cct atc act gaa cag ctg ccc     3112
Met Gly Phe Thr Ala Ile Trp Ile Ser Pro Ile Thr Glu Gln Leu Pro
                80                  85                  90

cag gat act gct gat ggt gaa gct tac cat gga tat tgg cag cag aag     3160
Gln Asp Thr Ala Asp Gly Glu Ala Tyr His Gly Tyr Trp Gln Gln Lys
            95                  100                 105

at  gtatgcgctc ctccttccca tatcgtaggc ttactctcag gcggcgactg          3212
Ile

acttgacag a tac gac gtg aac tcc aac ttc ggc act gca gat gac ctc     3261
            Tyr Asp Val Asn Ser Asn Phe Gly Thr Ala Asp Asp Leu
                110                 115                 120
```

```
aag tcc ctc tca gat gcg ctt cat gcc cgc gga atg tac ctc atg gtg     3309
Lys Ser Leu Ser Asp Ala Leu His Ala Arg Gly Met Tyr Leu Met Val
            125                 130                 135

gac gtc gtc cct aac cac atg gtaagtgctg cttcagcatc cttatcagtg       3360
Asp Val Val Pro Asn His Met
        140

aactccaagt gccaacgcta actgtaccag ggc tac gcc ggc aac ggc aac gat   3414
                                 Gly Tyr Ala Gly Asn Gly Asn Asp
                                 145                 150

gta gac tac agc gtc ttc gac ccc ttc gat tcc tcc tcc tac ttc cac     3462
Val Asp Tyr Ser Val Phe Asp Pro Phe Asp Ser Ser Ser Tyr Phe His
        155                 160                 165

cca tac tgc ctg atc aca gat tgg gac aac ttg acc atg gtc caa gat     3510
Pro Tyr Cys Leu Ile Thr Asp Trp Asp Asn Leu Thr Met Val Gln Asp
    170                 175                 180

tgt tgg gag ggt gac acc atc gta tct ctg cca gac cta aac acc acc     3558
Cys Trp Glu Gly Asp Thr Ile Val Ser Leu Pro Asp Leu Asn Thr Thr
185                 190                 195                 200

gaa act gcc gtg aga aca atc tgg tat gac tgg gta gcc gac ctg gta     3606
Glu Thr Ala Val Arg Thr Ile Trp Tyr Asp Trp Val Ala Asp Leu Val
                205                 210                 215

tcc aat tat tca g gtgcgaattc caacccaatt taaaataacc atatactaag      3659
Ser Asn Tyr Ser
            220

tgaaatcacc ag tc  gac gga ctc cgc atc gac agt gtc ctc gaa gtc gaa   3709
              Val Asp Gly Leu Arg Ile Asp Ser Val Leu Glu Val Glu
                                225                 230

cca gac ttc ttc ccg ggc tac cag gaa gca gca ggt gtc tac tgc gtc     3757
Pro Asp Phe Phe Pro Gly Tyr Gln Glu Ala Ala Gly Val Tyr Cys Val
    235                 240                 245

ggc gaa gtc gac aac ggc aac cct gcc ctc gac tgc cca tac cag aag     3805
Gly Glu Val Asp Asn Gly Asn Pro Ala Leu Asp Cys Pro Tyr Gln Lys
250                 255                 260                 265

gtc ctg gac ggc gtc ctc aac tat ccg at  gtacatcccc ctatacattg       3854
Val Leu Asp Gly Val Leu Asn Tyr Pro Ile
                270                 275

ttcattagat cttcgctaac tccaaccag c tac tgg caa ctc ctc tac gcc ttc   3908
                                  Tyr Trp Gln Leu Leu Tyr Ala Phe
                                                  280

gaa tcc tcc agc ggc agc atc agc aac ctc tac aac atg atc aaa tcc     3956
Glu Ser Ser Ser Gly Ser Ile Ser Asn Leu Tyr Asn Met Ile Lys Ser
    285                 290                 295

gtc gca agc gac tgc tcc gat ccg aca cta ctc ggc aac ttc atc gaa     4004
Val Ala Ser Asp Cys Ser Asp Pro Thr Leu Leu Gly Asn Phe Ile Glu
300                 305                 310                 315

aac cac gac aat ccc cgt ttc gcc tc  gtatgtccca cccctcccc            4050
Asn His Asp Asn Pro Arg Phe Ala Ser
                320

tccctacaat cacactcact aatacatcta acag c tac acc tcc gac tac tcg     4103
                                        Tyr Thr Ser Asp Tyr Ser
                                        325                 330

caa gcc aaa aac gtc ctc agc tac atc ttc ctc tcc gac ggc atc ccc     4151
Gln Ala Lys Asn Val Leu Ser Tyr Ile Phe Leu Ser Asp Gly Ile Pro
                335                 340                 345

atc gtc tac gcc ggc gaa gaa cag cac tac tcc ggc ggc aag gtg ccc     4199
Ile Val Tyr Ala Gly Glu Glu Gln His Tyr Ser Gly Gly Lys Val Pro
            350                 355                 360

tac aac cgc gaa gcg acc tgg ctt tca ggc tac gac acc tcc gca gag     4247
Tyr Asn Arg Glu Ala Thr Trp Leu Ser Gly Tyr Asp Thr Ser Ala Glu
        365                 370                 375
```

```
ctg tac acc tgg ata gcc acc acg aac gcg atc cgc aaa cta gcc atc     4295
Leu Tyr Thr Trp Ile Ala Thr Thr Asn Ala Ile Arg Lys Leu Ala Ile
    380                 385                 390

tca gct gac tcg gcc tac att acc tac gcg gttcgtcctt ccctcccacc       4345
Ser Ala Asp Ser Ala Tyr Ile Thr Tyr Ala
395                 400

ctttaccccc caccctacaa acatcccaca tactaacaac atttcaataa tgaaatag     4403

aat gat gca ttc tac act gac agc aac acc atc gca atg cgc aaa ggc     4451
Asn Asp Ala Phe Tyr Thr Asp Ser Asn Thr Ile Ala Met Arg Lys Gly
405                 410                 415                 420

acc tca ggg agc caa gtc atc acc gtc ctc tcc aac aaa ggc tcc tca     4499
Thr Ser Gly Ser Gln Val Ile Thr Val Leu Ser Asn Lys Gly Ser Ser
                425                 430                 435

gga agc agc tac acc ctg acc ctc agc gga agc ggc tac aca tcc ggc     4547
Gly Ser Ser Tyr Thr Leu Thr Leu Ser Gly Ser Gly Tyr Thr Ser Gly
            440                 445                 450

acg aag ctg atc gaa gcg tac aca tgc aca tcc gtg acc gtg gac tcg     4595
Thr Lys Leu Ile Glu Ala Tyr Thr Cys Thr Ser Val Thr Val Asp Ser
        455                 460                 465

agc ggc gat att ccc gtg ccg atg gcg tcg gga tta ccg aga gtt ctt     4643
Ser Gly Asp Ile Pro Val Pro Met Ala Ser Gly Leu Pro Arg Val Leu
    470                 475                 480

ctg ccc gcg tcc gtc gtc gat agc tct tcg ctc tgt ggc ggg agc gga     4691
Leu Pro Ala Ser Val Val Asp Ser Ser Ser Leu Cys Gly Gly Ser Gly
485                 490                 495                 500

aga tta tac gtc gag taattccgga gtggtcggtt actgtgacgt tgccggtggg     4746
Arg Leu Tyr Val Glu
                505

gacaaccttt gagtataagt ttattaaggt ggagtcggat gggactgtta cttgggagag   4806

tgatccgaat cgggagtata cggtgcccga gtgtgggagt ggggagacgg tggttgatac   4866

ttggaggtag atggtttggt cttattgttt tattaagtgt gatgagggtg gtttggaatg   4926

tatgtagttt gggctttggt agtgttgggt tgggttgggt taatgatttt gttattgtat   4986

tgtttttggt ggttgtgacc atggatttga aatgagattt tgtaggggct acggaagtgt   5046

attgtggaca tgtatgtgag ttaattcatc tgggtatgta caaagttggt tagccagtgg   5106

gcttgaagaa aagtctcctg ggtctctggt ttgagtaccc atgttaagag caagcataaa   5166

aacatgaaat attgggaata caaagggtat ttaaaactcg tgagcattag ctcctgggta   5226

gaatgcaatc ataacagaaa gtacagccag cgctgtgtca taaagaagtc cagttgggaa   5286

acgaaagact agaatcaaac taaaagtaat ccggccgata tggcttcacg tgcgaagtct   5346

cgccttgagg ggacattgtc cttgcaggtg attgaccatt gcgttcatat ggcgcgatgt   5406

ttggtagtgt gggtgtagcc ggtgacctca cggaaggact gaaggccaca tacccttctg   5466

agggcctctt ttcttcgtgg ccggagctct cgaatgggtt ctcgacaggt acactcgttt   5526

ggatgtggtc atttgaaggt ctgcgttcgg tcattgttcg cgcaggcgag ctgactgagg   5586

gattgaaagc tgcatagcca tcattggcat gcgttaattc gccaaagctt agcggcgaaa   5646

caggcctgac ctctaaccca tgcatctgct ctgcactcga ttgttcgtgg tgtccttgcg   5706

aagaaagaga agccttggac tcggatgact ttctggacga ggtggtagga tcatcatgat   5766

tgtaatgaga ctgtagcaca tcatgcgaat cattcgacac acggtgtctg cccgagctga   5826

cgtcagcatc ggtatgcatt tcgatatgat cctcatggtt ctcagcatgt ccctcgagag   5886

gggactcatt tccagcggca ggattataag caacataatt gtcatgtggt tgcgaccttt   5946
```

```
cgtgagactc cgagtttgat ctcactgtgg actcatgggc gatatgcggc tcatcatgat   6006

cttcgaatgg agaaaaatgg ttgaagtcgg aggacacggg tgatttagca gcagggttga   6066

atgcaacaca gccggtctcg cgctcttcat gtgagctata tgagtcatgt ggcctgtcat   6126

ggtccagagg ctccggatgc tcatggctag attcatcgtg tgccgaaatc gcgtcactag   6186

caaagggcga ggttgacaca ttggctgcag gactgaacgc cacataacca ctctcaggct   6246

cttcatggga gttataggag ctgtgtggca tatcatagtc ctgaggttca cgatgctcat   6306

ggctggattc atcgtgtgcc gaaatagcgt gactagcaaa aggcgagggc gaagcattgg   6366

ttgcaggact gaacgccaca tagccgtccc cattggccga attgactggt gacaacgtcc   6426

tacccatggc gtcggcgggg gcagcggttt ggtgagagcg aagaccatga gaaatagctg   6486

ggctgaacga tcgcagttgg tattcgtttt cttgagctgg ataggggggct gcgtcaggct   6546

ggctgaaagg tgagaatgtt cgggttgctg ctctatcacc agggaaggca gacgctggag   6606

tcaaagaacg agtgtttgga tcaattgccg gactgtatga acggaaagga gtgctagatg   6666

gagggccata aggatcgtaa tgaggctgat atgtttcata tggcctgtag ccttcgctag   6726

gacctcgtgg ttcggggacc gttggcccat acccaggagc tggtgtataa ttggaacgcg   6786

acacgggtgt ttgattgcgc agaatttgcg gtgccggcga ggcgtgatca atctggctgt   6846

aacctgggcc tggggtgtag tttgagacag gtgtttgtgt tcgtggcatt tgtggcgctg   6906

gcgacgctct gtcagtcggc ccatatccag gcgccgaagg tgtg                    6950
```

<210> SEQ ID NO 28
<211> LENGTH: 505
<212> TYPE: PRT
<213> ORGANISM: Artificial sequence
<220> FEATURE:
<223> OTHER INFORMATION: Synthetic Construct

<400> SEQUENCE: 28

```
Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ala Asp
                85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190
```

```
Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Val Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Lys Val Pro Tyr Asn Arg Glu Ala Thr
        355                 360                 365

Trp Leu Ser Gly Tyr Asp Thr Ser Ala Glu Leu Tyr Thr Trp Ile Ala
    370                 375                 380

Thr Thr Asn Ala Ile Arg Lys Leu Ala Ile Ser Ala Asp Ser Ala Tyr
385                 390                 395                 400

Ile Thr Tyr Ala Asn Asp Ala Phe Tyr Thr Asp Ser Asn Thr Ile Ala
                405                 410                 415

Met Arg Lys Gly Thr Ser Gly Ser Gln Val Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Ser Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Arg Leu Tyr Val Glu
            500                 505


<210> SEQ ID NO 29
<211> LENGTH: 24
<212> TYPE: DNA
<213> ORGANISM: artificial sequence
<220> FEATURE:
<223> OTHER INFORMATION: Forward primer

<400> SEQUENCE: 29

cgtacacctt gggattatgc gctg                                             24


<210> SEQ ID NO 30
<211> LENGTH: 24
<212> TYPE: DNA
<213> ORGANISM: artificial sequence
<220> FEATURE:
```

<223> OTHER INFORMATION: Reverse primer

<400> SEQUENCE: 30
cacaaaggcg caaagcatac catc 24

<210> SEQ ID NO 31
<211> LENGTH: 29
<212> TYPE: DNA
<213> ORGANISM: artificial sequence
<220> FEATURE:
<223> OTHER INFORMATION: Primer pyr-F

<400> SEQUENCE: 31
ttaattaaac taaatgacgt ttgtgaaca 29

<210> SEQ ID NO 32
<211> LENGTH: 42
<212> TYPE: DNA
<213> ORGANISM: artificial sequence
<220> FEATURE:
<223> OTHER INFORMATION: Primer pyr-R

<400> SEQUENCE: 32
ctaccgccag gtgtcagtca ccctcaaagt ccaactcttt tc 42

<210> SEQ ID NO 33
<211> LENGTH: 38
<212> TYPE: DNA
<213> ORGANISM: artificial sequence
<220> FEATURE:
<223> OTHER INFORMATION: Primer Tamg-F

<400> SEQUENCE: 33
agagttggac tttgagggtg actgacacct ggcggtag 38

<210> SEQ ID NO 34
<211> LENGTH: 83
<212> TYPE: DNA
<213> ORGANISM: artificial sequence
<220> FEATURE:
<223> OTHER INFORMATION: Primer Tamg-R

<400> SEQUENCE: 34
gcatgcacta gctagttgaa gttcctatac tatttgaaga ataggaactc ggaataggaa 60
cttcaaccta gaggagagag ttg 83

<210> SEQ ID NO 35
<211> LENGTH: 2143
<212> TYPE: DNA
<213> ORGANISM: artificial sequence
<220> FEATURE:
<223> OTHER INFORMATION: The A.nidulans pyrG gene with flanking
sequences in pHUda794
<220> FEATURE:
<221> NAME/KEY: misc_feature
<222> LOCATION: (2)..(36)
<223> OTHER INFORMATION: Primer pyr-F
<220> FEATURE:
<221> NAME/KEY: promoter
<222> LOCATION: (15)..(553)
<220> FEATURE:
<221> NAME/KEY: CDS
<222> LOCATION: (554)..(1378)
<220> FEATURE:
<221> NAME/KEY: misc_feature
<222> LOCATION: (1360)..(1401)
<223> OTHER INFORMATION: Primer pyr-R
<220> FEATURE:

```
<221> NAME/KEY: misc_feature
<222> LOCATION: (1364)..(1401)
<223> OTHER INFORMATION: Primer Tamg-F
<220> FEATURE:
<221> NAME/KEY: terminator
<222> LOCATION: (1379)..(2071)
<223> OTHER INFORMATION: The A. niger glucoamylase terminator
<220> FEATURE:
<221> NAME/KEY: misc_feature
<222> LOCATION: (2061)..(2143)
<223> OTHER INFORMATION: Primer Tamg-R
<220> FEATURE:
<221> NAME/KEY: misc_feature
<222> LOCATION: (2078)..(2127)
<223> OTHER INFORMATION: FRT-F3

<400> SEQUENCE: 35

attaattaac ctagtactaa atgacgtttg tgaacagccc aaagcctaca aattcaactg      60

cgcacaacgc gcccacggca acttcctcga gaacgcgccg cagacaatgc tctctatcct     120

ggtggcaggc gtcaagtacc cagaggcagc agcgggctta ggagcggcct gggttgttct     180

ccgcaccctc tacatgctgg gctatattta tagcgacaag ccgaacggca ccggcaggta     240

caatggttcg ctgtacttgc ttgcgcaagc gggtctttgg ggattgagcg catttggtgt     300

tgcaaaggat ttgatgtaaa tgtagtcgac atcttagcac agaggggaga gttgataaaa     360

tgtggtctgt ttgaatgata gtcgggttcg tgacctatat tcgtgatagt ggagataggt     420

ctgcgcctat cttatcgggc cggagcaaaa attccaccgc agcggggtga gttttcgtta     480

tacagccatc ccacttccag cttcaaattg tcagtttaat ccagcccaat tcaatcattg     540

gagaaccgcc atc atg tct tcg aag tcc cac ctc ccc tac gca att cgc       589
               Met Ser Ser Lys Ser His Leu Pro Tyr Ala Ile Arg
               1               5                   10

gca acc aac cat ccc aac cct tta aca tct aaa ctc ttc tcc atc gcc      637
Ala Thr Asn His Pro Asn Pro Leu Thr Ser Lys Leu Phe Ser Ile Ala
        15                  20                  25

gag gag aag aaa acc aac gtc acc gtc tcc gca gac gtt act act tcc      685
Glu Glu Lys Lys Thr Asn Val Thr Val Ser Ala Asp Val Thr Thr Ser
    30                  35                  40

gcc gag ctc ctc gat ctt gct gac cgc cta ggc ccc tat atc gca gtt      733
Ala Glu Leu Leu Asp Leu Ala Asp Arg Leu Gly Pro Tyr Ile Ala Val
45                  50                  55                  60

ctg aaa acc cac atc gac atc ctc acc gat ctc acc ccg tcg acc ctt      781
Leu Lys Thr His Ile Asp Ile Leu Thr Asp Leu Thr Pro Ser Thr Leu
                65                  70                  75

tcc tcg ctc caa tcc ctc gcg aca aag cac aac ttc ctc atc ttt gag      829
Ser Ser Leu Gln Ser Leu Ala Thr Lys His Asn Phe Leu Ile Phe Glu
            80                  85                  90

gac cgc aag ttc atc gac atc ggc aac acc gtg caa aag cag tac cac      877
Asp Arg Lys Phe Ile Asp Ile Gly Asn Thr Val Gln Lys Gln Tyr His
        95                  100                 105

ggt ggc gct ctc cgc atc tcc gaa tgg gca cac atc atc aac tgc gcc      925
Gly Gly Ala Leu Arg Ile Ser Glu Trp Ala His Ile Ile Asn Cys Ala
    110                 115                 120

atc ctg ccg ggc gaa ggg atc gtc gag gcc ctc gca cag aca acc aag      973
Ile Leu Pro Gly Glu Gly Ile Val Glu Ala Leu Ala Gln Thr Thr Lys
125                 130                 135                 140

tct cct gac ttt aaa gac gcg aat caa cga ggt ctc ctg att ctt gcc     1021
Ser Pro Asp Phe Lys Asp Ala Asn Gln Arg Gly Leu Leu Ile Leu Ala
                145                 150                 155

gag atg acg agt aag gga tct ctt gcg aca ggg gag tac acg gca cgc     1069
Glu Met Thr Ser Lys Gly Ser Leu Ala Thr Gly Glu Tyr Thr Ala Arg
            160                 165                 170
```

```
tcg gtt gag tac gcg cgg aag tat aag ggg ttt gtg atg gga ttc gtg      1117
Ser Val Glu Tyr Ala Arg Lys Tyr Lys Gly Phe Val Met Gly Phe Val
        175                 180                 185

agt aca agg gcg ttg agt gag gtg ctg ccc gaa cag aaa gag gag agc      1165
Ser Thr Arg Ala Leu Ser Glu Val Leu Pro Glu Gln Lys Glu Glu Ser
    190                 195                 200

gag gat ttt gtc gtc ttt acg act ggg gtg aat ctg tcg gat aag ggg      1213
Glu Asp Phe Val Val Phe Thr Thr Gly Val Asn Leu Ser Asp Lys Gly
205                 210                 215                 220

gat aag ctg ggg cag cag tat cag aca cct ggg tcg gcg gtt ggg cga      1261
Asp Lys Leu Gly Gln Gln Tyr Gln Thr Pro Gly Ser Ala Val Gly Arg
                225                 230                 235

ggt gcg gac ttt atc att gcg ggt agg ggc atc tat aag gcg gac gat      1309
Gly Ala Asp Phe Ile Ile Ala Gly Arg Gly Ile Tyr Lys Ala Asp Asp
            240                 245                 250

cca gtc gag gcg gtt cag agg tac cgg gag gaa ggc tgg aaa gct tac      1357
Pro Val Glu Ala Val Gln Arg Tyr Arg Glu Glu Gly Trp Lys Ala Tyr
        255                 260                 265

gag aaa aga gtt gga ctt tga gggtgactga cacctggcgg tagacaatca       1408
Glu Lys Arg Val Gly Leu
    270

atccatttcg ctatagttaa aggatgggga tgagggcaat tggttatatg atcatgtatg   1468

tagtgggtgt gcataatagt agtgaaatgg aagccaagtc atgtgattgt aatcgaccga   1528

cggaattgag gatatccgga aatacagaca ccgtgaaagc catggtcttt ccttcgtgta   1588

gaagaccaga cagacagtcc ctgatttacc cttgcacaaa gcactagaaa attagcattc   1648

catccttctc tgcttgctct gctgatatca ctgtcattca atgcatagcc atgagctcat   1708

cttagatcca agcacgtaat tccatagccg aggtccacag tggagcagca acattcccca   1768

tcattgcttt ccccaggggc ctcccaacga ctaaatcaag agtatatctc taccgtccaa   1828

tagatcgtct tcgcttcaaa atctttgaca attccaagag ggtccccatc catcaaaccc   1888

agttcaataa tagccgagat gcatggtgga gtcaattagg cagtattgct ggaatgtcgg   1948

ggccagttgg ccgggtggtc attggccgcc tgtgatgcca tctgccacta aatccgatca   2008

ttgatccacc gcccacgagg cgcgtctttg ctttttgcgc ggcgtccagg ttcaactctc   2068

tcctctaggt tgaagttcct attccgagtt cctattcttc aaatagtata ggaacttcaa   2128

ctagctagtg catgc                                                     2143


<210> SEQ ID NO 36
<211> LENGTH: 274
<212> TYPE: PRT
<213> ORGANISM: artificial sequence
<220> FEATURE:
<223> OTHER INFORMATION: Synthetic Construct

<400> SEQUENCE: 36

Met Ser Ser Lys Ser His Leu Pro Tyr Ala Ile Arg Ala Thr Asn His
1               5                   10                  15

Pro Asn Pro Leu Thr Ser Lys Leu Phe Ser Ile Ala Glu Glu Lys Lys
            20                  25                  30

Thr Asn Val Thr Val Ser Ala Asp Val Thr Thr Ser Ala Glu Leu Leu
        35                  40                  45

Asp Leu Ala Asp Arg Leu Gly Pro Tyr Ile Ala Val Leu Lys Thr His
    50                  55                  60

Ile Asp Ile Leu Thr Asp Leu Thr Pro Ser Thr Leu Ser Ser Leu Gln
65                  70                  75                  80
```

```
Ser Leu Ala Thr Lys His Asn Phe Leu Ile Phe Glu Asp Arg Lys Phe
                85                  90                  95

Ile Asp Ile Gly Asn Thr Val Gln Lys Gln Tyr His Gly Gly Ala Leu
            100                 105                 110

Arg Ile Ser Glu Trp Ala His Ile Ile Asn Cys Ala Ile Leu Pro Gly
        115                 120                 125

Glu Gly Ile Val Glu Ala Leu Ala Gln Thr Thr Lys Ser Pro Asp Phe
    130                 135                 140

Lys Asp Ala Asn Gln Arg Gly Leu Leu Ile Leu Ala Glu Met Thr Ser
145                 150                 155                 160

Lys Gly Ser Leu Ala Thr Gly Glu Tyr Thr Ala Arg Ser Val Glu Tyr
                165                 170                 175

Ala Arg Lys Tyr Lys Gly Phe Val Met Gly Phe Val Ser Thr Arg Ala
            180                 185                 190

Leu Ser Glu Val Leu Pro Glu Gln Lys Glu Glu Ser Glu Asp Phe Val
        195                 200                 205

Val Phe Thr Thr Gly Val Asn Leu Ser Asp Lys Gly Asp Lys Leu Gly
    210                 215                 220

Gln Gln Tyr Gln Thr Pro Gly Ser Ala Val Gly Arg Gly Ala Asp Phe
225                 230                 235                 240

Ile Ile Ala Gly Arg Gly Ile Tyr Lys Ala Asp Asp Pro Val Glu Ala
                245                 250                 255

Val Gln Arg Tyr Arg Glu Glu Gly Trp Lys Ala Tyr Glu Lys Arg Val
            260                 265                 270

Gly Leu


<210> SEQ ID NO 37
<211> LENGTH: 33
<212> TYPE: DNA
<213> ORGANISM: artificial sequence
<220> FEATURE:
<223> OTHER INFORMATION: Primer xln-F

<400> SEQUENCE: 37

gcatgcttaa ttaatggaag tgcgttgatc att                                 33


<210> SEQ ID NO 38
<211> LENGTH: 19
<212> TYPE: DNA
<213> ORGANISM: artificial sequence
<220> FEATURE:
<223> OTHER INFORMATION: Primer xln-R

<400> SEQUENCE: 38

ggatcccctg tcagttggg                                                 19


<210> SEQ ID NO 39
<211> LENGTH: 2477
<212> TYPE: DNA
<213> ORGANISM: artificial sequence
<220> FEATURE:
<223> OTHER INFORMATION: The synthetic version of FLP (sFLP) expression
      parts in pHUda996
<220> FEATURE:
<221> NAME/KEY: misc_feature
<222> LOCATION: (1)..(33)
<223> OTHER INFORMATION: Primer xln-F
<220> FEATURE:
<221> NAME/KEY: promoter
<222> LOCATION: (16)..(663)
<223> OTHER INFORMATION: Aspergillus nidulans xlnA promoter
```

```
<220> FEATURE:
<221> NAME/KEY: misc_feature
<222> LOCATION: (651)..(669)
<223> OTHER INFORMATION: Primer xln-R
<220> FEATURE:
<221> NAME/KEY: CDS
<222> LOCATION: (673)..(1941)
<223> OTHER INFORMATION: sFLP encoding
<220> FEATURE:
<221> NAME/KEY: terminator
<222> LOCATION: (1951)..(2450)
<223> OTHER INFORMATION: The niaD terminator, TniaD.

<400> SEQUENCE: 39

gcatgcttaa ttaatggaag tgcgttgatc attattcccc gaaaatgtag tacccagtaa      60

gtggtctagc ggtggctatg gtaggacatc tatgcctaag ctggagttct cattgaacgt     120

gtaccggccg attgccctaa actctgattg agagccggaa acctcatcta cctgatgctc     180

aggggccatc caatagcttc cgatagcatt acagacagat ggactcgtct tggcccacgg     240

gtctagaaca gtcgccggaa ctgcctctat ttgaaacgga gctgaaccat gatacttaag     300

cgtgccaagc ggcgccgttt cccactggaa caaggagcaa tagaattctg cagagattct     360

tcattcaggc tattcagcaa ttcggtttgt ggagcggatc ggggtccact gggtttagtc     420

tggggttttt ctttgcccgc atgggctcta gcacatgcac agcttgcagt tgctgctacg     480

ctatctggga aaacgaatgg ctattcagga gtttataacc aaaagagccg gaaacaggct     540

gattgccctc tcacggggag acgttgtact tctgatccag aggctattaa ccggacacta     600

cctataaagg aggtagcatt cctttctgtc cggctcccag attccaacaa cccaactgac     660

aggggatcca cc atg ccc cag ttc gat atc ctc tgc aag acc ccc ccc aag     711
              Met Pro Gln Phe Asp Ile Leu Cys Lys Thr Pro Pro Lys
              1               5                   10

gtc ctc gtc cgc cag ttc gtc gag cgc ttc gag cgc ccc tcc ggc gag      759
Val Leu Val Arg Gln Phe Val Glu Arg Phe Glu Arg Pro Ser Gly Glu
    15                  20                  25

aag atc gcc ctc tgc gcc gcc gag ctc acc tac ctc tgc tgg atg atc      807
Lys Ile Ala Leu Cys Ala Ala Glu Leu Thr Tyr Leu Cys Trp Met Ile
30                  35                  40                  45

acc cat aac ggc acc gcc atc aag cgc gcc acc ttc atg tcc tac aac      855
Thr His Asn Gly Thr Ala Ile Lys Arg Ala Thr Phe Met Ser Tyr Asn
                50                  55                  60

acc atc atc tcc aac tcc ctc tcc ttc gat atc gtc aac aag tcc ctc      903
Thr Ile Ile Ser Asn Ser Leu Ser Phe Asp Ile Val Asn Lys Ser Leu
            65                  70                  75

cag ttc aag tac aag acc cag aag gcc acc atc ctg gag gcc tcc ctc      951
Gln Phe Lys Tyr Lys Thr Gln Lys Ala Thr Ile Leu Glu Ala Ser Leu
        80                  85                  90

aag aag ctc atc ccc gcc tgg gag ttc acc atc atc ccc tac tac ggc      999
Lys Lys Leu Ile Pro Ala Trp Glu Phe Thr Ile Ile Pro Tyr Tyr Gly
    95                  100                 105

cag aag cat cag tcc gat atc acc gat atc gtc tcc tcc ctc cag ctc     1047
Gln Lys His Gln Ser Asp Ile Thr Asp Ile Val Ser Ser Leu Gln Leu
110                 115                 120                 125

cag ttc gag tcc tcc gag gag gcc gat aag ggc aac tcc cat tcc aag     1095
Gln Phe Glu Ser Ser Glu Glu Ala Asp Lys Gly Asn Ser His Ser Lys
                130                 135                 140

aag atg ctc aag gcc ctc ctc tcc gag ggc gag tcc atc tgg gag atc     1143
Lys Met Leu Lys Ala Leu Leu Ser Glu Gly Glu Ser Ile Trp Glu Ile
            145                 150                 155

acc gag aag atc ctc aac tcc ttc gag tac acc tcc cgc ttc acc aag     1191
Thr Glu Lys Ile Leu Asn Ser Phe Glu Tyr Thr Ser Arg Phe Thr Lys
```

```
        160                 165                 170

acc aag acc ctc tac cag ttc ctc ttc ctc gcc acc ttc atc aac tgc     1239
Thr Lys Thr Leu Tyr Gln Phe Leu Phe Leu Ala Thr Phe Ile Asn Cys
    175                 180                 185

ggc cgc ttc tcc gat atc aag aac gtc gat ccc aag tcc ttc aag ctc     1287
Gly Arg Phe Ser Asp Ile Lys Asn Val Asp Pro Lys Ser Phe Lys Leu
190                 195                 200                 205

gtc cag aac aag tac ctc ggc gtc atc atc cag tgc ctc gtc acc gag     1335
Val Gln Asn Lys Tyr Leu Gly Val Ile Ile Gln Cys Leu Val Thr Glu
            210                 215                 220

acc aag acc tcc gtc tcc cgc cat atc tac ttc ttc tcc gcc cgc ggc     1383
Thr Lys Thr Ser Val Ser Arg His Ile Tyr Phe Phe Ser Ala Arg Gly
            225                 230                 235

cgc atc gat ccc ctc gtc tac ctc gat gag ttc ctc cgc aac tcc gag     1431
Arg Ile Asp Pro Leu Val Tyr Leu Asp Glu Phe Leu Arg Asn Ser Glu
        240                 245                 250

ccc gtc ctc aag cgc gtc aac cgc acc ggc aac tcc tcc tcc aac aag     1479
Pro Val Leu Lys Arg Val Asn Arg Thr Gly Asn Ser Ser Ser Asn Lys
    255                 260                 265

cag gag tac cag ctc ctc aag gat aac ctc gtc cgc tcc tac aac aag     1527
Gln Glu Tyr Gln Leu Leu Lys Asp Asn Leu Val Arg Ser Tyr Asn Lys
270                 275                 280                 285

gcc ctc aag aag aac gcc ccc tac tcc atc ttc gcc atc aag aac ggc     1575
Ala Leu Lys Lys Asn Ala Pro Tyr Ser Ile Phe Ala Ile Lys Asn Gly
            290                 295                 300

ccc aag tcc cat atc ggc cgc cat ctc atg acc tcc ttc ctc tcc atg     1623
Pro Lys Ser His Ile Gly Arg His Leu Met Thr Ser Phe Leu Ser Met
            305                 310                 315

aag ggc ctc acc gag ctc acc aac gtc gtc ggc aac tgg tcc gat aag     1671
Lys Gly Leu Thr Glu Leu Thr Asn Val Val Gly Asn Trp Ser Asp Lys
        320                 325                 330

cgc gcc tcc gcc gtc gcc cgc acc acc tac acc cat cag atc acc gcc     1719
Arg Ala Ser Ala Val Ala Arg Thr Thr Tyr Thr His Gln Ile Thr Ala
    335                 340                 345

atc ccc gat cat tac ttc gca cta gtc tcc cgc tac tac gcc tac gat     1767
Ile Pro Asp His Tyr Phe Ala Leu Val Ser Arg Tyr Tyr Ala Tyr Asp
350                 355                 360                 365

ccc atc tcc aag gag atg atc gcc ctc aag gat gag acc aac ccc atc     1815
Pro Ile Ser Lys Glu Met Ile Ala Leu Lys Asp Glu Thr Asn Pro Ile
            370                 375                 380

gag gag tgg cag cat atc gag cag ctc aag ggc tcc gcc gag ggc tcc     1863
Glu Glu Trp Gln His Ile Glu Gln Leu Lys Gly Ser Ala Glu Gly Ser
            385                 390                 395

atc cgc tac ccc gcc tgg aac ggc atc atc tcc cag gag gtc ctc gat     1911
Ile Arg Tyr Pro Ala Trp Asn Gly Ile Ile Ser Gln Glu Val Leu Asp
        400                 405                 410

tac ctc tcc tcc tac atc aac cgc cgc atc tgagtcgaga ttatccaagg       1961
Tyr Leu Ser Ser Tyr Ile Asn Arg Arg Ile
    415                 420

gaatgactta atgagtatgt aagacatggg tcataacggc gttcgaaaca tatacagggt   2021

tatgtttggg aatagcacac gaataataac gttaataggt accaaagtcc ttgatacatt   2081

agcacggtag aaaaagaata atacaacgag ctgggaatat tctttaatat aaaactccaa   2141

gaagagctgg tgcggtggag cttgttttcg actctcagta atatttcctc atatccaagc   2201

gcgctaggag gtggtcgaat acacatgtag gcgcttctct ggatgcaaaa gtcgtgccgg   2261

acctgccgaa agactttgaa gatgcgttca cgccatctaa gttgcgtaga taattcacaa   2321

aaagggatgt ttgtttccgg aatgtagcaa agagctgata ggcaatagcc tcactttcgt   2381
```

```
ggcgcacgcc gctcgttcca tccatcctcg acaatggagc aaatgtcaaa atcgtaccga   2441

aaatactttg ctagcgaagt tcctatactt tctaga                               2477


<210> SEQ ID NO 40
<211> LENGTH: 423
<212> TYPE: PRT
<213> ORGANISM: artificial sequence
<220> FEATURE:
<223> OTHER INFORMATION: Synthetic Construct

<400> SEQUENCE: 40

Met Pro Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Leu Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
```

```
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420
```

<210> SEQ ID NO 41
<211> LENGTH: 81
<212> TYPE: DNA
<213> ORGANISM: artificial sequence
<220> FEATURE:
<223> OTHER INFORMATION: Primer Pna-F

<400> SEQUENCE: 41

```
gaattcatct tgaagttcct attccgagtt cctattctct agaaagtata ggaacttcgc     60

tagccgagag cagcttgaag a                                               81
```

<210> SEQ ID NO 42
<211> LENGTH: 29
<212> TYPE: DNA
<213> ORGANISM: artificial sequence
<220> FEATURE:
<223> OTHER INFORMATION: Primer Pna-R

<400> SEQUENCE: 42

```
ggatccccca gttgtgtata tagaggatt                                       29
```

<210> SEQ ID NO 43
<211> LENGTH: 24
<212> TYPE: DNA
<213> ORGANISM: artificial sequence
<220> FEATURE:
<223> OTHER INFORMATION: Forward primer

<400> SEQUENCE: 43

```
tcgagtgcgg ccgacgcgta cgtc                                            24
```

<210> SEQ ID NO 44
<211> LENGTH: 20
<212> TYPE: DNA
<213> ORGANISM: artificial sequence
<220> FEATURE:
<223> OTHER INFORMATION: Reverse primer

<400> SEQUENCE: 44

```
cagagagtgt tggtcacgta                                                 20
```

<210> SEQ ID NO 45
<211> LENGTH: 33
<212> TYPE: DNA
<213> ORGANISM: artificial sequence
<220> FEATURE:
<223> OTHER INFORMATION: Primer 3ku-F

<400> SEQUENCE: 45

```
gactagttcta gaagccgtgg gtatttttat gaa                                 33
```

<210> SEQ ID NO 46
<211> LENGTH: 34
<212> TYPE: DNA
<213> ORGANISM: artificial sequence
<220> FEATURE:
<223> OTHER INFORMATION: Primer 3ku-R

<400> SEQUENCE: 46
gaattcgttt aaacttggcg gctgccaagc ttcc 34

<210> SEQ ID NO 47
<211> LENGTH: 28
<212> TYPE: DNA
<213> ORGANISM: artificial sequence
<220> FEATURE:
<223> OTHER INFORMATION: Primer 5ku-F

<400> SEQUENCE: 47
gcggccgctc attcagagag ctacccgt 28

<210> SEQ ID NO 48
<211> LENGTH: 30
<212> TYPE: DNA
<213> ORGANISM: artificial sequence
<220> FEATURE:
<223> OTHER INFORMATION: Primer 5ku-R

<400> SEQUENCE: 48
actagttaat taagaggacc gcatctttga 30

<210> SEQ ID NO 49
<211> LENGTH: 6133
<212> TYPE: DNA
<213> ORGANISM: artificial sequence
<220> FEATURE:
<223> OTHER INFORMATION: The A.niger ku70 gene and flanking sequences of pHUda801
<220> FEATURE:
<221> NAME/KEY: misc_feature
<222> LOCATION: (1)..(1319)
<223> OTHER INFORMATION: 5' flanking pHUda801 region
<220> FEATURE:
<221> NAME/KEY: CDS
<222> LOCATION: (1165)..(1230)
<220> FEATURE:
<221> NAME/KEY: CDS
<222> LOCATION: (1288)..(1899)
<220> FEATURE:
<221> NAME/KEY: CDS
<222> LOCATION: (1959)..(2805)
<220> FEATURE:
<221> NAME/KEY: CDS
<222> LOCATION: (2870)..(2973)
<220> FEATURE:
<221> NAME/KEY: CDS
<222> LOCATION: (3038)..(3265)
<220> FEATURE:
<221> NAME/KEY: CDS
<222> LOCATION: (3339)..(3440)
<220> FEATURE:
<221> NAME/KEY: misc_feature
<222> LOCATION: (4100)..(6133)
<223> OTHER INFORMATION: 3' flanking pHUda801 region

<400> SEQUENCE: 49
cacagctcat tcagagagct acccgtagta gaacaggaat actgggggta ttgcgaaaac 60
gcgaccgcac gaccgccctt cccattgcca aaaccatctt ccagcaattg tgtgtacatt 120
tgttccgtca gcgggttggc gtagcggaag gcaacgtacg gcttgtgagg cgcagtctcc 180

```
gggttgatct tgtccagcag cttgcacatt tcctcgcatt ggtattccga ccattttctt    240

atgggtgagc ctccaccgat gtccgcatac tgtttttgaa tcttgggtgt gcgtcgtttc    300

gaaataagag gcccgaggta atgctggaac ttgccaagag gaatcaaatc gccgtcggcc    360

ttgaatagaa gtagaatgtt agaaacggag caaccaaaat gacagcttgc catagtcgga    420

gacgtacaaa gagccggctg aggaaatctt ctacttcgtc tgtcgtcgag ggccctccca    480

tgttcaggaa gaccatggct gtagggccct tagagcctgt tgcatcctgg gtaaccggag    540

gcactgttgt cgccagccca catctttgtt cttgcttgta tccgaacagg gtgcgagaag    600

ccggtcgcag caattgccgg ggaagggtaa acgggcggcg gagagccatg acaggtaatt    660

gtactgaatt cggttgacct agtcaatggg ggtataagaa aagaccgttc gtatcgcgca    720

agcagatgaa ctattcaagc ccgcattcaa tacttaaaag atagacgagt ggcaagaaca    780

ggtagtgggt gtatgcaaca gcgcaaggcc ttctggaagc tgaaaagtcc agaacggctt    840

gatgacggag caccgagacc acgaccaact ccgactcccg acagccaatg accggccagc    900

tagcgtcatc aattaccggg cggacatcac atgatgttcg tgtctccccg cgtctttctg    960

cccaccggtt tgatcgcgtc cctcgcgacc ggatccagtg acgatataga tctcccctcg   1020

gctgcaggca gcagaggcca aacaggcaga cacaacagcc ccacttgttc ctggttacga   1080

ttcaagttgt cttaaccttt atacttccct ctttcaattt cgataatatc ttgattgctt   1140

taaacgattc cacaacattc tact atg gcg gac ggt aac cca cat cgg gaa     1191
                           Met Ala Asp Gly Asn Pro His Arg Glu
                           1               5

gat gag gcg gcc gag gaa gaa gag gag att gat gag act gtacgcaaat     1240
Asp Glu Ala Ala Glu Glu Glu Glu Glu Ile Asp Glu Thr
10                  15                  20

ttacccatga acttggactg gaactctgga actgacaata agatcag agc tac aaa    1296
                                                    Ser Tyr Lys
                                                            25

cca gtc aaa gat gcg gtc ctc ttc gca atc gat gtc agc gat tcc atg    1344
Pro Val Lys Asp Ala Val Leu Phe Ala Ile Asp Val Ser Asp Ser Met
                30                  35                  40

ttg acg ccg cgc ccc tcg gca gat cct aag aaa cac acc caa gaa tca    1392
Leu Thr Pro Arg Pro Ser Ala Asp Pro Lys Lys His Thr Gln Glu Ser
            45                  50                  55

ccc acc acg gca gcg ctc aaa tgc gcc tat cac ttc atg caa caa cga    1440
Pro Thr Thr Ala Ala Leu Lys Cys Ala Tyr His Phe Met Gln Gln Arg
        60                  65                  70

atc ata tca aat cca caa gac atg atg ggt gtt ttg ctg ttc ggg acc    1488
Ile Ile Ser Asn Pro Gln Asp Met Met Gly Val Leu Leu Phe Gly Thr
    75                  80                  85

cag gcg tcc aag ttc ttt gaa gaa gat gaa gac agt cgg gga gac ctg    1536
Gln Ala Ser Lys Phe Phe Glu Glu Asp Glu Asp Ser Arg Gly Asp Leu
90                  95                  100                 105

tcc tac ccc aac tgc tac ctc ttc act gat ctg gat gtt cct tcg gct    1584
Ser Tyr Pro Asn Cys Tyr Leu Phe Thr Asp Leu Asp Val Pro Ser Ala
                110                 115                 120

cat gag gtc aaa gaa ctt cga gca ctg gta gat gat gaa gga gac tca    1632
His Glu Val Lys Glu Leu Arg Ala Leu Val Asp Asp Glu Gly Asp Ser
            125                 130                 135

agg gag gtt cta tct cca gcg aaa gag cag gtc tct atg gca aac gtc    1680
Arg Glu Val Leu Ser Pro Ala Lys Glu Gln Val Ser Met Ala Asn Val
        140                 145                 150

cta ttt tgc gcc aac cag ata ttc aca tcc aga gcg cca aat ttc ctc    1728
Leu Phe Cys Ala Asn Gln Ile Phe Thr Ser Arg Ala Pro Asn Phe Leu
    155                 160                 165
```

```
tcc cgg cgt ttg ttc atc ata acc gac aat gac aac ccc cat ggt gat      1776
Ser Arg Arg Leu Phe Ile Ile Thr Asp Asn Asp Asn Pro His Gly Asp
170                 175                 180                 185

gat aaa acc ctg cgg tca gcg gcg act gta cgt gct aag gat ctt tac      1824
Asp Lys Thr Leu Arg Ser Ala Ala Thr Val Arg Ala Lys Asp Leu Tyr
                190                 195                 200

gat ctt ggt gtc aca att gag ctg ttt ccg atc tca cgc cct gag cat      1872
Asp Leu Gly Val Thr Ile Glu Leu Phe Pro Ile Ser Arg Pro Glu His
            205                 210                 215

gag ttc aag aac agc aag ttc tat gac gtaagctatc atactctata           1919
Glu Phe Lys Asn Ser Lys Phe Tyr Asp
        220                 225

gcaaagtggc aggggtcgat actcactaca gatacaaag gat att atc tac aag      1973
                                           Asp Ile Ile Tyr Lys
                                                       230

tca ttg ccc agc gat cca gag gcg cct gca tat cta caa tct gat tca      2021
Ser Leu Pro Ser Asp Pro Glu Ala Pro Ala Tyr Leu Gln Ser Asp Ser
            235                 240                 245

aaa gcg gcg act gcg acc ggg gac ggg att tca ctc ctc aac acg ctt      2069
Lys Ala Ala Thr Ala Thr Gly Asp Gly Ile Ser Leu Leu Asn Thr Leu
        250                 255                 260

ctg tcc agt att aat tcg aga acg gtt ccg cgt cgc act cat ttt tcg      2117
Leu Ser Ser Ile Asn Ser Arg Thr Val Pro Arg Arg Thr His Phe Ser
    265                 270                 275

aac atg cct tta gaa ctt ggc cca gac ttc aga att tcg gta tcg ggc      2165
Asn Met Pro Leu Glu Leu Gly Pro Asp Phe Arg Ile Ser Val Ser Gly
280                 285                 290                 295

tat ata ctc tta cga agg caa gcg ccc gct aga aac tcc ttc atc tgg      2213
Tyr Ile Leu Leu Arg Arg Gln Ala Pro Ala Arg Asn Ser Phe Ile Trp
                300                 305                 310

ctg aac ggc gag aag cct gtg gtc gcg aaa gga gtg act tcc cac tcc      2261
Leu Asn Gly Glu Lys Pro Val Val Ala Lys Gly Val Thr Ser His Ser
            315                 320                 325

gca gat gat act ggc cgg act gtc gag aaa tgg gag atc aga aag gca      2309
Ala Asp Asp Thr Gly Arg Thr Val Glu Lys Trp Glu Ile Arg Lys Ala
        330                 335                 340

tat aag ttc ggt ggc gac caa gta acc ttt tcg cct gat gag cag aag      2357
Tyr Lys Phe Gly Gly Asp Gln Val Thr Phe Ser Pro Asp Glu Gln Lys
    345                 350                 355

gcg ctt agg gat ttc ggt gag cca gta atc cgg gtt att ggg ttc aag      2405
Ala Leu Arg Asp Phe Gly Glu Pro Val Ile Arg Val Ile Gly Phe Lys
360                 365                 370                 375

cct atc act gcg ctt cca ttc tgg gca aac gtc aag cac cca tat ttt      2453
Pro Ile Thr Ala Leu Pro Phe Trp Ala Asn Val Lys His Pro Tyr Phe
                380                 385                 390

atc tat cca tcc gag gaa gac tat gta ggc tcc tcg cga gta ttt tcc      2501
Ile Tyr Pro Ser Glu Glu Asp Tyr Val Gly Ser Ser Arg Val Phe Ser
            395                 400                 405

gca ttg cat cag act ctt ttg cgt tcc aag aag atg gca ctc gtc tgg      2549
Ala Leu His Gln Thr Leu Leu Arg Ser Lys Lys Met Ala Leu Val Trp
        410                 415                 420

ttc att gcg cgc aag ggt gct ggc ccc gtt ctc gcc gct atg atc gca      2597
Phe Ile Ala Arg Lys Gly Ala Gly Pro Val Leu Ala Ala Met Ile Ala
    425                 430                 435

ggc gaa gaa aag ctt gat gag aat ggc gta caa aaa tac cct cct ggc      2645
Gly Glu Glu Lys Leu Asp Glu Asn Gly Val Gln Lys Tyr Pro Pro Gly
440                 445                 450                 455

atg tgg att ctt ccc ctc ccc ttc gca gac gat atc cgg cag aac ccc      2693
Met Trp Ile Leu Pro Leu Pro Phe Ala Asp Asp Ile Arg Gln Asn Pro
```

```
            460                 465                 470

gaa aca acg ttg aat gtc gcc ccg gag tca ttg att gat cag atg cgc      2741
Glu Thr Thr Leu Asn Val Ala Pro Glu Ser Leu Ile Asp Gln Met Arg
            475                 480                 485

gtg gtc gtc cag caa ctg cag ctg ccg aag gga gtg tac gag cct ctc      2789
Val Val Val Gln Gln Leu Gln Leu Pro Lys Gly Val Tyr Glu Pro Leu
        490                 495                 500

aaa tac ccc aat cca t gtaagtcact gctgtcttgc attgctcgta tacgatgaac   2845
Lys Tyr Pro Asn Pro
    505

gagaagttga cagcccgtga tcag cc  ctt caa tgg cat tac cgc atc cta      2895
                           Ser Leu Gln Trp His Tyr Arg Ile Leu
                               510                 515

caa gct ctc gca tta gac gaa gat ctc cct gaa aaa cca gaa gac aaa      2943
Gln Ala Leu Ala Leu Asp Glu Asp Leu Pro Glu Lys Pro Glu Asp Lys
        520                 525                 530

acc att ccg aaa tac cgc caa atc gac aag gtaaaaccac tacacccaag       2993
Thr Ile Pro Lys Tyr Arg Gln Ile Asp Lys
    535                 540

aaacaaccct ccacgcattc aacctactga caattgcacc gcag cgc gcc ggt gac    3049
                                                 Arg Ala Gly Asp
                                                     545

tac gta tta tcc tgg gcc gac gaa ctc gaa aag caa tac gcc aaa acc      3097
Tyr Val Leu Ser Trp Ala Asp Glu Leu Glu Lys Gln Tyr Ala Lys Thr
        550                 555                 560

tca gca gcg gcc cct cgc cca acc agc acc ctc gtg aaa cga gga tca      3145
Ser Ala Ala Ala Pro Arg Pro Thr Ser Thr Leu Val Lys Arg Gly Ser
    565                 570                 575

aaa gac cga gca agc gaa acc gag gac tcc aag cca tcg aaa aag atc      3193
Lys Asp Arg Ala Ser Glu Thr Glu Asp Ser Lys Pro Ser Lys Lys Ile
580                 585                 590                 595

aag gtt gag gaa gac tct gga agc cta gag gag gaa gtc cgc agg cat      3241
Lys Val Glu Glu Asp Ser Gly Ser Leu Glu Glu Glu Val Arg Arg His
                600                 605                 610

cac aag aag gga acg cta tcc aag gtaagccacc acaggctttc tacacgtcct    3295
His Lys Lys Gly Thr Leu Ser Lys
            615

cgtgatggca aatatgacat cgtattaacc ggcggttttc tag ctt acg gtc gct     3350
                                                Leu Thr Val Ala
                                                620

atc ctc aag gac ttc ttg act tcc aat gga cgc tca aat gcc ggt aag      3398
Ile Leu Lys Asp Phe Leu Thr Ser Asn Gly Arg Ser Asn Ala Gly Lys
    625                 630                 635

aag gcg gat ctt att gag cgg gta gag gag ttc ttg gag cag              3440
Lys Ala Asp Leu Ile Glu Arg Val Glu Glu Phe Leu Glu Gln
640                 645                 650

tgacatggcg ggattgttgg attcgctagt gcgcttctgt tggtggatgt cgttatgtgg   3500

tgtcttatct cgggttaggc gttcgtgacc tgaggacatg agcttgtaat taatgatggg   3560

ttggatgtcg cggtattcgt tcttcagcga aacgtaatgg acacgtattt taggcgatgt   3620

acagttataa aaatcgaatt cgctgggcta gccggacatg tcaaaacgaa gagtattagg   3680

agagacatca ggtccaagtg ctatttttca aaccagtcgc ttaagaccac cgaggccttt   3740

atctccagaa aatataccgg ttcagcaggt gcgcgtatcc cgaattcaaa ttaatattgg   3800

aacgatcgta aataaccgcc cagattcgcc gtaaaacgat agtagtcagg ctttgccgcc   3860

gacagaaggg gacgagtatg tcaactgagt caacttgaac cgagcagccc ctctaaacaa   3920

cgccacgctg tttgtaatat ccctttagaa acgtgttgtc gctggcaatt atccacaaaa   3980
```

```
aatgagtcta aacgggcgaa aaaagtcacc aaaatgggag aatatgtgga aagaagaaag   4040
aaagagagac caaagcaaga gagcgccgaa aggaagctat cgtaatatat acaagtagaa   4100
gccgtgggta tttttatgaa agcagaaacg ttaacggtat gcgtacaatg atcaacattg   4160
tccataaact tgacagtagc agacttcttc gtcgggacag ctgagagtag cgaagtgtta   4220
gtatttagga cgcattcagc aggtagacgg gggaggtgtg caaaggcaac atactatatt   4280
gattctttgc cgaatatgac atgccagaga aattccatga cacggccact actggcgtca   4340
tccttgtcgg tatcgattat ccactggcgg atcttgatgt agtcctctcg tggtcgttgg   4400
tggacctgct cccgggacac ggcgaattgc gcacagcacg ccgcgccaat ctgtttcggc   4460
atttgcagga acttctggta tttagcttcg tcgtattcat cttgcatcgt aaggcccccg   4520
gtggagttca aaggcggggt gctggtgccc tcaaatatct ctgcaaagac ttcttccgtc   4580
acgtgctggt tggtgcgatg gccctgcttg caccccgggt tccagttgca gcggaggttg   4640
acatagccat tgtcttggac gaagttgaga cgcagggatt tcatcgcaat gacattgtcg   4700
tgtaagggcg catctacatg ccaggccatc aggaaacccg agcgatggga atgaaggaaa   4760
gcaatagtgg atggtagggt gtcgtagtga tcaattaggt aggtgagata agccatggac   4820
tcgtgaccct tgttcagcgg ggttgtgagt gttgtgccgt cagctgcgac ctttttggag   4880
ggattcacga tgtatatggc acgttgccag ctgtggaggg aagctattag tgcgccgaaa   4940
cattgggttg ggaaggggag gacaaaaaaa actcactctg gtagctcctg ctcgacccat   5000
tcagtgtgct cttcctgtag cctggccatc acaatcactt tatcccctgg tgtgacagga   5060
cgagagccat ttaatgtgtt catcggcggg cgcaaatcca gccaattgat cagatatgcg   5120
cccgcgcgat actgatcgca aaggtcctcg aggtggatct tcaagagata taagggcaag   5180
atgagtgcta gactagcaca tagtgctatg cgagcgcccc atctcatgat gaatggctaa   5240
aggacggtag cttctgtgca cggtacggga ctgtttccag aagaattggt gaaaacgcca   5300
acgaggacca atatcgaaag gccgttatcg atgtaatgca ggttaaaatc tgttcctctc   5360
ttctgcaggt gacgaaatca taggactatg aaggtggatg ttgtcacaac acgggttggt   5420
gtaaggaatg acttgagtcg ggaaagaccg agaaagatga aagacggaga ggatagtttc   5480
gagcattaaa aggagggtca atcctattga ggaagaatcc aaaagaagga aaagaggaaa   5540
aatcgaaaaa ggagggtagg tcttggaggg gctatatgtg aaccatattg cgagaaacag   5600
aggacgagag taggaagaga gaagacggac gagaggggtc aaggcgaggt aatcaggaaa   5660
ggagactgga ggaccgttga ttaacctatt cgtctgccta ccaaggcggt aggtgcagta   5720
gtaggagaag tagtcaaggc accaggtact tttagtgact ttggactaaa atagtcacta   5780
agacgagtaa gttagtggtg gaagggaagg tccatcgaat gcttccaatt caagccccca   5840
tctgcctcct tctgtttcgc ccgctctcag gcacttcgaa tctttcaatc cgtctgtctg   5900
tctttttggg tggcgcggca tgggggcagt ggggcgtaac cggacccccc actggctggc   5960
cacgcgttaa aattgttgct atcgtttggc tccccaaaga tgaagactaa gggggaatgg   6020
aagaggctgt cataggctgt tgagagacgg aggtcccctc agacaatcgc aaaccttaag   6080
ggaaccactt tcttccttag cgggccttag cggggaagct tggcagccgc caa          6133
```

<210> SEQ ID NO 50
<211> LENGTH: 653
<212> TYPE: PRT
<213> ORGANISM: artificial sequence
<220> FEATURE:

<223> OTHER INFORMATION: Synthetic Construct

<400> SEQUENCE: 50

```
Met Ala Asp Gly Asn Pro His Arg Glu Asp Glu Ala Ala Glu Glu Glu
1               5                   10                  15

Glu Glu Ile Asp Glu Thr Ser Tyr Lys Pro Val Lys Asp Ala Val Leu
            20                  25                  30

Phe Ala Ile Asp Val Ser Asp Ser Met Leu Thr Pro Arg Pro Ser Ala
        35                  40                  45

Asp Pro Lys Lys His Thr Gln Glu Ser Pro Thr Thr Ala Ala Leu Lys
    50                  55                  60

Cys Ala Tyr His Phe Met Gln Gln Arg Ile Ile Ser Asn Pro Gln Asp
65                  70                  75                  80

Met Met Gly Val Leu Leu Phe Gly Thr Gln Ala Ser Lys Phe Phe Glu
                85                  90                  95

Glu Asp Glu Asp Ser Arg Gly Asp Leu Ser Tyr Pro Asn Cys Tyr Leu
            100                 105                 110

Phe Thr Asp Leu Asp Val Pro Ser Ala His Glu Val Lys Glu Leu Arg
        115                 120                 125

Ala Leu Val Asp Asp Glu Gly Asp Ser Arg Glu Val Leu Ser Pro Ala
    130                 135                 140

Lys Glu Gln Val Ser Met Ala Asn Val Leu Phe Cys Ala Asn Gln Ile
145                 150                 155                 160

Phe Thr Ser Arg Ala Pro Asn Phe Leu Ser Arg Arg Leu Phe Ile Ile
                165                 170                 175

Thr Asp Asn Asp Asn Pro His Gly Asp Asp Lys Thr Leu Arg Ser Ala
            180                 185                 190

Ala Thr Val Arg Ala Lys Asp Leu Tyr Asp Leu Gly Val Thr Ile Glu
        195                 200                 205

Leu Phe Pro Ile Ser Arg Pro Glu His Glu Phe Lys Asn Ser Lys Phe
    210                 215                 220

Tyr Asp Asp Ile Ile Tyr Lys Ser Leu Pro Ser Asp Pro Glu Ala Pro
225                 230                 235                 240

Ala Tyr Leu Gln Ser Asp Ser Lys Ala Ala Thr Ala Thr Gly Asp Gly
                245                 250                 255

Ile Ser Leu Leu Asn Thr Leu Leu Ser Ser Ile Asn Ser Arg Thr Val
            260                 265                 270

Pro Arg Arg Thr His Phe Ser Asn Met Pro Leu Glu Leu Gly Pro Asp
        275                 280                 285

Phe Arg Ile Ser Val Ser Gly Tyr Ile Leu Leu Arg Arg Gln Ala Pro
    290                 295                 300

Ala Arg Asn Ser Phe Ile Trp Leu Asn Gly Glu Lys Pro Val Val Ala
305                 310                 315                 320

Lys Gly Val Thr Ser His Ser Ala Asp Asp Thr Gly Arg Thr Val Glu
                325                 330                 335

Lys Trp Glu Ile Arg Lys Ala Tyr Lys Phe Gly Gly Asp Gln Val Thr
            340                 345                 350

Phe Ser Pro Asp Glu Gln Lys Ala Leu Arg Asp Phe Gly Glu Pro Val
        355                 360                 365

Ile Arg Val Ile Gly Phe Lys Pro Ile Thr Ala Leu Pro Phe Trp Ala
    370                 375                 380

Asn Val Lys His Pro Tyr Phe Ile Tyr Pro Ser Glu Glu Asp Tyr Val
385                 390                 395                 400
```

```
Gly Ser Ser Arg Val Phe Ser Ala Leu His Gln Thr Leu Leu Arg Ser
                405                 410                 415

Lys Lys Met Ala Leu Val Trp Phe Ile Ala Arg Lys Gly Ala Gly Pro
            420                 425                 430

Val Leu Ala Ala Met Ile Ala Gly Glu Glu Lys Leu Asp Glu Asn Gly
        435                 440                 445

Val Gln Lys Tyr Pro Pro Gly Met Trp Ile Leu Pro Leu Pro Phe Ala
    450                 455                 460

Asp Asp Ile Arg Gln Asn Pro Glu Thr Thr Leu Asn Val Ala Pro Glu
465                 470                 475                 480

Ser Leu Ile Asp Gln Met Arg Val Val Val Gln Gln Leu Gln Leu Pro
                485                 490                 495

Lys Gly Val Tyr Glu Pro Leu Lys Tyr Pro Asn Pro Ser Leu Gln Trp
            500                 505                 510

His Tyr Arg Ile Leu Gln Ala Leu Ala Leu Asp Glu Asp Leu Pro Glu
        515                 520                 525

Lys Pro Glu Asp Lys Thr Ile Pro Lys Tyr Arg Gln Ile Asp Lys Arg
    530                 535                 540

Ala Gly Asp Tyr Val Leu Ser Trp Ala Asp Glu Leu Glu Lys Gln Tyr
545                 550                 555                 560

Ala Lys Thr Ser Ala Ala Ala Pro Arg Pro Thr Ser Thr Leu Val Lys
                565                 570                 575

Arg Gly Ser Lys Asp Arg Ala Ser Glu Thr Glu Asp Ser Lys Pro Ser
            580                 585                 590

Lys Lys Ile Lys Val Glu Glu Asp Ser Gly Ser Leu Glu Glu Glu Val
        595                 600                 605

Arg Arg His His Lys Lys Gly Thr Leu Ser Lys Leu Thr Val Ala Ile
    610                 615                 620

Leu Lys Asp Phe Leu Thr Ser Asn Gly Arg Ser Asn Ala Gly Lys Lys
625                 630                 635                 640

Ala Asp Leu Ile Glu Arg Val Glu Glu Phe Leu Glu Gln
                645                 650
```

<210> SEQ ID NO 51
<211> LENGTH: 21
<212> TYPE: DNA
<213> ORGANISM: artificial sequence
<220> FEATURE:
<223> OTHER INFORMATION: Forward primer

<400> SEQUENCE: 51
acggtatgcg tacaatgatc a 21

<210> SEQ ID NO 52
<211> LENGTH: 21
<212> TYPE: DNA
<213> ORGANISM: artificial sequence
<220> FEATURE:
<223> OTHER INFORMATION: Reverse primer

<400> SEQUENCE: 52
atttgagggc accagcaccc c 21

<210> SEQ ID NO 53
<211> LENGTH: 24
<212> TYPE: DNA
<213> ORGANISM: artificial sequence
<220> FEATURE:
<223> OTHER INFORMATION: Forward primer

<400> SEQUENCE: 53
tcgagtgcgg ccgacgcgta cgtc 24

<210> SEQ ID NO 54
<211> LENGTH: 20
<212> TYPE: DNA
<213> ORGANISM: artificial sequence
<220> FEATURE:
<223> OTHER INFORMATION: Reverse primer

<400> SEQUENCE: 54
cagagagtgt tggtcacgta 20

<210> SEQ ID NO 55
<211> LENGTH: 30
<212> TYPE: DNA
<213> ORGANISM: artificial sequence
<220> FEATURE:
<223> OTHER INFORMATION: Primer 3fcy-F

<400> SEQUENCE: 55
tctagaattg aaagctagtt ctggtcgcat 30

<210> SEQ ID NO 56
<211> LENGTH: 32
<212> TYPE: DNA
<213> ORGANISM: artificial sequence
<220> FEATURE:
<223> OTHER INFORMATION: Primer 3fcy-R

<400> SEQUENCE: 56
gtttaaactc cttgcttcgc atacatgccc ac 32

<210> SEQ ID NO 57
<211> LENGTH: 30
<212> TYPE: DNA
<213> ORGANISM: artificial sequence
<220> FEATURE:
<223> OTHER INFORMATION: Primer 5fcy-F

<400> SEQUENCE: 57
gcggccgccg ccgccgaaga actgagcaaa 30

<210> SEQ ID NO 58
<211> LENGTH: 29
<212> TYPE: DNA
<213> ORGANISM: artificial sequence
<220> FEATURE:
<223> OTHER INFORMATION: Primer 5fcy-R

<400> SEQUENCE: 58
actagtatat cttcttatcg cagagattg 29

<210> SEQ ID NO 59
<211> LENGTH: 5230
<212> TYPE: DNA
<213> ORGANISM: artificial sequence
<220> FEATURE:
<223> OTHER INFORMATION: The A.niger fcy1 gene and flanking sequences in pHUda1043
<220> FEATURE:
<221> NAME/KEY: misc_feature
<222> LOCATION: (2)..(2052)
<223> OTHER INFORMATION: 5' flanking pHUda 1043 region
<220> FEATURE:
<221> NAME/KEY: CDS
<222> LOCATION: (2606)..(2764)
<220> FEATURE:
<221> NAME/KEY: CDS
<222> LOCATION: (2834)..(3099)
<220> FEATURE:
<221> NAME/KEY: CDS
<222> LOCATION: (3117)..(3195)
<220> FEATURE:
<221> NAME/KEY: misc_feature
<222> LOCATION: (3261)..(5218)
<223> OTHER INFORMATION: 3' flanking pHUda 1043 region

<400> SEQUENCE: 59

```
ccgccgccga agaactgagc aaagaggtcc tcggcgccca tgccaccgcc agcaccgcca     60
tgctcaagac cctcctcacc gagctggtcg tagaggctac gcttctgggg atcggagagg    120
gtctcgtaag cggcagacaa ttccttgaac ttctcagcgg cttcggggtt gtttgtgttc    180
ttgtctgtaa agatatcgcg ttagtaaaga cccctagatc tttcgtgaaa agcaccgctt    240
tcgcgattca agttgactta ccagggtggt acttcagggc acccttcttg taggcagtct    300
tgagttgggc ctcagaggcc gtcgggggaa cctaaccgcc tcaccgttag tttctgtgac    360
gtgcaaaacc agccaaactt ggcgaaaacc cagaacatac ccccaggatg tcgtagaact    420
tagtttcctt gaccattgtg atctgtgtct agaagagaga aaaaaatcga aaggcgaaag    480
ttgggcgacg gggagaagcc gagggaaaat atagaagaaa caagaacttt tcggagggac    540
gagacggggc aatccgatcc tagaaaacct tacaccgggg tatggaacag gcgaaacaaa    600
gagggctcga aaccaaggag tgtagagaaa tccttgaaaa agagggagga gtttgaggag    660
acgaggggag aggagtctcg aaggcgtgag gggggacaag taagaggtgg aaggaagaag    720
gaagagttgg agagagagag ggtccgtccg ggtgataatc aaagccagga gagcgagaga    780
gagaagagag aaagcggcga cagggcggcg gctgagacaa gtgagagggt atcgtatgtg    840
taatctgatt accaggacca ggcaccaatc gacctttgat ttgccgcacg agcgcagtga    900
agactcgcca agagtttcaa gatgggcgta tcaaataccg gagatacgat ggggcgaaac    960
tccgggagta tagaaatgct ggagaagatg agcgaccgcg cttcaactgg ctggaactgg   1020
aattatatag aaaaaggtgg atagtggttc tgaaaagatc agatcttaac atgaaaggag   1080
agatcgtcgt atgcttttga acaaattggc atgtccacga tgacaacgtc tcaggctgaa   1140
tggagttgtt ctctttgctt cgacaagccc cgtcacccgc agccttgatg gcccgagcgt   1200
ggcttccgac tgcttcgatg cgattccgtg tccttccacc gctttcgcac cctttccatc   1260
gctgacaatc gccctggtaa ttaccggttc gtgaccacgg agagcgttgg ttgcatccca   1320
tttctggatg tctgaccaaa tgtatcaccg ggacttttct atcttgttcg atactacagt   1380
agggaggggt ggtcctaagt aagctagttc tttcatgcct cggtaggatg cggcaaggtc   1440
tacctgggta ttacggtcca atcatacacc attcacgggg atcctcgtct tcatactact   1500
actactaagt actactactt actgcggtgt attgtgtagc atccctccat ccaccatcac   1560
tactcatcat cttacatgta taaaatacct acccagtata ttacacccgg aaactccaag   1620
cacaaaaaaa gaaaaagaaa ataaggaaac tgtaaaatta aagtttgatg tagccgcccg   1680
gatctgcctt tgtctcccaa gtcagattct tttcttcctg gcacacagcg ccatttgcct   1740
caggcacttg gaattgtggc gggcggtggt tgattgccgg cttatcgata aggagaggcg   1800
attagctcga tgcggaagga ggggaagaaa aaagcctgtc gggattcccc acctggagat   1860
tcgtcgcgat ccccaattgc cggctggctt cggttcaact ggctcatgcc tggtgtactc   1920
tactgttctt ctgctgctgc agaggcaatt aatggttcaa ttccggagta ccagacagaa   1980
```

```
attggcttct gtggttcttg ccatgatcgt ggatcagagg ttcagagaac aatctctgcg   2040

ataagaagat atactagtaa atagtgcgtg gcatggggtc tgcgcgagat gaaccccgag   2100

tttatcagcc actgccagtt tgatcttgta aattgtgaaa ctgtgaatta atggttacaa   2160

gtgataagga cgttaccatc gggctctatg catctagatc ggatgtctca tatacaatca   2220

gctcaatttg tattcagtta tagttgtata caaggcatga aatattaagc atctttctta   2280

cgcttatgca tgtcgatccc caagcacacc aaagaagcac tttatgcata ccataaccca   2340

agaaagtcta tcacatgcac acattatcca tgaaaatact attcaatacg aatgtaacaa   2400

cgtcctctat cagtctcaat gacagcagct atcttgttat catggagctc cgcacgtcca   2460

gcccgatgcg ggtcagtccg gcagttaacc acacagagtt tgctccgtct tgatgctacc   2520

ccatctttct atctctctcc caattacccc tccaatcgct ctatatttca tatctcaata   2580

cagcatacaa caagcacata ccatc atg gag acc gat ccc gga ttc atc gct      2632
                            Met Glu Thr Asp Pro Gly Phe Ile Ala
                            1               5

gct gtg gaa gaa gcc aag caa ggc gct gct gag ggt ggt gtg ccc att      2680
Ala Val Glu Glu Ala Lys Gln Gly Ala Ala Glu Gly Gly Val Pro Ile
10                  15                  20                  25

gga gct tgt ttg gtc tcc aag gat ggc aag att cta ggc cgc ggc cac      2728
Gly Ala Cys Leu Val Ser Lys Asp Gly Lys Ile Leu Gly Arg Gly His
                30                  35                  40

aat atg cgc gtc cag aag ggt agt ccc gtg ttg cat gttcgttgat           2774
Asn Met Arg Val Gln Lys Gly Ser Pro Val Leu His
            45                  50

cccatccctt gccttctgag ggtcgtctgg ggttctaatt ctaatctcta ccgtcatag     2833

gct gag atg tcc gcg ctc gag aac tcc ggt cgt ctg ccc gct tcg gcc      2881
Ala Glu Met Ser Ala Leu Glu Asn Ser Gly Arg Leu Pro Ala Ser Ala
    55                  60                  65

tac gaa ggc gct act atg tac acg acc ctg tcg cca tgc gac atg tgc      2929
Tyr Glu Gly Ala Thr Met Tyr Thr Thr Leu Ser Pro Cys Asp Met Cys
70                  75                  80                  85

acc ggt gcc tgc atc ctc tac aag gtt aag cgc gtt gtt gtg ggc gag      2977
Thr Gly Ala Cys Ile Leu Tyr Lys Val Lys Arg Val Val Val Gly Glu
                90                  95                  100

aac aag agc ttc atg ggt ggc gag gac tat ctt aag agc cgt ggg aag      3025
Asn Lys Ser Phe Met Gly Gly Glu Asp Tyr Leu Lys Ser Arg Gly Lys
            105                 110                 115

gag gtt gtg gtt ttg gat aat gca gag tgt aag cag ctg atg gag aag      3073
Glu Val Val Val Leu Asp Asn Ala Glu Cys Lys Gln Leu Met Glu Lys
        120                 125                 130

ttc atg aag gag aag ccg gag ctt tg  gtaggtttcc catgcat c tca ctg     3123
Phe Met Lys Glu Lys Pro Glu Leu Cys                      Ser Leu
    135                 140

gac tgg tct agt ctt ttg ttg gaa tgt acg ctg act gta cga tgt ctt      3171
Asp Trp Ser Ser Leu Leu Leu Glu Cys Thr Leu Thr Val Arg Cys Leu
145                 150                 155                 160

tgc agg aat gag gac att tcc gtc tgagcttttg aattcgtgaa ggtgtcaact     3225
Cys Arg Asn Glu Asp Ile Ser Val
                165

atattgctgg ctaggctctc atgtacataa taaagaattg aaagctagtt ctggtcgcat   3285

tgagcaccca atttagaccg tcagacggtg gatctcttcg aagaagaact tgagatcatc   3345

cgggttgacg aaaggagtca cacctgtgat acattagcat ttattgaata acccagctgt   3405

ggcagtgctc accgtgaccc aagttggcaa tccagccttg cttgcccttc tcgaatcccc   3465
```

```
gaaccatagt ctccacagcc tccgtgatag cctcgcgtcc tccatagaga acaccagggt   3525

cagcattacc ctggatcgtc acacgaccat tggcaatccg cctagcctca gcggggtcgt   3585

gcagccagtc caagccaaca acattgtagc ccgactcgca gagatcctca agaccaaacc   3645

acgcaccctt cgcgaagact gtcatcggaa caggctccag acccatctcc ttcaacttct   3705

tcggcagatt cgccgaaatg tgacgcaggt agggaagaga gaatgacttg aaagcggccg   3765

gagacagctc acccgcccag gaatcgaaga cctgtaccag ctgagcacca gcagcaacct   3825

gaagcgccag gtattcaaca cagatctcgg cgatcttctg caggagagcc tgcgactcct   3885

tggggtactt gtagatccac ttcttcgact ggacgaacag tttcgtgccg cctccctcta   3945

ccatgtagca cagcagagtc cacggggcac cgcaaaagcc gatcaacggc acacgaccct   4005

gcagcttgtg gcgggtgagg gtaatggcct tgtagacgta gtcgagctcc gacttgacat   4065

ccacatcctt ctgcatcact ttctcgtact gtccatcatc gggcgactgg agcggctcgg   4125

ggaagtgggg tcccttcttg tcgaccatct caacctgcat tcccatggcc tggggaatga   4185

ccagaatatc ggagaagatg atcgcagcat cgatgagtcc ggcgtagcgg tcgatgggct   4245

ggatcgtcaa cgtcgatgcg acttcggggt cgcggcagca ttcgaaaaag tcgcggccgg   4305

ctttggcttc atggtattcg gggagataac ggccagctat ataagaagca caatgtggtc   4365

agttataaga gagacatact tggatccggg actcgtaaga gtgcgaagag agtagtttgt   4425

agagagaggc gtaccttgcc gcataaccca tatcggagga cgctggactt tctcgcctgc   4485

aatgatatca gtcccatctc tttgaatata atggtttaaa atcagaatta cccctagcag   4545

ccctcagcaa gaggtcgttc ttcaatggct cgaattgatg ctgcattttg atgtgggatg   4605

tgtgagtgat ggaggggacc ttgcggagga ggggccttcg acatgcaagt cctgccaccg   4665

ttcgcggcct cgggccggaa ctcgactggt cgtccgtggc tcaggtaagc ttcaagccgt   4725

tcgcaagtct ggaacatctg cttactctac ttcgattaag atggcataat ttacgcagct   4785

cgagaataac tatgaggcaa tgcgatgttg attttattga catgtatgtg ctattaagta   4845

ccgagaatat tcctccctcg cgtcccgaca gcgacgacca atacaatgcc ccacaaatcc   4905

ttcgcaacaa acaacagcct caagtactac gctcttctag tcgctacttg aacacaaacc   4965

ccaggacaag cctctgaggt aatgaacagc gcgacggcct tacgtccggg gctacattga   5025

atctgtgaac ctgaaagctg ttagctatca gaccattgaa agtaatgcgt gacaaatggc   5085

aagttgaatg gaatggtgtc agcaaaaaat tagagtgttt gttgttgctg tttttgttcg   5145

tcaaagcaag tagctctggg ttaaaaatgt atcatcatat caccggggag tgggcatgta   5205

tgcgaagcaa ggaaaaccaa atgat                                         5230
```

```
<210> SEQ ID NO 60
<211> LENGTH: 168
<212> TYPE: PRT
<213> ORGANISM: artificial sequence
<220> FEATURE:
<223> OTHER INFORMATION: Synthetic Construct

<400> SEQUENCE: 60

Met Glu Thr Asp Pro Gly Phe Ile Ala Ala Val Glu Glu Ala Lys Gln
1               5                   10                  15

Gly Ala Ala Glu Gly Gly Val Pro Ile Gly Ala Cys Leu Val Ser Lys
            20                  25                  30

Asp Gly Lys Ile Leu Gly Arg Gly His Asn Met Arg Val Gln Lys Gly
        35                  40                  45
```

```
Ser Pro Val Leu His Ala Glu Met Ser Ala Leu Glu Asn Ser Gly Arg
    50                  55                  60

Leu Pro Ala Ser Ala Tyr Glu Gly Ala Thr Met Tyr Thr Thr Leu Ser
65                  70                  75                  80

Pro Cys Asp Met Cys Thr Gly Ala Cys Ile Leu Tyr Lys Val Lys Arg
                85                  90                  95

Val Val Val Gly Glu Asn Lys Ser Phe Met Gly Gly Glu Asp Tyr Leu
            100                 105                 110

Lys Ser Arg Gly Lys Glu Val Val Val Leu Asp Asn Ala Glu Cys Lys
        115                 120                 125

Gln Leu Met Glu Lys Phe Met Lys Glu Lys Pro Glu Leu Cys Ser Leu
    130                 135                 140

Asp Trp Ser Ser Leu Leu Leu Glu Cys Thr Leu Thr Val Arg Cys Leu
145                 150                 155                 160

Cys Arg Asn Glu Asp Ile Ser Val
                165


<210> SEQ ID NO 61
<211> LENGTH: 26
<212> TYPE: DNA
<213> ORGANISM: artificial sequence
<220> FEATURE:
<223> OTHER INFORMATION: Forward primer

<400> SEQUENCE: 61

gaaagctagt tctggtcgca ttgagc                                            26


<210> SEQ ID NO 62
<211> LENGTH: 24
<212> TYPE: DNA
<213> ORGANISM: artificial sequence
<220> FEATURE:
<223> OTHER INFORMATION: Reverse primer

<400> SEQUENCE: 62

gaagttgaag gagatgggtc tgga                                              24


<210> SEQ ID NO 63
<211> LENGTH: 85
<212> TYPE: DNA
<213> ORGANISM: artificial sequence
<220> FEATURE:
<223> OTHER INFORMATION: Primer 3na2-F

<400> SEQUENCE: 63

tctagattga agttcctatt ccgagttcct attcttcaaa tagtatagga acttcatgtc      60

tccatgtttc ttgagcggaa gtact                                             85


<210> SEQ ID NO 64
<211> LENGTH: 30
<212> TYPE: DNA
<213> ORGANISM: artificial sequence
<220> FEATURE:
<223> OTHER INFORMATION: Primer 3na2-R

<400> SEQUENCE: 64

gtttaaacga agactgatat tatggcggaa                                        30


<210> SEQ ID NO 65
<211> LENGTH: 30
<212> TYPE: DNA
<213> ORGANISM: artificial sequence
```

<220> FEATURE:
<223> OTHER INFORMATION: Primer 5na2-F

<400> SEQUENCE: 65
gcggccgcaa gagtcaaaag atagcagagc 30

<210> SEQ ID NO 66
<211> LENGTH: 79
<212> TYPE: DNA
<213> ORGANISM: artificial sequence
<220> FEATURE:
<223> OTHER INFORMATION: Primer 5na2-R

<400> SEQUENCE: 66
actagtgcta gcgaagttcc tatacttgaa taggaactcg gaataggaac ttcaagatga 60
attcgcggcc ggccgcatg 79

<210> SEQ ID NO 67
<211> LENGTH: 30
<212> TYPE: DNA
<213> ORGANISM: artificial sequence
<220> FEATURE:
<223> OTHER INFORMATION: Primer fcy-F

<400> SEQUENCE: 67
gctagcgcga ggctatcacg gaggctgtgg 30

<210> SEQ ID NO 68
<211> LENGTH: 30
<212> TYPE: DNA
<213> ORGANISM: artificial sequence
<220> FEATURE:
<223> OTHER INFORMATION: Primer fcy-R

<400> SEQUENCE: 68
gctagcttct gtggttcttg ccatgatcgt 30

<210> SEQ ID NO 69
<211> LENGTH: 12700
<212> TYPE: DNA
<213> ORGANISM: artificial sequence
<220> FEATURE:
<223> OTHER INFORMATION: The A.niger NA2 gene with flanking sequences in pHUda1078
<220> FEATURE:
<221> NAME/KEY: misc_feature
<222> LOCATION: (27)..(1992)
<223> OTHER INFORMATION: 5' flanking pHUda 1078
<220> FEATURE:
<221> NAME/KEY: CDS
<222> LOCATION: (5056)..(5223)
<220> FEATURE:
<221> NAME/KEY: CDS
<222> LOCATION: (5279)..(5317)
<220> FEATURE:
<221> NAME/KEY: CDS
<222> LOCATION: (5404)..(5519)
<220> FEATURE:
<221> NAME/KEY: CDS
<222> LOCATION: (5589)..(5697)
<220> FEATURE:
<221> NAME/KEY: CDS
<222> LOCATION: (5766)..(5994)
<220> FEATURE:
<221> NAME/KEY: CDS
<222> LOCATION: (6053)..(6215)
<220> FEATURE:
<221> NAME/KEY: CDS
<222> LOCATION: (6281)..(6427)
<220> FEATURE:

<221> NAME/KEY: CDS
<222> LOCATION: (6493)..(6733)
<220> FEATURE:
<221> NAME/KEY: CDS
<222> LOCATION: (6813)..(7097)
<220> FEATURE:
<221> NAME/KEY: misc_feature
<222> LOCATION: (10618)..(12659)
<223> OTHER INFORMATION: 3' flanking pHUda 1078

<400> SEQUENCE: 69

```
gctcagcgat acttcccggg aaaatcaaga gtcaaaagat agcagagctt gaagaacgac     60
ttcggcagtt tgctcttaaa cgcgagggat cgaaaacatt actgtacaac acaaagaaag    120
accttattag actccgcgct gagaaagaca gtgtcaaagg agaaaaagaa cgcctcctga    180
aggaaagagc tacagaggag acatggtggt cttacatctc gtccttaatg ataggaaaca    240
cggtggaatt caaccagcgg agacaacgac gagagcgtga gataactgac tcgattggga    300
aacaacggac gaaggaatgg aatattgatc ttaaactggc ggaggttcaa tatcttgaaa    360
gaatgctcga ttctatctct tctgctgaga ttgaaatcaa agttgagata acgaaaatag    420
aagagcgctg gcgcgaaagg ctatcattgc aggaaatgga aagggtattg gcgaaatgga    480
aaaatcaaag ataattagcg aagggaactc gagtagcaac acggcataga tctacgaagg    540
cagaaactat agccatcagt catatattca aaaaattgtg gtagagtata gcgaagtgtg    600
ctaagtggtg ccaactgaag aataatcagt ggcaggagga actttggtgg atttgggacg    660
aaatacacac gtggtaagaa atgtccttgt atgagaggat acaagcgacg gaagccgcgc    720
tgagtcaccc cagtgcatag ttacgtttta atacagaagc tggtaacaga tgtccggagg    780
aatagtcgta aaaaagctta gcctaatccc gattagggct tctcaaacat aggaagagta    840
taaacatttg cgccattttt gcaacctagt gtaaacgaat ggaatcaaaa aacacatgtg    900
ttaagccatc caccaagtcg taaactcatt atatggccca agttcgttga accgtctgct    960
ttcacatcaa cctcctctat gtctcgaaga atattctcta tgtattcacc tgcaccgcta   1020
agtttcatta taagtgcgat agcacgatga acatcaagga gccgccgtga gggcgtatca   1080
attacacgag tgggactaag ggttaaagtc cgcgtgactg ggaagagtgg atcacgtaaa   1140
aatggacttc gctctgttga atcaattttg tactgatatg gcacgcctgt gggttcgaaa   1200
taaatctgaa attcaccgaa catacgatga tagtcgagcg ttaaagtaag ggcgttaatg   1260
gggctgtcaa tcttcggacc atcaattaga tggatgacac cagggtcaaa catatctaaa   1320
atccgaagca cattcttttt cgagtcgctc tatggaacta tgttagcgga gcgatgaagc   1380
atgttttaga tcagacatac taggtctgca tctccagagg aaactgttgt aagacaatgt   1440
ggtagaatat gggccacttc caggaactga aagcggtcac ttgattcgtt tttcaattct   1500
attccttcat cgtccttgca atcttcccca tactgctcga aacgttttct agcctcgctc   1560
ttatcaaatt ttcgagaaat tacgcaacga tagcgatcac gcacaaggca actttttcgc   1620
aagatagata cacggtatgg tgtgccggag ggcgtagatg tttgtattgc ggataatgat   1680
gcaggcgtcg gttgcggagt cttgacagat gaagctcgga ctgtgatcat ccaagttaaa   1740
tagtgcttct cacagtagaa tggtcaatag ccaacatacg cggaaggagg aaattctcaa   1800
tgatgtaatc agcgaattct tcgatcgcgc tctttgcttt gttcttctcg tctggactcc   1860
aagacgtaaa gttatcgaag aacgtcaaga caatcgtaat atcagaatca atcaaatcag   1920
caggctgtga acatagattt tcgtatatcg acgagaaaaa gaacgttaaa aatgtatcct   1980
tagctaccac atgctcatat gtggccttaa taagtgccgc tggcttgtaa ccttttcgtg   2040
```

```
cactcctttc ggggccataa cactgaatta agacctgaag aaggttggct gccgattgac   2100
tttggtgggg tggtaatgag aaaggttttg agaagttcag gactttttct aaagatgact   2160
ggtgtcgatg caaaggatgt gaaggcatca tcgataagcc caatccattg tgtgaggtgt   2220
gcagaggaag ccaaccaagg atgtttctac aacgcgcctc aggtcacgtg gttgggagat   2280
cgtcgggttc ttgtcaagtc gagaactgtt aaaaagttag ttgctcatgt acccgctagt   2340
cccacttaag actgtatcgt tatcggttta tataataaat cttggatgac tgtaacaata   2400
tatatatata ttccagtagt taattgggct agtgacgggt taagctatgg aacaatacga   2460
tcgattcaac gcgctttggt ctcagtcatg tctgtattgg ttggcccaat ctctaatgtc   2520
gctaacgaac cggcgtgcga caccaattat cacccccttgc ttgacgaaga agtctgggtc   2580
ttccttcgaa acctgttgaa ggtctaatcc attttccaac gccacatcac gtgctttttt   2640
aatatggtct ctataaatct cacggccaac acgcgacaag tgccaattgg catattcctc   2700
cactgcatca tctaagaacc caggaatatc aacagagtca atacagttgg gacttgagct   2760
tgactgctca gccgtaacag atctgtctgt taggctttgc gatgactgcg cggggaggac   2820
attgatattg attggtggac aaattgatcc acttgcggaa tgcttcgggt tcttttgttt   2880
ttcaagccgc agtgcctcct ctgcatagag ttgttcacgg acatcgtcag gaatatcatc   2940
atgcgtatcc aagatgcctc caccctcaac gtatttgaca agtctcctca gatggtgcgt   3000
tctaagtttg taatgcttct ttccaacagg gtccagccag caatactgcc cttcatggcg   3060
gcagggtggc ccaggacaac gcatcgtttg atacacttcc cgccaatatg gacgttgtcc   3120
agaagcctgt tcagcatcga tctgggcgtc tcgttctgta agcattctcc tagttactga   3180
tgactttcct ctcttatctg tattccgtga aagaggaggg ccactgtcct ctatatagtt   3240
tatggatata aaaagtttga gcttcttgcc aatatgaaac agatttcccc acattaagag   3300
ctgtttctct ataggtttcc aatcaatatt agtgccgtca aaacgtttgt tcagatcaga   3360
ttgtccacgt tcgtttacag atactctgac tgtagtatca tctgatctca cacgttggtt   3420
gtgacgtatt tttcgacgca taacattttc agcatcctgt gttatcttcg cccagtgtga   3480
actgggtgct acagccaagt cctgttcagt gtcctttgac acagttcggt tgttcagagt   3540
taccttccac tcaatagtat aatgaataca aggctttcct ctatgttgcc tcgtagtcct   3600
ttcttcgggc tcctggaaga aacccagatg attgggctgg gattgatgca agggagtata   3660
aggttcatca agtacatgtt caggtgatgg gcaaaatacg gatggcgtac gatctctacc   3720
gaagtcacca ggggtggggg catacgatgg agtttgtatc cacggatcag gtggctgaag   3780
ctgagaggca tcgtcatcgt agtaaggact aaacgtcatc ccctcaaggc agtagatgcc   3840
actgagaagc ctagtgttgg gatcatcata tgttagccta caccatatgg gtgtcccagc   3900
aagagtgtcc gtgagggaag aggtgcagct aacaaaacca gtaaaatgat caggttcatg   3960
gacaatgaac taagacaggt acagtattgt agccctaccc gtcttggtta acctggtaag   4020
gtcaaaaagg atcgaaccgt ggctcagtac aaacaaaagg aatgttaaca gtttgcggga   4080
gatgcaaggc acatgctttg tcatgtttga cgcgtttgca gtgtagaagc ttccagctac   4140
cgtagattac tgatacaaac tcaatacact atttctataa ccttactgtt caatacagta   4200
cgatcaaaat ttccggaata ttaatgttac ggttaccttc catatgtaga ctagcgcact   4260
tggcattagg gttcgaaata cgatcaaaga gtattggggg gggtgacagc agtaatgact   4320
ccaactgtaa atcggcttct aggcgcgctc catctaaatg ttctggctgt ggtgtacagg   4380
```

```
ggcataaaat tacgcactac ccgaatcgat agaactactc atttttatat agaagtcaga   4440

attcatggtg ttttgatcat tttaaatttt tatatggcgg gtggtgggca actcgcttgc   4500

gcgggcaact cgcttaccga ttacgttagg gctgatattt acgtaaaaat cgtcaaggga   4560

tgcaagacca aagtactaaa accccggagt caacagcatc caagcccaag tccttcacgg   4620

agaaacccca gcgtccacat cacgagcgaa ggaccacctc taggcatcgg acgcaccatc   4680

caattagaag cagcaaagcg aaacagccca agaaaaaggt cggcccgtcg gccttttctg   4740

caacgctgat cacgggcagc gatccaacca acaccctcca gagtgactag ggcggaaat    4800

ttatcgggat taatttccac tcaaccacaa atcacagtcg tccccggtat tgtcctgcag   4860

aatgcaattt aaactcttct gcgaatcgct tggattcccc gcccctggcc gtagagctta   4920

aagtatgtcc cttgtcgatg cgatgtatca caacatataa atactagcaa gggatgccat   4980

gcttggagga tagcaaccga caacatcaca tcaagctctc ccttctctga acaataaacc   5040

ccacagaagg catttt atg atg gtc gcg tgg tgg tct cta ttt ctg tac ggc   5091
                 Met Met Val Ala Trp Trp Ser Leu Phe Leu Tyr Gly
                 1               5                   10

ctt cag gtc gcg gca cct gct ttg gct gca acg cct gcg gac tgg cga     5139
Leu Gln Val Ala Ala Pro Ala Leu Ala Ala Thr Pro Ala Asp Trp Arg
        15                  20                  25

tcg caa tcc att tat ttc ctt ctc acg gat cga ttt gca agg acg gat     5187
Ser Gln Ser Ile Tyr Phe Leu Leu Thr Asp Arg Phe Ala Arg Thr Asp
    30                  35                  40

ggg tcg acg act gcg act tgt aat act gcg gat cag gtgtgttgtt          5233
Gly Ser Thr Thr Ala Thr Cys Asn Thr Ala Asp Gln
45                  50                  55

acctactagc tttcagaaag aggaatgtaa actgacttga tatag aaa tac tgt ggt   5290
                                                  Lys Tyr Cys Gly
                                                              60

gga aca tgg cag ggc atc atc gac aag gtaaattgcc cctttatcaa           5337
Gly Thr Trp Gln Gly Ile Ile Asp Lys
                65

aaaaaaaaga aggaaaagca gaagaaaaat aaaataaaaa gaactctagt cctaaccatc   5397

acatag ttg gac tat atc cag gga atg ggc ttc aca gcc atc tgg atc      5445
       Leu Asp Tyr Ile Gln Gly Met Gly Phe Thr Ala Ile Trp Ile
       70                  75                  80

acc ccc gtt aca gcc cag ctg ccc cag acc acc gca tat gga gat gcc     5493
Thr Pro Val Thr Ala Gln Leu Pro Gln Thr Thr Ala Tyr Gly Asp Ala
    85                  90                  95

tac cat ggc tac tgg cag cag gat at  gtaagtcgat ttctttaaat           5539
Tyr His Gly Tyr Trp Gln Gln Asp Ile
100                 105

atctacctgt catcttttac atcaatatga actaacttga tggttttag a tac tct     5595
                                                        Tyr Ser
                                                            110

ctg aac gaa aac tac ggc act gca gat gac ttg aag gcg ctc tct tcg     5643
Leu Asn Glu Asn Tyr Gly Thr Ala Asp Asp Leu Lys Ala Leu Ser Ser
                115                 120                 125

gcc ctt cat gag agg ggg atg tat ctt atg gtc gat gtg gtt gct aac     5691
Ala Leu His Glu Arg Gly Met Tyr Leu Met Val Asp Val Val Ala Asn
            130                 135                 140

cat atg gttcgtggtc ctttgcaact gacttcgcgg atatggttca tttcagtact      5747
His Met

gacaatgagt aatatcag ggc tat gat gga gcg ggt agc tca gtc gat tac     5798
                    Gly Tyr Asp Gly Ala Gly Ser Ser Val Asp Tyr
                    145                 150                 155
```

```
agt gtg ttt aaa ccg ttc agt tcc caa gac tac ttc cac ccg ttc tgt     5846
Ser Val Phe Lys Pro Phe Ser Ser Gln Asp Tyr Phe His Pro Phe Cys
                160                 165                 170

ttc att caa aac tat gaa gat cag act cag gtt gag gat tgc tgg cta     5894
Phe Ile Gln Asn Tyr Glu Asp Gln Thr Gln Val Glu Asp Cys Trp Leu
            175                 180                 185

gga gat aac act gtc tcc ttg cct gat ctc gat acc acc aag gat gtg     5942
Gly Asp Asn Thr Val Ser Leu Pro Asp Leu Asp Thr Thr Lys Asp Val
        190                 195                 200

gtc aag aat gaa tgg tac gac tgg gtg gga tca ttg gta tcg aac tac     5990
Val Lys Asn Glu Trp Tyr Asp Trp Val Gly Ser Leu Val Ser Asn Tyr
    205                 210                 215

tcc a gtaagatatt tctccctcat tctacaactt ggctgatcga tgatacttac       6044
Ser
220

gaaatcag tt  gac ggc ctc cgt atc gac aca gta aaa cac gtc cag aag    6093
         Ile Asp Gly Leu Arg Ile Asp Thr Val Lys His Val Gln Lys
                        225                 230

gac ttc tgg ccc ggg tac aac aaa gcc gca ggc gtg tac tgt atc ggc     6141
Asp Phe Trp Pro Gly Tyr Asn Lys Ala Ala Gly Val Tyr Cys Ile Gly
235                 240                 245                 250

gag gtg ctc gac ggt gat ccg gcc tac act tgt ccc tac cag aac gtc     6189
Glu Val Leu Asp Gly Asp Pro Ala Tyr Thr Cys Pro Tyr Gln Asn Val
                255                 260                 265

atg gac ggc gta ctg aac tat ccc at  gtatggttcc tccaaccatg           6235
Met Asp Gly Val Leu Asn Tyr Pro Ile
            270                 275

agccttcttg caagtctcat ctcctaacga aacggctaaa accag t tac tat cca     6290
                                                    Tyr Tyr Pro

ctc ctc aac gcc ttc aag tca acc tcc ggc agc atg gac gac ctc tac     6338
Leu Leu Asn Ala Phe Lys Ser Thr Ser Gly Ser Met Asp Asp Leu Tyr
    280                 285                 290

aac atg atc aac acc gtc aaa tcc gac tgt cca gac tca aca ctc ctg     6386
Asn Met Ile Asn Thr Val Lys Ser Asp Cys Pro Asp Ser Thr Leu Leu
295                 300                 305                 310

ggc aca ttc gtc gag aac cac gac aac cca cgg ttc gct tc              6427
Gly Thr Phe Val Glu Asn His Asp Asn Pro Arg Phe Ala Ser
                315                 320

gtaagtcttc ccttttattt tccgttccca atttccacac agaaccccac ctaacaagag   6487

caaag t tac acc aac gac ata gcc ctc gcc aag aac gtc gca gca ttc     6535
        Tyr Thr Asn Asp Ile Ala Leu Ala Lys Asn Val Ala Ala Phe
        325                 330                 335

atc atc ctc aac gac gga atc ccc atc atc tac gcc ggc caa gaa cag     6583
Ile Ile Leu Asn Asp Gly Ile Pro Ile Ile Tyr Ala Gly Gln Glu Gln
    340                 345                 350

cac tac gcc ggc gga aac gac ccc gcg aac cgc gaa gca acc tgg ctc     6631
His Tyr Ala Gly Gly Asn Asp Pro Ala Asn Arg Glu Ala Thr Trp Leu
355                 360                 365                 370

tcg ggc tac ccg acc gac agc gag ctg tac aag tta att gcc tcc gcg     6679
Ser Gly Tyr Pro Thr Asp Ser Glu Leu Tyr Lys Leu Ile Ala Ser Ala
                375                 380                 385

aac gca atc cgg aac tat gcc att agc aaa gat aca gga ttc gtg acc     6727
Asn Ala Ile Arg Asn Tyr Ala Ile Ser Lys Asp Thr Gly Phe Val Thr
            390                 395                 400

tac aag gtaagcacaa cctctaagca taccctaatg gcctatcttc agagtatctg      6783
Tyr Lys

acacaagaga ctaatcactg gcaatacag aac tgg ccc atc tac aaa gac gac     6836
                                Asn Trp Pro Ile Tyr Lys Asp Asp
                                405                 410
```

```
aca acg atc gcc atg cgc aag ggc aca gat ggg tcg cag atc gtg act     6884
Thr Thr Ile Ala Met Arg Lys Gly Thr Asp Gly Ser Gln Ile Val Thr
        415                 420                 425

atc ttg tcc aac aag ggt gct tcg ggt gat tcg tat acc ctc tcc ttg     6932
Ile Leu Ser Asn Lys Gly Ala Ser Gly Asp Ser Tyr Thr Leu Ser Leu
    430                 435                 440

agt ggt gcg ggt tac aca gcc ggc cag caa ttg acg gag gtc att ggc     6980
Ser Gly Ala Gly Tyr Thr Ala Gly Gln Gln Leu Thr Glu Val Ile Gly
445                 450                 455                 460

tgc acg acc gtg acg gtt ggt tcg gat gga aat gtg cct gtt cct atg     7028
Cys Thr Thr Val Thr Val Gly Ser Asp Gly Asn Val Pro Val Pro Met
                465                 470                 475

gca ggt ggg cta cct agg gta ttg tat ccg act gag aag ttg gca ggt     7076
Ala Gly Gly Leu Pro Arg Val Leu Tyr Pro Thr Glu Lys Leu Ala Gly
            480                 485                 490

agc aag atc tgt agt agc tcg tgaagggtgg agagtatatg atggtactgc        7127
Ser Lys Ile Cys Ser Ser Ser
        495

tattcaatct ggcattggac agtgagtttg agtttgatgt acataaccaa ggttgtgtct   7187

gtataaatata tacatgtaag atacatgagc ttcggtgata taatacagaa gtaccataca  7247

gtaccgcgtt atgaaaacac attaatccgg atcctttcct ataatagact agcgtgcttg   7307

gcattagggt tcgaaaaaca atcgaagagt ataaggggat gacagcagta acgactccaa   7367

ctgtagccca catcttgagt tcggcaacta ctgttggcac gtgaccctgt gccttgtggt   7427

agctccttaa ctttgtcatc attcgaagaa ttttcgtccc ttcccaggta ccatccaaaa   7487

gacaagcatc cgtcgcttca ctctgagatc agatgagagt aatattgttg actgcgtttg   7547

tgatgcgggt gatgtcctct gcgatcggcc gcaagctgtt tagtttgccc cggatcttct   7607

gtgccgacgg ttgctccccg aattttctta gctagtgtaa tcacgctatt cagaaaggct   7667

tccaagaatt aggccggtag ttcggcgcgt ttggtgtcgt caagctccag cagtgctggg   7727

gcctcggcta tgatatggtt agaatgctcg gggtgggtca cggcaggaca cccgacactg   7787

caacgtctac cacatttgag cgttattggc agacttgcgg cgagataacg accgctagct   7847

tgtatcaacc aaatccaact gaaattattg ctttgccatc ccaacagtgg atttcggagg   7907

agggaggggg gaagatatac gatgaacgga agactggaca agatacgtta cataaagcag   7967

tactacttgt ttcaaactgt gtacacacca gggctctcgc ttcagcggag agtgtcgaaa   8027

gattcagtaa aacatcgcca ggggtgatgg aaaggggtta agctagacac agaaacatag   8087

aggaatcaag aatgagagaa gacgttgtga agctttgttc gacgtatttc gcagagcata   8147

tttctgagca gcggacacga tttgtaacgt agccgtagac tcttgggact gaagcttcac   8207

gaagggcaga agaaagtgaa gtgcagcgtc tgaatcgata ttctgcctat acagccgata   8267

gttttcccct gaatctatca aatggccaag tgttcgcagc acttctgggc gccttccgct   8327

taaacgtatg ccctgaagga gcccagtgaa cgagtaaaaa tcgcgcaggc gataaaattt   8387

ctgcggtcgg tttagtatga accaaggcaa gggaaggaga taattaccag cgccaattga   8447

tccaacttta gatacaaagc cggttcagta gctgagcatt cctctgctgc tcggcaaata   8507

ctgttccacc acctattcag agctgtcaaa gggtcgccgc tacccttctt caccatttcg   8567

acggtgagct cctgaaagag ggaaagagct gctgccgtaa gctctgctgc cagtgcctcc   8627

agttcctcca gctccgtgtg gtagagtttg tcaagaaatg cagtttgagt attgaagtct   8687

tgcgaacaga caacttctgg acttctgtag aaatttcgga agcgtacggc cagagcttca   8747
```

```
agttggcaat ggataagggc gatcgggttg tcttttgaga ggactgcttt tatcggatcc   8807
gtgataaatc gagcatcaat gttgtattcc gtgtatcgcc gattacaaac gcattcacac   8867
gcatgataca ccgctccgga cagaaagggg tctgcggtaa atttctctaa agtctttgag   8927
gcgtcaggat atgcagtgga tggataggaa gcggaagggt gatacatttg tcaagcctag   8987
atacttctca aactcgttca agtgccttct gaggtagtaa tacagaatca cgcttagccc   9047
atcatactta gactcaagcg ccttgacaat aggtgatgag cgatcccttg cttcttgcac   9107
ccagtcctcg aattgaacaa gaggaaagta cctttcactc tcgtcaatca gttgctgcgc   9167
aattgtgttg gcatcggaat cccatgacga acgcggttgc cacttccaac gaatggagtc   9227
cagtgcttct ggtatcttgg gtacgtttgt accggatgac tcaaagcgga atccaatcaa   9287
ctgcgaatga aattgtggcg gctggctaga tggtttttcg cccgtaagca aaacaggttc   9347
gagttctaca tcataggcag ttgtggcaac gctcaacgaa gatcgctcgc aaggtaatag   9407
aaagatcatg gtgaaaagaa atctagcaga agattcgaac tgaggtagta gacgagcatt   9467
ctagcaggaa ttgtggtacg tttatatgga atacttgatg ccggcgccgc aataagtagc   9527
aaagggattg cagaaagttc tataggggac aacacagtaa aaaggcggag attgcagaaa   9587
aatacaggga gacagcagat ttgaagatcc aggccttgat ctggactggg aggacaccga   9647
cctcggcagt ggctgcatct tactggtgga tatggttggg tgttcaaaca ggtcacaccc   9707
tctatcctat caggcgagag gctacccata gtgcactgtc cttcctgctt tacggcacat   9767
ccagcacccg attgaaatag gggccgtcga ggtgtcctct cctccgacct gcgtcaagga   9827
aacctactcc tttttctgcc ctcgtcaagc tgttcacttt tccttgaaaa tggtcaaaca   9887
aactcgactt cctcttctac ttgcagaagc attgccttgt cgcctagacc gtattcaggc   9947
caaatttacg gagcaatgca aggatctgaa accggacgcc tttctccagc ttacagttct  10007
tctcagccag attgaacaca tagttggaat tcattacaca ccaggagttt caacatcagc  10067
tagcacaaaa cctacttgcg tcgtctgcgg ccgatcatac tcaagaatat cttccctgaa  10127
ctctcatatc tcgctagccc atcagtatct gcggcggatc attgaagcca gatcttgcaa  10187
ttcttgcgac aatgaattcg actccccaag gcaacttgtc taccatgaga gatcgattca  10247
caaggcagcg tatctgtcca gagcagactt tatctggcca ggatttgaac aactgaactc  10307
aagagaaggt gggagtgacc gtgcattgac aagactggcg aatagatgct aatttatcgt  10367
tccagcgcag aagtctttcc tgagaaccct ggcaggcgat gaggaagagc caaaagttta  10427
tgaatttgtg ggggaagcag ctgacacaaa acggacaact ttagagccgg gggaagcggt  10487
agaagggaga cgttttgatg agcaatattc tatcagcggt gacggacatt tgcaatacga  10547
tttagggtat tatggggata tagactcctg gttactaccg tattcaccgg cttgtaacgg  10607
atccgtctga tgtctccatg tttcttgagc ggaagtacta tacatcccta gtcaatcaaa  10667
cggtcgttgt tgcaaatata ctatctcggc caaaattccg gcctgtcctt gaatgtaagg  10727
tattctccag tccttcatcc atcccgcaac acagatgctg ttttccgcca tcgttagaga  10787
cttcgtgagt agaatgtcag aatgacttac atatcggttc cgcttagcaa aacgcttttc  10847
cgtaagtgtt cgtttggagt gaaatattcg aatatccaag tagaattgct ttgaccaccg  10907
aggtgaaaca cgttgatgag tttaagatcg ggcaaaccgc tggatggcac gaagaggctg  10967
ttgcttttat tcatttcgcg ctttcgaaaa cggcccggaa gatatgtgcc ttcgtccacc  11027
cggagaaact gcttaacggc ctgaacaatt agcccagaag ctctataaac tcttggtatt  11087
ctatacagac atcattatgc tcgatttgcc tctgctctat tgtggcatcg aggaaagttt  11147
```

```
gattttgcat cacaatccag ccgtccacca tgaactttct tcgcgtatcg ataacttgtc  11207

ccttgtcgcg gacagaaaca gaatcaactg agccatcgcg aaaaaggaag ctgacgactg  11267

atgaactcat attgctcgct ggttgctgta tcgttgaccc cgccagtcgt gtgcggggca  11327

gattcatgaa tgtcggaagg gcggacagca cgtgagagtg ggcgaagagg gacactggag  11387

cgactttctc gagtcaggaa aggaacatcc agttcttcgt agtggagcac tcaccacttc  11447

cagcttggca gctaatccat atctcattat tatccgccat aatgacaata aaattttgtc  11507

tttgattggt ttattcactc taggacgcca aagatgaaca atatatgagt ggaaaggatg  11567

ggaaatggaa ggtagtcgtc gggtggaagc aatgtgaaga ctttgggaag ttcaacggtc  11627

aggtttctc cctcaatctc aattctgcgg ataaagcgag agaagtaatt gcagtatgtt  11687

ttttctaagc gactacagat aatactttga gcaaaggcct actataaatc gttacgtcgc  11747

aaaaatactg aatacgtttg ccgattacga agaggacagg gcaggattag gcaacagcgc  11807

agaaagtaca agagagattg cagtattaac caggcagaaa acggataata ttctgagcaa  11867

aggcttacca taaatcggca cgtcgcagaa atactggata cgtttgcaga ttacgaagag  11927

gataaggcag gtgcagaagg ttcaagagag attgcagtta ttaatcaagt ggttatccta  11987

taatcaagtt atctcattgg atgagccgta cgttaccatt aactagtgtt catgctaaat  12047

acatagttgg ctcacggcca agtaggtggt tcatcgcatg ccttctttgg cagcaaaatt  12107

agtctactcc cactcccgtc cctacttagt atcatagcac caccccttcaa ggagaggaag  12167

tgtacattat cccgtaccac ttactcaaat tgtagggga cgctaccgcg acaccggcca  12227

ggctgcctcc acaccagcct ccgcttacgc cacatccttc cgcctacctt aataggtaag  12287

gctcgctccc tataaggtaa ggcttgcttt tctgagccag cacaataata ccgcctaccc  12347

gttttgaggc agtagtttat tatctcaggc agtacaactg gtgtctcaag caagaataac  12407

tctatattag gaaagcagta atattacact ggctataaga agtgggcctt atcttatagg  12467

gagtgaacct tacctaccaa ggtaggcaga agcatgtggc atgagcggag gctggtgtcg  12527

cggtagcgcc tcccaagtta taaactcatc tgtgtgatgc aatgcggaac aactctacta  12587

gtacatgttt gccttagaaa caaagtaaca actgcaacca gcccgcaacc ttccgccata  12647

atatcagtct tctaatcttc cgacatgtta cattaatgcc catgcgatac gta         12700
```

```
<210> SEQ ID NO 70
<211> LENGTH: 499
<212> TYPE: PRT
<213> ORGANISM: artificial sequence
<220> FEATURE:
<223> OTHER INFORMATION: Synthetic Construct

<400> SEQUENCE: 70

Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
            20                  25                  30

Tyr Phe Leu Leu Thr Asp Arg Phe Ala Arg Thr Asp Gly Ser Thr Thr
        35                  40                  45

Ala Thr Cys Asn Thr Ala Asp Gln Lys Tyr Cys Gly Gly Thr Trp Gln
    50                  55                  60

Gly Ile Ile Asp Lys Leu Asp Tyr Ile Gln Gly Met Gly Phe Thr Ala
65                  70                  75                  80

Ile Trp Ile Thr Pro Val Thr Ala Gln Leu Pro Gln Thr Thr Ala Tyr
```

```
                85                  90                  95

Gly Asp Ala Tyr His Gly Tyr Trp Gln Gln Asp Ile Tyr Ser Leu Asn
            100                 105                 110

Glu Asn Tyr Gly Thr Ala Asp Asp Leu Lys Ala Leu Ser Ser Ala Leu
        115                 120                 125

His Glu Arg Gly Met Tyr Leu Met Val Asp Val Val Ala Asn His Met
    130                 135                 140

Gly Tyr Asp Gly Ala Gly Ser Ser Val Asp Tyr Ser Val Phe Lys Pro
145                 150                 155                 160

Phe Ser Ser Gln Asp Tyr Phe His Pro Phe Cys Phe Ile Gln Asn Tyr
                165                 170                 175

Glu Asp Gln Thr Gln Val Glu Asp Cys Trp Leu Gly Asp Asn Thr Val
            180                 185                 190

Ser Leu Pro Asp Leu Asp Thr Thr Lys Asp Val Val Lys Asn Glu Trp
        195                 200                 205

Tyr Asp Trp Val Gly Ser Leu Val Ser Asn Tyr Ser Ile Asp Gly Leu
    210                 215                 220

Arg Ile Asp Thr Val Lys His Val Gln Lys Asp Phe Trp Pro Gly Tyr
225                 230                 235                 240

Asn Lys Ala Ala Gly Val Tyr Cys Ile Gly Glu Val Leu Asp Gly Asp
                245                 250                 255

Pro Ala Tyr Thr Cys Pro Tyr Gln Asn Val Met Asp Gly Val Leu Asn
            260                 265                 270

Tyr Pro Ile Tyr Tyr Pro Leu Leu Asn Ala Phe Lys Ser Thr Ser Gly
        275                 280                 285

Ser Met Asp Asp Leu Tyr Asn Met Ile Asn Thr Val Lys Ser Asp Cys
    290                 295                 300

Pro Asp Ser Thr Leu Leu Gly Thr Phe Val Glu Asn His Asp Asn Pro
305                 310                 315                 320

Arg Phe Ala Ser Tyr Thr Asn Asp Ile Ala Leu Ala Lys Asn Val Ala
                325                 330                 335

Ala Phe Ile Ile Leu Asn Asp Gly Ile Pro Ile Ile Tyr Ala Gly Gln
            340                 345                 350

Glu Gln His Tyr Ala Gly Gly Asn Asp Pro Ala Asn Arg Glu Ala Thr
        355                 360                 365

Trp Leu Ser Gly Tyr Pro Thr Asp Ser Glu Leu Tyr Lys Leu Ile Ala
    370                 375                 380

Ser Ala Asn Ala Ile Arg Asn Tyr Ala Ile Ser Lys Asp Thr Gly Phe
385                 390                 395                 400

Val Thr Tyr Lys Asn Trp Pro Ile Tyr Lys Asp Asp Thr Thr Ile Ala
                405                 410                 415

Met Arg Lys Gly Thr Asp Gly Ser Gln Ile Val Thr Ile Leu Ser Asn
            420                 425                 430

Lys Gly Ala Ser Gly Asp Ser Tyr Thr Leu Ser Leu Ser Gly Ala Gly
        435                 440                 445

Tyr Thr Ala Gly Gln Gln Leu Thr Glu Val Ile Gly Cys Thr Thr Val
    450                 455                 460

Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Ser Ser Ser
```

```
<210> SEQ ID NO 71
<211> LENGTH: 1515
<212> TYPE: DNA
<213> ORGANISM: artificial sequence
<220> FEATURE:
<223> OTHER INFORMATION: The nucleotide sequence of A.niger fcy1 in
      pHUda1078 & 1067
<220> FEATURE:
<221> NAME/KEY: CDS
<222> LOCATION: (620)..(778)
<220> FEATURE:
<221> NAME/KEY: CDS
<222> LOCATION: (848)..(1113)
<220> FEATURE:
<221> NAME/KEY: CDS
<222> LOCATION: (1131)..(1209)

<400> SEQUENCE: 71

ttctgtggtt cttgccatga tcgtggatca gaggttcaga gaacaatctc tgcgataaga     60

agatatacta gtaaatagtg cgtggcatgg ggtctgcgcg agatgaaccc cgagtttatc    120

agccactgcc agtttgatct tgtaaattgt gaaactgtga attaatggtt acaagtgata    180

aggacgttac catcgggctc tatgcatcta gatcggatgt ctcatataca atcagctcaa    240

tttgtattca gttatagttg tatacaaggc atgaaatatt aagcatcttt cttacgctta    300

tgcatgtcga tccccaagca caccaaagaa gcactttatg cataccataa cccaagaaag    360

tctatcacat gcacacatta tccatgaaaa tactattcaa tacgaatgta acaacgtcct    420

ctatcagtct caatgacagc agctatcttg ttatcatgga gctccgcacg tccagcccga    480

tgcgggtcag tccggcagtt aaccacacag agtttgctcc gtcttgatgc taccccatct    540

ttctatctct ctcccaatta cccctccaat cgctctatat ttcatatctc aatacagcat    600

acaacaagca cataccatc atg gag acc gat ccc gga ttc atc gct gct gtg     652
                     Met Glu Thr Asp Pro Gly Phe Ile Ala Ala Val
                     1               5                   10

gaa gaa gcc aag caa ggc gct gct gag ggt ggt gtg ccc att gga gct      700
Glu Glu Ala Lys Gln Gly Ala Ala Glu Gly Gly Val Pro Ile Gly Ala
            15                  20                  25

tgt ttg gtc tcc aag gat ggc aag att cta ggc cgc ggc cac aat atg      748
Cys Leu Val Ser Lys Asp Gly Lys Ile Leu Gly Arg Gly His Asn Met
        30                  35                  40

cgc gtc cag aag ggt agt ccc gtg ttg cat gttcgttgat cccatccctt        798
Arg Val Gln Lys Gly Ser Pro Val Leu His
    45                  50

gccttctgag ggtcgtctgg ggttctaatt ctaatctcta ccgtcatag gct gag atg    856
                                                      Ala Glu Met
                                                          55

tcc gcg ctc gag aac tcc ggt cgt ctg ccc gct tcg gcc tac gaa ggc      904
Ser Ala Leu Glu Asn Ser Gly Arg Leu Pro Ala Ser Ala Tyr Glu Gly
            60                  65                  70

gct act atg tac acg acc ctg tcg cca tgc gac atg tgc acc ggt gcc      952
Ala Thr Met Tyr Thr Thr Leu Ser Pro Cys Asp Met Cys Thr Gly Ala
        75                  80                  85

tgc atc ctc tac aag gtt aag cgc gtt gtt gtg ggc gag aac aag agc     1000
Cys Ile Leu Tyr Lys Val Lys Arg Val Val Val Gly Glu Asn Lys Ser
    90                  95                  100

ttc atg ggt ggc gag gac tat ctt aag agc cgt ggg aag gag gtt gtg     1048
Phe Met Gly Gly Glu Asp Tyr Leu Lys Ser Arg Gly Lys Glu Val Val
105                 110                 115                 120

gtt ttg gat aat gca gag tgt aag cag ctg atg gag aag ttc atg aag     1096
Val Leu Asp Asn Ala Glu Cys Lys Gln Leu Met Glu Lys Phe Met Lys
                125                 130                 135
```

```
gag aag ccg gag ctt tg  gtaggtttcc catgcat c tca ctg gac tgg tct    1146
Glu Lys Pro Glu Leu Cys                      Ser Leu Asp Trp Ser
            140                                          145

agt ctt ttg ttg gaa tgt acg ctg act gta cga tgt ctt tgc agg aat    1194
Ser Leu Leu Leu Glu Cys Thr Leu Thr Val Arg Cys Leu Cys Arg Asn
        150                 155                 160

gag gac att tcc gtc tgagcttttg aattcgtgaa ggtgtcaact atattgctgg    1249
Glu Asp Ile Ser Val
    165

ctaggctctc atgtacataa taaagaattg aaagctagtt ctggtcgcat tgagcaccca   1309

atttagaccg tcagacggtg gatctcttcg aagaagaact tgagatcatc cgggttgacg   1369

aaaggagtca cacctgtgat acattagcat ttattgaata acccagctgt ggcagtgctc   1429

accgtgaccc aagttggcaa tccagccttg cttgcccttc tcgaatcccc gaaccatagt   1489

ctccacagcc tccgtgatag cctcgc                                        1515


<210> SEQ ID NO 72
<211> LENGTH: 168
<212> TYPE: PRT
<213> ORGANISM: artificial sequence
<220> FEATURE:
<223> OTHER INFORMATION: Synthetic Construct

<400> SEQUENCE: 72

Met Glu Thr Asp Pro Gly Phe Ile Ala Ala Val Glu Glu Ala Lys Gln
1               5                   10                  15

Gly Ala Ala Glu Gly Gly Val Pro Ile Gly Ala Cys Leu Val Ser Lys
            20                  25                  30

Asp Gly Lys Ile Leu Gly Arg Gly His Asn Met Arg Val Gln Lys Gly
        35                  40                  45

Ser Pro Val Leu His Ala Glu Met Ser Ala Leu Glu Asn Ser Gly Arg
    50                  55                  60

Leu Pro Ala Ser Ala Tyr Glu Gly Ala Thr Met Tyr Thr Thr Leu Ser
65                  70                  75                  80

Pro Cys Asp Met Cys Thr Gly Ala Cys Ile Leu Tyr Lys Val Lys Arg
                85                  90                  95

Val Val Val Gly Glu Asn Lys Ser Phe Met Gly Gly Glu Asp Tyr Leu
            100                 105                 110

Lys Ser Arg Gly Lys Glu Val Val Val Leu Asp Asn Ala Glu Cys Lys
        115                 120                 125

Gln Leu Met Glu Lys Phe Met Lys Glu Lys Pro Glu Leu Cys Ser Leu
    130                 135                 140

Asp Trp Ser Ser Leu Leu Leu Glu Cys Thr Leu Thr Val Arg Cys Leu
145                 150                 155                 160

Cys Arg Asn Glu Asp Ile Ser Val
                165


<210> SEQ ID NO 73
<211> LENGTH: 24
<212> TYPE: DNA
<213> ORGANISM: artificial sequence
<220> FEATURE:
<223> OTHER INFORMATION: Forward primer

<400> SEQUENCE: 73

tcgagtgcgg ccgacgcgta cgtc                                            24
```

<210> SEQ ID NO 74
<211> LENGTH: 20
<212> TYPE: DNA
<213> ORGANISM: artificial sequence
<220> FEATURE:
<223> OTHER INFORMATION: Reverse primer

<400> SEQUENCE: 74
cagagagtgt tggtcacgta 20

<210> SEQ ID NO 75
<211> LENGTH: 52
<212> TYPE: DNA
<213> ORGANISM: artificial sequence
<220> FEATURE:
<223> OTHER INFORMATION: Primer bac-F

<400> SEQUENCE: 75
tctagagaat aggaactcgg aataggaact tcaagatgaa ttcgcggccg cg 52

<210> SEQ ID NO 76
<211> LENGTH: 77
<212> TYPE: DNA
<213> ORGANISM: artificial sequence
<220> FEATURE:
<223> OTHER INFORMATION: Primer bac-R

<400> SEQUENCE: 76
tctagattga agttcctatt ccgagttcct attcttcaaa tagtatagga acttcagcat 60
gcaagcttgg cctccgc 77

<210> SEQ ID NO 77
<211> LENGTH: 30
<212> TYPE: DNA
<213> ORGANISM: artificial sequence
<220> FEATURE:
<223> OTHER INFORMATION: Primer FLP-F

<400> SEQUENCE: 77
ttaattaatg gaagtgcgtt gatcattatt 30

<210> SEQ ID NO 78
<211> LENGTH: 30
<212> TYPE: DNA
<213> ORGANISM: artificial sequence
<220> FEATURE:
<223> OTHER INFORMATION: Primer FLP-R

<400> SEQUENCE: 78
ttaattaaac tagtggagcg aaccaagtga 30

<210> SEQ ID NO 79
<211> LENGTH: 24
<212> TYPE: DNA
<213> ORGANISM: artificial sequence
<220> FEATURE:
<223> OTHER INFORMATION: Forward primer

<400> SEQUENCE: 79
tcgagtgcgg ccgacgcgta cgtc 24

<210> SEQ ID NO 80
<211> LENGTH: 20
<212> TYPE: DNA
<213> ORGANISM: artificial sequence
<220> FEATURE:

<223> OTHER INFORMATION: Reverse primer

<400> SEQUENCE: 80
cagagagtgt tggtcacgta 20

<210> SEQ ID NO 81
<211> LENGTH: 27
<212> TYPE: DNA
<213> ORGANISM: artificial sequence
<220> FEATURE:
<223> OTHER INFORMATION: Primer 126-F

<400> SEQUENCE: 81
ggatccacca tgcggctctc cacatcc 27

<210> SEQ ID NO 82
<211> LENGTH: 30
<212> TYPE: DNA
<213> ORGANISM: artificial sequence
<220> FEATURE:
<223> OTHER INFORMATION: Primer 126-R

<400> SEQUENCE: 82
cacgtgtgat tacggacaca atccgttatt 30

<210> SEQ ID NO 83
<211> LENGTH: 1815
<212> TYPE: DNA
<213> ORGANISM: artificial sequence
<220> FEATURE:
<223> OTHER INFORMATION: The nucleotide sequence of the JA126 amylase gene
<220> FEATURE:
<221> NAME/KEY: misc_feature
<222> LOCATION: (1)..(1798)
<223> OTHER INFORMATION: Amylase JA126 coding sequence

<400> SEQUENCE: 83
atgcggctct ccacatcctc cctcttcttg tccgtctcct tgctcggaaa gttggccttg 60
ggcgcgacgt cggacgattg gaagggtaag gccatttacc agttgctcac ggaccgattc 120
ggtcgcgcag atgactcgac ctcgaactgt tcgaacctct cgaactactg tggtggcact 180
tacgagggca tcactaaaca tctcgactac atctccggta tgggcttcga tgcaatttgg 240
atttcgccga tccctaagaa ctcggacggt ggataccacg gttactgggc cacagacttc 300
tatcagctca actcgaactt cggcgacgag tcgcagttga aagcgctcat ccaggcggcc 360
catgagcggg acatgtatgt catgctcgat gtggtggcaa accacgccgg cccgacttcg 420
aacggatact cgggttacac tttcggtgat gcctccctct accatccgaa atgtaccatc 480
gattacaacg atcagacatc gatcgaacag tgttgggtcg ccgatgagtt gcccgatatc 540
gacaccgaaa actcggacaa cgtcgcaatc ctcaacgaca tcgtctccgg ctgggtgggt 600
aactactcgt tcgatggtat tcggatcgac accgtcaagc acatccgcaa ggacttctgg 660
acaggttacg ccgaagccgc gggtgtgttc gcgaccggag aggtgttcaa cggagacccc 720
gcatacgtgg gaccctatca gaaatacttg ccttccctca tcaactatcc catgtactac 780
gccctcaacg acgtcttcgt ctcgaagtcg aagggtttct ccaggatttc cgagatgttg 840
ggctcgaacc gtaacgcctt cgaagatact tccgtcctca ccacgttcgt ggacaaccac 900
gacaaccctc gattcttgaa ctcccagtcc gacaaagccc tcttcaagaa cgcgctcaca 960
tacgtgttgc tcggcgaagg aatccccatc gtctactatg gatcggaaca gggcttctcg 1020

```
ggcggtgcag accctgccaa ccgagaagtc ctctggacta cgaactacga cacgtcgtcg   1080

gatctctacc agttcatcaa gaccgtcaac tcggtgcgta tgaagtcgaa caaggcggtg   1140

tacatggaca tttacgtggg cgataacgcg tatgcattca agcatggaga cgccttggtg   1200

gtcctcaaca actacggctc gggttcgacc aaccaggtgt ccttctcggt gtcgggaaag   1260

ttcgactccg gcgcctccct catggatatc gtgtccaaca tcacaactac tgtctcctcg   1320

gatggcacag tcactttcaa cttgaaggat ggcctcccgg cgattttcac ctccgcaact   1380

ggcggcacca ctacgacggc tacccccact ggctccggca gcgtgacctc gaccagcaag   1440

accaccgcga ctgccagcaa gaccagcacc agtacgtcat caacctcctg taccactccc   1500

accgccgtgg ctgtgacttt cgatctgaca gctaccacca cctacggcga gaacatctac   1560

ctggtcggat cgatctctca gctgggtgac tgggaaacca gcgacggcat agctctgagt   1620

gctgacaagt acacttccag cgacccgctc tggtatgtca ctgtgactct gccggctggt   1680

gagtcgtttg agtacaagtt tatccgcatt gagagcgatg actccgtgga gtgggagagt   1740

gatcccaacc gagaatacac cgttcctcag gcgtgcggaa cgtcgaccgc gacggtgact   1800

gacacctggc ggtag                                                    1815
```

```
<210> SEQ ID NO 84
<211> LENGTH: 604
<212> TYPE: PRT
<213> ORGANISM: Artificial sequence
<220> FEATURE:
<223> OTHER INFORMATION: The amino acid sequence of the JA126 amylase
<220> FEATURE:
<221> NAME/KEY: SIGNAL
<222> LOCATION: (1)..(21)
<223> OTHER INFORMATION: Secretion signal from A.niger acid stable
      amylase
<220> FEATURE:
<221> NAME/KEY: DOMAIN
<222> LOCATION: (22)..(459)
<223> OTHER INFORMATION: Catalytic amylase domain from Rhizomucor
      pusillus
<220> FEATURE:
<221> NAME/KEY: DOMAIN
<222> LOCATION: (460)..(604)
<223> OTHER INFORMATION: Linker and starch-binding domain from A. niger
      glucoamylase

<400> SEQUENCE: 84

Met Arg Leu Ser Thr Ser Ser Leu Phe Leu Ser Val Ser Leu Leu Gly
1               5                   10                  15

Lys Leu Ala Leu Gly Ala Thr Ser Asp Asp Trp Lys Ser Lys Ala Ile
            20                  25                  30

Tyr Gln Leu Leu Thr Asp Arg Phe Gly Arg Ala Asp Asp Ser Thr Ser
        35                  40                  45

Asn Cys Ser Asn Leu Ser Asn Tyr Cys Gly Gly Thr Tyr Glu Gly Ile
    50                  55                  60

Thr Lys His Leu Asp Tyr Ile Ser Gly Met Gly Phe Asp Ala Ile Trp
65                  70                  75                  80

Ile Ser Pro Ile Pro Lys Asn Ser Asp Gly Gly Tyr His Gly Tyr Trp
                85                  90                  95

Ala Thr Asp Phe Tyr Gln Leu Asn Ser Asn Phe Gly Asp Glu Ser Gln
            100                 105                 110

Leu Lys Ala Leu Ile Gln Ala Ala His Glu Arg Asp Met Tyr Val Met
        115                 120                 125

Leu Asp Val Val Ala Asn His Ala Gly Pro Thr Ser Asn Gly Tyr Ser
    130                 135                 140
```

```
Gly Tyr Thr Phe Gly Asp Ala Ser Leu Tyr His Pro Lys Cys Thr Ile
145                 150                 155                 160

Asp Tyr Asn Asp Gln Thr Ser Ile Glu Gln Cys Trp Val Ala Asp Glu
                165                 170                 175

Leu Pro Asp Ile Asp Thr Glu Asn Ser Asp Asn Val Ala Ile Leu Asn
            180                 185                 190

Asp Ile Val Ser Gly Trp Val Gly Asn Tyr Ser Phe Asp Gly Ile Arg
        195                 200                 205

Ile Asp Thr Val Lys His Ile Arg Lys Asp Phe Trp Thr Gly Tyr Ala
    210                 215                 220

Glu Ala Ala Gly Val Phe Ala Thr Gly Glu Val Phe Asn Gly Asp Pro
225                 230                 235                 240

Ala Tyr Val Gly Pro Tyr Gln Lys Tyr Leu Pro Ser Leu Ile Asn Tyr
                245                 250                 255

Pro Met Tyr Tyr Ala Leu Asn Asp Val Phe Val Ser Lys Ser Lys Gly
            260                 265                 270

Phe Ser Arg Ile Ser Glu Met Leu Gly Ser Asn Arg Asn Ala Phe Glu
        275                 280                 285

Asp Thr Ser Val Leu Thr Thr Phe Val Asp Asn His Asp Asn Pro Arg
    290                 295                 300

Phe Leu Asn Ser Gln Ser Asp Lys Ala Leu Phe Lys Asn Ala Leu Thr
305                 310                 315                 320

Tyr Val Leu Leu Gly Glu Gly Ile Pro Ile Val Tyr Tyr Gly Ser Glu
                325                 330                 335

Gln Gly Phe Ser Gly Gly Ala Asp Pro Ala Asn Arg Glu Val Leu Trp
            340                 345                 350

Thr Thr Asn Tyr Asp Thr Ser Ser Asp Leu Tyr Gln Phe Ile Lys Thr
        355                 360                 365

Val Asn Ser Val Arg Met Lys Ser Asn Lys Ala Val Tyr Met Asp Ile
    370                 375                 380

Tyr Val Gly Asp Asn Ala Tyr Ala Phe Lys His Gly Asp Ala Leu Val
385                 390                 395                 400

Val Leu Asn Asn Tyr Gly Ser Gly Ser Thr Asn Gln Val Ser Phe Ser
                405                 410                 415

Val Ser Gly Lys Phe Asp Ser Gly Ala Ser Leu Met Asp Ile Val Ser
            420                 425                 430

Asn Ile Thr Thr Thr Val Ser Ser Asp Gly Thr Val Thr Phe Asn Leu
        435                 440                 445

Lys Asp Gly Leu Pro Ala Ile Phe Thr Ser Ala Thr Gly Gly Thr Thr
    450                 455                 460

Thr Thr Ala Thr Pro Thr Gly Ser Gly Ser Val Thr Ser Thr Ser Lys
465                 470                 475                 480

Thr Thr Ala Thr Ala Ser Lys Thr Ser Thr Ser Thr Ser Ser Thr Ser
                485                 490                 495

Cys Thr Thr Pro Thr Ala Val Ala Val Thr Phe Asp Leu Thr Ala Thr
            500                 505                 510

Thr Thr Tyr Gly Glu Asn Ile Tyr Leu Val Gly Ser Ile Ser Gln Leu
        515                 520                 525

Gly Asp Trp Glu Thr Ser Asp Gly Ile Ala Leu Ser Ala Asp Lys Tyr
    530                 535                 540

Thr Ser Ser Asp Pro Leu Trp Tyr Val Thr Val Thr Leu Pro Ala Gly
545                 550                 555                 560
```

```
Glu Ser Phe Glu Tyr Lys Phe Ile Arg Ile Glu Ser Asp Asp Ser Val
                565                 570                 575

Glu Trp Glu Ser Asp Pro Asn Arg Glu Tyr Thr Val Pro Gln Ala Cys
            580                 585                 590

Gly Thr Ser Thr Ala Thr Val Thr Asp Thr Trp Arg
        595                 600


<210> SEQ ID NO 85
<211> LENGTH: 29
<212> TYPE: DNA
<213> ORGANISM: artificial sequence
<220> FEATURE:
<223> OTHER INFORMATION: Forward primer

<400> SEQUENCE: 85

tcgaacttcg gcgacgagtc gcagttgaa                                      29


<210> SEQ ID NO 86
<211> LENGTH: 30
<212> TYPE: DNA
<213> ORGANISM: artificial sequence
<220> FEATURE:
<223> OTHER INFORMATION: Reverse primer

<400> SEQUENCE: 86

cccaacatct cggaaatcct ggagaaaccc                                     30


<210> SEQ ID NO 87
<211> LENGTH: 27
<212> TYPE: DNA
<213> ORGANISM: artificial sequence
<220> FEATURE:
<223> OTHER INFORMATION: Primer 172449

<400> SEQUENCE: 87

gacgaattcc gatgaatgtg tgtcctg                                        27


<210> SEQ ID NO 88
<211> LENGTH: 60
<212> TYPE: DNA
<213> ORGANISM: artificial sequence
<220> FEATURE:
<223> OTHER INFORMATION: Primer 172450

<400> SEQUENCE: 88

gacgaattct ctagaagatc tctcgaggag ctcaagcttc tgtacagtga ccggtgactc     60


<210> SEQ ID NO 89
<211> LENGTH: 27
<212> TYPE: DNA
<213> ORGANISM: artificial sequence
<220> FEATURE:
<223> OTHER INFORMATION: Primer X4407C0

<400> SEQUENCE: 89

cagggatccg tctaggctgc aataggc                                        27


<210> SEQ ID NO 90
<211> LENGTH: 18
<212> TYPE: DNA
<213> ORGANISM: artificial sequence
<220> FEATURE:
<223> OTHER INFORMATION: Primer X4407C07

<400> SEQUENCE: 90
```

ggagaattcg gtcacatc 18

<210> SEQ ID NO 91
<211> LENGTH: 26
<212> TYPE: DNA
<213> ORGANISM: artificial sequence
<220> FEATURE:
<223> OTHER INFORMATION: Primer X7164D09

<400> SEQUENCE: 91
gacactagtc gtcggcagca ccggtg 26

<210> SEQ ID NO 92
<211> LENGTH: 28
<212> TYPE: DNA
<213> ORGANISM: artificial sequence
<220> FEATURE:
<223> OTHER INFORMATION: Primer X7164D10

<400> SEQUENCE: 92
cagaagcttc agagtgaaat agacgcgg 28

<210> SEQ ID NO 93
<211> LENGTH: 79
<212> TYPE: DNA
<213> ORGANISM: artificial sequence
<220> FEATURE:
<223> OTHER INFORMATION: Primer T5483H12

<400> SEQUENCE: 93
gcacatatga tttaaatccc taatgttgac cctaatgttg accctaatgt tgagcggccg 60
cgtttaaacg aattcgccc 79

<210> SEQ ID NO 94
<211> LENGTH: 71
<212> TYPE: DNA
<213> ORGANISM: artificial sequence
<220> FEATURE:
<223> OTHER INFORMATION: Primer T5483G10

<400> SEQUENCE: 94
cgtaagctta tttaaatccc taatgttgac cctaatgttg accctaatgt tgagaccggt 60
gactctttct g 71

<210> SEQ ID NO 95
<211> LENGTH: 27
<212> TYPE: DNA
<213> ORGANISM: artificial sequence
<220> FEATURE:
<223> OTHER INFORMATION: Primer D5831F08

<400> SEQUENCE: 95
gacgaattcg gcgtgggaaa ttcctgg 27

<210> SEQ ID NO 96
<211> LENGTH: 18
<212> TYPE: DNA
<213> ORGANISM: artificial sequence
<220> FEATURE:
<223> OTHER INFORMATION: Primer D5831F09

<400> SEQUENCE: 96
ccctacacct ggggtacc 18

<210> SEQ ID NO 97
<211> LENGTH: 29
<212> TYPE: DNA
<213> ORGANISM: artificial sequence
<220> FEATURE:
<223> OTHER INFORMATION: Primer D5775F04

<400> SEQUENCE: 97
gacgcggccg cgctttgcta aaactttgg 29

<210> SEQ ID NO 98
<211> LENGTH: 30
<212> TYPE: DNA
<213> ORGANISM: artificial sequence
<220> FEATURE:
<223> OTHER INFORMATION: Primer D5775D07

<400> SEQUENCE: 98
gacaagctta tgctcgatgg aaacgtgcac 30

<210> SEQ ID NO 99
<211> LENGTH: 30
<212> TYPE: DNA
<213> ORGANISM: artificial sequence
<220> FEATURE:
<223> OTHER INFORMATION: Primer D5775D08

<400> SEQUENCE: 99
gacaagctta cagtagttgg actactttac 30

<210> SEQ ID NO 100
<211> LENGTH: 28
<212> TYPE: DNA
<213> ORGANISM: artificial sequence
<220> FEATURE:
<223> OTHER INFORMATION: Primer D5775F05

<400> SEQUENCE: 100
gacgcggccg cgacgagcaa ctgacggc 28

<210> SEQ ID NO 101
<211> LENGTH: 60
<212> TYPE: DNA
<213> ORGANISM: artificial sequence
<220> FEATURE:
<223> OTHER INFORMATION: Primer F3-1

<400> SEQUENCE: 101
gatccttgaa gttcctattc cgagttccta ttcttcaaat agtataggaa cttcactgca 60

<210> SEQ ID NO 102
<211> LENGTH: 50
<212> TYPE: DNA
<213> ORGANISM: artificial sequence
<220> FEATURE:
<223> OTHER INFORMATION: Primer F3-2

<400> SEQUENCE: 102
tgaagttcct atactatttg aagaatagga actcggaata ggaacttcaa 50

<210> SEQ ID NO 103
<211> LENGTH: 55
<212> TYPE: DNA
<213> ORGANISM: artificial sequence
<220> FEATURE:
<223> OTHER INFORMATION: Primer F-1

<400> SEQUENCE: 103
gtaccttgaa gttcctattc cgagttccta ttctctagaa agtataggaa cttca 55

<210> SEQ ID NO 104
<211> LENGTH: 54
<212> TYPE: DNA
<213> ORGANISM: artificial sequence
<220> FEATURE:
<223> OTHER INFORMATION: Primer F-2

<400> SEQUENCE: 104
gtactgaagt tcctatactt tctagagaat aggaagtcgg aataggaact tcaa 54

<210> SEQ ID NO 105
<211> LENGTH: 2091
<212> TYPE: DNA
<213> ORGANISM: Artificial sequence
<220> FEATURE:
<223> OTHER INFORMATION: A Talaromyces emersonii AMG gene containing introns optimized for expression in Aspergillus.

<400> SEQUENCE: 105
ggatccacca tggcctcgct cgtcgcagga gccctctgta tcctcggctt gacacctgca 60
gccttcgcac gagcacccgt cgcagcacgg gcaaccggtt cgttggattc cttcctcgca 120
accgaaactc ctatcgccct ccagggcgtg ctcaacaaca tcggacccaa cggtgcggac 180
gtcgcaggag cgtccgcagg cattgtcgtc gcctcgccct ccaggtccga tcccaactgt 240
aggttctttc ccaccagaaa ttacttattt aaatcagccc tctgacaggt tgaagacttc 300
tattcgtgga cgagggatgc agcgttgaca gcgaaatacc tcgtcgatgc cttcattgcc 360
ggaaacaaag acttggagca gacaatccag cagtacatct cggcacaggc gaaggtgcag 420
accatctcga accccctccgg tgacttgtcg acaggcggat tgggcgaacc caaattcaac 480
gtcaacgaga ccgccttcac aggaccctgg ggtcgacccc agagggacgg acctgccctc 540
agggcaaccg cactcatcgc gtacgccaac tacttgattg taagcttctg ctcgctgccc 600
ttctctctgc tcgtatgcta agtagtcctg tcaggataac ggagaggcgt ccacagccga 660
tgagatcatc tggcctatcg tccagaacga cctctcctac atcacccagt actggaactc 720
ctccacgttc ggtaggcaaa tgaatattcc cgacacagcg tggtactaat ttgattcaga 780
tttgtgggag gaggtcgaag gctcgtcctt cttcactaca gccgtgcagc atcgagcctt 840
ggtggaaggt aacgcgttgg cgacgcgatt gaaccacaca tgttccaact gtgtgtccca 900
ggcaccgcag gtcctctgtt tcctccagtc ctactggact ggatcgtacg tcttggcgaa 960
cttcggtggc tccggcaggt ccggcaagga cgtgaactcc atcctcggct ccatccatac 1020
attcgatcct gccggaggat gtgatgactc gaccttccag ccctgttccg caagggcctt 1080
ggcaaaccat aaggtcgtca ccgattcgtt ccgctcgatc tacgcgatca actccggcat 1140
cgccgaaggt tcggcagtgg cagtgggtcg ataccccgaa gacgtctatc agggtggcaa 1200
cccctggtat ctcgcaacag ccgcagcggc agagcagctc tacgacgcaa tctatcagtg 1260
gaagaagatt ggttcgattt ccattaccga cgtgtccctc ccgttcttcc aggatatcta 1320
cccgtcggca gccgtcggaa cctataactc gggctccaca accttcaacg acatcatttc 1380
ggcagtccag acgtatggag atggctattt gtcgatcgtg gtacgttttg ccttagattc 1440
tcaggtgtaa agaaaaaaat ggaactaact cagttctagg aaaagtacac accctccgat 1500
ggatcgctca cggagcagtt ctcgcgcacg gatggaaccc ccttgtccgc gtcggcattg 1560

```
acgtggtcgt atgcctcgtt gttgactgcc tcggcacgac ggcagtccgt cgtccctgcc   1620

tcgtggggag agtcgtcggc gtcgtcggtc cctgcagtct gttccgcaac ttcggccact   1680

ggcccttatt ccactgcaac caacactgtc tggccttcgt cgggctccgg atcgtcgaca   1740

accacgtcgt cggcaccttg taccacgcct acatccgtcg ccgtcacctt cgacgagatc   1800

gtgtcgacct cgtacggtga aactatctac ctcgcaggat cgatccccga gctcggcaac   1860

tggtcgaccg cgtccgccat ccccctccga gccgacgcat acacaaactc caacccccttg   1920

tggtatgtca cggtgaactt gcctcctggc acctccttcg agtacaagtt cttcaaaaac   1980

cagaccgatg gtaccatcgt ctgggaggac gaccccaacc gttcgtatac cgtccctgcg   2040

tactgtggtc agactaccgc cattctcgat gactcctggc agtgactcga g            2091
```

```
<210> SEQ ID NO 106
<211> LENGTH: 1272
<212> TYPE: DNA
<213> ORGANISM: Artificial sequence
<220> FEATURE:
<223> OTHER INFORMATION: Encoding thermostable FLP recombinase variant
      designated "FLPe" having amino acid alterations P2S, L33S, Y108N,
      S294P.
<220> FEATURE:
<221> NAME/KEY: CDS
<222> LOCATION: (1)..(1269)
<223> OTHER INFORMATION: Encoding thermostable FLP recombinase variant
      designated "FLPe" having amino acid alterations P2S, L33S, Y108N,
      S294P.

<400> SEQUENCE: 106

atg tcc cag ttc gat atc ctc tgc aag acc ccc ccc aag gtc ctc gtc       48
Met Ser Gln Phe Asp Ile Leu Cys Lys Thr Pro Pro Lys Val Leu Val
1               5                   10                  15

cgc cag ttc gtc gag cgc ttc gag cgc ccc tcc ggc gag aag atc gcc       96
Arg Gln Phe Val Glu Arg Phe Glu Arg Pro Ser Gly Glu Lys Ile Ala
            20                  25                  30

tcc tgc gcc gcc gag ctg acc tac ctc tgc tgg atg atc acc cat aac      144
Ser Cys Ala Ala Glu Leu Thr Tyr Leu Cys Trp Met Ile Thr His Asn
        35                  40                  45

ggc acc gcc atc aag cgc gcc acc ttc atg tcc tac aac acc atc atc      192
Gly Thr Ala Ile Lys Arg Ala Thr Phe Met Ser Tyr Asn Thr Ile Ile
    50                  55                  60

tcc aac tcc ctc tcc ttc gat atc gtc aac aag tcc ctc cag ttc aag      240
Ser Asn Ser Leu Ser Phe Asp Ile Val Asn Lys Ser Leu Gln Phe Lys
65                  70                  75                  80

tac aag acc cag aag gcc acc atc ctg gag gcc tcc ctc aag aag ctc      288
Tyr Lys Thr Gln Lys Ala Thr Ile Leu Glu Ala Ser Leu Lys Lys Leu
                85                  90                  95

atc ccc gcc tgg gag ttc acc atc atc ccc tac aac ggc cag aag cat      336
Ile Pro Ala Trp Glu Phe Thr Ile Ile Pro Tyr Asn Gly Gln Lys His
            100                 105                 110

cag tcc gat atc acc gat atc gtc tcc tcc ctc cag ctc cag ttc gag      384
Gln Ser Asp Ile Thr Asp Ile Val Ser Ser Leu Gln Leu Gln Phe Glu
        115                 120                 125

tcc tcc gag gag gcc gat aag ggc aac tcc cat tcc aag aag atg ctc      432
Ser Ser Glu Glu Ala Asp Lys Gly Asn Ser His Ser Lys Lys Met Leu
    130                 135                 140

aag gcc ctc ctc tcc gag ggc gag tcc atc tgg gag atc acc gag aag      480
Lys Ala Leu Leu Ser Glu Gly Glu Ser Ile Trp Glu Ile Thr Glu Lys
145                 150                 155                 160

atc ctc aac tcc ttc gag tac acc tcc cgc ttc acc aag acc aag acc      528
Ile Leu Asn Ser Phe Glu Tyr Thr Ser Arg Phe Thr Lys Thr Lys Thr
                165                 170                 175
```

```
ctc tac cag ttc ctc ttc ctc gcc acc ttc atc aac tgc ggc cgc ttc      576
Leu Tyr Gln Phe Leu Phe Leu Ala Thr Phe Ile Asn Cys Gly Arg Phe
            180                 185                 190

tcc gat atc aag aac gtc gat ccc aag tcc ttc aag ctc gtc cag aac      624
Ser Asp Ile Lys Asn Val Asp Pro Lys Ser Phe Lys Leu Val Gln Asn
        195                 200                 205

aag tac ctc ggc gtc atc atc cag tgc ctc gtc acc gag acc aag acc      672
Lys Tyr Leu Gly Val Ile Ile Gln Cys Leu Val Thr Glu Thr Lys Thr
    210                 215                 220

tcc gtc tcc cgc cat atc tac ttc ttc tcc gcc cgc ggc cgc atc gat      720
Ser Val Ser Arg His Ile Tyr Phe Phe Ser Ala Arg Gly Arg Ile Asp
225                 230                 235                 240

ccc ctc gtc tac ctc gat gag ttc ctc cgc aac tcc gag ccc gtc ctc      768
Pro Leu Val Tyr Leu Asp Glu Phe Leu Arg Asn Ser Glu Pro Val Leu
                245                 250                 255

aag cgc gtc aac cgc acc ggc aac tcc tcc tcc aac aag cag gag tac      816
Lys Arg Val Asn Arg Thr Gly Asn Ser Ser Ser Asn Lys Gln Glu Tyr
            260                 265                 270

cag ctc ctc aag gat aac ctc gtc cgc tcc tac aac aag gcc ctc aag      864
Gln Leu Leu Lys Asp Asn Leu Val Arg Ser Tyr Asn Lys Ala Leu Lys
        275                 280                 285

aag aac gcc ccc tac ccc atc ttc gcc atc aag aac ggc ccc aag tcc      912
Lys Asn Ala Pro Tyr Pro Ile Phe Ala Ile Lys Asn Gly Pro Lys Ser
    290                 295                 300

cat atc ggc cgc cat ctc atg aca agc ttc ctc tcc atg aag ggc ctc      960
His Ile Gly Arg His Leu Met Thr Ser Phe Leu Ser Met Lys Gly Leu
305                 310                 315                 320

acc gag ctc acc aac gtc gtc ggc aac tgg tcc gat aag cgc gcc tcc     1008
Thr Glu Leu Thr Asn Val Val Gly Asn Trp Ser Asp Lys Arg Ala Ser
                325                 330                 335

gcc gtc gcc cgc acc acc tac acc cat cag atc acc gcc atc ccc gat     1056
Ala Val Ala Arg Thr Thr Tyr Thr His Gln Ile Thr Ala Ile Pro Asp
            340                 345                 350

cat tac ttc gca cta gtc tcc cgc tac tac gcc tac gat ccc atc tcc     1104
His Tyr Phe Ala Leu Val Ser Arg Tyr Tyr Ala Tyr Asp Pro Ile Ser
        355                 360                 365

aag gag atg atc gcc ctc aag gat gag acc aac ccc atc gag gag tgg     1152
Lys Glu Met Ile Ala Leu Lys Asp Glu Thr Asn Pro Ile Glu Glu Trp
    370                 375                 380

cag cat atc gag cag ctc aag ggc tcc gcc gag ggc tcc atc cgc tac     1200
Gln His Ile Glu Gln Leu Lys Gly Ser Ala Glu Gly Ser Ile Arg Tyr
385                 390                 395                 400

ccc gcc tgg aac ggc atc atc tcc cag gag gtc ctc gat tac ctc tcc     1248
Pro Ala Trp Asn Gly Ile Ile Ser Gln Glu Val Leu Asp Tyr Leu Ser
                405                 410                 415

tcc tac atc aac cgc cgc atc tga                                     1272
Ser Tyr Ile Asn Arg Arg Ile
            420
```

```
<210> SEQ ID NO 107
<211> LENGTH: 423
<212> TYPE: PRT
<213> ORGANISM: Artificial sequence
<220> FEATURE:
<223> OTHER INFORMATION: Synthetic Construct

<400> SEQUENCE: 107

Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
```

```
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420
```

<210> SEQ ID NO 108

<211> LENGTH: 20
<212> TYPE: DNA
<213> ORGANISM: Artificial sequence
<220> FEATURE:
<223> OTHER INFORMATION: Primer oJaL132

<400> SEQUENCE: 108
cagatactgg ttccttacgg 20

<210> SEQ ID NO 109
<211> LENGTH: 40
<212> TYPE: DNA
<213> ORGANISM: Artificial sequence
<220> FEATURE:
<223> OTHER INFORMATION: Primer oJaL133

<400> SEQUENCE: 109
cgtccacgcg gggattatgc gtagaatgca gagatagctg 40

<210> SEQ ID NO 110
<211> LENGTH: 20
<212> TYPE: DNA
<213> ORGANISM: Artificial sequence
<220> FEATURE:
<223> OTHER INFORMATION: Primer X1111C07

<400> SEQUENCE: 110
gcataatccc cgcgtggacg 20

<210> SEQ ID NO 111
<211> LENGTH: 19
<212> TYPE: DNA
<213> ORGANISM: Artificial sequence
<220> FEATURE:
<223> OTHER INFORMATION: Primer oJaL114

<400> SEQUENCE: 111
ccaacagccg actcaggag 19

<210> SEQ ID NO 112
<211> LENGTH: 40
<212> TYPE: DNA
<213> ORGANISM: Artificial sequence
<220> FEATURE:
<223> OTHER INFORMATION: Primer oJaL134

<400> SEQUENCE: 112
cgataagctc cttgacgggg ttgagcactg cttttggatc 40

<210> SEQ ID NO 113
<211> LENGTH: 20
<212> TYPE: DNA
<213> ORGANISM: Artificial sequence
<220> FEATURE:
<223> OTHER INFORMATION: Primer oJaL135

<400> SEQUENCE: 113
gctcacccgg cataagttgc 20

<210> SEQ ID NO 114
<211> LENGTH: 20
<212> TYPE: DNA
<213> ORGANISM: Artificial sequence
<220> FEATURE:
<223> OTHER INFORMATION: Primer X1111C08

<400> SEQUENCE: 114
ccccgtcaag gagcttatcg 20

<210> SEQ ID NO 115
<211> LENGTH: 19
<212> TYPE: DNA
<213> ORGANISM: Artificial sequence
<220> FEATURE:
<223> OTHER INFORMATION: Primer oJaL113

<400> SEQUENCE: 115
gagctgctgg atttggctg 19

<210> SEQ ID NO 116
<211> LENGTH: 28
<212> TYPE: DNA
<213> ORGANISM: artificial sequence
<220> FEATURE:
<223> OTHER INFORMATION: Primer 3PAY-F

<400> SEQUENCE: 116
ttgcttctag acttctattt cctaatat 28

<210> SEQ ID NO 117
<211> LENGTH: 27
<212> TYPE: DNA
<213> ORGANISM: artificial sequence
<220> FEATURE:
<223> OTHER INFORMATION: Primer 3PAY-R

<400> SEQUENCE: 117
ttgtttaaac ttaattaacc gcgccat 27

<210> SEQ ID NO 118
<211> LENGTH: 30
<212> TYPE: DNA
<213> ORGANISM: artificial sequence
<220> FEATURE:
<223> OTHER INFORMATION: Primer 5PAY-F

<400> SEQUENCE: 118
ggtggcggcc gcgccgacgg tgctggagga 30

<210> SEQ ID NO 119
<211> LENGTH: 75
<212> TYPE: DNA
<213> ORGANISM: artificial sequence
<220> FEATURE:
<223> OTHER INFORMATION: Primer 5PAY-R

<400> SEQUENCE: 119
tttactagtg aagttcctat actttctaga gaataggaac tcggaatagg aacttcaaga 60
tgaattccta gtcgg 75

<210> SEQ ID NO 120
<211> LENGTH: 85
<212> TYPE: DNA
<213> ORGANISM: artificial sequence
<220> FEATURE:
<223> OTHER INFORMATION: Primer pyrG-F

<400> SEQUENCE: 120
ttagtacttt gaagttccta ttccgagttc ctattcttca aatagtatag gaacttcaac 60
tagctagtgc atgcctagtg gagcg 85

<210> SEQ ID NO 121
<211> LENGTH: 29
<212> TYPE: DNA
<213> ORGANISM: artificial sequence
<220> FEATURE:
<223> OTHER INFORMATION: Primer pyrG-R

<400> SEQUENCE: 121
aagtctagaa gcaagggcga attccagca 29

<210> SEQ ID NO 122
<211> LENGTH: 30
<212> TYPE: DNA
<213> ORGANISM: artificial sequence
<220> FEATURE:
<223> OTHER INFORMATION: Primer fcy-F

<400> SEQUENCE: 122
gctagcgcga ggctatcacg gaggctgtgg 30

<210> SEQ ID NO 123
<211> LENGTH: 30
<212> TYPE: DNA
<213> ORGANISM: artificial sequence
<220> FEATURE:
<223> OTHER INFORMATION: Primer fcy-R

<400> SEQUENCE: 123
gctagcttct gtggttcttg ccatgatcgt 30

<210> SEQ ID NO 124
<211> LENGTH: 24
<212> TYPE: DNA
<213> ORGANISM: artificial sequence
<220> FEATURE:
<223> OTHER INFORMATION: T.c.GA coding region forward primer

<400> SEQUENCE: 124
tcgagtgcgg ccgacgcgta cgtc 24

<210> SEQ ID NO 125
<211> LENGTH: 20
<212> TYPE: DNA
<213> ORGANISM: artificial sequence
<220> FEATURE:
<223> OTHER INFORMATION: T.c.GA coding region reverse primer

<400> SEQUENCE: 125
cagagagtgt tggtcacgta 20

<210> SEQ ID NO 126
<211> LENGTH: 29
<212> TYPE: DNA
<213> ORGANISM: artificial sequence
<220> FEATURE:
<223> OTHER INFORMATION: JA126 coding region forward primer

<400> SEQUENCE: 126
tcgaacttcg gcgacgagtc gcagttgaa 29

<210> SEQ ID NO 127
<211> LENGTH: 30
<212> TYPE: DNA
<213> ORGANISM: artificial sequence
<220> FEATURE:
<223> OTHER INFORMATION: JA126 coding region reverse primer

<400> SEQUENCE: 127
cccaacatct cggaaatcct ggagaaaccc 30

<210> SEQ ID NO 128
<211> LENGTH: 115
<212> TYPE: DNA
<213> ORGANISM: artificial sequence
<220> FEATURE:
<223> OTHER INFORMATION: Primer FLPe1

<400> SEQUENCE: 128
ggatctacca tgtcccagtt cgatatcctc tgcaagaccc cccccaaggt cctcgtccgc 60
cagttcgtcg agcgcttcga gcgcccctcc ggcgagaaga tcgcctcctg cgccg 115

<210> SEQ ID NO 129
<211> LENGTH: 30
<212> TYPE: DNA
<213> ORGANISM: artificial sequence
<220> FEATURE:
<223> OTHER INFORMATION: Primer FLPe2

<400> SEQUENCE: 129
atgcttctgg ccgttgtagg ggatgatggt 30

<210> SEQ ID NO 130
<211> LENGTH: 30
<212> TYPE: DNA
<213> ORGANISM: artificial sequence
<220> FEATURE:
<223> OTHER INFORMATION: Primer FLPe3

<400> SEQUENCE: 130
accatcatcc cctacaacgg ccagaagcat 30

<210> SEQ ID NO 131
<211> LENGTH: 30
<212> TYPE: DNA
<213> ORGANISM: artificial sequence
<220> FEATURE:
<223> OTHER INFORMATION: Primer FLPe4

<400> SEQUENCE: 131
ttgatggcga agatggggta gggggcgttc 30

<210> SEQ ID NO 132
<211> LENGTH: 30
<212> TYPE: DNA
<213> ORGANISM: artificial sequence
<220> FEATURE:
<223> OTHER INFORMATION: Primer FLPe5

<400> SEQUENCE: 132
gaacgccccc taccccatct tcgccatcaa 30

<210> SEQ ID NO 133
<211> LENGTH: 30
<212> TYPE: DNA
<213> ORGANISM: artificial sequence
<220> FEATURE:
<223> OTHER INFORMATION: Primer FLPe6

<400> SEQUENCE: 133
ttcggatcag atgcggcggt tgatgtagga 30

<210> SEQ ID NO 134
<211> LENGTH: 29
<212> TYPE: DNA
<213> ORGANISM: artificial sequence
<220> FEATURE:
<223> OTHER INFORMATION: JA126 coding region forward primer

<400> SEQUENCE: 134
tcgaacttcg gcgacgagtc gcagttgaa 29

<210> SEQ ID NO 135
<211> LENGTH: 30
<212> TYPE: DNA
<213> ORGANISM: artificial sequence
<220> FEATURE:
<223> OTHER INFORMATION: JA126 coding region reverse primer

<400> SEQUENCE: 135
cccaacatct cggaaatcct ggagaaaccc 30

<210> SEQ ID NO 136
<211> LENGTH: 29
<212> TYPE: DNA
<213> ORGANISM: artificial sequence
<220> FEATURE:
<223> OTHER INFORMATION: Primer K6763E12

<400> SEQUENCE: 136
gacgcggccg ccgcgtggag gtctaggac 29

<210> SEQ ID NO 137
<211> LENGTH: 27
<212> TYPE: DNA
<213> ORGANISM: artificial sequence
<220> FEATURE:
<223> OTHER INFORMATION: Primer K6763F01

<400> SEQUENCE: 137
gacaagctta caaacccgtg acactcc 27

<210> SEQ ID NO 138
<211> LENGTH: 28
<212> TYPE: DNA
<213> ORGANISM: artificial sequence
<220> FEATURE:
<223> OTHER INFORMATION: Primer K6763F02

<400> SEQUENCE: 138
gacaagctta cgcatgtatg tatgtgtc 28

<210> SEQ ID NO 139
<211> LENGTH: 28
<212> TYPE: DNA
<213> ORGANISM: artificial sequence
<220> FEATURE:
<223> OTHER INFORMATION: Primer K6763F03

<400> SEQUENCE: 139
gacgtttaaa cggatgggtt tgccatac 28

<210> SEQ ID NO 140
<211> LENGTH: 25
<212> TYPE: DNA
<213> ORGANISM: artificial sequence
<220> FEATURE:
<223> OTHER INFORMATION: Primer Forward (069083)

<400> SEQUENCE: 140
aaaaaacaaa catcccgttc ataac 25

<210> SEQ ID NO 141
<211> LENGTH: 25
<212> TYPE: DNA
<213> ORGANISM: artificial sequence
<220> FEATURE:
<223> OTHER INFORMATION: Primer Reverse (069084)

<400> SEQUENCE: 141
aacaaggttt accggtttcg aaaag 25

<210> SEQ ID NO 142
<211> LENGTH: 22
<212> TYPE: DNA
<213> ORGANISM: artificial sequence
<220> FEATURE:
<223> OTHER INFORMATION: Primer 5' Recombination Forward (#0611526)

<400> SEQUENCE: 142
ttcccttcct ctagtgttga at 22

<210> SEQ ID NO 143
<211> LENGTH: 22
<212> TYPE: DNA
<213> ORGANISM: artificial sequence
<220> FEATURE:
<223> OTHER INFORMATION: Primer Reverse No integration (#0611527)

<400> SEQUENCE: 143
tcgtcgaata ctaacatctt gc 22

<210> SEQ ID NO 144
<211> LENGTH: 22
<212> TYPE: DNA
<213> ORGANISM: artificial sequence
<220> FEATURE:
<223> OTHER INFORMATION: Primer Reverse Integration (#0611528)

<400> SEQUENCE: 144
cacggacctc gaacctttat at 22

<210> SEQ ID NO 145
<211> LENGTH: 25
<212> TYPE: DNA
<213> ORGANISM: artificial sequence
<220> FEATURE:
<223> OTHER INFORMATION: Primer 3' Recombination Forward (#999661)

<400> SEQUENCE: 145
cagcgagagc ctgacctatt gcatc 25

<210> SEQ ID NO 146
<211> LENGTH: 25
<212> TYPE: DNA
<213> ORGANISM: artificial sequence
<220> FEATURE:
<223> OTHER INFORMATION: Primer Reverse No integration (#069084)

<400> SEQUENCE: 146
aacaaggttt accggtttcg aaaag 25

<210> SEQ ID NO 147

-continued

```
<211> LENGTH: 24
<212> TYPE: DNA
<213> ORGANISM: artificial sequence
<220> FEATURE:
<223> OTHER INFORMATION: Primer Reverse Integration (#0611648)

<400> SEQUENCE: 147

gtggctgccg aggtgtgtat acca                                              24
```